US010954216B2

(12) United States Patent
Hashizume et al.

(10) Patent No.: US 10,954,216 B2
(45) Date of Patent: Mar. 23, 2021

(54) BMP-SIGNAL-INHIBITING COMPOUND

(71) Applicants: RIKEN, Saitama (JP); THE UNIVERSITY OF TOKYO, Tokyo (JP)

(72) Inventors: Yoshinobu Hashizume, Saitama (JP); Katsuhiko Sekimata, Saitama (JP); Hirokazu Kubota, Saitama (JP); Hirofumi Yamamoto, Saitama (JP); Yasuko Koda, Saitama (JP); Hiroo Koyama, Saitama (JP); Tomonori Taguri, Saitama (JP); Tomohiro Sato, Saitama (JP); Akiko Tanaka, Saitama (JP); Kohei Miyazono, Tokyo (JP)

(73) Assignees: RIKEN, Saitama (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 16/473,850

(22) PCT Filed: Dec. 26, 2017

(86) PCT No.: PCT/JP2017/046508
§ 371 (c)(1),
(2) Date: Jun. 26, 2019

(87) PCT Pub. No.: WO2018/124001
PCT Pub. Date: Jul. 5, 2018

(65) Prior Publication Data
US 2019/0337926 A1 Nov. 7, 2019

(30) Foreign Application Priority Data
Dec. 27, 2016 (JP) .............................. JP2016-254414

(51) Int. Cl.
| | | |
|---|---|---|
| *C07D 401/14* | (2006.01) | |
| *C07D 405/14* | (2006.01) | |
| *C07D 471/08* | (2006.01) | |
| *C07D 487/08* | (2006.01) | |
| *C07D 471/04* | (2006.01) | |
| *C07D 417/14* | (2006.01) | |
| *C07D 413/14* | (2006.01) | |
| *A61P 19/08* | (2006.01) | |

(52) U.S. Cl.
CPC ............ *C07D 401/14* (2013.01); *A61P 19/08* (2018.01); *C07D 405/14* (2013.01); *C07D 413/14* (2013.01); *C07D 417/14* (2013.01); *C07D 471/04* (2013.01); *C07D 471/08* (2013.01); *C07D 487/08* (2013.01)

(58) Field of Classification Search
CPC ...... C07D 401/14; C07D 405/14; A61P 19/08
See application file for complete search history.

(56) References Cited

FOREIGN PATENT DOCUMENTS

| | | |
|---|---|---|
| JP | 2007-517825 | 7/2007 |
| JP | 2008-516962 | 5/2008 |
| WO | 2005/068452 | 7/2005 |
| WO | 2006/044509 | 4/2006 |
| WO | 2009/114180 | 9/2009 |
| WO | 2011/025927 A1 | 3/2011 |
| WO | 2014/138088 | 9/2014 |
| WO | 2015/148654 | 10/2015 |
| WO | 2016/121908 | 8/2016 |

OTHER PUBLICATIONS

Kim. BMB Reports, 2011, 619-634 (Year: 2011).*
Holderfield . Cancer Cell, 2013, 23, 594-602 (Year: 2013).*
Japanese and English version of International Preliminary Report on Patentability of Chapter I, Application No. PCT/JP2017/046508, dated Jul. 2, 2019.
International Search Report and Search Opinion, Application No. PCT/JP2017/046508, dated Feb. 13, 2018.
Waite et al., Nat. Rev. Genet., vol. 4, 763-773, 2003.
Weiss et al., N. Engl. J. Med., vol. 352, 1011-1023, 2005.
Yu et al., Nat. Chem. Biol., vol. 4, 33-41, 2008.
Shore et al., Nat. Genet., vol. 38, 525-527, 2006.
Kaplan et al., Expert Opinion on Orphan Drugs, vol. 1, 637-649, 2013.
Katagiri et al., Biol. Chem., vol. 394, 703-714, 2013.
Pignolo et al., J. Bone and Mineral Res., vol. 31, 650-656, 2016.
Chaikuad et al., J. Biol. Chem., vol. 290, 3390-3404, 2015.
Fukuda et al., J. Biol. Chem., vol. 284, 7149-7156, 2009.
Economides et al., Sci. Transl. Med. vol. 7, 303ra137, 2015.
Hopkins, Expert Opinion on Therapeutic Patents vol. 26, 1115-1128, 2016.
Murakami et al., Rinsho Seikei Geka (Clinical Orthopaedic Surgery), vol. 23, 397-402, 1988.
Koga et al., Rinsho Seikei Geka (Clinical Orthopaedic Surgery), vol. 33, 385-391, 1998.
Yonemori et al., Am. J. Pathol., vol. 186, 1335-1347, 1997.

(Continued)

*Primary Examiner* — Noble E Jarrell
(74) *Attorney, Agent, or Firm* — Greenblum & Bernstein P.L.C.

(57) ABSTRACT

The present invention relates to novel and excellent small-molecule-compounds that specifically antagonize BMP signal pathways, and these compounds can be used to modulate cell growth, differentiation, proliferation, and apoptosis, and thus can be used to treat diseases or pathological symptoms related to BMP signal pathway including inflammation, cardiovascular diseases, hematopoietic diseases, cancer, osteodystrophia, or the like, particularly, fibrodysplasia ossificans progressiva, and the present invention relates to provision of a pharmaceutical and pharmacological agent used for specifically antagonizing the BMP signal pathways and acting on the BMP signal pathways in the prevention and treatment or experimental application since the compounds can be beneficial for regulating cell differentiation and/or cell proliferation.

26 Claims, No Drawings

(56) References Cited

OTHER PUBLICATIONS

Inamasu et al., Neurosurgery vol. 58, 1027-1039, 2006.
Yu et al., J. Biol. Chem., vol. 280, 24443-24450, 2005.
Moustakas, Miyazono et al., Cytokine Growth Factor Rev., 81-92, 2016.
Imamura et al., Oncogene vol. 27, 6322-6333, 2008.
Jones et al., Nature. Genet., vol. 46, 457-461, 2014.
Becher et al., Nature Genet., vol. 46, 451-456, 2014.
Baker et al., Nature Genet., vol. 46, 444-450, 2014.
Ligon et al., Nature Genet., vol. 46, 462-466, 2014.
Kim et al., Nature Immunol. vol. 7, 1057-1065, 2006.
Kersten et al., BMC, Immunol., vol. 6, 9-21, 2005.
Levi et al., J. Bone Joint Surg., vol. 97, 1001-1011, 2015.
Shaifur et al., Bone Res., vol. 3, 1-20, 2015.
Randy et al., Am. J. Orthop., vol. 40, E232-E235, 2011.
Cushner et al., Orthopaedic Rev., vol. 21, 1319-1326, 1992.
Levi et al., Ann. Surg., vol. 259, 993-998, 2014.
Levi et al., Stem Cells Dev. vol. 24, 205-213, 2015.
Bostrom et al., J. Clin. Invest. vol. 91, 1800-1809, 1993.
Tyson et al., Alterioscler. Thromb. Vasc, Biol., vol. 23, 489-494, 2003.
Botchkarev et al., Differentiation vol. 72, 512-526, 2004.
Kaiser et al., J. Invest. Dermatol., vol. 111, 1145-1152, 1998.
Plikus et al., Nature vol. 451, 340-344, 2008.
Blessing et al., J. Cell Biol., vol. 135, 227-239, 1996.
Andreev et al., Exp. Eye. Res., vol. 83, 1162-1170, 2006.
Mishina et al., PLoS One vol. 10, e0141345, 2015.
Mishina et al., Bone vol. 88, 74-84, 2016.
Miriyala et al., Circulation vol. 113, 2818-2825, 2006.
Fantozzi et al., Am. J. Physiol. Lung Cell. Mol. Physiol., vol. 291, L993-1004, 2006.
Frank et al., Circ. Res. vol. 97, 496-504, 2005.
Nakano et al., Am. J. Physiol. Heart Circ. Physiol., vol. 293, H3396-H3403, 2007.
Pietras et al., Blood vol. 117, 6999-7006, 2011.
Kwon et al., Alterioscler. Thromb. Vasc, Biol., vol. 35, 2020-2031, 2015.
Yamashita et al., J. Neurochem., vol. 105, 1471-1479, 2008.
Yamashita et al., J. Cell. Biol., vol. 173, 47-58, 2006.
Yamashita et al., Brain Res., vol. 118, 74-86, 2007.
Lin et al., J. Biol. Chem., vol. 280, 29820-29827, 2005.
Schluesener et al., Acta. Neuropathol., vol. 90, 76-79, 1995.
Grinspan et al., J. Neurosci. Res., vol. 86, 125-135, 2008.
Itoh et al., J. Biol. Chem., vol. 282, 15843-15850, 2007.
O'Connor et al., J. Neurosci., vol. 27, 7740-7750, 2007.
Jo et al., Circulation vol. 116, 1258-1266, 2007.
Demer et al., J. Clin. Invest., vol. 91, 1800-1809, 1993.
Daemen et al., Alterioscler. Thromb. Vasc, Biol., vol. 21, 1998-2003, 2001.
Hruska et al., Circ. Res., vol. 97, 105-112, 2005.
Bostrom et al., Crit. Rev. Eukar. Gene. Expr., vol. 10, 151-158, 2000.
Yokode et al., Circulation vol. 103, 2955-2960, 2001.
Yu et al., Alterioscler. Thromb. Vasc, Biol., vol. 32, 613-622, 2012.
Yamanaka et al., Curr. Stem Cell Res. Ther., vol. 1, 103-111, 2006.
Choi et al., Development vol. 131, 2749-2762, 2004.
Chien et al., Cell vol. 117, 373-386, 2004.
Fukuda et al., Nat. Biotechnol., vol. 23, 607-611, 2005.
Extended European Search Report, European Patent Office, Application No. 17888576.0, dated May 12, 2020.
Gregory J Anderson et al: "Small-molecule dissection of BMP signaling", Nature Chemical Biology, Nature Publishing Group, Basingstoke, vol. 4, No. 1, Jan. 2008.

* cited by examiner

BMP-SIGNAL-INHIBITING COMPOUND

TECHNICAL FIELD

The present invention relates to novel and excellent small-molecule compounds that specifically antagonize BMP (bone morphogenetic protein) signal pathways, and these compounds can be used to modulate cell growth, differentiation, proliferation, and apoptosis, and thus can be used to treat diseases or pathological symptoms related to BMP signal pathway including inflammation, cardiovascular diseases, hematopoietic diseases, cancer, osteodystrophia, or the like, particularly, fibrodysplasia ossificans progressiva, and the present invention relates to provision of a pharmaceutical and pharmacological agent used for specifically antagonizing the BMP signal pathways and acting on the BMP signal pathways in the prevention and treatment or experimental application since the compounds can be beneficial for regulating cell differentiation and/or cell proliferation.

BACKGROUND ART

BMP and TGF-β signal pathways are essential for normal organ development and pattern formation, and also essential for normal remodeling and pathological remodeling of mature tissues. Defects in the BMP signal pathway have been suggested as causes of many congenital and acquired disease processes including hereditary hemorrhagic telangiectasia, primary pulmonary hypertension, familial juvenile polyposis, and sporadic renal cell carcinoma and prostate cancer.

It has been suggested that attenuation in BMP signal can cause certain disease conditions related to defects in signaling components. However, it has been suggested that, excessive BMP signal can cause expression of pathological symptoms in some situations (Non Patent Literature 1).

An ability to regulate BMP signal is used to provide a method of preventing or treating such symptoms, a method of studying the same, and a method of determining underlying causes of such symptoms.

(Treatment of Anemia Including Anemia Due to Iron Deficiency and Chronic Diseases)

For an overview, see (Non Patent Literature 2).

Inflammatory anemia (also called anemia of chronic diseases) is observed in patients with chronic infections, autoimmune diseases (systemic lupus erythematosus and rheumatoid arthritis, and Castleman's disease, etc.), inflammatory bowel disease, cancer (including multiple myeloma), and renal failure.

Inflammatory anemia is often caused by inappropriate expression of the peptide hormone hepcidin. Hepcidin causes decomposition of ferroportin of important proteins enabling iron transportation from intracellular stores of macrophages and iron transportation from intestinal epithelial cells. Many patients with renal failure have erythropoietin deficiency and excessive hepcidin expression in combination. BMP signal induces hepcidin expression, and inhibition of hepcidin expression with a BMP signal inhibitor increases an iron level. The BMP signal inhibitor described in this specification can be used to treat anemia due to chronic diseases or inflammation and anemia related to a high hepcidin state.

Increased IL-6 in inflammatory anemia due to various causes, the effect of chronic IL-6 administration in vivo, protection of IL-6-deficient rodents from anemia (Non Patent Literature 2), and pro-inflammatory cytokine IL-6 are thought to be intrinsic causes of increased hepcidin expression in inflammatory conditions. Stimulation of hepatocellular carcinoma cell lines due to IL-6 induces hepcidin expression, and on the other hand, it has been described that a treatment with a BMP signal inhibitor inhibits IL-6-induced hepcidin expression (Non Patent Literature 3). In addition, it has been described that systemic iron administration in mice and zebra fish quickly activates BMP responsive SMAD and hepcidin expression in the liver, and BMP antagonistic action effectively blocks such response (Non Patent Literature 3). Such data suggest that iron-mediated and inflammation-mediated regulation of hepcidin and circulating iron levels require BMP signal transduction. The BMP signal inhibitor described in this specification can be used to change availability of iron in various situations for therapeutic benefits.

The BMP signal inhibitor described in this specification, (i) enhances efficacy of dietary iron and oral iron supplementation (these are safer than intravenous iron administration) and increases a serum iron concentration; (ii) increases accumulation of hemoglobin in the blood before surgery or allows oneself to donate blood before surgery; and (iii) enhances efficacy of erythropoietin and its related substances, and thus can be used in anemic conditions, and accordingly can reduce a dosage of erythropoietin to be administered for anemia, and can minimize known erythropoietin toxicity and side effects (hypertension, cardiovascular events, and tumor proliferation).

(Treatment of Fibrodysplasia Ossificans Progressiva (FOP))

Fibrodysplasia ossificans progressiva (FOP) is a hereditary disease in which cartilage tissues and bone tissues are ectopically formed in soft tissues such as skeletal muscle, tendons, and ligaments in which bone tissues are not generally formed (Non Patent Literatures 5 and 6). In this disease, ectopic ossification occurs throughout the body including the face, ectopic bone tissues and existing bone tissues are combined together, a movable range of joints is significantly reduced, and deformation of the body is caused (Non Patent Literatures 5 and 6).

In ectopic ossification in FOP, in addition to chronically progressing according to this growth, acute ectopic ossification that proceeds with symptoms called flare-up caused by muscle damage, viral infections or the like is known (Non Patent Literature 7). Flare-up is swelling in which an inflammation reaction and long term pain are main symptoms, and is induced by bruises, falls, intramuscular injections, and the like which cause muscle damage, and also sudden cases in which causes are not clear are known. In FOP, since ectopic bone tissues are formed after flare-up, invasive medical procedures such as biopsy and surgery are contraindicated, and ectopic bone tissues cannot be surgically removed. In addition, since ectopic bone tissues formed due to FOP are formed by normal chondrocytes and osteoblasts, and metabolized in the same manner as in normal bone tissues, it is not possible to remove only ectopic bone tissues through internal medicine using drugs and the like.

Currently, no fundamental treatment methods for preventing ectopic ossification in FOP have been found, and only symptomatic therapies for inflammation, pain, and the like are being performed. Therefore, it is very difficult to remove ectopic bone tissues formed due to FOP, and the development of drugs that can be expected to have a preventive effect before ectopic ossification begins is awaited.

Regarding genes responsible for FOP, the activin-like kinase 2 (ALK2) gene that encodes one type of receptor for bone morphogenetic proteins (BMPs) that induce ectopic osteogenesis in soft tissues including skeletal muscle tissue has been identified (Non Patent Literature 4). ALK2 is the same as a gene called activin A type receptor 1 (ACVR1). ALK2 with amino acid substitution has been found in familial and sporadic FOP cases (Non Patent Literature 4).

Human and mouse ALK2 is a single-pass type transmembrane protein having a signal peptide composed of 509 amino acids, and functions as a transmembrane serine/threonine kinase receptor that binds to BMP (Non Patent Literatures 5 and 6), and this binds to BMP in the extracellular domain at the N terminal side, and activates a downstream intracellular information transmission system at intracellular serine/threonine kinase sites.

BMP receptors are classified into two types: a type I receptor containing ALK2 and a type II receptor according to their structures and functions (Non Patent Literatures 5 and 6). The type II receptor is a constitutively active enzyme that exhibits kinase activity without binding to BMP. On the other hand, the type I receptor containing ALK2 is an inactive enzyme when it does not bind to BMP and exhibits kinase activity depending on binding to BMP. This is thought to be caused by the fact that, due to binding to BMP, a kinase for the type II receptor phosphorylates the intracellular domain of the type I receptor as a substrate, changes a three-dimensional structure, and activates the type I receptor (Non Patent Literatures 5 and 6).

It is known that, when a specific amino acid in the intracellular domain of the type I receptor is substituted, a constitutively active receptor is activated independently from the type II receptor (Non Patent Literatures 5 and 6). When this constitutively active mutant of the type I receptor is over-expressed, an intracellular information transmission system is activated even if a BMP stimulation is not applied. Therefore, the type I receptor is thought to be a molecule responsible for transmitting BMP signal from the outside of cells to the inside of cells.

ALK2 mutations identified from familial and typical sporadic FOP cases were R206H mutants in which Arg206 was substituted with His (Non Patent Literature 4). It has been found that all gene mutations identified from FOP cases so far cause amino acid mutations in the ALK2 intracellular domain. Many of such FOP case mutations are concentrated near an ATP binding region in the ALK2 intracellular domain (Non Patent Literature 8).

When ALK2 mutants identified in FOP are over-expressed in cultured cells, a BMP intracellular information transmission system is activated even if a BMP stimulation is not applied (Non Patent Literature 9). Thus, regarding FOP therapeutic agents, small-molecule inhibitors for ALK2 kinase, RNAi and exon skipping methods for specifically inhibiting expression of genetically mutated ALK2, downstream transcription factor inhibitors for ALK2 receptors, activin neutralizing antibodies, ALK2 antibodies, and osteoblast differentiation inhibitors using BMP signal inhibition, and the like have been developed (Patent Literatures 1 to 4, and Non Patent Literatures 5, 6, 10, and 11).

In recent years, several small-molecule compounds having a BMP signal inhibitory effect have been reported. For example, pyrazolo[1,5-a]pyrimidine derivatives are disclosed in WO2009/114180 (Patent Literature 1), and WO2014/138088 (Patent Literature 2), and 3,5-diarylpyridine derivatives are disclosed in WO2015/148654 (Patent Literature 3). For FOP therapeutic agents, it is necessary to exhibit pharmaceutical efficacy according to oral administration rather than injection having a risk of muscle damage that contributes to flare-up, but BMP signal inhibitors that allow oral absorption have not been reported yet. In addition, FOP therapeutic agents based on nucleic acids such as RNAi that specifically inhibit expression of genetically mutated ALK2 do not have established effective drug delivery methods. An antibody medicine (Patent Literature 4) in which act on the ALK2 extracellular domain to inhibit signals and activin neutralizing antibodies (Non Patent Literature 7) are expected to express ALK2-signal specific pharmacological effects. However, there are concerns that intravenous administration having a high risk of the occurrence of flare-up in FOP patients is required, and drugs are poorly distributed in muscle tissues.

As described above, in the development of BMP signal inhibitors so far, pharmacokinetics has been major problem. However, a small-molecule BMP signal inhibitor in the present invention has an excellent pharmacokinetic profile that is expected to express pharmaceutical efficacy via oral administration. In the present invention, in pharmacokinetic studies using rodents, clinical development candidates showed a high bioavailability (>90%).

In order to prevent excessive osteogenesis in response to trauma, musculoskeletal stress or inflammation, the small-molecule BMP signal inhibitor of the present invention can be administered systemically or locally to concentrate or limit the effect in a trauma or inflammation site.

The small-molecule BMP signal inhibitor in the present invention can be used as a chronic treatment to reduce spontaneous osteogenesis in highly susceptible individuals. In individuals with FOP in whom osteoma or affected bone occurs most frequently in connection with trauma, in order to prevent abnormal osteogenesis, a temporary treatment can be performed before, during, or after such a traumatic event.

A temporary treatment using the small-molecule BMP signal inhibitor in the present invention can be performed before, during or immediately after necessary or urgent medical procedures or surgical procedures (and also important immune treatments and tooth extraction) in individuals with FOP in order to prevent pathological calcification. A combination treatment with other bone inhibitors, immunomodulative drugs or anti-inflammatory drugs (such as NSAIDs, steroids, cyclosporin, cyclophosphamide, azathioprine, methotrexate, rituximab, etanercept, or similar drugs) can inhibit ectopic osteogenesis in the above disorders and increase efficacy of the BMP signal inhibitor.

(Treatment of Ligament Ossification)

Involvement of ossification of the posterior longitudinal ligament (OPLL), ossification of the yellow ligament (OYL), and ossification of the anterior longitudinal ligament (OALL) with systemic factors and local factors has been reported (Non Patent Literature 12), and it has been reported that BMP is involved in such ossification procedures (Non Patent Literature 13). In addition, it has been reported that BMP receptors and activin receptors are highly expressed in OPLL patient tissues (Non Patent Literature 14, and Non Patent Literature 15).

Specific inhibitors of BMP signal such as compounds described in this specification can be used to prevent osteogenesis in ligaments in response to trauma, musculoskeletal stress or inflammation. The compounds can also be used to ease regression of affected bone. The BMP signal inhibitor can be administered systemically or locally to concentrate or limit the effect in a trauma or inflammation site.

(Treatment of Cancer)

Excessive BMP signal transduction (this can be caused due to BMP overexpression, or paradoxically, as a result of deficiency in BMP type II receptor expression (Non Patent Literature 1, and Non Patent Literature 16)) can contribute to tumorigenesis, some solid tumors (including breast cancer and prostate cancer), and bone cancer, lung cancer and renal cell carcinoma proliferation (Non Patent Literature 17) or metastasis (Non Patent Literature 18). In addition, the presence of constitutively active mutation forms of ALK2 in children with high-grade glioma and medium to high-grade astrocytoma has been reported (Non Patent Literature 19).

When BMP overexpression, increased BMP signal activity related to BMP type II receptor deficiency, or BMP signal enhancement due to the presence of constitutively active mutation forms of ALK2 contributing to pathogenesis, inhibiting BMP signal activity at the level of the BMP type I receptor (downstream of both ligands and type II receptors) using the BMP inhibitor described in this specification can be an effective method of normalizing BMP signal activity and then potentially inhibiting tumor proliferation or metastasis.

As either an auxiliary chemical treatment or a primary chemical treatment, the BMP signal inhibitor described in this specification can be used to slow down or stop proliferation or metastasis of the above tumor cells (as well as other tumor constituting cell types) for clinical advantages. Similarly, the BMP signal inhibitor described in this specification can also be used to reduce bone metastatic properties of certain types of cancer (for example, adenocarcinoma such as prostate cancer and breast cancer). In addition, the compounds described in this specification can be used to inhibit osteoblast activity in either bone-forming tumors or bone-derived tumors (such as osteosarcoma) (as an auxiliary chemical treatment or a primary chemical treatment). In addition, the compounds described in this specification can be used to inhibit osteoclastic activity (also regulated by BMP through the action of RANKL in BMP target genes), and osteoclastic activity which is abnormally increased in medical conditions such as multiple myeloma and other bone targeting tumors. When the BMP inhibitor is applied in such medical conditions, the presence of osteolytic lesions and bone fractures due to involvement of a tumor can be reduced.

(Immune Regulation)

It has been reported that BMP attenuates inflammatory responses or immune responses (Non Patent Literature 20), and BMP can impair an individual's ability to fight infectious diseases (specifically, viral infections, bacterial infections, fungal infections, parasitic infections, or human type *Mycobacterium tuberculosis* infections). Thus, the BMP signal inhibitor described in this specification can enhance inflammatory responses or immune responses, which can allow an individual to more quickly eliminate infectious diseases.

There is increasing evidence that BMP receptors are expressed on cell surfaces of lymphocytes and other immune cells, and thus BMP regulates differentiation and maturation of various humoral and cellular immunological compartments, and BMP also regulates humoral and cellular immune responses in mature organisms. Like the effects of many immunologically important cytokines that are generally known, effects of BMP signals on immune cells can be situation-specific and thus effects of BMP signals increasing or decreasing differentiation or functions of a specific lymphocyte population are empirically determined. The BMP antagonistic action using the compounds described in this specification can be an effective strategy for intentionally biasing differentiation of cellular immune compartments, congenital immune compartments, or humoral immune compartments for treatments, or a strategy for therapeutically biasing immune responses in the mature immune system. Such strategies can target innate disorders in cellular immunity, innate immunity or humoral immunity, or can target disorders in which immune responses are inappropriately weak (for example, if immune treatments using other methods are difficult or ineffective, the compound can be used as an adjuvant for promoting favorable antigen sensitization or can target disorders in which immune responses are excessive or inappropriate (for example, autoimmunity and autosensitization)).

The BMP signal inhibitor described in this specification can also be effective in intentional induction of immune tolerance in some situations (that is, in allogenic transplantation or autoimmunity).

(Treatment of Pathological Osteogenesis)

The BMP signal inhibitor described in this specification can be used to improve pathological osteogenesis/bone fusion in inflammatory disorders such as ankylosing spondylitis or other seronegative spondylarthroses (autoimmunity and inflammation in the above disorders stimulate osteogenesis) (Non Patent Literature 21). As one application of the above compounds, the compounds are used to prevent excessive osteogenesis in patients with specifically spondylitis or chronic rheumatoid arthritis after joint surgery. The BMP signal inhibitor described in this specification can also be used to prevent calcinosis (dystrophic soft tissue calcification) in diseases such a systemic lupus erythematosus, scleroderma, and dermatomyositis.

Due to blunt traumatic damage to muscles, in certain individuals, abnormal osteogenesis in muscles is caused, and thereby a disorder called traumatic myositis ossificans can occur (Non Patent Literature 22). Head trauma and burns can induce ectopic osteogenesis (Non Patent Literature 23), which can significantly impair patient rehabilitation and recovery. A treatment using the BMP signal inhibitor described in this specification, or a treatment with an anti-inflammatory drug (for example, non-steroidal anti-inflammatory drugs such as indomethacin and ibuprofen) that is generally prescribed to treat the above symptoms as necessary, is useful to prevent pathological osteogenesis in individuals susceptible to pathological osteogenesis or is useful to reduce or regress lesions in individuals with pathological osteogenesis that has developed recently or previously. Although reports of ossification developing in other muscles (including myocardium) in the presence of damage or trauma are very rare, similar treatments with the BMP signal inhibitor described in this specification are useful in such situations.

(Treatment of Ectopic Osteogenesis and Maladaptive Osteogenesis)

BMP signals and their transcriptional target are suggested as the cause of initial vascular remodeling and medium-term vascular remodeling and calcification in Monckeberg vascular calcification diseases and atherosclerotic vascular diseases (Non Patent Literature 24). BMP and BMP-induced bone differentiation are also suggested as the cause of heart valve calcification. Innate heart valves can be calcified specifically if they are abnormal for a long time. A typical example is the aortic bicuspid valves, and such valves generally cause calcification, which results in stenosis. Cardiac surgery is often required for patients with calcific aortic stenosis for valve replacement. Abnormal calcification can adversely affect the functions of the prosthetic vascular grafts or heart valve. For example, prosthetic heart valves cause stenosis and calcification which often lead to leakage.

The BMP signal inhibitor described in this specification can be used to inhibit only vascular or valve calcific diseases, and can be used to inhibit vascular or valve calcific diseases combined with atherosclerotic diseases, renal diseases, renal osteodystrophy or parathyroid diseases.

The BMP signal inhibitor described in this specification is administered systemically or administered locally, or directly incorporated into a prosthetic material or other grafts (for example, into a mixture having polymers covering or constituting all or a part of a graft or a prosthetic component), and thus can be used to inhibit calcification of a prosthetic vascular material or a valve material.

In some cases, it is desirable to intentionally inhibit bone fracture healing at specific sites to delay bone fracture healing after bone fracture or to prevent functional damage due to misadaptive osteogenesis. For example, when bone fracture has occurred but it is not possible to perform surgery immediately due to medical or practical reasons, until final surgery or treatment can be performed, bone fracture healing can be delayed or stopped temporarily by use of the BMP signal inhibitor described in this specification. This is so that, for example, the need for later intentional bone refracturing to secure an appropriate positional relationship between fractured bone surfaces of bone fragments can be reduced. When a treatment period is relatively short, it is anticipated that a normal bone fracture healing process will occur upon discontinuation of a BMP signal inhibitor. In other cases, for example, when bone fracture directly affects joints, new bone growth can impair functions with even a small amount. In this case, systemic or local inhibition of BMP activity (by systemic delivery of the BMP signal inhibitor described in this specification or by the local delivery of the BMP signal inhibitor described in this specification through the diffusion from a local graft or a matrix) can be used in a target region to inhibit bone fracture healing or prevent fracture calluses.

(Treatment of Skin Diseases)

In proliferation of keratinocytes cultured in vitro, BMP inhibits keratinocyte proliferation and promotes differentiation (Non Patent Literature 25). For patients who need skin grafts (for example, after burns), skin grafts are prepared from cultured keratinocytes. Keratinocytes can be derived from other animals (xenograft), but they are only temporary because they are rejected by the immune system. Keratinocytes can be derived from patients themselves and can be grown on a cell sheet in a laboratory (cultured epithelial autograft). Patients do not reject keratinocytes derived from their own body. The BMP signal inhibitor described in this specification can be added to a keratinocyte culture to promote keratinocyte proliferation, and thereby patients can receive grafts faster.

Improvement in Epithelialization:

BMP6 is highly expressed in skin injury lesions, and BMP6 at a high level is detected in chronic human wounds with various causes (Non Patent Literature 26). In mice in which BMP5 is overexpressed in the skin, improvement in epithelialization with significantly delayed re-epithelialization and skin wound recovery (Non Patent Literature 26) can reduce scar formation. Superficial administration or systemic administration of the BMP signal inhibitor described in this specification can be used to improve skin wound epithelialization, for example, in treatments of decubital ulcers (bed sores) or skin scars that have not healed or have not sufficiently healed (for example, in patients with peripheral vascular diseases, diabetes mellitus, and venous insufficiency). The compounds are also expected to reduce scar formation.

Promotion of Body Hair Growth:

hair follicle growth of the scalp has a cycle with three phases: a growth phase (proliferation phase), a regression phase (retrogression phase), and a resting phase (telogen phase). Recent evidence suggests that BMP signals delay transition from the resting phase to the growth phase (Non Patent Literature 27). Inhibition of BMP signal transduction using the BMP signal inhibitor described in this specification can shorten the resting phase and increase the number of hair follicles in the growth phase. The BMP signal inhibitor described in this specification can be used in treatment situations in which there are insufficient hair follicles are or when body hairs are lost at a higher frequency than they grow. Such situations include androgenic alopecia (male pattern alopecia), alopecia areata, and telogen effluvium.

Treatment of Psoriasis:

Psoriasis is an inflammatory skin disorder that occurs often in skin trauma and subsequent repair and after inflammation (Koebner phenomenon). Since overexpression of BMP6 in the skin of mice leads to skin lesions similar to those observed in patients with psoriasis (Non Patent Literature 28), BMP may be involved in an inflammatory mechanism causing psoriasis and its repair. The BMP signal inhibitor described in this specification can be superficially or systemically administered to treat established psoriasis or prevent the onset of psoriasis after skin damage.

Treatment of Corneal Scarring:

BMP6 expression is related to conjunctiva scarring (Non Patent Literature 29). The BMP signal inhibitor described in this specification can be used to prevent or treat corneal scarring and consequent blindness.

(Prevention or Treatment of Osteoporosis)

It has been reported that, in BMPR1A conditional KO mice, bone elasticity and toughness have been enhanced and become more effective in combination with exercise (Non Patent Literature 30). In addition, it can be clearly understood that, in this mechanism, attenuation of BMP signals promotes cross-link formation of collagen in osteogenesis and promotes accumulation of minerals in the femur (Non Patent Literature 31). The BMP signal inhibitor described in this specification that inhibits BMP signal transduction can be used to increase bone mass and bone density.

In addition, the BMP signal inhibitor described in this specification can be used to provide a bone mass loss ameliorating agent that allows a long-term stay in space. That is, this provides a guideline that administration of the BMP signal inhibitor is effective for a reduction in the bone mass in a microgravity environment which is one of space medical problems. In addition, in Japan with the declining birthrate and aging population, it is predicted that the number of bedridden elderly people will be 2.3 million in 2025 and that there will be 2.60 million middle-aged people (Annual Report on Health, Labor and Welfare 2011). The BMP signal inhibitor described in this specification can be used to develop a bone mass reduction preventive drug or an osteoporosis therapeutic agent for elderly people.

(Treatment of Systemic Hypertension)

Injection of BMP4 induces systemic hypertension in mice (Non Patent Literature 32). Vascular smooth muscle cells express various BMP ligands. BMP increases expression of voltage-gated potassium channels, and accordingly, increases contraction of vascular smooth muscles (Non Patent Literature 33), and the BMP signal inhibitor described in this specification that inhibits BMP signal transduction can be used to lower a blood pressure. A sustained reduction in blood pressure in patients with hypertension is expected to prevent myocardial infarction, congestive heart failures, cerebrovascular diseases, and renal failure. The BMP inhibitor described in this specification can be used to target hypertension in specific vascular beds such as pulmonary hypertension via local delivery (for example, via an aerosol).

(Treatment of Pulmonary Hypertension)

BMP signal transduction contributes to the cause of pulmonary hypertension. For example, mice with a reduced BMP4 level are protected from pulmonary hypertension and pulmonary vascular remodeling induced due to breathing over the long term at a low oxygen concentration (Non Patent Literature 34). In addition, mutations in genes that encode type II BMP receptors (BMPRII) are frequently observed in patients with sporadic and familial pulmonary arterial hypertension. It is expected that reduction in BMP signal transduction will cause pulmonary hypertension. However, Yu et al have reported that BMPRII deficiency paradoxically increases BMP signal transduction according to some BMP ligands (Non Patent Literature 16), and thereby a modulation in BMP signal transduction using the BMP signal inhibitor described in this specification can actually contribute to the improvement of pulmonary hypertension.

The BMP signal inhibitor described in this specification can be used to prevent the development of the disease in patients at risk of pulmonary arterial hypertension (for example, patients with BMPRII mutations) or treat patients with idiopathic or acquired pulmonary arterial hypertension. Reduction in pulmonary hypertension in individuals treated with the BMP signal inhibitor described in this specification is expected to reduce short breath, right ventricular hypertrophy, and right ventricular failures.

(Treatment of Ventricular Hypertrophy)

A BMP10 level increases in hypertrophied ventricles of rats with hypertension, and the BMP ligands induce hypertrophy in cultured neonatal rat ventricular myocytes (Non Patent Literature 35). According to inhibition of BMP10 signal transduction using the BMP signal inhibitor described in this specification, ventricular hypertrophy can be prevented and treated. Ventricular hypertrophy can lead to congestive heart failures due to diastolic dysfunction. The BMP signal inhibitor described in this specification is expected to prevent and treat congestive heart failures.

(Treatment of Angiogenesis)

There are two types of age-related macular degeneration: atrophy type and exudative type. In the exudative type, there is accompanying neovascularity from the vascular choroid, and bleeding and exudation under the retina occur, rapidly progress, and cause deterioration in eyesight. The cause is thought to be secretion of cytokines such as a vascular endothelial growth factor (VEGF) and induction of choroidal neovascularization, and an anti-VEGF drug therapy in which neovascularity is prevented by neutralizing increased VEGF in the eye due to age-related macular degeneration is performed. Anti-VEGF drugs that can be used clinically in Japan include RNA aptamer preparations, humanized anti-VEGF neutralizing antibodies, and soluble decoy receptor fusion proteins. Such anti-VEGF drugs significantly reduce intraocular VEGF when repeatedly administered through intravitreal injection every 4 to 8 weeks, and regress choroidal neovascularization, and as a result, the eyesight can be improved and maintained. However, there are cases in which it is not possible to completely eliminate exudative changes even if intravitreal injection is performed monthly, and there are cases in which there is repeated recurrence during the course of long term treatment and the eyesight deteriorates. It is suggested that there are many factors other than VEGF that affect the development and progression of age-related macular degeneration and BMP is involved as one of them.

Involvement of signals in angiogenesis through ALK1 receptors has been reported and the relationship of signal transduction activation by its ligand BMP9 with blood vessel extension in tumor proliferation has been revealed (Non Patent Literature 36). Such findings suggest that the BMP signal inhibitor can be used as an anti-cancer agent that has an effect of preventing angiogenesis, and inhibition of BMP signal using the BMP signal inhibitor described in this specification could be an effective method of potentially inhibiting tumor proliferation or metastasis. In addition, there is a limit to treatment in which only VEGF is inhibited in order to prevent angiogenesis in exudative type age-related macular degeneration, and a treatment in which other factors are inhibited is desirable. Therefore, it is expected that the BMP signal inhibitor described in this specification would be locally (such as eye drops) or systemically administered as a small-molecule drug, and prevent bleeding and exudation under the retina, and as a result, prevent and treat blindness.

(Treatment of Neurological Disorders)

Treatment of Spinal Cord Injury and Neurological Disorders:

BMP is a potent inhibitory factor for axonal regeneration in the adult spinal cord after spinal cord injury (Non Patent Literature 37). It has been reported that BMP expression increases in oligodendrocytes and astrocytes around an injury site after spinal cord contusion. Intrathecal administration of noggin as a BMP signal inhibitor leads to enhancement in motor activity and significant regrowth of the corticospinal tract after spinal cord contusion.

Repulsive guidance molecule a (RGMa) inhibits axon proliferation and recovery, and synapse re-formation after spinal cord injury, and the effects of RGMa are blocked by antibodies for RGMa (Non Patent Literature 38). RGMa enhances BMP signal transduction (Non Patent Literature 39), and this suggests that BMP signal transduction can be the cause of axon proliferation and recovery interruption.

Based on this consideration, the BMP signal inhibitor described in this specification is expected to enhance axon proliferation and recovery after spinal cord injury. The BMP signal inhibitor described in this specification is expected to prevent and treat neurological disorders related to a wide range of disorders including diabetes mellitus. The BMP signal inhibitor described in this specification is expected to treat any of pains and motor dysfunctions related to neurological disorders.

Treatment of Neurological Disorders Related to Central Nervous System Inflammation:

BMP4 and BMP5 are detected in multiple sclerosis and Creutzfeldt-Jakob disease lesions (Non Patent Literature 40). BMP is also detected in mice with experimental autoimmune encephalomyelitis (animal models with multiple sclerosis) (Non Patent Literature 41). The BMP signal inhibitor described in this specification can be used to prevent and treat multiple sclerosis and other neurological disorders that are related to central nervous system inflammation or related to misadaptive damage repair processes mediated by BMP signals.

Treatment of Dementia:

A BMP signal transduction inhibitor can promote neurogenesis in neural progenitor cells of mice (Non Patent Literature 42). The BMP signal inhibitor described in this specification can be used to enhance neurogenesis in various neurological disorders involving an accelerated loss of neurons (including cerebrovascular diseases and Alzheimer's disease, and other dementias).

Change in Memory and Learning:

BMP signal transduction has an important role in the development and maintenance of neurons involved in memory and cognitive activity. For example, mice deficient in chordin as a BMP signal inhibitor had improved spatial learning but had degraded exploratory behavior in a novel environment (Non Patent Literature 43). The BMP signal inhibitor described in this specification can be used to change or prevent memories or learning (including, for example, amnesia in anesthesia or other situations in which pain is caused), and can be used to prevent post-traumatic stress disorders.

(Treatment of Arteriosclerosis)

Much evidence suggests that BMP ligands are pro-inflammatory and proatherogenic in blood vessel walls (Non Patent Literature 44). Knockdown of BMP4 expression reduces inflammatory signals and on the other hand, knockdown of BMP inhibitors (for example, follistatin or noggin) increases inflammatory signals. The BMP signal inhibitor described in this specification can be used to reduce vascular inflammation related to atherosclerotic arteriosclerosis, autoimmune diseases, and other vasculitis. The BMP signal inhibitor described in this specification is expected to reduce acute coronary syndromes (angina pectoris and heart attack), transient ischemic attack, strokes, peripheral vascular diseases, and other vascular ischemia events due to the reduced atherosclerotic arteriosclerosis. In addition, in so far as atherosclerotic arteriosclerosis contributes to the cause of aneurysm formation, the BMP signal inhibitor described in this specification can be used to slow the progress of aneurysm formation, which can reduce frequent occurrence of aneurysm structures and the need for vascular surgery.

Since BMP and many BMP-inducible gene products that affect matrix remodeling are overexpressed in initial atherosclerotic lesions, BMP signals can promote plaque formation and progress (Non Patent Literature 45). BMP signal transduction activity in atherosclerotic plaque can therefore represent a form of maladaptive damage repair or can contribute to inflammation. BMP signals can gradually induce differentiation of resident vascular cell populations or neovascular cell populations into osteoblast-like cells, which can lead to short-term or medium-term calcification of blood vessels (Non Patent Literature 46). Calcific vascular diseases or arteriosclerosis is related to a reduced vascular index and an increased risk of cardiovascular events and an increased mortality rate, and is particularly problematic when associated with potential atherosclerotic diseases (Non Patent Literature 47). However, when signals contributing to the progress of atherosclerotic lesions and calcific lesions are blocked, all such lesions can regress (Non Patent Literature 48). Yu et al. found that the inhibitor against the BMP type I receptor activity is effective in treatments for atherosclerotic plaque and vascular calcification (Non Patent Literature 49), and the inhibitors against the BMP type I receptor activity described in this specification can be used to inhibit the progress of atherosclerotic plaque and vascular calcification in vivo.

(Proliferation, Engraftment and Differentiation of Progenitor Cells Including Embryonic Cells and Adult Stem Cells In Vitro and In Vivo)

BMP signals are important to regulate differentiation and regeneration of progenitor cell populations and stem cell populations (in addition, tissues in some situations), and this regulation prevents differentiation into differentiation lines (and on the other hand, directs differentiation in other situations). The BMP signal inhibitor described in this specification can be used (i) to maintain a pluripotent state of stem cell populations or pluripotent cell populations in vivo or in vitro; (ii) to proliferate stem cell populations or pluripotent cell populations in vivo or in vitro; (iii) to direct differentiation of stem cell populations or pluripotent cell populations in vivo or in vitro; (iv) to manipulate or direct differentiation of stem cell populations or pluripotent cell populations in vivo or in vitro (either alone, in a combination with other treatments, or in series with other treatments); and (v) to regulate dedifferentiation from differentiation cell populations to pluripotent populations or precursor populations.

BMP signals are required for many stem cell lines and precursor series to determine whether they proliferate, differentiate into specific tissue lines, reach and integrate specific tissue types, or cause programmed cell death. Often, BMP signals interact with signals provided by growth factors (bFGF, PDGF, VEGF, HBEGF, PlGF, and others), sonic hedgehog, notch, and the Wnt signal pathway and affect the above changes (Non Patent Literature 50). The BMP signal inhibitor described in this specification can be used to direct differentiation of stem cells (for example, embryonic stem cells) or tissue precursor cells into specific lines for therapeutic applications (Non Patent Literature 51). In addition, in certain cell populations, the BMP signal inhibitor described in this specification can be effective in preventing differentiation and promoting proliferation in order to produce a sufficient number of cells effective for clinical applications. Exact combinations of BMP signal inhibitors, growth factors or signaling molecules can be very specific to cells and tissue types.

For example, some embryonic stem cell lines need to be co-cultured with a leukemia inhibitory factor (LIF) in order to inhibit differentiation of some cultured embryonic stem cell lines and maintain pluripotency (Non Patent Literature 50). The use of the BMP signal inhibitor described in this specification can be used to maintain pluripotency in the absence of LIF. Other ES cell lines need to be co-cultured with specific feeder cell layers in order to maintain pluripotency. The use of the BMP signal inhibitor described in this specification, alone or an in combination with other drugs, can be effective in maintaining pluripotency when contamination with feeder cell layers is a concern or a DNA or protein component makes it difficult or prevents the use of cells for human treatment.

In another example, in some situations, inhibition of BMP signals with proteins such as noggin just before LIF inhibition in the culture can induce differentiation into myocardium cell differentiation lines (Non Patent Literature 52). The use of the pharmacological BMP signal inhibitor described in this specification can have similar (if not, potent) effects. The differentiation cells can be therapeutically introduced into pathological myocardium. In addition, such a treatment can actually be more effective for engrafted progenitor cells that have already reached pathological myocardium. A systemic treatment using a BMP signal proteinaceous inhibitor (such as noggin) is very expensive and requires a complex dosing method. Systemic or local delivery of the BMP signal inhibitor described in this specification can bias differentiation of the progenitor cells in situ to functional myocardium cells.

(Application of Compounds Having Varying Degrees of Selectivity: A Compound that Inhibits BMP Signal Transduction Via a Specific BMP Type I Receptor or a Compound that Affects Signal Transduction Via TGF-β and an Activin Receptor)

The BMP signal inhibitor described in this specification inhibits activity of BMP receptors: ALK2, ALK3, and ALK6. Some of them inhibit ALK2 and ALK3 to a higher degree than ALK6, and have a relatively higher selectivity with respect to a specific BMP receptor. It is thought that certain diseases can be caused due to signal transduction dysfunction of certain specific receptors.

For example, fibrodysplasia ossificans progressiva (FOP) is a disease caused by abnormal (constitutively active) ALK2 functions (Non Patent Literature 4). In addition, the presence of constitutively active mutation forms of ALK2 in pediatric high-grade glioma and medium to high grade astrocyte species has been reported (Non Patent Literature 19). In such examples, the BMP signal inhibitor described in this specification that specifically antagonizes a function of some BMP receptors can have advantages of reduced toxicity or side effects or higher efficacy, or can have all of these advantages.

Some of the BMP signal inhibitors described in this specification can have a high degree of selectivity for BMP compared with TGF-β, and activin receptor signal transduction. Other compounds can have a lower specificity and target other pathways in addition to BMP signal. For example, in a tumor treatment, when specific tumor molecular phenotyping of a certain patient exhibits dysregulation of a plurality of pathways, a drug that inhibits BMP signal and one or more of the above pathways can have a beneficial effect (for example, reduction in size of tumor).

(Application of Compound in Species Other than Human)

The BMP signal inhibitor described in this specification can be used to treat subjects (for example, humans, household pets, livestock, and other animals) according to the use of a dosage and a dosage regimen that are appropriately determined by those skilled in the art, and parameters of the dosage and the dosage regimen can be changed depending on, for example, the type and degree of a disorder to be treated, overall health conditions of a subject, a therapeutic index of the compound and an administration pathway. A standard clinical test can be used to optimize the dosage and frequency of administration for a certain specific pharmaceutical composition of the present invention. Examples of administration pathways that can be used include oral administration, parenteral administration, intravenous administration, intraarterial administration, subcutaneous administration, intramuscular administration, surface administration, intracranial administration, intraorbital administration, ocular administration, intraventricular administration, intracapsular administration, intravertebral administration, intracisternal administration, intraperitoneal administration, intranasal administration, aerosol administration, and suppository administration.

(Inhibition of BMP Signal Transduction in Insects)

Some of the BMP signal inhibitors described in this specification can have activity for arthropod BMP receptors, and presumably, have selectivity for arthropod BMP receptors relative to chordate BMP receptors. Inhibition of BMP signal transduction in arthropod larvae or eggs can cause serious developmental abnormalities and probably can cause impairment in their reproductive ability (for example, dorsalization similar to that observed when the pathway is inhibited in zebra fish and *Drosophila*). When the BMP signal inhibitor described in this specification has a much stronger selectivity for arthropod BMP receptors than human BMP receptors, the BMP signal inhibitor described in this specification can be used as an insecticide or a pest control agent that is apparently less toxic and safer than current strategies from a viewpoint of protection of the environment.

In addition to administration to patients in a treatment method, the BMP signal inhibitor described in this specification can be used to treat cells and tissues transplanted into patients and structural materials ex vivo. For example, the compounds can be used to treat explanted tissues that can be used, for example, in transplantation.

While the present invention is generally described here, the present invention will be more easily understood with reference to the following examples. The following examples are included to simply exemplify specific aspects and embodiments of the present invention, and do not limit the present invention.

CITATION LIST

Patent Literature

[Patent Literature 1] International Publication No. WO2009/114180
[Patent Literature 2] International Publication No. WO2014/138088
[Patent Literature 3] International Publication No. WO2015/148654
[Patent Literature 4] International Publication No. WO2016/121908

Non-Patent Literature

[Non-Patent Literature 1] Waite et al., Nat. Rev. Genet., vol. 4, 763-773, 2003
[Non-Patent Literature 2] Weiss et al., N. Engl. J. Med., vol. 352, 1011-1023, 2005
[Non-Patent Literature 3] Yu et al., Nat. Chem. Biol., vol. 4, 33-41, 2008
[Non-Patent Literature 4] Shore et al., Nat. Genet., vol. 38, 525-527, 2006
[Non-Patent Literature 5] Kaplan et al., Expert Opinion on Orphan Drugs, vol. 1, 637-649, 2013
[Non-Patent Literature 6] Katagiri et al., Biol. Chem., vol. 394, 703-714, 2013
[Non-Patent Literature 7] Pignolo et al., J. Bone and Mineral Res., vol. 31, 650-656, 2016
[Non-Patent Literature 8] Chaikuad et al., J. Biol. Chem., vol. 290, 3390-3404, 2015
[Non-Patent Literature 9] Fukuda et al., J. Biol. Chem., vol. 284, 7149-7156, 2009
[Non-Patent Literature 10] Economides et al., Sci. Transl. Med. vol. 7, 303ra137, 2015
[Non-Patent Literature 11] Hopkins, Expert Opinion on Therapeutic Patents vol. 26, 1115-1128, 2016
[Non-Patent Literature 12] Murakami et al., Rinsho Seikei Geka (Clinical Orthopaedic Surgery), vol. 23, 397-402, 1988
[Non-Patent Literature 13] Koga et al., Rinsho Seikei Geka (Clinical Orthopaedic Surgery), vol. 33, 385-391, 1998
[Non-Patent Literature 14] Yonemori et al., Am. J. Pathol., vol. 186, 1335-1347, 1997
[Non-Patent Literature 15] Inamasu et al., Neurosurgery vol. 58, 1027-1039, 2006
[Non-Patent Literature 16] Yu et al., J. Biol. Chem., vol. 280, 24443-24450, 2005
[Non-Patent Literature 17] Moustakas, Miyazono et al., Cytokine Growth Factor Rev., 81-92, 2016
[Non-Patent Literature 18] Imamura et al., Oncogene vol. 27, 6322-6333, 2008

[Non-Patent Literature 19]
(1) Jones et al., Nature. Genet., vol. 46, 457-461, 2014
(2) Becher et al., Nature Genet., Vol. 46, 451-456, 2014
(3) Baker et al., Nature Genet., vol. 46, 444-450, 2014
(4) Ligon et al., Nature Genet., vol. 46, 462-466, 2014
[Non-Patent Literature 20]
(1) Kim et al., Nature Immunol. vol. 7, 1057-1065, 2006
(2) Kersten et al., BMC, Immunol., vol. 6,9-21, 2005
[Non-Patent Literature 21]
(1) Levi et al., J. Bone Joint Surg., vol. 97, 1001-1011, 2015
(2) Shaifur et al., Bone Res., vol. 3, 1-20, 2015
(3) Randy et al., Am. J. Orthop., vol. 40, E232-E235, 2011
[Non-Patent Literature 22] Cushner et al., Orthopaedic Rev., vol. 21, 1319-1326, 1992
[Non-Patent Literature 23]
(1) Levi et al., Ann. Surg., vol. 259, 993-998, 2014
(2) Levi et al., Stem Cells Dev. vol. 24, 205-213, 2015
[Non-Patent Literature 24]
(1) Bostrom et al., J. Clin. Invest. vol. 91, 1800-1809, 1993
(2) Tyson et al., Alterioscler. Thromb. Vasc, Biol., vol. 23, 489-494, 2003
[Non-Patent Literature 25] Botchkarev et al., Differentiation vol. 72, 512-526, 2004
[Non-Patent Literature 26] Kaiser et al., J. Invest. Dermatol., vol. 111, 1145-1152, 1998
[Non-Patent Literature 27] Plikus et al., Nature vol. 451, 340-344, 2008
[Non-Patent Literature 28] Blessing et al., J. Cell Biol. vol. 135, 227-239, 1996
[Non-Patent Literature 29] Andreev et al., Exp. Eye. Res., vol. 83, 1162-1170, 2006
[Non-Patent Literature 30] Mishina et al., PLoS ONE vol. 10, e0141345, 2015
[Non-Patent Literature 31] Mishina et al., Bone vol. 88, 74-84, 2016
[Non-Patent Literature 32] Miriyala et al., Circulation vol. 113, 2818-2825, 2006
[Non-Patent Literature 33] Fantozzi et al., Am. J. Physiol. Lung Cell. Mol. Physiol., vol. 291, L993-1004, 2006
[Non-Patent Literature 34] Frank et al., Circ. Res. vol. 97, 496-504, 2005
[Non-Patent Literature 35] Nakano et al., Am. J. Physiol. Heart Circ. Physiol., vol. 293, H3396-H3403, 2007
[Non-Patent Literature 36]
(1) Pietras et al., Blood vol. 117, 6999-7006, 2011
(2) Kwon et al., Alterioscler. Thromb. Vasc, Biol., vol. 35, 2020-2031, 2015
[Non-Patent Literature 37] Yamashita et al., J. Neurochem., vol. 105, 1471-1479, 2008
[Non-Patent Literature 38]
(1) Yamashita et al., J. Cell. Biol., vol. 173, 47-58, 2006
(2) Yamashita et al., Brain Res., vol. 118, 74-86, 2007
[Non-Patent Literature 39] Lin et al., J. Biol. Chem., vol. 280, 29820-29827, 2005
[Non-Patent Literature 40] Schluesener et al., Acta. Neuropathol., vol. 90, 76-79, 1995
[Non-Patent Literature 41] Grinspan et al., J. Neurosci. Res., vol. 86, 125-135, 2008
[Non-Patent Literature 42] Itoh et al., J. Biol. Chem., vol. 282, 15843-15850, 2007
[Non-Patent Literature 43] O'Connor et al., J. Neurosci., vol. 27, 7740-7750, 2007
[Non-Patent Literature 44] Jo et al., Circulation vol. 116, 1258-1266, 2007
[Non-Patent Literature 45]
(1) Demer et al., J. Clin. Invest., vol. 91, 1800-1809, 1993
(2) Daemen et al., Alterioscler. Thromb. Vasc, Biol., vol. 21, 1998-2003, 2001
[Non-Patent Literature 46] Hruska et al., Circ. Res., vol. 97, 105-112, 2005
[Non-Patent Literature 47] Bostrom et al., Crit. Rev. Eukar. Gene. Expr., vol. 10, 151-158, 2000
[Non-Patent Literature 48] Yokode et al., Circulation vol. 103, 2955-2960, 2001
[Non-Patent Literature 49] Yu et al., Alterioscler. Thromb. Vasc, Biol., vol. 32, 613-622, 2012
[Non-Patent Literature 50] Yamanaka et al., Curr. Stem Cell Res. Ther., vol. 1, 103-111, 2006
[Non-Patent Literature 51]
(1) Choi et al., Development vol. 131, 2749-2762, 2004
(2) Chien et al., Cell vol. 117, 373-386, 2004
[Non-Patent Literature 52] Fukuda et al., Nat. Biotechnol., vol. 23, 607-611, 2005

SUMMARY OF INVENTION

Problem to be Solved

The inventors and the like conducted extensive studies for many years regarding synthesis of derivatives having an effect of specifically antagonizing BMP signal pathways, and its pharmacological activity, and as a result, found novel derivatives having a completely different structure from known compounds and having excellent effects, and thereby completed the present invention.

Solution to Problem

Novel derivatives of the present invention are a compound of Formula (I) or a pharmacologically acceptable salt thereof or an ester thereof,

[C1]

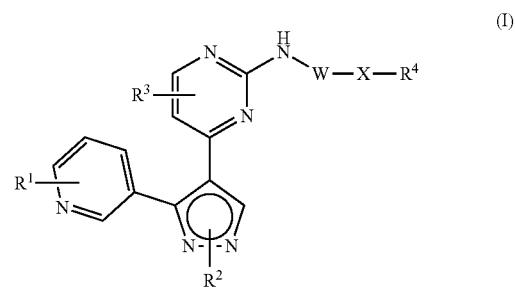

[wherein,
$R^1$ is a group selected from H and a "substituent group A",
$R^2$ is a group selected from
H;
a lower alkyl group;
a lower alkyl group substituted with 1 to 3 substituents selected from a "substituent group B" or an oxo group; and
the "substituent group B,"
$R^3$ is
H,
a halogen atom or
a lower alkyl group, W is a group selected from
a phenylene group;
a phenylene group substituted with 1 to 3 substituents selected from the "substituent group A";
a bivalent group in which a phenylene group and a heterocyclyl group are condensed;
a bivalent group in which a phenylene group and a heterocyclyl group are condensed and substituted with 1 to 3 substituents selected from the "substituent group A",
a bivalent pyridyl group;
a bivalent group in which a pyridyl group and a heterocyclyl group are condensed; and
a bivalent pyrazolyl group;
X is a group selected from among
a single bond;
a group selected from a "substituent group C" including the sequences in reverse order;
a lower alkylene group; and
a lower alkylene group substituted with groups selected from the "substituent group C" including the sequences in reverse order.
$R^4$ is a group selected from
H;
a lower alkyl group;
a lower alkyl group substituted with 1 to 3 substituents selected from the "substituent group B", an oxo group and a lower alkyl group;
a $C_{3-6}$ cycloalkyl group;
a —C(O)$R^5$ group;
a heteroaryl group;
a heteroaryl group substituted with 1 to 3 substituents selected from a "substituent group E";
a heterocyclyl group; and
a heterocyclyl group substituted with 1 to 3 substituents selected from a "substituent group D,"
$R^5$ is
an OH group,
a lower alkyl group, or
a lower alkoxy group,
$R^6$ is H or a lower alkyl group;
$R^7$ is H or a lower alkyl group; or
$R^6$ and $R^7$, together, form a lower alkylene group or a lower alkylene group in which one carbon atom is replaced with an —O— group, an —NR$^8$— group, or an —S(O)$_p$— group (p is 0, 1 or 2);
$R^8$ is H or a lower alkyl group;
the "substituent group A" is
a lower alkyl group,
a lower alkoxy group,
a cyano group,
a nitro group,
an —N(R$^6$)R$^7$ group or
a halogen atom,
the "substituent group B" is
an OH group;
an —N(R$^6$)R$^7$ group;
an —N(R$^6$)COR$^5$ group;
a halogen atom;
a —C(O)R$^5$ group;
a —C(O)N(R$^6$)R$^7$ group;
a $C_{3-6}$ cycloalkyl group;
a halo-lower alkyl group;
a heterocyclyl group;
a heterocyclyl group substituted with 1 to 3 substituents selected from the "substituent group A";
an aryl group;
an aryl group substituted with 1 to 3 substituents selected from the "substituent group A";
a pyridyl group;
a pyridyl group substituted with 1 to 3 substituents selected from the "substituent group A";
a lower alkoxy group;
a halo-lower alkoxy group; or
a $C_{3-6}$ cycloalkyl lower alkoxy group,
the "substituent group C" is
an —O— group,
a —C(O)— group,
a —C(O)O— group,
a —C(O)NR$^8$— group,
an —NR$^8$— group,
an —S— group,
an —S(O)— group,
an —S(O)$_2$— group,
an —S(O)$_2$NR$^8$— group or
an —NR$^8$S(O)$_2$— group;
the "substituent group D" is
a lower alkyl group;
a lower alkyl group substituted with 1 to 3 substituents selected from the "substituent group B" and an oxo group;
an oxo group;
a cyano group;
a halogen atom;
an —N(R$^6$)R$^7$ group;
an —N(R$^6$)COR$^5$ group;
a —CO-lower alkylene-OH group;
a —C(O)R$^5$ group;
a —C(O)N(R$^6$)R$^7$ group;
a heterocyclyl group;
a heterocyclyl group substituted with 1 to 3 substituents selected from the "substituent group A";
a $C_{3-6}$ cycloalkyl group;
an aryl group;
a lower alkyl group substituted with 1 to 3 substituents selected from the "substituent group B," an oxo group and a COOH group, or
an aryl group substituted with 1 to 3 substituents selected from the "substituent group A," and
the "substituent group E" is
an OH group;
a halogen atom;
a lower alkyl group;
a halo-lower alkyl group;
a lower alkyl group substituted with 1 to 3 substituents selected from the "substituent group B" and an oxo group;
a heterocyclyl group; or
a heterocyclyl group substituted with 1 to 3 substituents selected from the "substituent group D."
Preferably, $R^1$ is H or a halogen atom,
$R^2$ is a group selected from
a lower alkyl group;
a lower alkyl group substituted with 1 to 3 substituents selected from the "substituent group B" and an oxo group; and
the "substituent group B," and
more preferably is a group selected from
a lower alkyl group;
a lower alkyl group substituted with 1 to 3 substituents selected from the "substituent group B" and an oxo group;
a $C_{3-6}$ cycloalkyl and heterocyclyl groups,
$R^3$ is H or a halogen atom, W is a group selected from
a phenylene group;
a phenylene group substituted with 1 to 3 substituents selected from the "substituent group A";
a bivalent group in which a phenylene group and a heterocyclyl group are condensed;
a bivalent pyridyl group; and
a bivalent pyrazolyl groups,
more preferably
a phenylene group,
a bivalent group in which a phenylene group and a heterocyclyl group are condensed;
a bivalent pyridyl group; and
a bivalent pyrazolyl groups,
X is a group selected from
a single bond;
an —O— group, a —C(O)— group, a —C(O)NR$^8$— group, an —NR$^8$C(O)— group, an —S(O)$_2$— group, an —S(O)$_2$NR$^8$— group, or an —NR$^8$S(O)$_2$— group including the sequences in reverse order;
a lower alkylene group; and
a lower alkylene groups substituted with an —O— group, a —C(O)— group, a —C(O)NR$^8$— group, an —NR$^8$C(O)— group, an —S(O)$_2$— group, an —S(O)$_2$NR$^8$— group, or an —NR$^8$S(O)$_2$— group including the sequences in reverse order, more preferably
a single bond;
an —O— group, a —C(O)— group, a —C(O)NR$^8$— group, an —S(O)$_2$— group, or an —S(O)$_2$NR$^8$— group including the sequences in reverse order;
a lower alkylene group; and
a lower alkylene groups substituted with an —O— group or a —C(O)— group including the sequences in reverse order.
R$^4$ is a group selected from
H;
a lower alkyl group;
a lower alkyl group substituted with 1 to 3 substituents selected from the "substituent group B," an oxo group and a lower alkyl group;
a C$_{3-6}$ cycloalkyl group;
a —C(O)R$^5$ group;
a heteroaryl group;
a heteroaryl group substituted with 1 to 3 substituents selected from the "substituent group E";
a heterocyclyl group;
a heterocyclyl group substituted with 1 to 3 substituents selected from the "substituent group D," and
more preferably,
H;
a lower alkyl group;
a lower alkyl group substituted with 1 to 3 substituents selected from the "substituent group B," an oxo group and a lower alkyl group;
a C$_{3-6}$ cycloalkyl group;
a heteroaryl group;
a heteroaryl group substituted with 1 to 3 substituents selected from the "substituent group E";
a heterocyclyl group; and
a heterocyclyl group substituted with 1 to 3 substituents selected from the "substituent group D,"
still more preferably,
a "heterocyclyl" group in the "heterocyclyl" group and the "heterocyclyl" group substituted with 1 to 3 substituents selected from the "substituent group D" in R$^4$ is a group selected from the followings:

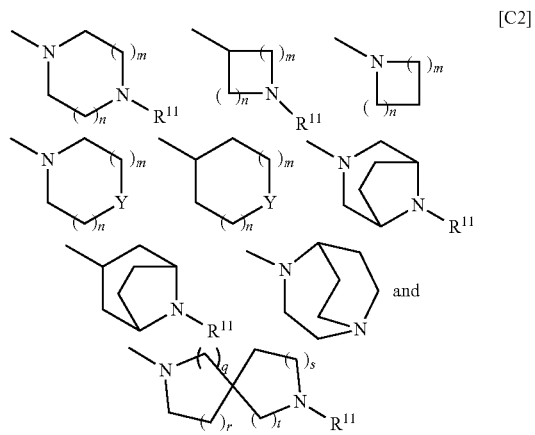

[C2]

wherein, R$^{11}$ is H or a "substituent group D," Y is an —O— group, or —S(O)$_p$— group, m and n may be the same as or different from each other; 1 or 2, p is 0, 1 or 2, and q, r, s and t may be the same as or different from each other; 0, 1 or 2; provided that q and t are not both 0,
R$^5$ is an OH group or a lower alkyl group,
R$^6$ and R$^7$, together, form a lower alkylene group,
the "substituent group A" is a lower alkyl group, a cyano group or a halogen atom,
the "substituent group B" is an OH group, an —N(R$^6$)R$^7$ group, a halogen atom, a C$_{3-6}$ cycloalkyl group, a heterocyclyl group, an aryl group, an aryl group substituted with 1 to 3 substituents selected from the "substituent group A," a pyridyl group, a lower alkoxy group, a halo-lower alkoxy group, a —C(O)N(R$^5$)R$^7$ group, or a C$_{3-6}$ cycloalkyl lower alkoxy group, more preferably, an OH group, an —N(R$^6$)R$^7$ group, a halogen atom, a C$_{3-6}$ cycloalkyl group, a heterocyclyl group, an aryl group, an aryl group substituted with 1 to 3 substituents selected from the "substituent group A," a lower alkoxy group, a halo-lower alkoxy group, or a C$_{3-6}$ cycloalkyl lower alkoxy group,
the "substituent group C" is an —O— group, a —C(O)— group, a —C(O)NR$^8$— group, an —S(O)$_2$— group, or an —S(O)$_2$NR$^8$— group, more preferably, the "substituent group C" is an —O— group, a —C(O)— group, a —C(O)NR$^8$— group, or an —S(O)$_2$NR$^8$— group,
the "substituent group D" is a lower alkyl group; a lower alkyl group substituted with 1 to 3 substituents selected from the "substituent group B" and an oxo group; an oxo group; a cyano group; a halogen atom; an —N(R$^6$)R$^7$ group; an —N(R$^6$)COR$^5$ group; a —CO-lower alkylene-OH group; a —C(O)R$^5$ group; a C(O)N(R$^6$)R$^7$ group; a heterocyclyl group; a heterocyclyl group substituted with 1 to 3 substituents selected from the "substituent group A"; a C$_{3-6}$ cycloalkyl group; or an aryl group, more preferably a lower alkyl group; a lower alkyl group substituted with 1 to 3 substituents selected from the "substituent group B" and an oxo group; a halogen atom; an oxo group; a cyano group; an —N(R$^6$)R$^7$ group; an —N(R$^6$)COR$^5$ group; a —CO-lower alkylene-OH group; a —C(O)R$^5$ group; a —C(O)N(R$^6$)R$^7$ group; a heterocyclyl group; a C$_{3-6}$ cycloalkyl group; or an aryl group,
the "substituent group E" is a lower alkyl group; a halo-lower alkyl group; a lower alkyl group substituted with 1 to 3 substituents selected from the "substituent group B" and an oxo group; a heterocyclyl group; or a heterocyclyl group substituted with 1 to 3 substituents selected from the "substituent group D", more preferably a lower alkyl group; a halo-lower alkyl group; or a heterocyclyl group.

Examples of —W—X—R⁴ are as follows,

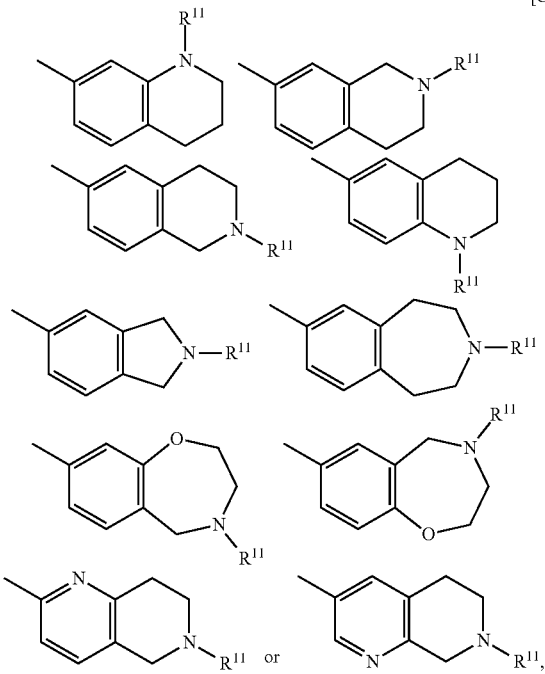

[C3]

and represented by compounds in which $R^{11}$ is H or a "substituent group D."

Preferable individual compounds include, (4-(tert-butyl)piperazin-1-yl) (4-((4-(1-ethyl-3-(pyridin-3-yl)-1H-pyrazol-4-yl)pyrimidin-2-yl)amino)phenyl)methanone;

(4-((4-(1-ethyl-3-(pyridin-3-yl)-1H-pyrazol-4-yl)pyrimidin-2-yl)amino)phenyl) (4-(4-fluorophenyl)piperazine-1-yl)methanone;

2-methyl-N-(4-(1-(oxetan-3-yl)-3-(pyridin-3-yl)-1H-pyrazol-4-yl)pyrimidin-2-yl)-1,2,3,4-tetrahydroisoquinolin-6-amine;

2-methyl-N-(4-(3-(pyridin-3-yl)-1-((tetrahydrofuran-3-yl)methyl)-1H-pyrazol-4-yl)pyrimidin-2-yl)-1,2,3,4-tetrahydroisoquinolin-6-amine;

N-(4-(1-(2-methoxyethyl)piperidin-4-yl)phenyl)-4-(1-(oxetan-3-yl)-3-(pyridin-3-yl)-1H-pyrazol-4-yl)pyrimidin-2-amine;

4-(1-ethyl-3-(pyridin-3-yl)-1H-pyrazol-4-yl)-N-(4-(4-(oxetan-3-yl)piperazin-1-yl)phenyl)pyrimidin-2-amine;

4-(1-ethyl-3-(pyridin-3-yl)-1H-pyrazol-4-yl)-N-(4-(4-isopropylpiperazin-1-yl)phenyl)pyrimidin-2-amine;

4-(1-ethyl-3-(pyridin-3-yl)-1H-pyrazol-4-yl)-N-(4-(4-(2-methoxyethyl)piperazin-1-yl)phenyl)pyrimidin-2-amine;

N-(4-(1-ethyl-1H-pyrazol-4-yl)phenyl)-4-(1-ethyl-3-(pyridin-3-yl)-1H-pyrazol-4-yl)pyrimidin-2-amine;

2-(4-(4-((4-(1-ethyl-3-(pyridin-3-yl)-1H-pyrazol-4-yl)pyrimidin-2-yl)amino)phenyl)piperazin-1-yl)-1-(piperidin-1-yl)ethan-1-one;

N-(4-(4-cyclopropylpiperazin-1-yl)phenyl)-4-(1-ethyl-3-(pyridin-3-yl)-1H-pyrazol-4-yl)pyrimidin-2-amine;

N-(4-(4-(cyclopropylmethyl)piperazin-1-yl)phenyl)-4-(1-ethyl-3-(pyridin-3-yl)-1H-pyrazol-4-yl)pyrimidin-2-amine;

N-(4-(4-(cyclopropylmethyl)piperazin-1-yl)phenyl)-4-(1-(2-methoxyethyl)-3-(pyridin-3-yl)-1H-pyrazol-4-yl)pyrimidin-2-amine;

4-(1-(2-methoxyethyl)-3-(pyridin-3-yl)-1H-pyrazol-4-yl)-N-(4-(4-(2-methoxyethyl)piperazin-1-yl)phenyl)pyrimidin-2-amine;

N-(4-(1H-1,2,4-triazol-1-yl)phenyl)-4-(1-ethyl-3-(pyridin-3-yl)-1H-pyrazol-4-yl)pyrimidin-2-amine;

4-(1-ethyl-3-(pyridin-3-yl)-1H-pyrazol-4-yl)-N-(4-(2-(4-(2-methoxyethyl)piperazin-1-yl)ethyl)phenyl)pyrimidin-2-amine;

N-(4-(1H-imidazol-1-yl)phenyl)-4-(1-ethyl-3-(pyridin-3-yl)-1H-pyrazol-4-yl)pyrimidin-2-amine;

4-(1-ethyl-3-(pyridin-3-yl)-1H-pyrazol-4-yl)-N-(3-fluoro-4-(1-methylpiperidin-4-yl)phenyl)pyrimidin-2-amine;

4-(1-ethyl-3-(pyridin-3-yl)-1H-pyrazol-4-yl)-N-(4-(4-methylpiperazin-1-yl)phenyl)pyrimidin-2-amine;

4-(1-ethyl-3-(pyridin-3-yl)-1H-pyrazol-4-yl)-N-(3-methoxy-4-(4-methylpiperazin-1-yl)phenyl)pyrimidin-2-amine;

4-(1-ethyl-3-(pyridin-3-yl)-1H-pyrazol-4-yl)-N-(4-(piperidin-1-yl)phenyl)pyrimidin-2-amine;

4-(1-ethyl-3-(pyridin-3-yl)-1H-pyrazol-4-yl)-N-(4-(1-(2-methoxyethyl)pyrrolidin-3-yl)phenyl)pyrimidin-2-amine;

N-(4-(4-(2-(2,2-difluoroethoxy)ethyl)piperazin-1-yl)phenyl)-4-(1-ethyl-3-(pyridin-3-yl)-1H-pyrazol-4-yl)pyrimidin-2-amine;

1-(4-(4-((4-(1-ethyl-3-(pyridin-3-yl)-1H-pyrazol-4-yl)pyrimidin-2-yl)amino)-1H-pyrazol-1-yl)piperidin-1-yl)-2-methylpropan-2-ol;

4-(1-ethyl-3-(pyridin-3-yl)-1H-pyrazol-4-yl)-N-(1-(1-(2-methoxyethyl)piperidin-4-yl)-1H-pyrazol-4-yl)pyrimidin-2-amine oxalate;

4-(1-ethyl-3-(pyridin-3-yl)-1H-pyrazol-4-yl)-N-(4-(1-(2-methoxyethyl)piperidin-4-yl)phenyl)pyrimidin-2-amine, N-(4-(1-(2-methoxyethyl)-3-(pyridin-3-yl)-1H-pyrazol-4-yl)pyrimidin-2-yl)-2-methylisoindolin-5-amine;

N-(4-(1-ethyl-3-(pyridin-3-yl)-1H-pyrazol-4-yl)pyrimidin-2-yl)-2-(2-methoxyethyl)isoindolin-5-amine;

N-(4-(1-(2-methoxyethyl)-3-(pyridin-3-yl)-1H-pyrazol-4-yl)pyrimidin-2-yl)-2-methyl-1,2,3,4-tetrahydroisoquinolin-6-amine;

2-methyl-1-(4-(2-((2-methyl-1,2,3,4-tetrahydroisoquinolin-6-yl)amino)pyrimidin-4-yl)-3-(pyridin-3-yl)-1H-pyrazol-1-yl)propan-2-ol;

3-cyclopropyl-N-(4-(1-ethyl-3-(pyridin-3-yl)-1H-pyrazol-4-yl)pyrimidin-2-yl)-2,3,4,5-tetrahydro-1H-benzo[d]azepin-7-amine;

N-(4-(1-ethyl-3-(pyridin-3-yl)-1H-pyrazol-4-yl)pyrimidin-2-yl)-4-methyl-2,3,4,5-tetrahydrobenzo[f][1,4]oxazepin-8-amine;

N-(4-(4-(dimethylamino)-4-methylpiperidin-1-yl)phenyl)-4-(1-ethyl-3-(pyridin-3-yl)-1H-pyrazol-4-yl)pyrimidin-2-amine, 4-(1-(2-methoxyethyl)-3-(pyridin-3-yl)-1H-pyrazol-4-yl)-N-(4-(piperazin-1-yl)phenyl)pyrimidin-2-amine;

N-(4-(4-(2-methoxyethyl)piperazin-1-yl)phenyl)-4-(3-(pyridin-3-yl)-1-(tetrahydrofuran-3-yl)-1H-pyraze-4-yl)pyrimidin-2-amine;

N-(4-(4-(2-methoxyethyl)piperazin-1-yl)phenyl)-4-(1-((3-methyloxetan-3-yl)methyl)-3-(pyridin-3-yl))-1H-pyrazol-4-yl)pyrimidin-2-amine;

4-(1-ethyl-3-(pyridin-3-yl)-1H-pyrazol-4-yl)-N-(4-(4-((1-methylpyrrolidin-2-yl)methyl)piperazin-1-yl)phenyl)pyrimidin-2-amine;

1-(4-(2-((4-(4-(2-methoxyethyl)piperazin-1-yl)phenyl) amino)pyrimidin-4-yl)-3-(pyridin-3-yl)-1H-pyrazol-1-yl)-2-methylpropan-2-ol;

2-((4-(2-((4-(4-(2-methoxyethyl)piperazin-1-yl)phenyl) amino)pyrimidin-4-yl)-3-(pyridin-3-yl)-1H-pyrazol-1-yl) methyl)benzonitrile;

4-(1-ethyl-3-(pyridin-3-yl)-1H-pyrazol-4-yl)-N-(4-(8-(2-methoxyethyl)-8-azabicyclo[3.2.1]octan-3-yl)phenyl)pyrimidin-2-amine;

N-(4-(1-ethyl-3-(pyridin-3-yl)-1H-pyrazol-4-yl)pyrimidin-2-yl)-2-((tetrahydrofuran-2-yl)methyl)-1,2,3,4-tetrahydroisoquinoline-7-amine;

N-(4-(1-ethyl-3-(pyridin-3-yl)-1H-pyrazol-4-yl)pyrimidin-2-yl)-2-((tetrahydrofuran-2-yl)methyl)-1,2,3,4-tetrahydroisoquinolin-6-amine;

N-(4-(1-ethyl-3-(pyridin-3-yl)-1H-pyrazol-4-yl)pyrimidin-2-yl)-3-(2-methoxyethyl)-2,3,4,5-tetrahydro-1H-benzo[d]azepin-7-amine;

N-(4-(4-((4,4-dimethyloxetan-2-yl)methyl)piperazin-1-yl) phenyl)-4-(1-ethyl-3-(pyridin-3-yl)-1H-pyrazol-4-yl)pyrimidin-2-amine;

4-(1-ethyl-3-(pyridin-3-yl)-1H-pyrazol-4-yl)-N-(4-(4-((tetrahydrofuran-3-yl)methyl)piperazin-1-yl)phenyl)pyrimidin-2-amine;

4-(1-(oxetan-3-yl)-3-(pyridin-3-yl)-1H-pyrazol-4-yl)-N-(4-(4-(oxetan-3-yl)piperazin-1-yl)phenyl)pyrimidin-2-amine;

N-(4-(4-(2-methoxyethyl)piperazin-1-yl)phenyl)-4-(1-(oxetan-3-ylmethyl)-3-(pyridin-3-yl)-1H-pyrazol-4-yl) pyrimidin-2-amine;

1-(4-(4-((4-(1-ethyl-3-(pyridin-3-yl)-1H-pyrazol-4-yl)pyrimidin-2-yl)amino)phenyl)piperazin-1-yl)-2-methylpropan-2-ol;

1-(4-(4-((4-(1-ethyl-3-(pyridin-3-yl)-1H-pyrazol-4-yl)pyrimidin-2-yl)amino)phenyl)piperazin-1-yl)-3-methoxypropan-2-ol;

1-(7-((4-(1-ethyl-3-(pyridin-3-yl)-1H-pyrazol-4-yl)pyrimidin-2-yl)amino)-3,4-dihydroisoquinoline-2(1H)-yl)-2-methylpropan-2-ol;

1-(6-((4-(1-ethyl-3-(pyridin-3-yl)-1H-pyrazol-4-yl)pyrimidin-2-yl)amino)-3,4-dihydroisoquinolin-2(1H)-yl)-3-methoxypropan-2-ol;

4-(1-ethyl-3-(pyridin-3-yl)-1H-pyrazol-4-yl)-N-(4-(1-methylpiperidin-3-yl)phenyl)pyrimidin-2-amine;

4-(1-ethyl-3-(pyridin-3-yl)-1H-pyrazol-4-yl)-N-(3-(1-methylpiperidin-4-yl)phenyl)pyrimidin-2-amine;

N-(4-(1-ethyl-3-(pyridin-3-yl)-1H-pyrazol-4-yl)pyrimidin-2-yl)-3-methyl-2,3,4,5-tetrahydro-1H-benzo[d]azepin-7-amine;

(4-((4-(1-ethyl-3-(pyridin-3-yl)-1H-pyrazol-4-yl)pyrimidin-2-yl)amino)phenyl) (8-methyl-3,8-diazabicyclo[3.2.1]octan-3-yl)methanone;

(8-cyclopentyl-3,8-diazabicyclo[3.2.1]octan-3-yl) (4-((4-(1-ethyl-3-(pyridin-3-yl)-1H-pyrazol-4-yl)pyrimidin-2-yl) amino)phenyl)methanone;

(4-((4-(1-ethyl-3-(pyridin-3-yl)-1H-pyrazol-4-yl)pyrimidin-2-yl)amino)phenyl) (4-isopropylpiperazin-1-yl)methanone;

(4-cyclohexylpiperazin-1-yl) (4-((4-(1-ethyl-3-(pyridin-3-yl)-1H-pyrazol-4-yl)pyrimidin-2-yl)amino)phenyl) methanone;

N-(4-(1-ethyl-3-(pyridin-3-yl)-1H-pyrazol-4-yl)pyrimidin-2-yl)-3-(oxetan-3-yl)-2,3,4,5-tetrahydro-1H-benzo[d] azepin-7-amine;

N-(4-(1-ethyl-3-(pyridin-3-yl)-1H-pyrazol-4-yl)pyrimidin-2-yl)-2-(2-methoxyethyl)-1,2,3,4-tetrahydroisoquinolin-6-amine;

N-(4-(1-ethyl-3-(pyridin-3-yl)-1H-pyrazol-4-yl)pyrimidin-2-yl)-2-methyl-1,2,3,4-tetrahydroisoquinolin-6-amine;

4-(1-ethyl-3-(pyridin-3-yl)-1H-pyrazol-4-yl)-N-(4-(4-(tetrahydro-2H-pyran-4-yl)piperazin-1-yl)phenyl)pyrimidin-2-amine;

2-methyl-1-(4-(2-((2-(oxetan-3-yl)-1,2,3,4-tetrahydroisoquinolin-6-yl)amino)pyrimidin-4-yl)-3-(pyridin-3-yl)-1H-pyrazol-1-yl)propan-2-ol;

4-(1,1-dimethylethyl)-3-(pyridin-3-yl)-1H-pyrazol-4-yl)-N-(4-(piperazin-1-yl)phenyl)pyrimidin-2-amine;

4-(1-(oxetan-3-yl)-3-(pyridin-3-yl)-1H-pyrazol-4-yl)-N-(4-(piperazin-1-yl)phenyl)pyrimidin-2-amine;

4-(1-phenethyl-3-(pyridin-3-yl)-1H-pyrazol-4-yl)-N-(4-(piperazin-1-yl)phenyl)pyrimidin-2-amine;

N-(4-(3,8-diazabicyclo[3.2.1]octan-3-yl)phenyl)-4-(1-ethyl-3-(pyridin-3-yl)-1H-pyrazol-4-yl)pyrimidin-2-amine;

N-(4-(azetidin-3-yloxy)phenyl)-4-(1-ethyl-3-(pyridin-3-yl)-1H-pyrazol-4-yl)pyrimidin-2-amine;

N-(4-(4-aminopiperidin-1-yl)phenyl)-4-(1-ethyl-3-(pyridin-3-yl)-1H-pyrazol-4-yl)pyrimidin-2-amine;

4-(1-ethyl-3-(5-fluoropyridin-3-yl)-1H-pyrazol-4-yl)-N-(4-(piperazin-1-yl)phenyl)pyrimidin-2-amine;

4-(1-(2,2-difluoroethyl)-3-(pyridin-3-yl)-1H-pyrazol-4-yl)-N-(4-(piperazin-1-yl)phenyl)pyrimidine-2-amine;

4-(1-ethyl-3-(pyridin-3-yl)-1H-pyrazol-4-yl)-N-(4-(piperazin-1-yl)phenyl)pyrimidin-2-amine;

4-(1-ethyl-3-(pyridin-3-yl)-1H-pyrazol-4-yl)-N-(3-fluoro-4-(piperazin-1-yl)phenyl)pyrimidin-2-amine;

N-(3,5-difluoro-4-(piperazin-1-yl)phenyl)-4-(1-ethyl-3-(pyridin-3-yl)-1H-pyrazol-4-yl)pyrimidin-2-amine;

4-(1-ethyl-3-(pyridin-3-yl)-1H-pyrazol-4-yl)-N-(3-methyl-4-(piperazin-1-yl)phenyl)pyrimidin-2-amine;

4-(1-ethyl-3-(pyridin-3-yl)-1H-pyrazol-4-yl)-N-(6-(piperazin-1-yl)pyridin-3-yl)pyrimidin-2-amine;

3-((4-(2-((4-(piperazin-1-yl)phenyl)amino)pyrimidin-4-yl)-3-(pyridin-3-yl)-1H-pyrazol-1-yl)methyl)benzonitrile;

2-((4-(2-((4-(piperazin-1-yl)phenyl)amino)pyrimidin-4-yl)-3-(pyridin-3-yl)-1H-pyrazol-1-yl)methyl)benzonitrile;

4-(1-ethyl-3-(pyridin-3-yl)-1H-pyrazol-4-yl)-N-(4-(piperidin-4-yl)phenyl)pyrimidin-2-amine;

N-(4-(8-azabicyclo[3.2.1]octan-3-yl)phenyl)-4-(1-ethyl-3-(pyridin-3-yl)-1H-pyrazol-4-yl)pyrimidin-2-amine;

4-(1-ethyl-3-(pyridin-3-yl)-1H-pyrazol-4-yl)-N-(4-(1-(piperidin-4-yl)-1H-pyrazol-4-yl)phenyl)pyrimidin-2-amine;

N-(4-(1-ethyl-3-(pyridin-3-yl)-1H-pyrazol-4-yl)pyrimidin-2-yl)-1,2,3,4-tetrahydroisoquinolin-6-amine;

N-(4-(1-ethyl-3-(pyridin-3-yl)-1H-pyrazol-4-yl)pyrimidin-2-yl)-1,2,3,4-tetrahydroisoquinolin-7-amine;

N-(4-(1-ethyl-3-(pyridin-3-yl)-1H-pyrazol-4-yl)pyrimidin-2-yl)-2,3,4,5-tetrahydro-1H-benzo[d]azepin-7-amine;

2-(6-((4-(1-ethyl-3-(pyridin-3-yl)-1H-pyrazol-4-yl)pyrimidin-2-yl)amino)-3,4-dihydroisoquinolin-2(1H)-yl)acetic acid;

2-(4-(4-((4-(1-ethyl-3-(pyridin-3-yl)-1H-pyrazol-4-yl)pyrimidin-2-yl)amino)phenyl)piperazin-1-yl)acetic acid;

N-(4-(4-amino-4-methylpiperidin-1-yl)phenyl)-4-(1-ethyl-3-(pyridin-3-yl)-1H-pyrazol-4-yl)pyrimidin-2-amine;

N-(4-(4-amino-4-ethylpiperidin-1-yl)phenyl)-4-(1-ethyl-3-(pyridin-3-yl)-1H-pyrazol-4-yl)pyrimidin-2-amine;

2-(7-((4-(1-ethyl-3-(pyridin-3-yl)-1H-pyrazol-4-yl)pyrimidin-2-yl)amino)-3,4-dihydroisoquinolin-2(1H)-yl)ethan-1-ol; and 4-(1-ethyl-3-(pyridin-3-yl)-1H-pyrazol-4-yl)-N-(4-(3-(4-methylpiperazin-1-yl)-1H-1,2,4-triazol-1-yl)phenyl)pyrimidin-2-amine, Examples of more preferable compounds include,
4-(1-ethyl-3-(pyridin-3-yl)-1H-pyrazol-4-yl)-N-(4-(4-(oxetan-3-yl)piperazin-1-yl)phenyl)pyrimidin-2-amine;
4-(1-ethyl-3-(pyridin-3-yl)-1H-pyrazol-4-yl)-N-(4-(2-methoxyethyl)piperazin-1-yl)phenyl)pyrimidin-2-amine;
N-(4-(1-ethyl-1H-pyrazol-4-yl)phenyl)-4-(1-ethyl-3-(pyridin-3-yl)-1H-pyrazol-4-yl)pyrimidin-2-amine;
N-(4-(4-(cyclopropylmethyl)piperazin-1-yl)phenyl)-4-(1-ethyl-3-(pyridin-3-yl)-1H-pyrazol-4-yl)pyrimidin-2-amine;
N-(4-(1H-1,2,4-triazol-1-yl)phenyl)-4-(1-ethyl-3-(pyridin-3-yl)-1H-pyrazol-4-yl)pyrimidin-2-amine;
4-(1-ethyl-3-(pyridin-3-yl)-1H-pyrazol-4-yl)-N-(4-(4-methylpiperazin-1-yl)phenyl)pyrimidin-2-amine;
1-(4-(4-((4-(1-ethyl-3-(pyridin-3-yl)-1H-pyrazol-4-yl)pyrimidin-2-yl)amino)-1H-pyrazol-1-yl)piperidin-1-yl)-2-methylpropan-2-ol;
N-(4-(1-(2-methoxyethyl)-3-(pyridin-3-yl)-1H-pyrazol-4-yl)pyrimidin-2-yl)-2-methyl-1,2,3,4-tetrahydroisoquinolin-6-amine;
2-methyl-1-(4-(2-((2-methyl-1,2,3,4-tetrahydroisoquinolin-6-yl)amino)pyrimidin-4-yl)-3-(pyridin-3-yl)-1H-pyrazol-1-yl)propan-2-ol;
N-(4-(1-ethyl-3-(pyridin-3-yl)-1H-pyrazol-4-yl)pyrimidin-2-yl)-2-((tetrahydrofuran-2-yl)methyl)-1,2,3,4-tetrahydroisoquinolin-6-amine;
N-(4-(1-ethyl-3-(pyridin-3-yl)-1H-pyrazol-4-yl)pyrimidin-2-yl)-3-(2-methoxyethyl)-2,3,4,5-tetrahydro-1H-benzo[d]azepin-7-amine;
4-(1-(oxetan-3-yl)-3-(pyridin-3-yl)-1H-pyrazol-4-yl)-N-(4-(4-(oxetan-3-yl)piperazin-1-yl)phenyl)pyrimidin-2-amine;
N-(4-(1-ethyl-3-(pyridin-3-yl)-1H-pyrazol-4-yl)pyrimidin-2-yl)-2-methyl-1,2,3,4-tetrahydroisoquinolin-6-amine;
4-(1-(2,2-difluoroethyl)-3-(pyridin-3-yl)-1H-pyrazol-4-yl)-N-(4-(piperazin-1-yl)phenyl)pyrimidin-2-amine;
4-(1-ethyl-3-(pyridin-3-yl)-1H-pyrazol-4-yl)-N-(4-(piperazin-1-yl)phenyl)pyrimidin-2-amine;
4-(1-ethyl-3-(pyridin-3-yl)-1H-pyrazol-4-yl)-N-(6-(piperazin-1-yl)pyridin-3-yl)pyrimidin-2-amine;
N-(4-(1-ethyl-3-(pyridin-3-yl)-1H-pyrazol-4-yl)pyrimidin-2-yl)-1,2,3,4-tetrahydroisoquinolin-6-amine;
N-(4-(1-ethyl-3-(pyridin-3-yl)-1H-pyrazol-4-yl)pyrimidin-2-yl)-1,2,3,4-tetrahydroisoquinolin-7-amine;
N-(4-(1-ethyl-3-(pyridin-3-yl)-1H-pyrazol-4-yl)pyrimidin-2-yl)-2,3,4,5-tetrahydro-1H-benzo[d]azepin-7-amine; and
N-(4-(4-amino-4-ethylpiperidin-1-yl)phenyl)-4-(1-ethyl-3-(pyridin-3-yl)-1H-pyrazol-4-yl)pyrimidin-2-amine.

The novel compound of the present invention is a compound selected from among the above compounds, pharmacologically acceptable salts thereof or pharmacologically acceptable esters thereof, and a novel and excellent disease preventive agent or therapeutic agent of the present invention which specifically antagonizes BMP signal pathways includes a compound selected from among the above compounds, pharmacologically acceptable salts thereof or pharmacologically acceptable esters thereof as an active component.

In General Formula (I),
in $R^2$, $R^3$, $R^4$, $R^5$, $R^6$, $R^7$, $R^8$, the "substituent group A," the "substituent group D" and the "substituent group E," the "lower alkyl" group refers to a linear or branched alkyl group having 1 to 6 carbon atoms, for example, methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, or 2-ethylbutyl, and is preferably a linear or branched alkyl group having 1 to 4 carbon atoms, and more preferably methyl, ethyl, n-propyl, isopropyl, n-butyl, or tert-butyl.

The "lower alkyl group substituted with 1 to 3 substituents selected from the "substituent group B," an oxo group and a lower alkyl group" in the definition of $R^4$; the lower alkyl group substituted with 1 to 3 substituents selected from the "substituent group B" and an oxo group" in the definition of $R^2$, the "substituent group D" and the "substituent group E"; and the "lower alkyl group substituted with 1 to 3 substituents selected from the "substituent group B," an oxo group and a COOH group" in the definition of the "substituent group D" are respectively said "lower alkyl" group substituted with 1 to 3 substituents selected from the "substituent group B," an oxo group and a lower alkyl group"; said "lower alkyl" group substituted with 1 to 3 substituents selected from the "substituent group B" and an oxo group" and said "lower alkyl" group substituted with 1 to 3 substituents selected from the "substituent group B," an oxo group and a COOH group," for example, an OH group, an —$N(R^8)R^9$ group, an —$N(R^6)COR^5$ group, a —$C(O)R^5$ group, a —$C(O)N(R^6)R^7$ group, a "halogen atom" to be defined below, an oxo group, a "$C_{3-6}$ cycloalkyl" group to be defined below, a "heterocyclyl" group to be defined below, a "heterocyclyl" group to be defined below "substituted with 1 to 3 substituents selected from the "substituent group A", an "aryl" group to be defined below, an "aryl" group to be defined below "substituted with 1 to 3 substituents selected from the "substituent group A", a pyridyl group, a pyridyl group substituted with 1 to 3 substituents selected from the "substituent group A", said "lower alkyl" substituted with 1 to 3 substituents selected from a "lower alkoxy" group to be defined below, a "halo-lower alkoxy" group to be defined below, a "C3-6 cycloalkyl lower alkoxy" to be defined below and said "lower alkyl" group, preferably a benzyl group; a phenethyl group; a 3-phenylpropyl group; a benzyl group substituted with 1 to 3 substituents selected from the "substituent group A"; a phenethyl group substituted with 1 to 3 substituents selected from the "substituent group A"; a 3-phenylpropyl group substituted with 1 to 3 substituents selected from the "substituent group A"; a pyridylmethyl group; a 2-pyridylethyl group; a 3-pyridylpropyl group; a pyridylmethyl group substituted with 1 to 3 substituents selected from the "substituent group A"; a 2-pyridylethyl group substituted with 1 to 3 substituents selected from the "substituent group A"; a 3-pyridylpropyl group substituted with 1 to 3 substituents selected from the "substituent group A"; dihalogenomethyl, trihalogenomethyl, 2,2-dihalogenoethyl, 2,2,2-trihalogenoethyl, 3,3-dihalogenopropyl, and 3,3,3-trihalogenopropyl groups; an oxetanylmethyl group; an oxetanylmethyl group substituted with 1 to 3 substituents selected from the "substituent group A"; a tetrahydrofuranylmethyl group; a tetrahydrofuranylmethyl group substituted with 1 to 3 substituents selected from the "substituent group A"; a (tetrahydro-2H-pyranyl)methyl group; a (tetrahydro-2H-pyranyl)methyl group substituted with 1 to 3 substituents selected from the "substituent group A"; an azetidin-2-ylmethyl group; an azetidin-3-ylmethyl group; an azetidin-2-ylmethyl group substituted with 1 to 3 substituents selected from the "substituent group A"; an azetidin-3-ylmethyl group substituted with 1 to 3 substituents selected from the "substituent group A"; a 2-azetidinylethyl group; a 3-azetidinylpropyl group; a 2-azetidinylethyl group substituted with 1 to 3 substituents selected from the "substituent group A"; a 3-azetidinylpropyl group substituted with 1 to 3 substituents selected from the "substituent group A"; pyrrolidin-2-ylmethyl; pyrrolidin-3-ylmethyl; a pyrrolidin-2-ylmethyl group substituted with 1 to 3 substituents selected from the "substituent group A"; a pyrrolidin-3-ylmethyl group substituted with 1 to 3 substituents selected from the "substituent group A"; a 2-pyrrolidinylethyl group; a 2-pyrrolidinylethyl group substituted with 1 to 3 substituents selected from the "substituent group A"; a 3-pyrrolidinylpropyl group; a 3-pyrrolidinylpropyl substituted with 1 to 3 substituents selected from the "substituent group A"; a piperidin-2-ylmethyl group; a piperidin-3-ylmethyl group; a piperidin-4-ylmethyl group; a piperidine-2-ylmethyl group substituted with 1 to 3 substituents selected from the "substituent group A"; a piperidin-3-ylmethyl group substituted with 1 to 3 substituents selected from the "substituent group A"; a piperidin-4-ylmethyl group substituted with 1 to 3 substituents selected from the "substituent group A"; a 2-piperidinylethyl group; a 2-piperidinylethyl group substituted with 1 to 3 substituents selected from the "substituent group A"; a 3-piperidinylpropyl group; a 3-piperidinylpropyl group substituted with 1 to 3 substituents selected from the "substituent group A"; a morpholin-2-ylmethyl group; a morpholin-3-ylmethyl group; a morpholin-2-ylmethyl group substituted with 1 to 3 substituents selected from the "substituent group A"; a morpholin-3-ylmethyl group substituted with 1 to 3 substituents selected from the "substituent group A"; a 2-morpholinoethyl group; a 2-morpholinoethyl group substituted with 1 to 3 substituents selected from the "substituent group A"; a 3-morpholinopropyl group; a 3-morpholinopropyl group substituted with 1 to 3 substituents selected from the "substituent group A"; 2-(morpholin-2-yl)ethyl; 2-(morpholin-3-yl)ethyl; a 2-(morpholin-2-yl)ethyl group substituted with 1 to 3 substituents selected from the "substituent group A"; a 2-(morpholin-3-yl)ethyl group substituted with 1 to 3 substituents selected from the "substituent group A"; a 3-(morpholin-2-yl)propyl group; a 3-(morpholin-3-yl)propyl group; a 3-(morpholin-2-yl)propyl group substituted with 1 to 3 substituents selected from the "substituent group A"; a 3-(morpholin-3-yl)propyl group substituted with 1 to 3 substituents selected from the "substituent group A"; a $C_{3-6}$ cycloalkylmethyl group; a 2-($C_{3-6}$ cycloalkyl)ethyl group; a 3-($C_{3-6}$ cycloalkyl)propyl, 2-(lower alkoxy)ethyl group; a 3-(lower alkoxy)propyl group; a 2-(halo-lower alkoxy)ethyl group; a 3-(halo-lower alkoxy)propyl group; a 2-($C_{3-6}$ cycloalkoxy)ethyl group; a 3-($C_{3-6}$ cycloalkoxy)propyl group; a 2-($C_{3-6}$ cycloalkyl lower alkoxy)ethyl group; a 3-($C_{3-6}$ cycloalkyl lower alkoxy)propyl group; a 2-hydroxyethyl group; a 3-hydroxypropyl group; a 2,3-dihydroxypropyl group; a 3-(lower alkoxy)propyl group substituted with an OH group; a 3-(halo-lower alkoxy)propyl group substituted with an OH group; carboxymethyl, 2-carboxyethyl, 3-carboxypropyl, carbamoylmethyl, 2-carbamoylethyl, 3-carbamoylpropyl, N,N-dimethylcarbamoylmethyl, 2-(N,N-dimethylcarbamoyl)ethyl, and 3-(N,N-dimethylcarbamoyl)propyl groups; a 2-oxo-2-(pyrrolidin-1-yl)ethyl group, a 3-oxo-3-(pyrrolidin-1-yl)propyl group, a 4-oxo-4-(pyrrolidin-1-yl)butyl group, a 2-oxo-2-(piperidin-1-yl)ethyl group, a 3-oxo-3-(piperidine-1-yl)propyl group, a 4-oxo-4-(piperidine-1-yl)butyl group, a 2-oxo-2-morpholinoethyl group, a 3-oxo-3-morpholinopropyl group, or a 4-oxo-4-morpholinobutyl group, more preferably, a benzyl group, a phenethyl group, a benzyl group substituted with 1 to 3 substituents selected from the "substituent group A," a phenethyl group substituted with 1 to 3 substituents selected from the "substituent group A", a pyridylmethyl group, a 2-pyridylethyl group, a pyridylmethyl group substituted with 1 to 3 substituents selected from the "substituent group A", a 2-pyridylethyl group substituted with 1 to 3 substituents selected from the "substituent group A", difluoromethyl, trifluoromethyl, dichloromethyl, trichloromethyl, 2,2-difluoroethyl, 2,2,2-trifluoroethyl, 2,2-dichloroethyl, 2,2,2-trichloroethyl, 3,3-difluoropropyl, 3,3,3-trifluoropropyl, 3,3-dichloropropyl, 3,3,3-trichloropropyl, and oxetanylmethyl groups, an oxetanylmethyl substituted with 1 to 3 substituents selected from lower alkyl groups, a tetrahydrofuranylmethyl group, a tetrahydrofuranylmethyl group substituted with 1 to 3 substituents selected from lower alkyl groups, a (tetrahydro-2H-pyranyl)methyl group, a (tetrahydro-2H-pyranyl)methyl group substituted with 1 to 3 substituents selected from lower alkyl groups, an azetidin-2-ylmethyl group, an azetidin-3-ylmethyl group, an azetidin-2-ylmethyl group substituted with 1 to 3 substituents selected from lower alkyl groups, an azetidin-3-ylmethyl group substituted with 1 to 3 substituents selected from lower alkyl groups, a 2-azetidinylethyl group, a 3-azetidinylpropyl group, a 2-azetidinylethyl group substituted with 1 to 3 substituents selected from lower alkyl groups, a 3-azetidinylpropyl group substituted with 1 to 3 substituents selected from lower alkyl groups, a pyrrolidin-2-ylmethyl group, a pyrrolidin-3-ylmethyl group, a pyrrolidin-2-ylmethyl group substituted with 1 to 3 substituents selected from lower alkyl groups, a pyrrolidin-3-ylmethyl group substituted with 1 to 3 substituents selected from lower alkyl groups, a 2-pyrrolidinylethyl group, a 2-pyrrolidinylethyl group substituted with 1 to 3 substituents selected from lower alkyl groups, a 3-pyrrolidinylpropyl group, a 3-(pyrrolidinyl)propyl group substituted with 1 to 3 substituents selected from lower alkyl groups, a piperidin-2-ylmethyl group, a piperidin-3-ylmethyl group, a piperidin-4-ylmethyl group, a piperidin-2-ylmethyl group substituted with 1 to 3 substituents selected from lower alkyl groups, a piperidin-3-ylmethyl group substituted with 1 to 3 substituents selected from lower alkyl groups, a piperidin-4-ylmethyl group substituted with 1 to 3 substituents selected from lower alkyl groups, a 2-piperidinylethyl group, a 2-piperidinylethyl group substituted with 1 to 3 substituents selected from lower alkyl groups, a 3-piperidinyipropyl group, a 3-piperidinylpropyl group substituted with 1 to 3 substituents selected from lower alkyl groups, a morpholin-2-ylmethyl group, a piperidin-3-ylmethyl group, a morpholin-2-ylmethyl group substituted with 1 to 3 substituents selected from lower alkyl groups, a morpholin-3-ylmethyl group substituted with 1 to 3 substituents selected from lower alkyl groups, a 2-morpholinoethyl group, a 2-morpholinoethyl group substituted with 1 to 3 substituents selected from lower alkyl groups, a 3-morpholinopropyl group, a 3-morpholinopropyl group substituted with 1 to 3 substituents selected from lower alkyl groups, a 2-(morpholin-2-yl)ethyl group, a 2-(morpholin-3-yl)ethyl group, a 2-(morpholin-2-yl)ethyl group substituted with 1 to 3 substituents selected from lower alkyl groups, a 2-(morpholin-3-yl)ethyl group substituted with 1 to 3 substituents selected from lower alkyl groups, a 3-(morpholin-2-yl)propyl group, a 3-(morpholin-3-yl)propyl group, a 3-(morpholin-2-yl)propyl group substituted with 1 to 3 substituents selected from lower alkyl groups, a 3-(morpholin-3-yl)propyl group substituted with 1 to 3 substituents selected from lower alkyl groups, a $C_{3-6}$ cycloalkylmethyl group, a 2-($C_{3-6}$ cycloalkyl)ethyl group, a 3-($C_{3-6}$ cycloalkyl)propyl group, a 2-(lower alkoxy)ethyl group, a 3-(lower alkoxy)propyl group, a 2-(halo-lower alkoxy)ethyl group, a 3-(halo-lower alkoxy)propyl group, a 2-($C_{3-6}$ cycloalkoxy)ethyl group, a 3-($C_{3-6}$ cycloalkoxy)propyl group, a 2-(C$_{3-6}$ cycloalkyl lower alkoxy)ethyl group, a 3-(C$_{3-6}$ cycloalkyl lower alkoxy)propyl group, a 2-hydroxyethyl group, a 3-hydroxypropyl group, a 2-hydroxyethyl group substituted with 1 to 3 substituents selected from lower alkyl groups, a 3-hydroxypropyl group substituted with 1 to 3 substituents selected from lower alkyl groups, a 2,3-dihydroxypropyl group, a 3-(lower alkoxy)propyl group substituted with an OH group, a 3-(halo-lower alkoxy) propyl group substituted with an OH group, a carboxymethyl group, a 2-carboxyethyl group, a carbamoylmethyl group, a 2-carbamoylethyl group, a N,N-dimethylcarbamoylmethyl group, a 2-(N,N-dimethylcarbamoyl)ethyl group, a 2-oxo-2-(pyrrolidin-1-yl)ethyl group, a 3-oxo-3-(pyrrolidin-1-yl)propyl group, a 2-oxo-2-(piperidin-1-yl)ethyl group, a 3-oxo-3-(piperidine-1-yl)propyl group, a 2-oxo-2-morpholinoethyl group, or a 3-oxo-3-morpholinopropyl group, most preferably, a benzyl group; a phenethyl group; a benzyl group substituted with a lower alkyl group, a halogen atom, a cyano group, a nitro group and/or an —N(R$^6$)R$^7$ group; a pyridylmethyl group; a 2-pyridylethyl group; a pyridylmethyl group substituted with a lower alkyl group and/or a halogen atom; trifluoromethyl, 2,2-difluoroethyl, 2,2,2-trifluoroethyl, 3,3-difluoropropyl, and 3,3,3-trifluoropropyl groups; an oxetanylmethyl group; an oxetanylmethyl group substituted with 1 to 3 substituents selected from lower alkyl groups; a tetrahydrofuranylmethyl group; a tetrahydrofuranylmethyl group substituted with 1 to 3 substituents selected from lower alkyl groups; a (tetrahydro-2H-pyranyl)methyl group; a (tetrahydro-2H-pyranyl)methyl group substituted with 1 to 3 substituents selected from lower alkyl groups; a pyrrolidin-2-ylmethyl group; a pyrrolidin-3-ylmethyl group; a pyrrolidin-2-ylmethyl group substituted with 1 to 3 substituents selected from lower alkyl groups; a pyrrolidin-3-ylmethyl group substituted with 1 to 3 substituents selected from lower alkyl groups; a piperidin-2-ylmethyl group; a piperidin-3-ylmethyl group; a piperidin-4-ylmethyl group; a piperidin-2-ylmethyl group substituted with 1 to 3 substituents selected from lower alkyl groups; a piperidin-3-ylmethyl group substituted with 1 to 3 substituents selected from lower alkyl groups; a piperidin-4-ylmethyl group substituted with 1 to 3 substituents selected from lower alkyl groups; a morpholin-2-ylmethyl group; a piperidin-3-ylmethyl group; a morpholin-2-ylmethyl group substituted with 1 to 3 substituents selected from lower alkyl groups; a morpholin-3-ylmethyl group substituted with 1 to 3 substituents selected from lower alkyl groups; a Ca-6 cycloalkylmethyl group; a 2403-6 cycloalkyl)ethyl group; a 2-(lower alkoxy)ethyl group; a 3-(lower alkoxy)propyl group; a 2-(halo-lower alkoxy)ethyl group; a 3-(halo-lower alkoxy)propyl group; a 2403-6 cycloalkyl lower alkoxy)ethyl group; a 3-(C3-6 cycloalkyl lower alkoxy)propyl group; a 2-hydroxyethyl group; a 3-hydroxypropyl group; a 2-hydroxyethyl group substituted with 1 to 3 substituents selected from lower alkyl groups; a 3-hydroxypropyl group substituted with 1 to 3 substituents selected from lower alkyl groups; a 2,3-dihydroxypropyl group; a 3-(lower alkoxy)propyl group substituted with an OH group; a 3-(halo-lower alkoxy)propyl group substituted with an OH group; a carboxymethyl group; a carbamoylmethyl group; a N,N-dimethylcarbamoylmethyl group; a 2-oxo-2-(pyrrolidin-1-yl)ethyl group, an 2-oxo-2-(piperidin-1-yl)ethyl group, or a 2-oxo-2-morpholinoethyl group.

"Phenylene" in W includes -1,4-phenylene-, -1,3-phenylene-, -1,2-phenylene-, and is preferably -1,4-phenylene- or -1,3-phenylene-.

The "phenylene group substituted with 1 to 3 substituents selected from the "substituent group A" in W is the above "phenylene" group substituted with 1 to 3 substituents selected from the "substituent group A" and is preferably 2-fluoro-1,4-phenylene, 2-chloro-1,4-phenylene, 2-methyl-1,4-phenylene, 2-methoxy-1,4-phenylene, 2-cyano-1,4-phenylene, or 2,6-difluoro-1,4-phenylene.

The "bivalent group in which a phenylene group and a heterocyclyl group are condensed" in W refers to a bivalent group in which a phenyl group and a "heterocyclyl group" to be defined below are condensed, and examples thereof include isobenzofuranyl, chromenyl, xanthenyl, phenoxathiinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, carbazolyl, carborinyl, acridinyl, isoindolinyl, benzo[d]azepine, and benzo[f][1,4] oxazepine groups.

The following groups are preferable.

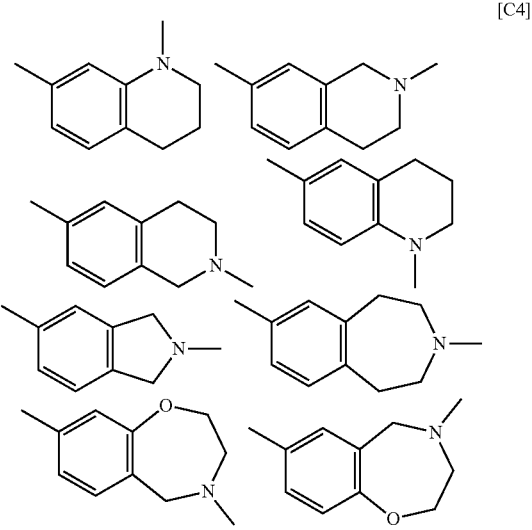

[C4]

The "a bivalent group in which a phenylene group and a heterocyclyl group are condensed" and substituted with 1 to 3 substituents selected from the "substituent group A" in W refers to said "a bivalent group in which a phenylene group and a heterocyclyl group are condensed" and substituted with 1 to 3 substituents selected from the "substituent group A" and is, for example, the above group substituted with 1 to 3 substituents selected from said "lower alkyl" group, a "lower alkoxy" group to be defined below and a "halogen" atom to be defined below, and preferably, a group such as isoquinolyl, quinolyl, isoindolyl, benzo[d]azepine, and benzo[f][1,4]oxazepine groups substituted with 1 substituent selected from a fluorine atom, a methyl group, and a methoxy group.

A "bivalent group in which a pyridyl group and a heterocyclyl group are condensed" in W refers to a bivalent group in which a pyridyl group and a "heterocyclyl group" to be defined below are condensed, and is, for example, 5,6,7,8-tetrahydro-1,6-naphthyridine, or 5,6,7,8-tetrahydro-1,7-naphthyridine, and preferably 5,6,7,8-tetrahydro-1,6-naphthyridine.

The "lower alkylene group" as defined in X and the "substituent group D" and represented by R$^6$ and R$^7$ together form an alkylene group having 1 to 6 carbon atoms, and is, for example, a linear or branched alkylene group having 1 to 6 carbon atoms such as methylene, methylmethylene, ethylene, propylene, trimethylene, tetramethylene, 1-methyltrimethylene, 2-methyltrimethylene, 3-methyltrimethylene, pentamethylene, and hexamethylene groups, and preferably a linear or branched alkylene group having 1 to 4 carbon atoms, and more preferably methylene, ethylene, trimethylene or tetramethylene.

The "lower alkylene group substituted with a groups selected from the "substituent group C" including the sequences in reverse order" in X refers to a group in which the terminal of the above "lower alkylene" group is substituted with an —O— group, a —C(O)— group, a —C(O)O— group, a —C(O)NR$^8$— group, an —NR$^8$— group, an —S— group, an —S(O)— group, an —S(O)$_2$— group, an —S(O)$_2$NR$^8$— group, an —OC(O)— group, an —NR$^8$C(O)— group, or an —NR$^8$S(O)$_2$— group, including the sequences in reverse order, and is preferably a group in which any one terminal of the "lower alkylene" group is substituted with a substituent, including the sequences in reverse order, and refers to, for example, -methylene-O—, —O-methylene-, -methylene-C(O)—, —C(O)-methylene-, -methylene-C(O)NR$^8$—, —C(O)NR$^8$-methylene-, -methylene-NR$^8$—, —NR$^8$-methylene-, -methylene-S(O)$_2$—, —S(O)$_2$-methylene-, -methylene-S(O)$_2$NR$^8$—, —S(O)$_2$NR$^8$-methylene-, -methylene-NR$^8$C(O)—, —NR$^8$C(O)-methylene-, -methylene-NR$^8$S(O)$_2$—, —NR$^8$S(O)$_2$-methylene-, and is preferably -methylene-O—, —O-methylene-, -methylene-C(O)—, —C(O)-methylene-, -methylene-C(O)NR$^8$—, —C(O)NR$^8$-methylene-, -methylene-S(O)$_2$—, —S(O)$_2$-methylene-, -methylene-S(O)$_2$NR$^8$—, or —S(O)$_2$NR$^8$-methylene-.

The "lower alkylene group in which one carbon atom is replaced with an —O— group, an —NR$^8$— group, or an —S(O)$_p$— group (p is 0, 1 or 2)" represented by R$^6$ and R$^7$ together refers to a cycloalkyl group (p is as defined above) in which one carbon atom is substituted with an —O— group, an —NR$^8$— group, or an —S(O)$_p$— group, and the —N(R$^6$)R$^7$ group refers to, for example, a morpholino group, a 1,4-oxazepan-4-yl group, a piperazin-1-yl group, a 1,4-diazepan-1-yl group, a thiomorpholino group, a 1,4-thiazepan-4-yl group, a 1-oxide thiomorpholino group, a 1,1-dioxide thiomorpholino group, a 1-oxide-1,4-thiazepan-4-yl group, or a 1,1-dioxide-1,4-thiazepan-4-yl group, and is preferably a morpholino group, a 1,4-oxazepan-4-yl group, a piperazin-1-yl group, a 1,4-diazepan-1-yl group, a thiomorpholino group, or a 1,1-dioxide thiomorpholino group.

The "heteroaryl" group in R$^4$ refers to a 5- to 7-membered heterocyclic group having 1 to 3 sulfur atoms, oxygen atoms and/or nitrogen atoms, and examples thereof include aromatic heterocyclic groups such as furyl, thienyl, pyrrolyl, azepinyl, pyrazolyl, imidazolyl, oxazolyl, isoxazolyl, thiazolyl, isothiazolyl, triazolyl, tetrazolyl, thiadiazolyl, pyranyl, pyridyl, pyridazinyl, pyrimidinyl, pyrazinyl, triazinyl, furyl, thienyl, imidazolyl, and oxadiazolyl groups, and preferably, a 5- to 7-membered heterocyclic group having at least one nitrogen atom and optionally having an oxygen atom or a sulfur atom, for example, aromatic heterocyclic groups such as pyrrolyl, azepinyl, pyrazolyl, imidazolyl, oxazolyl, isoxazolyl, thiazolyl, isothiazolyl, oxadiazolyl, triazolyl, tetrazolyl, thiadiazolyl, pyridyl, pyridazinyl, pyrimidinyl, and pyrazinyl groups, and more preferably, pyrazolyl, imidazolyl, oxadiazolyl, triazolyl, tetrazolyl, oxazolyl, isoxazolyl, thiazolyl, and pyridyl groups.

Here, the "heteroaryl" group may be condensed to another cyclic group, and examples thereof include isobenzofuranyl, chromenyl, xanthenyl, phenoxathiinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, carbazolyl, carborinyl, acridinyl, isoindolinyl, cinnolyl, benzofuranyl, benzothiophenyl, benzothiazolyl, benzoimidazolyl, benzoxazolyl, benzotriazolyl, imidazopyridyl, thienopyridyl, furopyridyl, pyrrolopyridyl, pyrazolopyridyl, imidazopyrimidinyl, pyrrolopyrimidinyl, and pyrazolopyrimidinyl groups.

The "heteroaryl group substituted with 1 to 3 substituents selected from the "substituent group E" in R$^4$ refers to the above "heteroaryl" group substituted with 1 to 3 substituents selected from the "substituent group E" and is, for example, a pyrazolyl group substituted with 1 to 3 substituents selected from the "substituent group E"; an imidazolyl group substituted with 1 to 3 substituents selected from the "substituent group E"; an oxadiazolyl group substituted with 1 to 3 substituents selected from the "substituent group E"; a triazolyl group substituted with 1 to 3 substituents selected from the "substituent group E"; an oxazolyl group substituted with 1 to 3 substituents selected from the "substituent group E"; an isoxazolyl group substituted with 1 to 3 substituents selected from the "substituent group E"; a thiazolyl group substituted with 1 to 3 substituents selected from the "substituent group E" or a pyridyl group substituted with 1 to 3 substituents selected from the "substituent group E," and more preferably a pyrazolyl group substituted with 1 to 3 substituents selected from the "substituent group E"; a triazolyl group substituted with 1 to 3 substituents selected from the "substituent group E"; an oxadiazolyl group substituted with 1 to 3 substituents selected from the "substituent group E" or a thiazolyl group substituted with 1 to 3 substituents selected from the "substituent group E", and most preferably a pyrazolyl group substituted with 1 to 3 substituents selected from lower alkyl groups; a pyrazolyl group substituted with a halo-lower alkyl group; a pyrazolyl group substituted with a heterocyclyl group; a pyrazolyl group substituted with a lower alkyl group substituted with 1 to 3 substituents selected from the "substituent group B" and an oxo group; a triazolyl group substituted with a lower alkyl group; a triazolyl group substituted with a heterocyclyl group; an oxadiazolyl group substituted with a lower alkyl group; or a thiazolyl group substituted with a lower alkyl group.

In the definitions R$^4$, the "substituent group B," the "substituent group D," and the "substituent group E," the "heterocyclyl" group indicates a 4- to 10-membered heterocyclic group having 1 to 3 sulfur atoms, oxygen atoms and/or nitrogen atoms. Examples thereof include partially or completely reduced groups of the above "heteroaryl" group such as morpholinyl, thiomorpholinyl, pyrrolidinyl, pyrrolinyl, imidazolidinyl, imidazolinyl, pyrazolidinyl, pyrazolinyl, piperidyl, and piperazinyl groups. Preferably, morpholinyl, thiomorpholinyl, pyrrolidinyl, pyrrolinyl, imidazolidinyl, imidazolinyl, pyrazolidinyl, pyrazolinyl, piperidyl, piperazinyl, azetidinyl, tetrahydro-2H-pyranyl, tetrahydrofuranyl, oxetanyl, and 1,4-diazepanyl groups are used.

In addition, the "heterocyclyl" group includes a 7- to 13-membered "heterocyclyl" group linked in a spiro type with other rings, and a cross-linked 7- to 11-membered "heterocyclyl" group. In this case, for example, 2,6-diazaspiro[3.3]heptan-2-yl, 2,6-diazaspiro[3.4]octan-6-yl, 2,7-diazaspiro[3.5]nonan-7-yl, 2,7-diazaspiro[4.4]nonan-2-yl, 2,8-diazaspiro[4.5]decan-8-yl, 3,9-diazaspiro[5.5]undecan-3-yl, 3,6-diazabicyclo[3.1.1]heptan-3-yl, 3,6-diazabicyclo[3.1.1]heptan-6-yl, 2,5-diazabicyclo[2.2.2]octan-2-yl, 3,8-diazabicyclo[3.2.1]octan-3-yl, 3,8-diazabicyclo[3.2.1]octan-8-yl, 1,4-diazabicyclo[3.2.2]nonan-4-yl, 1,4- diazatricyclo[3.3.1.1$^{3,7}$]decan-4-yl, 6-azabicyclo[3.1.1]heptan-3-yl, 6-azabicyclo[3.1.1]heptan-6-yl, 2-azabicyclo[2.2.2]octan-2-yl, 2-azabicyclo[2.2.2]octan-5-yl, 8-azabicyclo[3.2.1]octan-3-yl, 8-azabicyclo[3.2.1]octan-8-yl, and 2-azatricyclo[3.3.1.1$^{3,7}$]decan-2-yl are used. More preferably, 2,7-diazaspiro[3.5]nonan-7-yl, 2,8-diazaspiro[4.5]decan-8-yl, 1,4-diazabicyclo[3.2.2]nonan-4-yl, 3,8-diazabicyclo[3.2.1]octan-3-yl, 6-azabicyclo[3.1.1]heptan-3-yl, and 8-azabicyclo[3.2.1]octan-3-yl are used.

Here, as a preferable "heterocyclyl" group itself, for example, the following "heterocyclyl" groups can be exemplified.

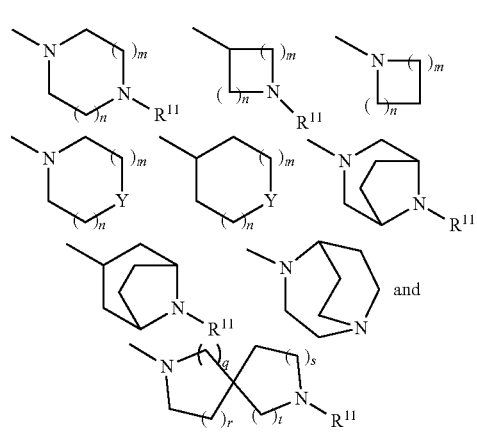

[C5]

(wherein, R$^{11}$ is H or a "substituent group D," Y is an —O— group or an —S(O)$_2$— group, m and n may be the same as or different from each other; 1 or 2, p is 0, 1 or 2, q, r, s and t may be the same as or different from each other; 0, 1 or 2; here q and t are not both 0).

In the definition of R$^4$ and the "substituent group E," the "heterocyclyl group substituted with 1 to 3 substituents selected from the "substituent group D" refers to the above "heterocyclyl" group in which substitution with 1 to 3 groups selected from the "substituent group D" occurs and is preferably a morpholinyl group substituted with 1 to 3 substituents selected from the "substituent group D"; a pyrrolidinyl group substituted with 1 to 3 substituents selected from the "substituent group D"; a piperidyl group substituted with 1 to 3 substituents selected from the "substituent group D"; a piperazinyl group substituted with 1 to 3 substituents selected from the "substituent group D"; an azetidinyl group substituted with 1 to 3 substituents selected from the "substituent group D"; a 1,4-diazepanyl group substituted with 1 to 3 substituents selected from the "substituent group D"; a 2,7-diazaspiro[3.5]nonan-7-yl group substituted with 1 to 3 substituents selected from the "substituent group D"; a 2,8-diazaspiro[4.5]decan-8-yl group substituted with 1 to 3 substituents selected from the "substituent group D"; a 3,8-diazabicyclo[3.2.1]octan-3-yl group substituted with 1 to 3 substituents selected from the "substituent group D"; a 6-azabicyclo[3.1.1]heptan-3-yl group substituted with 1 to 3 substituents selected from the "substituent group D" or an 8-azabicyclo[3.2.1]octan-3-yl group substituted with 1 to 3 substituents selected from the "substituent group D" and more preferably a pyrrolidinyl group substituted with 1 to 3 substituents selected from the "substituent group D"; a piperidyl group substituted with 1 to 3 substituents selected from the "substituent group D"; a piperazinyl group substituted with 1 to 3 substituents selected from the "substituent group D"; an azetidinyl group substituted with 1 to 3 substituents selected from the "substituent group D"; a 1,4-diazepanyl group substituted with 1 to 3 substituents selected from the "substituent group D"; a 2,7-diazaspiro[3.5]nonan-7-yl group substituted with 1 to 3 substituents selected from the "substituent group O"; a 3,8-diazabicyclo[3.2.1]octan-3-yl group substituted with 1 to 3 substituents selected from the "substituent group D" or an 8-azabicyclo[3.2.1]octan-3-yl group substituted with 1 to 3 substituents selected from the "substituent group D".

In the definition of the "substituent group B" and the "substituent group D," the "heterocyclyl group substituted with 1 to 3 substituents selected from the "substituent group A" refers to the above "heterocyclyl" group substituted with 1 to 3 substituents selected from the "substituent group A" and is preferably a morpholinyl group substituted with 1 to 3 substituents selected from the "substituent group A"; a thiomorpholinyl group substituted with 1 to 3 substituents selected from the "substituent group A"; a pyrrolidinyl group substituted with 1 to 3 substituents selected from the "substituent group A"; an imidazolidinyl group substituted with 1 to 3 substituents selected from the "substituent group A"; a pyrazolidinyl group substituted with 1 to 3 substituents selected from the "substituent group A"; a piperidyl group substituted with 1 to 3 substituents selected from the "substituent group A"; a piperazinyl group substituted with 1 to 3 substituents selected from the "substituent group A"; an azetidinyl group substituted with 1 to 3 substituents selected from the "substituent group A"; a tetrahydro-2H-pyranyl group substituted with 1 to 3 substituents selected from the "substituent group A"; a tetrahydrofuranyl group substituted with 1 to 3 substituents selected from the "substituent group A"; an oxetanyl group substituted with 1 to 3 substituents selected from the "substituent group A" or a 1,4-diazepanyl group substituted with 1 to 3 substituents selected from the "substituent group A" and more preferably a pyrrolidinyl group substituted with 1 to 3 substituents selected from lower alkyl groups; a piperidyl group substituted with 1 to 3 substituents selected from lower alkyl groups; a piperazinyl group substituted with 1 to 3 substituents selected from lower alkyl groups; an azetidinyl group substituted with 1 to 3 substituents selected from lower alkyl groups; a tetrahydro-2H-pyranyl group substituted with 1 to 3 substituents selected from lower alkyl groups; a tetrahydrofuranyl group substituted with 1 to 3 substituents selected from lower alkyl groups; an oxetanyl group substituted with 1 to 3 substituents selected from lower alkyl groups; and a 1,4-diazepanyl group substituted with 1 to 3 substituents selected from lower alkyl groups.

In the definition of the "substituent group B" and the "substituent group E," the "halo-lower alkyl" groups refers to a group in which a "halogen" atom to be defined below is bonded to the "lower alkyl group," and includes, for example, trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl, and 2,2-dibromoethyl groups, and is preferably, a trifluoromethyl, trichloromethyl, difluoromethyl, dichloromethyl, 2,2,2-trichloroethyl, 2,2,2-trifluoroethyl, or 2,2-difluoroethyl group, and more preferably a trifluoromethyl, difluoromethyl, 2,2,2-trifluoroethyl, or 2,2-difluoroethyl group.

The "halogen" atom in R$^3$, the "substituent group A," the "substituent group B," the "substituent group D," and the "substituent group E" represents a fluorine atom, a chlorine atom, a bromine atom or an iodine atom, and is preferably a fluorine atom or a chlorine atom.

The "$C_{3-6}$ cycloalkyl" group in the definition of $R^4$, the "substituent group B" and the "substituent group D" includes, for example, an optionally condensed 3- to 6-membered saturated cyclic hydrocarbon group such as cyclopropyl, cyclobutyl, cyclopentyl, and cyclohexyl groups, and is preferably a cyclopropyl group or a cyclopentyl group.

The "aryl" group in the definition of the "substituent group B" and the "substituent group D" includes, for example, an aromatic hydrocarbon group having 5 to 14 carbon atoms such as phenyl, indenyl, naphthyl, phenanthrenyl, and anthracenyl groups, and is preferably a phenyl group.

Here, the "aryl" group may be condensed with a cycloalkyl group having 3 to 10 carbon atoms, and includes, for example, a 2-indanyl group.

In the definition of the "substituent group B" and the "substituent group D," the "aryl group substituted with 1 to 3 substituents selected from the "substituent group A" refers to a group in which the "aryl" group is substituted with 1 to 3 substituents selected from the "substituent group A", and is, for example, a phenyl group substituted with 1 to 3 substituents selected from the "substituent group A"; an indenyl group substituted with 1 to 3 substituents selected from the "substituent group A"; a naphthyl group substituted with 1 to 3 substituents selected from the "substituent group A"; a phenanthrenyl group substituted with 1 to 3 substituents selected from the "substituent group A"; an anthracenyl group substituted with 1 to 3 substituents selected from the "substituent group A"; or a 2-indanyl group substituted with 1 to 3 substituents selected from the "substituent group A" and preferably a phenyl group substituted with 1 to 3 substituents selected from the "substituent group A"; or a naphthyl group substituted with 1 to 3 substituents selected from the "substituent group A"; and more preferably a phenyl group substituted with 1 to 3 substituents selected from a lower alkyl group, a halogen atom, a cyano group and an —$N(R^6)R^7$ group; or a phenyl group in which one atom is substituted with a nitro group.

In the definition of $R^6$, the "substituent group A," and the "substituent group B," the "lower alkoxy" group indicates a group in which the "lower alkyl group" is bonded to an oxygen atom, and includes, for example, a linear or branched alkoxy group having 1 to 6 carbon atoms such as methoxy, ethoxy, n-propoxy, isopropoxy, n-butoxy, isobutoxy, s-butoxy, tert-butoxy, n-pentoxy, isopentoxy, 2-methylbutoxy, neopentoxy, n-hexyloxy, 4-methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy, and 2,3-dimethylbutoxy groups, and is preferably a linear or branched alkoxy group having 1 to 4 carbon atoms, and more preferably, a methoxy, ethoxy, n-propoxy, isopropoxy, n-butoxy, isobutoxy, s-butoxy or tert-butoxy group.

In the definition of the "substituent group B," the "halo-lower alkoxy" group indicates a group in which the "halo-lower alkyl group" is bonded to an oxygen atom, and includes, for example, trifluoromethoxy, difluoromethoxy, dichloromethoxy, 2,2,2-trichloroethoxy, 2,2,2-trifluoroethoxy, 2-bromoethoxy, 2-chloroethoxy, 2-fluoroethoxy, 2,2-dichloroethoxy, and 2,2-difluoroethoxy groups, and is preferably a trifluoromethoxy, difluoromethoxy, 2,2,2-trifluoroethoxy, 2-bromoethoxy, 2-chloroethoxy, 2-fluoroethoxy, or 2,2-difluoroethoxy group.

In the definition of the "substituent group B," the pyridyl group substituted with 1 to 3 substituents selected from the "substituent group A" refers to a "pyridyl" group substituted with 1 to 3 groups selected from the "substituent group A" and is, for example, 2-methylpyridyl, 3-methylpyridyl, 4-methylpyridyl, 2-aminopyridyl, 3-chloropyridyl, or 3-fluoropyridyl, and is preferably 3-chloropyridyl.

In the definition of the "substituent group B," the "$C_{3-6}$ cycloalkyl lower alkoxy" group indicates a group in which the "$C_{3-6}$ cycloalkyl" group is bonded to the "lower alkoxy" group, and includes, for example, cyclopropylmethoxy, cyclobutylmethoxy, cyclopentylmethoxy, cyclohexylmethoxy, 2-cyclopropylethoxy, 2-cyclobutylethoxy, 2-cyclopentylethoxy, and 2-cyclohexylethoxy groups, and is preferably a cyclopropylmethoxy, cyclobutylmethoxy, cyclopentylmethoxy, cyclohexylmethoxy, or 2-cyclopropylethoxy group, and more preferably a cyclopropylmethoxy, cyclopentylmethoxy, cyclohexylmethoxy, or 2-cyclopropylethoxy group.

Depending on the type of substituents of the present invention, geometric isomers or tautomers may be present. However, the present invention includes those isomers when separated or mixtures thereof. In addition, compounds of the present invention may have an asymmetric carbon atom, and optical isomers with the (R) form and (S) form are present based thereon. The present invention includes all mixtures of such optical isomers and those isolated.

A compound (I) of the present invention may form acid addition salts, or salts with a base depending on the type of substituents. Such a salt is a pharmaceutically acceptable salt, and preferable examples thereof include those from an inorganic acid such as hydrochloric acid, hydrobromic acid, hydroiodic acid, sulfuric acid, nitric acid, and phosphoric acid, acid addition salts with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, benzenesulfonic acid, aspartic acid, and glutamic acid, an inorganic base such as sodium, potassium, magnesium, calcium, and aluminum, salts with an organic base such as methylamine, ethanolamine, ethylamine, lysine, and ornithine, and an ammonium salt.

In addition, the compound (I) of the present invention may absorb water, have adsorbed water attached thereto, or become a hydrate when left in the air. Such salts and additionally, some other solvents may be absorbed to obtain a solvate, and such salts and crystal polymorphs are also included in the present invention.

Since the compound (I) of the present invention can be an ester, "the ester" refers to such an ester. Such esters include, for example, "ester for a hydroxyl group" and "ester for a carboxy group," and are an ester in which each ester residue is a "general protecting group" or "a protecting group which is cleavable by a biological method such as hydrolysis in vivo."

The "general protecting group" refers to a protecting group which is cleavable by a chemical method such as hydrogenolysis, hydrolysis, electrolysis, or photolysis, and examples of the "general protecting group" like "ester for a hydroxyl group" include an "aliphatic acyl group," for example, an alkylcarbonyl group such as formyl, acetyl, propionyl, butyryl, isobutyryl, pentanoyl, and pivaloyl groups, a carboxylated alkylcarbonyl group such as a succinoyl group, a halogeno lower alkyl carbonyl group such as a trifluoroacetyl group, a lower alkoxy lower alkyl carbonyl group such as a methoxyacetyl, and an unsaturated alkylcarbonyl group such as an (E)-2-methyl-2-butenoyl group; an "aromatic acyl group," for example, an arylcarbonyl group such as a benzoyl group, a halogenoarylcarbonyl group, a lower alkylated arylcarbonyl group such as a 2,4,6-trimethylbenzoyl group and a 4-toluoyl group, a lower alkoxylated arylcarbonyl group such as a 4-anisoyl group, a carboxylated arylcarbonyl group such as a 2-carboxybenzoyl group, a 3-carboxybenzoyl group, and a 4-carboxybenzoyl group, a nitrated arylcarbonyl group, a lower alkoxy carboxylated arylcarbonyl group such as a 2-(methoxycarbonyl)benzoyl group, and an arylated arylcarbonyl group such as a 4-phenylbenzoyl group; a "tetrahydropyranyl or tetrahydrothiopyranyl group" such as tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl groups; a "tetrahydrofuranyl or tetrahydrothiofuranyl group" such as tetrahydrofuran-2-yl and tetrahydrothiofuran-2-yl groups; a "silyl group" such as trimethylsilyl, triethylsilyl, and tri lower alkylsilyl groups; an "alkoxymethyl group," for example, a lower alkoxymethyl group such as methoxymethyl and 1,1-dimethyl-1-methoxymethyl groups, a lower alkoxylated lower alkoxymethyl group such as a 2-methoxyethoxymethyl group, and a halogeno lower alkoxymethyl group such as 2,2,2-trichloroethoxymethyl and bis(2-chloroethoxy)methyl groups; an "substituted ethyl group," for example, a lower alkoxylated ethyl group such as 1-ethoxyethyl, and 1-(isopropoxy)ethyl groups, and a halogenated ethyl group such as a 2,2,2-trichloroethyl group; an "aralkyl group" such as a lower alkyl group substituted with 1 to 3 aryl groups (such as a benzyl group), in which an aryl ring may be substituted with a lower alkyl group, a lower alkoxy group, a nitro group, a halogen atom, a cyano group and the like; an "alkoxycarbonyl group," for example, a lower alkoxycarbonyl group such as methoxycarbonyl, ethoxycarbonyl, tert-butoxycarbonyl, and isobutoxycarbonyl groups and a lower alkoxycarbonyl group substituted with a halogen atom or a tri lower alkylsilyl group such as 2,2,2-trichloroethoxycarbonyl and 2-trimethylsilylethoxycarbonyl groups; an "alkenyloxycarbonyl group" such as vinyloxycarbonyl and allyloxycarbonyl groups; or an "aralkyloxycarbonyl group" in which an aryl ring may be substituted with 1 to 2 lower alkoxy groups or nitro groups such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl groups.

On the other hand, the "general protecting group" as a "ester for a carboxy group" is preferably a "lower alkyl group"; a "halogeno lower alkyl group" such as a trifluoromethyl group; a hydroxy "lower alkyl group"; a "lower alkyl group" substituted with 1 to 3 aryl groups such as a benzyl group and a phenethyl group; or an "aralkyl group" such as a lower alkyl group substituted with 1 to 3 aryl groups in which an aryl ring is substituted with a lower alkyl group, a lower alkoxy group, a nitro group, a halogen atom, a cyano group, or alkoxycarbonyl group.

The "protecting group which is cleavable by a biological method such as hydrolysis in vivo" refers to a protecting group which is cleaved by a biological method such as hydrolysis in the human body, and produces a free acid or a salt thereof, and it can be determined whether there are such derivatives by performing intravenous injection administration on experimental animals such as rats or mice, then examining body fluids of the animals, and detecting original compounds or pharmacologically acceptable salts thereof.

The "protecting group which is cleavable by a biological method such as hydrolysis in vivo" as the "ester for a hydroxy group" is, for example, 1-("aliphatic acyl" oxy) "lower alkyl group" such as a pivaloyloxymethyl group; a 1-(acyloxy) "lower alkyl group" such as a 1-("cycloalkyl" carbonyloxy) "lower alkyl group", and a 1-("aromatic acyl" oxy) "lower alkyl group" i.e. a benzoyloxymethyl group; an (alkoxycarbonyloxy)alkyl group such as methoxycarbonyloxymethyl, ethoxycarbonyloxymethyl, propoxycarbonyloxymethyl, and isopropoxycarbonyloxymethyl groups; a "phthalydyl group"; a "carbonyloxyalkyl group" such as an oxodioxolenylmethyl group, i.e. (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolene-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl, and (5-butyl-2-oxo-1,3-dioxolen-4-yl)methyl groups; an "aliphatic acyl group"; and an "aromatic acyl group" and on the other hand, as the "protecting group which is cleavable by a biological method such as hydrolysis in vivo" as the "ester for a carboxy group," specifically, an "alkoxy lower alkyl group," for example, a lower alkoxylated lower alkoxy lower alkyl group such as methoxymethyl and 1-ethoxyethyl groups, an "aryl" oxy "lower alkyl group" such as a phenoxymethyl group, and a halogenated lower alkoxy lower alkyl group such as 2,2,2-trichloroethoxymethyl and bis(2-chloroethoxy)methyl group: a "lower alkoxy" carbonyl "lower alkyl group" such as a methoxycarbonyl methyl; an acyloxy "lower alkyl group" such as an "aliphatic acyl" oxy "lower alkyl group," i.e. a 1-acetoxyethyl group, a "cycloalkyl" carbonyloxy "lower alkyl group" such as a cyclopentylcarbonyloxymethyl group, and a cyclohexylcarbonyloxymethyl group, and an "aromatic acyl" oxy "lower alkyl group" such as a benzoyloxymethyl group; an (alkoxycarbonyloxy)alkyl group such as a methoxycarbonyloxymethyl group, and an ethoxycarbonyloxymethyl group; "carbonyloxyalkyl group" such as a oxodioxolenylmethyl group, i.e., (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl, and (5-butyl-2-oxo-1,3-dioxolen-4-yl)methyl; the above "aryl group"; the above "lower alkyl group"; and a "carboxy alkyl group" such as a carboxymethyl group.

The "pharmacologically acceptable ester" refers to an ester having the "protecting group which is cleavable by a biological method such as hydrolysis in vivo" as an ester residue.

DESCRIPTION OF EMBODIMENTS

Derivatives having excellent effects of specifically antagonizing BMP signal pathways of the present invention can be produced by the following method.

(Production Method)

Compounds and pharmaceutically acceptable salts thereof according to the present invention can be produced using various known synthesis methods unless otherwise noted. In this case, in processes, desired compounds can be obtained by protecting or deprotecting functional groups as necessary. Protection and deprotection of functional groups can be performed by known methods, for example, methods described in "Protective Groups in Organic Synthesis," 4th edition, Greene and Wuts.

Examples of organic bases that can be used in processes include triethylamine, N,N-diisopropylethylamine, N-methylmorpholine, pyridine, picolin, 2,6-lutidine, 4-dimethyl-aminopyridine, imidazole, 1,4-diazabicyclo[2.2.2]octane, and 1,8-diazabicyclo[5.4.0]-7-undecene and the like.

Examples of inorganic bases that can be used in processes include sodium hydrogen carbonate, sodium carbonate, potassium carbonate, cesium carbonate, lithium hydroxide, sodium hydroxide, potassium hydroxide, and potassium phosphate.

Examples of carboxylates that can be used in processes include sodium acetate, potassium acetate, ammonium acetate, and ammonium formate.

Examples of alkali metal hydrides that can be used in processes include lithium hydride, and sodium hydride and the like.

Examples of metal alkoxides that can be used in processes include sodium methoxide, sodium ethoxide, sodium-tert-butoxide, and potassium-tert-butoxide and the like.

Examples of metal amides that can be used in processes include sodium amide, lithium diisopropyl amide, lithium hexamethyl disilazide, sodium hexamethyldisilazide, and potassium hexamethyldisilazide and the like.

Examples of organic lithiums that can be used in processes include n-butyl lithium.

Examples of organic acids that can be used in processes include formic acid, acetic acid, trifluoroacetic acid, methanesulfonic acid, trifluoromethanesulfonic acid, benzenesulfonic acid, p-toluenesulfonic acid, and 10-camphorsulfonic acid.

Examples of inorganic acids that can be used in processes include hydrochloric acid, hydrobromic acid, sulfuric acid, nitric acid, and phosphoric acid.

Examples of Lewis acids that can be used in processes include a boron trifluoride diethyl ether complex, aluminum chloride, zinc chloride, tin chloride, titanium tetrachloride, and titanium isopropoxide.

Representative production methods of compounds of the present invention will be described below, but the present invention is not limited thereto.

First production method

[C6]

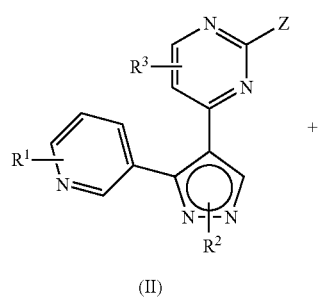

(II)

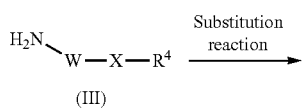

(III)

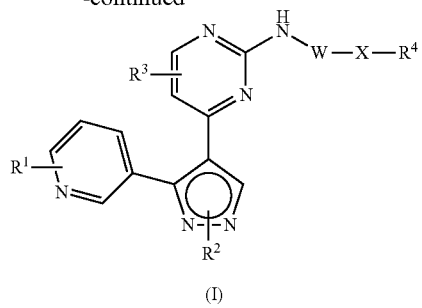

(I)

in the expression, Z is a leaving group, and $R^1$, $R^2$, $R^3$, $R^4$, W and X are as defined above.

Z is not particularly limited as long as it is a group which generally leaves as a nucleophile residue, and is preferably, a halogen atom such as a chlorine atom, a bromine atom, and an iodine atom; a lower alkoxycarbonyloxy group such as methoxycarbonyloxy and ethoxycarbonyloxy groups; an alkylcarbonyloxy group such as acetoxy and propionyloxy groups; an aliphatic acyloxy group such as a halogenated alkylcarbonyloxy group, i.e. chloroacetyloxy, dichloroacetyloxy, trichloroacetyloxy, and trifluoroacetyloxy groups, a lower alkoxyalkylcarbonyloxy group such as a methoxyacetyloxy group, and an unsaturated alkylcarbonyloxy group such as an (E)-2-methyl-2-butenoyloxy group; an aromatic acyloxy group, i.e. an arylcarbonyloxy group such as a benzoyloxy group, a halogenated arylcarbonyloxy group such as 2-bromobenzoyloxy, and 4-chlorobenzoyloxy groups, a lower alkylated arylcarbonyloxy group such as 2,4,6-trimethylbenzoyloxy, and 4-toluoyloxy groups, a lower alkoxylated arylcarbonyloxy group such as a 4-anisoyloxy group, and a nitrated arylcarbonyloxy group such as 4-nitrobenzoyloxy, and 2-nitrobenzoyloxy groups; a trihalogenomethyloxy group such as a trichloromethyloxy group; a lower alkanesulfonyloxy group such as methanesulfonyloxy, and ethanesulfonyloxy groups; a halogeno lower alkanesulfonyloxy group such as trifluoromethanesulfonyloxy and pentafluoroethanesulfonyloxy groups; and an arylsulfonyloxy group such as benzenesulfonyloxy, p-toluenesulfonyloxy, and p-nitrobenzenesulfonyloxy groups, and is preferably a halogen atom; a lower alkanesulfonyloxy group; or an arylsulfonyloxy group.

This production method is a method in which the compound (I) of the present invention is obtained by reacting pyrimidine derivatives represented by General Formula (II) with amine derivatives represented by General Formula (III) as shown in the above reaction formula.

The pyrimidine derivatives (II) that can be used in the first production method have a leaving group at the $2^{nd}$ position of their pyrimidine ring, and a desired compound (I) can be produced by a substitution reaction with amine derivatives (III) at that position.

This reaction occurs without a solvent or in an organic solvent inactive to the reaction, for example, a solvent such as tetrahydrofuran (THF), 1,4-dioxane, dichloromethane, N,N-dimethylformamide (DMF), dimethyl sulfoxide, N-methyl pyrrolidone, acetonitrile, toluene, methanol, ethanol, propanol, butanol, 1,2-dimethoxyethane, ethylene glycol, trifluoroethanol, and acetic acid. In some cases, the reaction can be promoted by adding organic bases, inorganic bases, organic acids, inorganic acids, Lewis acids or the like. In addition, in some cases, the reaction can be promoted by emitting microwaves using a microwave reaction device. The reaction temperature is appropriately selected from room temperature to 200° C., preferably 80° C. to 150° C. depending on the type of reaction derivatives and reaction conditions. The reaction time varies depending on reagents and solvents used, a reaction temperature, and the like, but it takes 10 minutes to 3 days.

In addition, this reaction can be performed with a coupling reaction using a palladium catalyst represented as a Buchwald-Hartwig reaction in a solvent inactive to the reaction, for example, a solvent such as THF, 1,4-dioxane, DMF, N-methyl pyrrolidone, toluene, 1,2-dimethoxyethane, and water. Examples of palladium catalysts used include palladium(II) acetate (Pd(OAc)$_2$), tetrakis(triphenylphosphine)palladium(O) (Pd(PPh$_3$)$_4$), dichlorobis(triphenylphosphine)palladium(II) (PdCl$_2$(PPh$_3$)$_2$), tris(dibenzylideneacetone)dipalladium(O) (Pd$_2$(dba)$_3$), bis(dibenzylideneacetone)palladium(O) (Pd(dba)$_2$), and [1,1'-bis(diphenylphosphino)ferrocene]palladium(II) dichloride (Pd(dppf)Cl$_2$). In some cases, the reaction can be promoted by adding inorganic bases or phosphine ligands.

Examples of phosphine ligands used include 2,2'-bis(diphenylphosphino)-1,1'-binaphthyl (BINAP), 2-dichlorohexylphosphino-2',4',6'-triisopropylbiphenyl (XPhos), 2-dichlorohexylphosphino-2',6'-dimethoxybiphenyl (SPhos), 2-dichlorohexylphosphino-2'-(N,N-dimethylamino)biphenyl (DavePhos), 2-(di-tert-butylphosphino)biphenyl (JohnPhos), and 4,5-bis(diphenylphosphino)-9,9-dimethylxanthene (XantPhos). The reaction can occur at room temperature to 150° C., and preferably 80° C. to 120° C. In some cases, the reaction can be promoted by emitting microwaves using a microwave reaction device. The reaction time varies depending on reagents and solvents used, a reaction temperature, and the like, but it takes 10 minutes to 3 days.

In addition, this reaction can be performed with a coupling reaction using a copper catalyst represented as a Goldberg reaction in the presence of inorganic bases, and a solvent inactive to the reaction, for example, a solvent such as THF, 1,4-dioxane, DMF, N-methyl pyrrolidone, and toluene. Examples of copper catalysts used include copper(I) iodide and copper oxide. In some cases, the reaction can be promoted by adding a ligand such as N,N'-dimethylethylenediamine (DMEDA). The reaction can occur at room temperature to 200° C., and preferably, 80° C. to 150° C. The reaction time varies depending on reagents and solvents used, a reaction temperature, and the like, but it takes 1 hour to 3 days.

Second production method

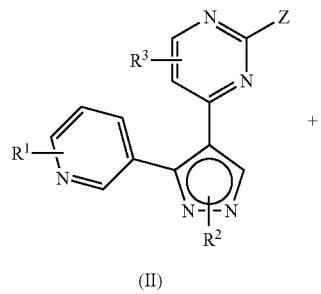

(II)

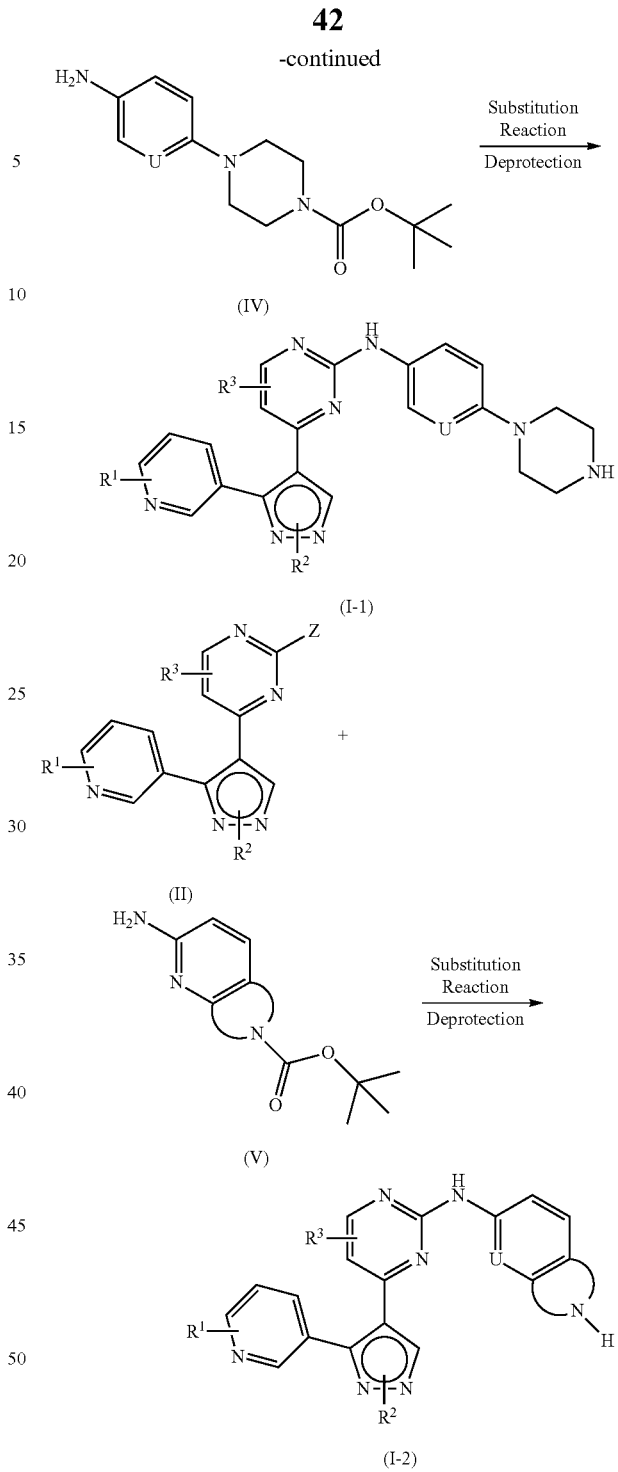

Wherein, U is CH or N, and R$^1$, R$^2$, R$^3$ and Z are as defined above.

This production method is a method in which a compound (I-1) or (I-2) of the present invention is obtained by reacting pyrimidine derivatives represented by General Formula (II) with amine derivatives represented by General Formula (IV) or (V) as shown in the above reaction formula.

The pyrimidine derivatives (II) that can be used in the second production method have a leaving group at the 2-position of their pyrimidine ring, and a desired compound (I-1) or (I-2) can be produced by one pot according to a substitution reaction with amine derivatives (IV) or (V) at that position and a subsequent deprotection reaction.

This reaction occurs in alcohols such as ethanol and propanol, or glycols such as ethylene glycol. In some cases, the reaction can be promoted by adding organic bases, inorganic bases, organic acids, inorganic acids, Lewis acids, or the like. The reaction can occur at room temperature to 200° C., and preferably 80° C. to 150° C. In some cases, the reaction can be promoted by emitting microwaves using a microwave reaction device. The reaction time varies depending on reagents and solvents used, a reaction temperature, and the like, but it takes 1 hour to 1 day.

Third production method

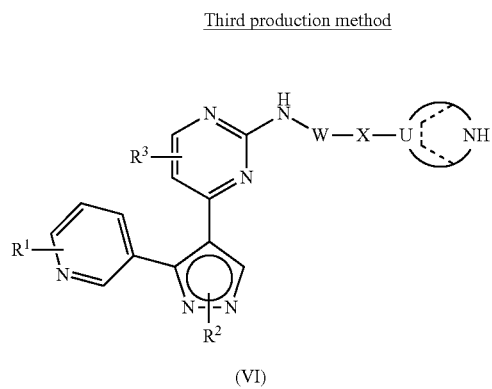

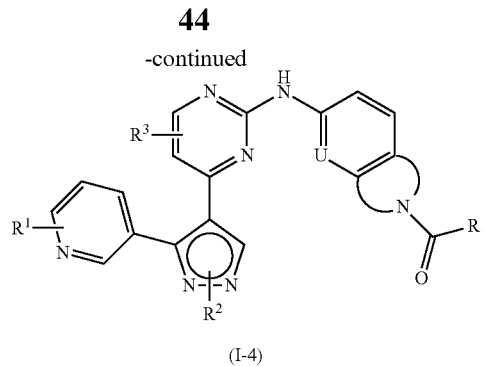

Wherein, U, $R^1$, $R^2$, $R^3$, W and X are as defined above, R is a group in the definition of $R^4$ in the present invention in a compound (I-3) of the present invention, and is, for example, an $R^5$ group, and the $R^4$ group itself in a compound (I-4) of the present invention.

This production method is a method in which the compound (I-3) or (I-4) of the present invention is obtained by subjecting amine derivatives represented by General Formula (VI) or (VIII) and carboxylic acid derivatives represented by General Formula (VII) to an amidation reaction as shown in the above reaction formula.

The carboxylic acid derivatives (VII) that can be used in the third production method are free carboxylic acids or reactive derivatives thereof, and examples of the reactive derivatives include an acid halide such as acid chloride, an active ester that can be prepared using N-hydroxysuccinimide or the like, and an acid anhydride. Such reactive derivatives are commercially available or can be produced by conventional methods.

When a free carboxylic acid is used, it is preferable to use a condensing agent such as 1-(3-dimethylaminopropyl)-3-ethylcarbodiimide or a carboxylic acid activating agent such as 1,1'-carbonyldiimidazole, and 1-hydroxybenzotriazole during the reaction.

This reaction can occur in a solvent inactive to the reaction, for example, a solvent such as THF, dichloromethane, 1,2-dichloroethane, DMF, ethyl acetate, and pyridine. The reaction temperature is appropriately selected from 0° C. to 120° C., preferably room temperature to 50° C. depending on the type of reactive derivatives. The reaction can be promoted by adding organic bases or inorganic bases depending on the type of reactive derivatives. The reaction time varies depending on reagents and solvents used, a reaction temperature, and the like, but it takes 1 hour to 1 day.

Fourth production method

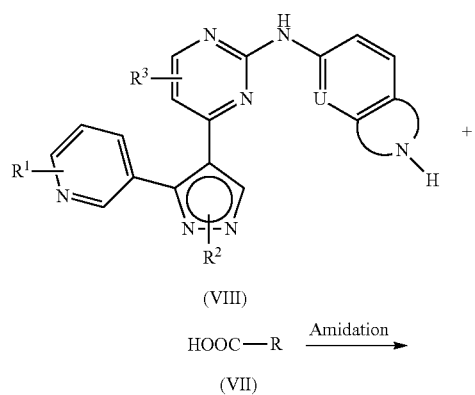

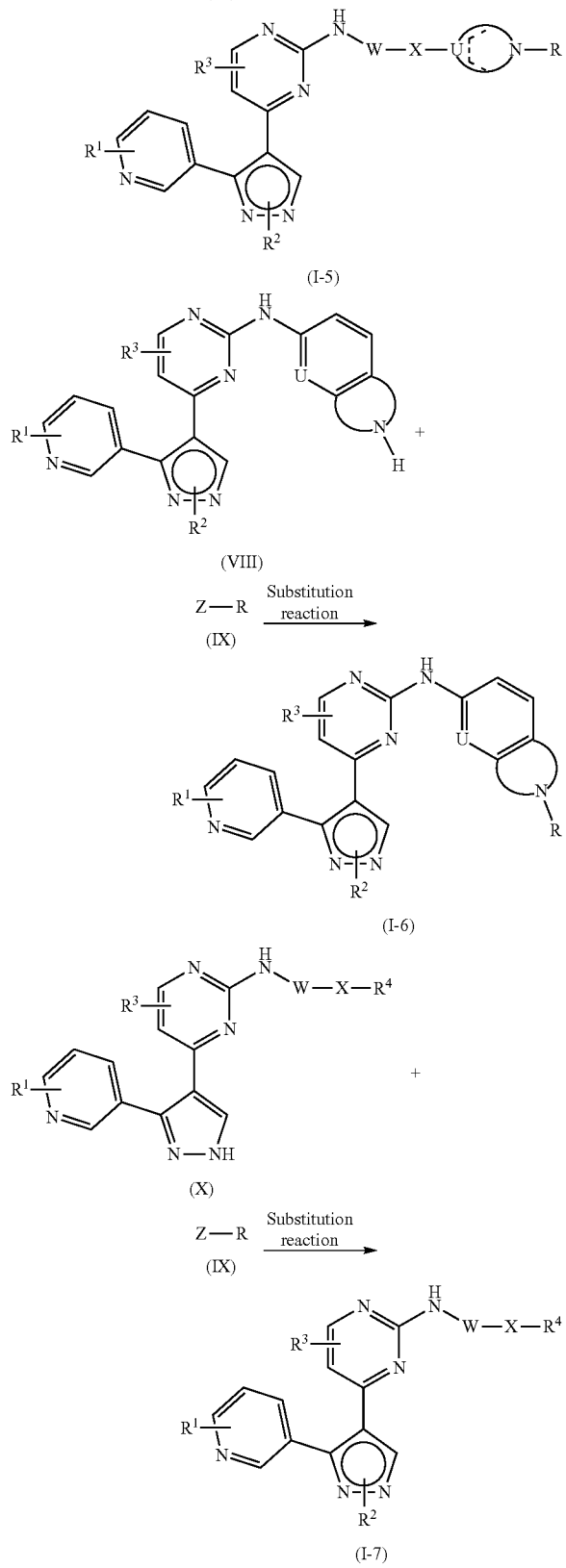

Wherein, U, $R^1$, $R^2$, $R^3$, Z, W and X are as defined above, and R in the upper and middle sections is a corresponding group in the definition of $R^4$ in the present invention and R in the lower section is a corresponding group in the definition of $R^2$ in the present invention.

This production method is a method in which a compound (I-5), (I-6) or (I-7) of the present invention is obtained by substituting amine derivatives represented by General Formula (VI) or (VIII), or pyrazole derivatives represented by General Formula (X) using a compound having a leaving group represented by General Formula (IX) as shown in the above reaction formula.

Examples of the compound (IX) having a leaving group that can be used in the fourth production method include an alkyl halide such as an alkyl bromide, a sulfonic acid ester of corresponding alcohol derivatives, and a carboxylic acid ester of corresponding alcohol derivatives. Such compounds are commercially available or can be produced by conventional methods.

This reaction occurs in a solvent inactive to the reaction, for example, a solvent such as THF, 1,4-dioxane, 1,2-dimethoxyethane, dichloromethane, DMF, N-methyl pyrrolidone, acetone, 2-butanone, and acetonitrile, or without a solvent. The reaction temperature is appropriately selected from 0° C. to 120° C., preferably room temperature to 100° C. depending on the type of reactive derivatives. The reaction can be promoted by adding organic bases or inorganic bases depending on the type of reaction agents. The reaction time varies depending on reagents and solvents used, a reaction temperature, and the like, but it takes 1 hour to 3 days.

Fifth production method

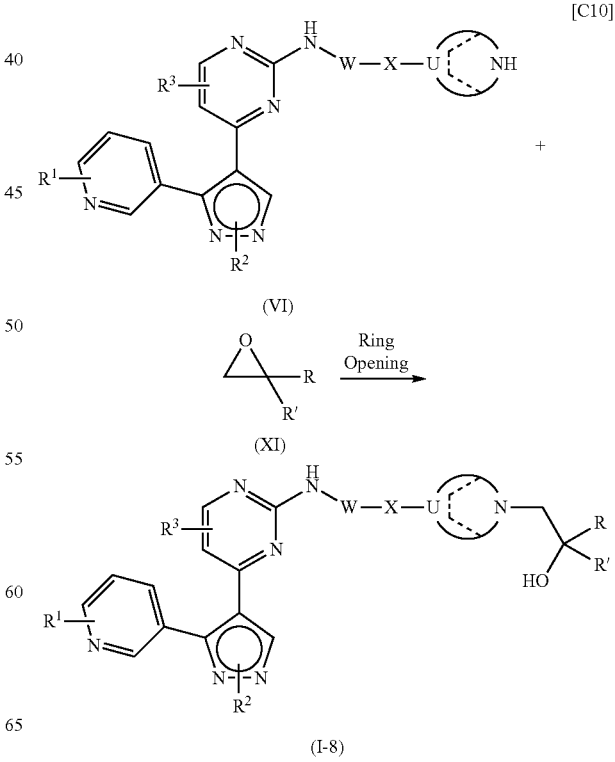

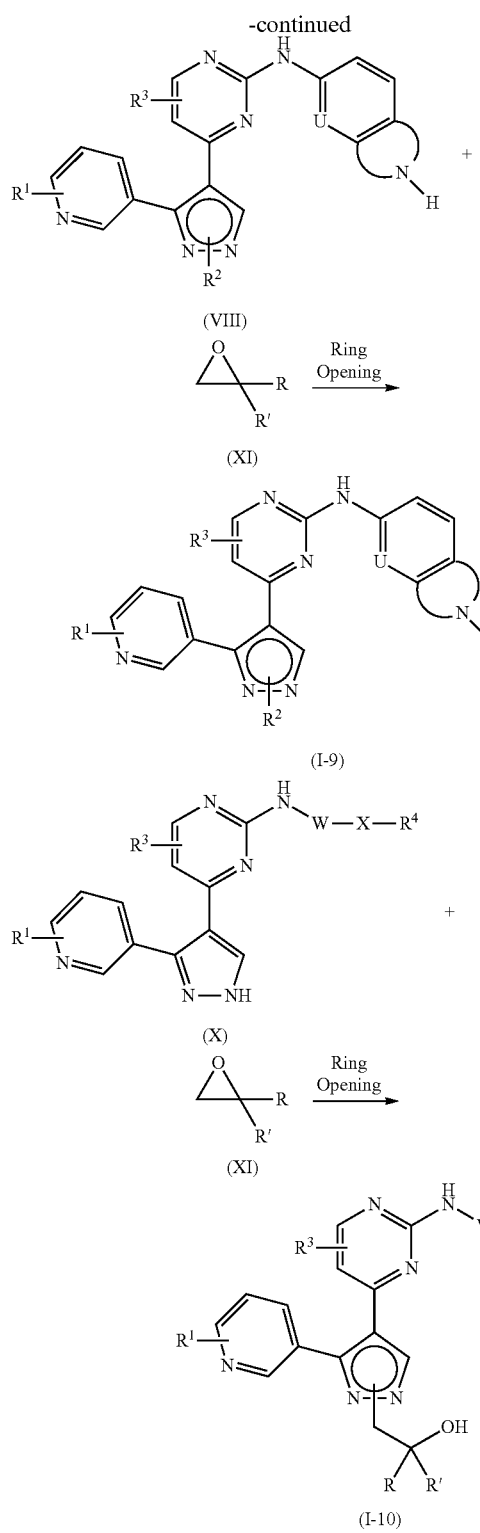

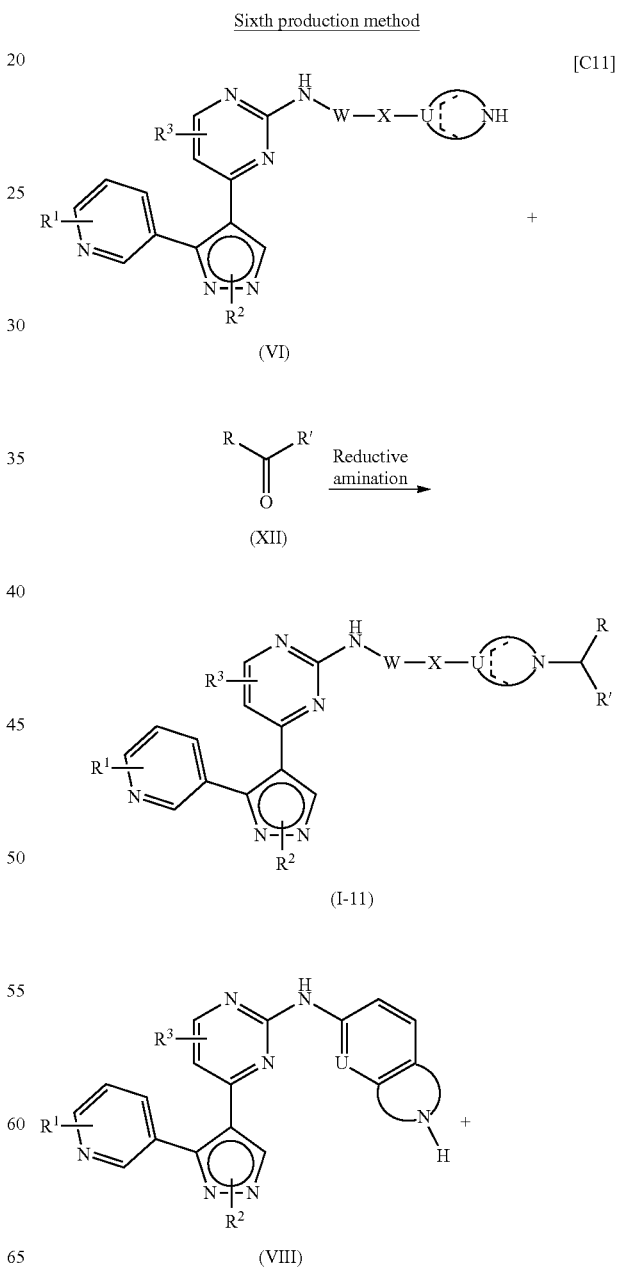

Wherein, $R^1$, $R^2$, $R^3$, $R^4$, U, W and X are as defined above, and R and R' are a corresponding group in the definition of $R^2$ and $R^4$ in the present invention, for example, a lower alkyl.

This production method is a method in which a compound (I-8), (I-9) or (I-10) of the present invention is obtained by alkylating amine derivatives represented by General Formula (VI) or (VIII) or pyrazole derivatives represented by General Formula (X) with epoxy derivatives represented by General Formula (XI) as shown in the above reaction formula.

This reaction occurs in a solvent inactive to the reaction, for example, a solvent such as THF, 1,4-dioxane, 1,2-dimethoxyethane, dichloromethane, DMF, acetone, 2-butanone, acetonitrile, ethanol, and isopropanol or without a solvent. The reaction temperature is appropriately selected from 0° C. to 120° C., preferably room temperature to 80° C. depending on the type of reaction derivatives. The reaction can be promoted by adding organic bases, Lewis acids or inorganic bases depending on the type of epoxy derivatives. The reaction time varies depending on reagents and solvents used, a reaction temperature, and the like, but it takes 1 hour to 3 days.

Sixth production method

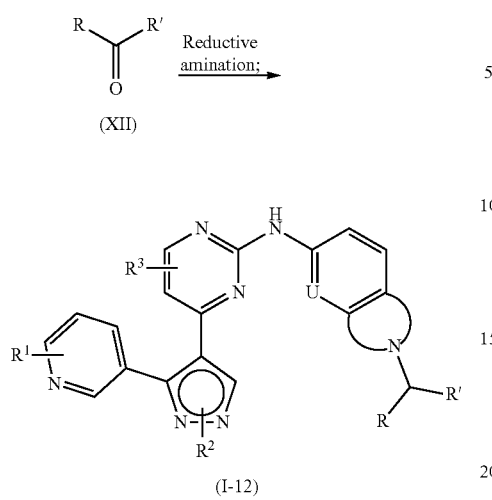

(XII)

(I-12)

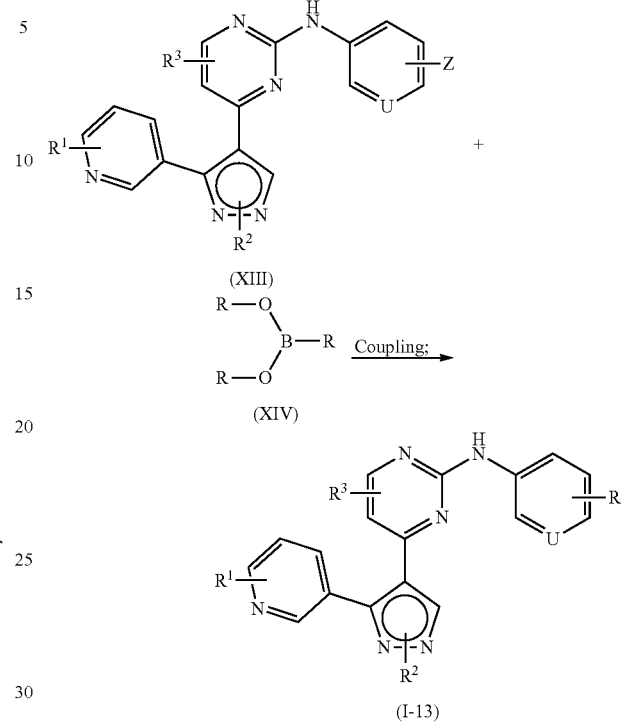

Seventh production method (XIII)

(XIV)

(I-13)

Wherein, $R^1$, $R^2$, $R^3$, U, W and X are as defined above, and R and R' are a corresponding group in the definition of $R^4$ in the present invention, for example, a lower alkyl group or a hydrogen atom (R and R' are not both a hydrogen atom).

This production method is a method in which a compound (I-11) or (I-12) of the present invention is obtained by subjecting amine derivatives represented by General Formula (VI) or (VIII) and carbonyl derivatives represented by General Formula (XII) to a reductive amination reaction as shown in the above reaction formula.

The carbonyl derivatives (XII) that can be used in the sixth production method are aldehyde derivatives or ketone derivatives, and are commercially available or can be produced by conventional methods.

This reductive amination reaction is performed by reacting amine derivatives with carbonyl derivatives in a solvent inactive to the reaction, for example, a solvent such as THF, 1,4-dioxane, 1,2-dimethoxyethane, dichloromethane, 1,2-dichloroethane, methanol, ethanol, and toluene, and reducing a produced Schiff base.

Regarding production of a Schiff base, removing produced water in the presence of Lewis acids, organic acids or inorganic acids or using a dehydrating agent such as a molecular sieve or a Dean-Stark trap is advantageous. The reaction temperature is appropriately set, but it is preferably from room temperature to that for refluxing. The reaction time varies depending on reagents and solvents used, a reaction temperature, and the like, but it takes 1 hour to 1 day.

Reduction of the Schiff base can be performed by adding a metal hydride complex such as sodium cyanoborohydride, sodium triacetoxyborohydride, and sodium borohydride, a borane complex such as picoline borane, or a reducing agent such as formic acid, and heating from −20° C. to that for refluxing. In addition, reduction can be performed by adding hydrogen using a catalyst such as palladium carbon, at room temperature to 50° C. in a solvent such as THF, methanol, and ethanol. The reaction time varies depending on reagents and solvents used, a reaction temperature, and the like, but it takes 1 hour to 1 day.

Wherein, $R^1$, $R^2$, $R^3$, U and Z are as defined above, and R is a corresponding group in the definition of —X—$R^4$ in the present invention.

This production method is a method in which a compound (I-13) of the present invention is obtained by reacting derivatives represented by General Formula (XIII) with boronic acid derivatives represented by General Formula (XIV) as shown in the above reaction formula.

Examples of boronic acid derivative (XIV) that can be used in this seventh production method include a free boronic acid and a boronic acid ester such as a pinacol ester. Such boronic acid derivatives are commercially available or can be produced by conventional methods.

This reaction occurs in the presence of a metal catalyst in a solvent inactive to the reaction, for example, a solvent such as THF, 1,4-dioxane, 1,2-dimethoxyethane, DMF, toluene, and water. The reaction can occur at room temperature to 150° C., and preferably from 80° C. to 120° C. In some cases, the reaction can be promoted by emitting microwaves using a microwave reaction device. The reaction time varies depending on reagents and solvents used, a reaction temperature, and the like, but it takes 10 minutes to 3 days.

Examples of the metal catalyst used in this reaction include a palladium catalyst such as $Pd(OAc)_2$, $Pd(PPh_3)_4$, $PdCl_2(PPh_3)_2$, $Pd_2(dba)_3$, $Pd(dba)_2$, and $Pd(dppf)Cl_2$; a nickel catalyst such as tetrakis(triphenylphosphine)nickel (0); and a copper catalyst such as copper oxide, and copper (I) iodide. In some cases, the reaction can be promoted by adding inorganic bases, carboxylic acid salts, and phosphine ligands. Examples of phosphine ligands used include tricyclohexylphosphine, tributylphosphine, XPhos, SPhos, DavePhos, JohnPhos, and XantPhos.

Eighth production method

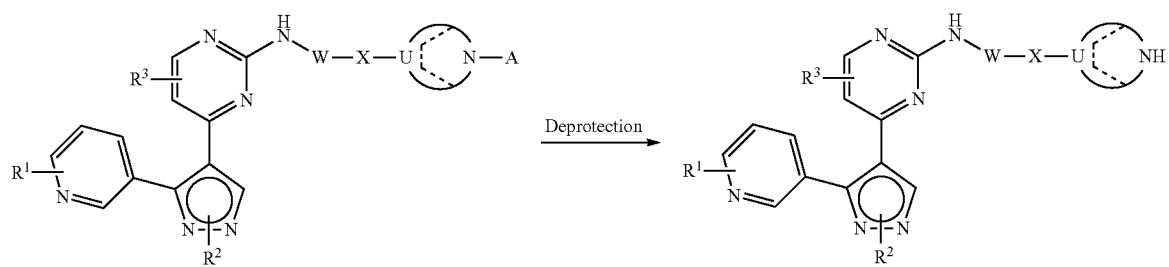

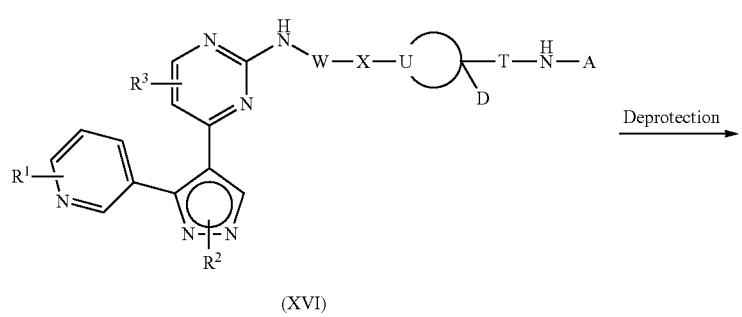

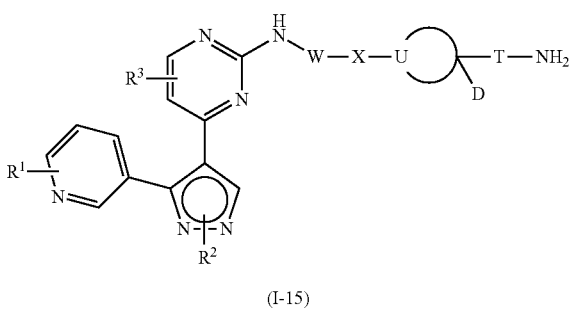

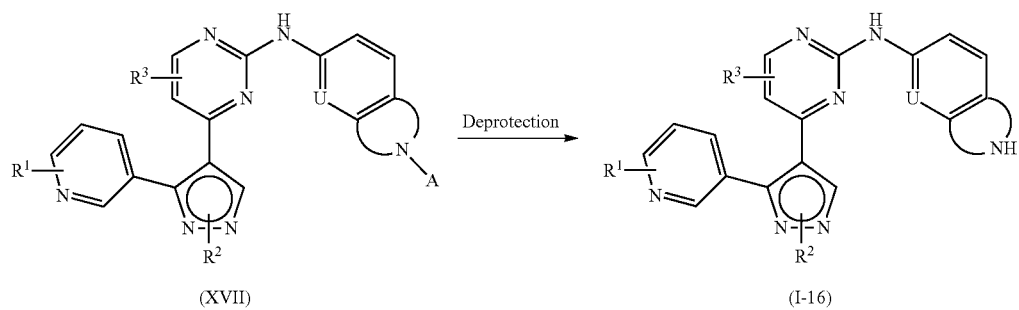

Wherein, $R^1$, $R^2$, $R^3$, U, W and X are as defined above, T is a single bond or a lower alkylene group, D is H or a lower alkyl group, and A is a protecting group.

This production method is a method in which a compound (I-14), (I-15) or (I-16) of the present invention is obtained by deprotecting derivatives represented by General Formula (XV), (XVI) or (XVII) as shown in the above reaction formula.

Generally, the protecting groups of the derivatives (XV), (XVI) or (XVII) are not limited as long as they are groups that can protect amino groups, and preferable examples thereof include a urethane-type protecting group such as a tert-butoxycarbonyl group and a benzyloxycarbonyl group; an amide-type protecting group such as an acetyl group and a benzoyl group; and an alkyl-type protecting group such as a benzyl group.

This reaction can be performed by known methods, for example, methods described in "Protective Groups in Organic Synthesis," 4th edition, Greene and Wuts.

Ninth production method

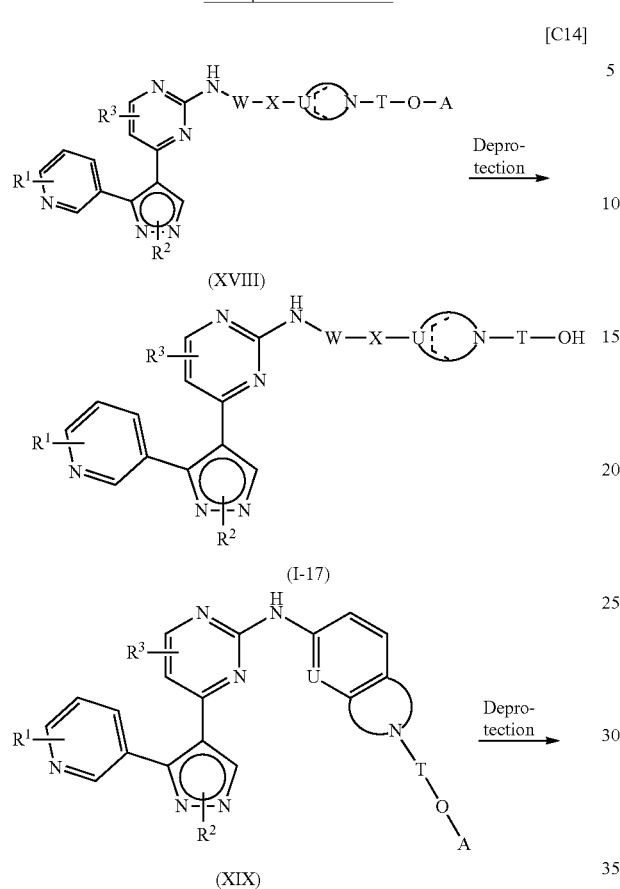

Wherein, $R^1$, $R^2$, $R^3$, A, U, W and X are as defined above, T is a lower alkylene having 2 carbon atoms or more, or a —C(O)-lower alkylene- group.

This production method is a method in which a compound (I-17) or (I-18) of the present invention is obtained by deprotecting derivatives represented by General Formula (XVIII) or (XIX) as shown in the above reaction formula.

Generally, the protecting group of the derivatives (XVIII) or (XIX) is not particularly limited as long as it can be used as a protecting group for a hydroxyl group, and preferable examples thereof include an ester-type protecting group such as an acetyl group and a benzoyl group; an ether-type protecting group such as a benzyl group; and a silyl ether-type protecting group such as a tert-butyldimethylsilyl group.

This reaction can be performed by known methods, for example, methods described in "Protective Groups in Organic Synthesis," 4th edition, Greene and Wuts.

Tenth production method

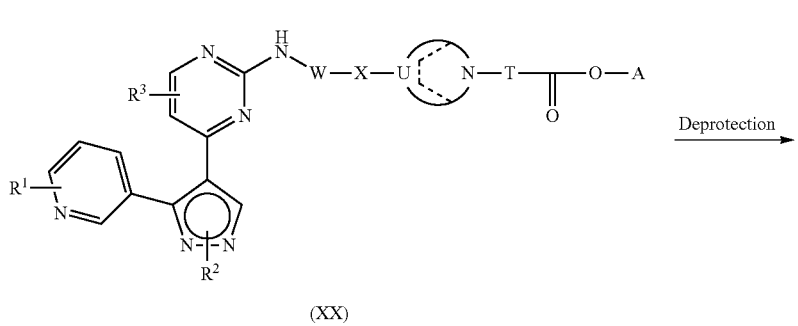

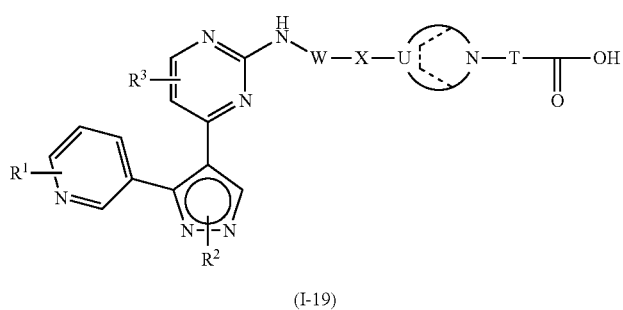

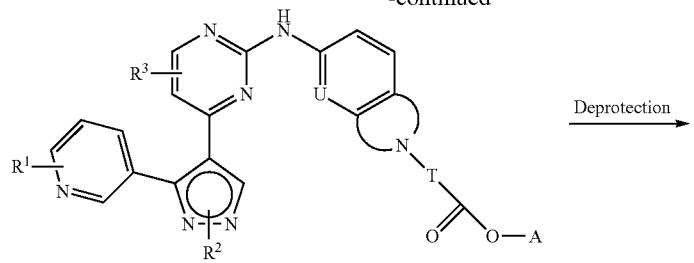

(XXI)

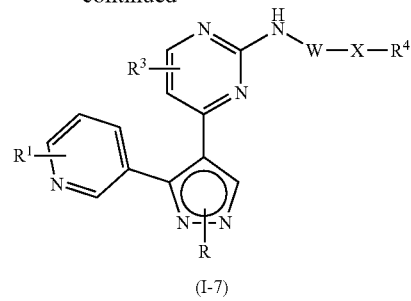

(I-20)

Wherein, $R^1$, $R^2$, $R^3$, A, U, W and X are as defined above, and T is a lower alkylene.

This production method is a method in which a compound (I-19) or (I-20) of the present invention is obtained by deprotecting a carboxy group of derivatives represented by General Formula (XX) or (XXI) as shown in the above reaction formula.

Generally, the protecting group of the derivatives (XX) or (XXI) is not particularly limited as long as it can be used as a protecting group for a carboxy group, and preferable examples thereof include an ester-type protecting group such as a methyl group and a tert-butyl group.

This reaction can be performed by known methods, for example, methods described in "Protective Groups in Organic Synthesis," 4th edition, Greene and Wuts.

Eleventh production method

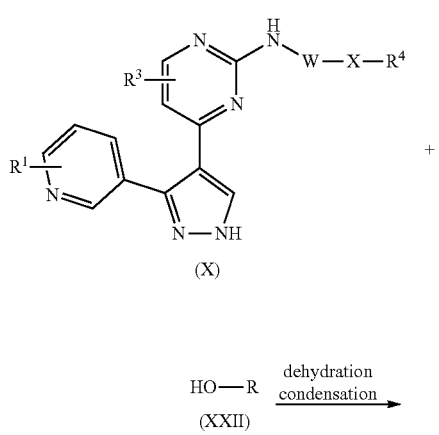

Wherein, $R^1$, $R^3$, $R^4$, W and X are as defined above, and R is a corresponding group to the definition of $R^2$ in the present invention.

This production method is a method in which a compound (I-7) of the present invention is obtained by a dehydration condensation reaction of pyrazole derivatives represented by General Formula (X) and alcohol derivatives represented by General Formula (XXII) as shown in the above reaction formula.

The alcohol derivatives (XXII) that can be used in this eleventh production method are commercially available or can be produced by conventional methods.

This reaction can be performed by a dehydration condensation reaction using azodicarboxylic acid derivatives and phosphine derivatives represented as a Mitsunobu reaction in a solvent inactive to the reaction, for example, a solvent such as THF, 1,4-dioxane, toluene, benzene, 1,2-dimethoxyethane, and acetonitrile. Examples of the azodicarboxylic acid derivatives used include diethyl azodicarboxylate, diisopropyl azodicarboxylate, di-tert-butyl azodicarboxylate, dimethyl azodicarboxylate, 1,1'-azobis(N,N-dimethylformamide), and 1,1'-(azodicarbonyl)dipiperidine. Examples of the phosphine derivatives used include triphenylphosphine, tributylphosphine, tricyclohexylphosphine, dicyclohexylphenylphosphine, and diphenyl-2-pyridylphosphine. The reaction occurs at 0° C. to 120° C., and preferably at room temperature to 100° C. The reaction time varies depending on reagents and solvents used, a reaction temperature, and the like, but it takes 1 hour to 3 days.

In addition, this reaction can be performed using phosphorane derivatives represented as a Tsunoda reagent in a solvent inactive to the reaction, for example, a solvent such as THF, 1,4-dioxane, toluene, benzene, 1,2-dimethoxyethane, and acetonitrile. Examples of the phosphorane derivatives used include cyanomethylene tributylphosphorane, and cyanomethylene trimethylphosphorane. The reaction occurs at 0° C. to 150° C., and preferably room temperature to 120° C. The reaction time varies depending on reagents and solvents used, a reaction temperature, and the like, but it takes 1 hour to 7 days.

Novel derivatives of the present invention have an excellent effect of specifically antagonizing BMP signal pathways and have no toxicity, and thus are useful as a preventive agent and a therapeutic agent for diseases and pathological symptoms related to BMP signal.

Examples of dosage forms of the compound (I) of the present invention include oral administration with tablets, capsules, granules, powders or syrups, or parenteral administration with injection agents, a suppository, and the like. Such formulations can be produced by well-known methods using additives, for example, an excipient (for example, sugar derivatives such as lactose, white sugar, glucose, mannitol, and sorbitol; starch derivatives such as corn starch, potato starch, a starch, and dextrin; cellulose derivatives such as crystalline cellulose; gum arabic; dextran; an organic excipient such as pullulan: and an inorganic excipient, i.e. silicate derivatives such as light anhydrous silica, synthetic aluminum silicate, calcium silicate, magnesium aluminometasilicate; a phosphate such as calcium hydrogen phosphate; a carbonate such as calcium carbonate; and a sulfate such as calcium sulfate), a lubricant (for example, stearic acid, calcium stearate, a stearic acid metal salt such as magnesium stearate; talc; colloidal silica; waxes such as Veegum and whale wax; boric acid; adipic acid; a sulfate such as sodium sulfate; glycols; fumaric acid; sodium benzoate; DL leucine; a fatty acid sodium salt; a lauryl sulfate such as sodium lauryl sulfate, and lauryl sulfate magnesium; silicas such as silicic anhydride and silicic acid hydrate; and the above starch derivatives), a binding agent (for example, hydroxypropyl cellulose, hydroxypropyl methyl cellulose, polyvinylpyrrolidone, macrogol, and the same compounds as for the excipient), a disintegrating agent (for example, cellulose derivatives such as low substituted hydroxypropyl cellulose, carboxymethyl cellulose, carboxymethylcellulose calcium, and internally cross-linked sodium carboxymethylcellulose; and chemically modified starch and celluloses such as carboxymethyl starch, sodium carboxymethyl starch, and crosslinked polyvinyl pyrrolidone), a stabilizer (para-hydroxybenzoic acid esters such as methyl paraben and propyl paraben; alcohols such as chlorobutanol, benzyl alcohol, and phenylethyl alcohol; benzalkonium chloride; phenols such as phenol and cresol; thimerosal; dehydroacetic acid; and sorbic acid), a flavoring agent (for example, a generally used sweetener, acidulant, perfume, and the like), a diluting agent, and the like.

An amount used varies depending on symptoms, age, administration methods, and the like. For example, desirably, in oral administration, one dosage is 0.01 mg/kg body weight (preferably 0.1 mg/kg body weight) as a lower limit and 30 mg/kg body weight (preferably 20 mg/kg body weight) as an upper limit, and in intravenous administration, one dosage is 0.001 mg/kg body weight (preferably 0.01 mg/kg body weight) as a lower limit and 10 mg/kg body weight (preferably 3 mg/kg body weight) as an upper limit, and administration is preferably performed once or several times per day depending on symptoms.

The present invention will be described below in further detail with reference to examples, production examples and test examples.

EXAMPLES

The compound of the present invention is not limited to compounds described in the following examples. In addition, production methods of raw material compounds used in an example will be described as production examples.

In the following examples, the following abbreviations may be used.

THF: Tetrahydrofuran
DMF: N,N-dimethylformamide
Pd/C: Palladium carbon
$^1$H NMR: Proton nuclear magnetic resonance
DMSO-$d_6$: Deuterated dimethyl sulfoxide
LC/MS: Liquid chromatography mass spectrometer
MS: Mass spectrometry using an electrospray ionization method
$[M+H]^+$, $[M+Na]^+$, $[M+2H]^{2+}$: Molecular ion peak
M: Molar concentration
N: Normal solution Production Example 1

A 1.3 M lithium hexadisilazide-THF solution (179 mL) was added dropwise to a mixture containing methyl nicotinate (16.0 g), 2-chloro-4-methyl pyrimidine (15.0 g) and THF (179 mL) under a nitrogen atmosphere while maintaining the internal temperature at about −30° C., and the mixture was stirred at −30° C. for 30 minutes, and then at room temperature for 1 hour. A saturated ammonium chloride aqueous solution was added to the reaction mixture, and extraction was performed using ethyl acetate. Then, an organic layer was dried with anhydrous sodium sulfate and concentrated under a reduced pressure. The obtained residue was purified through silica gel column chromatography (elution solvent: ethyl acetate), and then solidified in methyl tert-butyl ether, and thereby 2-(2-chloropyrimidin-4-yl)-1-(pyridin-3-yl)ethan-1-one (19.2 g) as an orange solid was obtained.

Production Example 2

A mixture containing 2-(2-chloropyrimidin-4-yl)-1-(pyridin-3-yl)ethan-1-one (Production Example 1, 54.5 g), DMF dimethyl acetal (33.4 g), toluene (1.4 L) and acetic acid (16.8 g) was stirred at 110° C. for 1 hour, and DMF dimethyl acetal (6.7 g) was added thereto, and the mixture was then stirred at 110° C. for 50 minutes. The reaction mixture was concentrated under a reduced pressure, ethanol (440 mL) was added to the obtained residue, acetic acid (16.8 g) and hydrazine monohydrate (11.7 g) were sequentially added thereto under ice cooling, and the mixture was then stirred for 40 minutes under ice cooling. Ice water was added to the reaction mixture, the mixture was stirred at room temperature for 1 hour, and the precipitated solid was then collected by filtration, washed with water, and then dried under a reduced pressure. The obtained solid was washed with ethyl acetate, and thereby 2-chloro-4-(3-(pyridin-3-yl)-1H-pyrazol-4-yl)pyrimidine (44.5 g) as a yellow-brown solid was obtained.

Production Example 3

A mixture containing 2-chloro-4-(3-(pyridin-3-yl)-1H-pyrazol-4-yl)pyrimidine (Production Example 2, 5.0 g), DMF (50 mL), iodoethane (1.72 mL), and potassium carbonate (5.36 g) was stirred at 60° C. for 3.5 hours. Ethyl acetate was added to the reaction mixture, the mixture was sequentially washed with water and a saturated saline solution. Then, an organic layer was dried with anhydrous sodium sulfate and concentrated under a reduced pressure. The obtained residue was purified through silica gel column chromatography (elution solvent: dichloromethane-ethyl acetate), and thereby 2-chloro-4-(1-ethyl-3-(pyridin-3-yl)-1H-pyrazol-4-yl)pyrimidine (2.17 g) as a light yellow powder was obtained.

Production Example 15

A mixture containing 4-(3-iodo-1H-pyrazol-4-yl)-2-(methylthio)pyrimidine (Synthesis literature 1, 2.00 g), bromoethane (2.48 g), potassium carbonate (0.75 g) and DMF (20 mL) was stirred at 50° C. for 5 hours. Ethyl acetate (600 mL) and a saturated saline solution (300 mL) were added to and distributed in the reaction solution, and the organic layer was dried with anhydrous sodium sulfate and then concentrated under a reduced pressure. Thereby, a mixture (2.21 g) containing 4-(1-ethyl-5-iodo-1H-pyrazol-4-yl)-2-(methylthio)pyrimidine and 4-(1-ethyl-3-iodo-1H-pyrazol-4-yl)-2-(methylthio)pyrimidine with a composition ratio of 1:2 as a yellow oily substance was obtained.

Production Example 17

A mixture containing 2-chloro-4-(3-(pyridin-3-yl)-1H-pyrazol-4-yl)pyrimidine (Production Example 2, 1.0 g), 2,2-dimethyloxirane (3.5 mL) and DMF (3.5 mL) was stirred at 50° C. overnight. The reaction mixture was dried under a nitrogen stream, and the obtained residue was purified through silica gel column chromatography (elution solvent: dichloromethane-methanol), and thereby 1-(4-(2-chloropyrimidin-4-yl)-3-(pyridin-3-yl)-1H-pyrazol-1-yl)-2-methylpropan-2-ol (497 mg) as a light brown foamy substance was obtained.

Production Example 18

A mixture containing 2-chloro-5-nitropyridine (158 mg), tert-butyl 3,8-diazabicyclo[3.2.1]octane-8-carboxylate (commercially available from JW Pharmaceutical, 212 mg), potassium carbonate (166 mg) and 1,4-dioxane (5 mL) was stirred at 120° C. After disappearance of the raw material was confirmed with LC/MS, the reaction mixture was concentrated under a reduced pressure, water was added to the obtained residue, and extraction was performed using dichloromethane. The organic layer was dried with anhydrous sodium sulfate and then concentrated under a reduced pressure. The obtained residue was purified through silica gel column chromatography (elution solvent: dichloromethane-ethyl acetate), and thereby tert-butyl 3-(5-nitropyridin-2-yl)-3,8-diazabicyclo[3.2.1]octane-8-carboxylate (280 mg) as a yellow powder was obtained.

Production Example 19

A mixture containing 1-benzyl-4-isopropyl-1,2,3,6-tetrahydropyridine (Synthesis literature 2, 1.52 g) and acetonitrile (0.74 mL) was added to concentrated sulfuric acid (3.2 mL), and the mixture was stirred at room temperature overnight. Ice water and sodium carbonate were sequentially added to the reaction mixture, and extraction was performed using ethyl acetate. Then, the organic layer was dried with anhydrous sodium sulfate and concentrated under a reduced pressure. The obtained residue was purified through silica gel column chromatography (elution solvent: chloroform-methanol), and thereby N-(2-(1-benzylpiperidin-4-yl)propan-2-yl)acetamide (808 mg) as a light yellow solid was obtained.

Production Example 20

A mixture containing N-(2-(1-benzylpiperidin-4-yl)propan-2-yl)acetamide (Production Example 19, 806 mg), 5% Pd/C (160 mg) and ethanol (10 mL) was stirred at room temperature overnight under a hydrogen atmosphere. Insoluble substances in the reaction mixture were filtered off. Then, the filtrate was concentrated under a reduced pressure, and ethanol (10 mL), acetic acid (0.5 mL) and 5% Pd/C (160 mg) were sequentially added to the obtained residue, and the mixture was stirred at room temperature for 4 days under a hydrogen atmosphere. Insoluble substances in the reaction mixture were filtered off. Then, the filtrate was concentrated under a reduced pressure, the obtained residue was purified through aminopropyl silica gel column chromatography (elution solvent: chloroform-methanol), and thereby N-(2-(piperidin-4-yl)propan-2-yl)acetamide (233 mg) as a colorless solid was obtained.

Production Example 21

A mixture containing 4-fluoronitrobenzene (0.2 mL), N-(4-methylpiperidin-4-yl)acetamide (Synthesis literature 3, 295 mg), potassium carbonate (313 mg) and N-methyl pyrrolidone (3 mL) was stirred at 80° C. overnight. The reaction mixture was cooled and water was then added thereto. The resulting solid was collected by filtration and then washed with water. The obtained solid was dissolved in chloroform, and washed with a saturated saline solution. Then, an organic layer was dried with anhydrous sodium sulfate and concentrated under a reduced pressure. The obtained yellow powder was washed with hexane, and thereby N-(4-methyl-1-(4-nitrophenyl)piperidin-4-yl)acetamide (393 mg) as a yellow powder was obtained.

Production Example 22

A mixture containing N-(1-benzyl-4-ethylpiperidin-4-yl)acetamide (Synthesis literature 4, 1.392 g), 5% Pd/C (280 mg), and ethanol (14 mL) was stirred at room temperature overnight under a hydrogen atmosphere. Insoluble substances in the reaction mixture were filtered off. Then, the filtrate was concentrated under a reduced pressure, and ethanol (14 mL), acetic acid (0.7 mL) and 5% Pd/C (280 mg) were added to the obtained residue, and the mixture was stirred at room temperature overnight under a hydrogen atmosphere. Insoluble substances in the reaction mixture were filtered off. Then, the filtrate was concentrated under a reduced pressure, the obtained residue was solidified in diisopropyl ether, and thereby N-(4-ethylpiperidin-4-yl)acetamide (1.018 g) as a colorless powder was obtained.

A mixture containing N-(4-ethylpiperidin-4-yl)acetamide (549 mg), 4-fluoronitrobenzene (0.2 mL), potassium carbonate (573 mg) and N-methyl pyrrolidone (6 mL) was stirred at 80° C. overnight. The reaction mixture was cooled and water was then added thereto. The resulting solid was collected by filtration and then washed with water. The obtained solid was dissolved in chloroform and washed with a saturated saline solution. Then, an organic layer was dried with anhydrous sodium sulfate and concentrated under a reduced pressure. The obtained yellow powder was washed with hexane, and thereby N-(4-ethyl-1-(4-nitrophenyl)piperidin-4-yl)acetamide (342 mg) as a yellow powder was obtained.

Production Example 24

A mixture containing tert-butyl 4-amino-4-methylpiperidine-1-carboxylate (commercially available from JW Pharmaceutical, 500 mg), paraformaldehyde (560 mg), sodium triacetoxyborohydride (1.95 g), 1,2-dichloroethane (10 mL) and acetic acid (0.5 mL) was stirred at 70° C. for 4 hours. Insoluble substances in the reaction mixture were filtered off. Then, the filtrate was washed with a potassium carbonate aqueous solution, and the organic layer was concentrated under a reduced pressure. Trifluoroacetic acid (3.5 mL) was added to the obtained residue, and the mixture was stirred at room temperature for 30 minutes and then concentrated under a reduced pressure. Potassium carbonate (2.21 g), 4-fluoronitrobenzene (621 mg), and DMF (20 mL) were added to the obtained residue, and the mixture was stirred at 100° C. for 14 hours. Insoluble substances in the reaction mixture were filtered off and the filtrate was then concentrated under a reduced pressure. The obtained residue was purified through silica gel column chromatography (elution solvent: dichloromethane-ethyl acetate), and thereby N,N,4-trimethyl-1-(4-nitrophenyl)piperidin-4-amine (263 mg) as a yellow solid was obtained.

Production Example 25

A mixture containing 4-nitrobenzene sulfonyl chloride (310 mg), dichloromethane (10 mL), diisobutylethylamine (576 mg) and tert-butyl 4-(methylamino)piperidine-1-carboxylate (commercially available from Tokyo Chemical Industry Co., Ltd., 360 mg) was stirred at room temperature for 2 hours. The reaction mixture was concentrated under a reduced pressure, the obtained residue was purified through silica gel column chromatography (elution solvent: dichloromethane-ethyl acetate), and thereby tert-butyl 4-((N-methyl-4-nitrophenyl)sulfonamido)piperidine-1-carboxylate (531 mg) as a colorless powder was obtained.

Production Example 26

A mixture containing 2,2-difluoroethanol (2 mL) and 60% sodium hydride (76 mg) was stirred at room temperature for 1 hour, and 1-(2-bromoethyl)-4-(4-nitrophenyl)piperazine (Synthesis literature 5, 200 mg) was then added thereto, and the mixture was stirred at room temperature for 3 days. Ice water was added to the reaction mixture, and extraction was then performed using chloroform. The organic layer was dried with anhydrous sodium sulfate and then concentrated under a reduced pressure. The obtained residue was purified through silica gel column chromatography (elution solvent: chloroform), and thereby 1-(2-(2,2-difluoroethoxy)ethyl)-4-(4-nitrophenyl)piperazine (202 mg) as a light brown oily substance was obtained.

Production Example 28

A mixture containing 4-(4-nitro-1H-pyrazol-1-yl)piperidine (Synthesis literature 6, 200 mg) and 2,2-dimethyloxirane (3.6 mL) was stirred at 65° C. overnight. The reaction mixture was concentrated under a reduced pressure, the obtained residue was purified through silica gel column chromatography (elution solvent: hexane-ethyl acetate), and thereby 2-methyl-1-(4-(4-nitro-1H-pyrazol-1-yl)piperidin-1-yl)propan-2-ol (160 mg) as a yellow solid was obtained.

Production Example 29

A 1.9 N diisopropyl azodicarboxylate-toluene solution (8.7 mL) was added to a mixture containing 4-nitro-1H-pyrazole (1.5 g), tert-butyl 3-hydroxyazetidine-1-carboxylate (commercially available from Tokyo Chemical Industry Co., Ltd., 2.3 g), triphenyl phosphine (4.35 g) and THF (50 mL), and the mixture was stirred at room temperature overnight. Magnesium chloride (3.15 g) was added to the reaction mixture, and the mixture was then stirred at 60° C. for 2 hours, cooled, and filtered. The filtrate was concentrated, and the obtained residue was distributed in water and ethyl acetate. The organic layer was washed with a saturated saline solution, and dried over anhydrous sodium sulfate, and then concentrated under a reduced pressure. The obtained residue was purified through silica gel column chromatography (elution solvent: hexane-ethyl acetate), and thereby tert-butyl 3-(4-nitro-1H-pyrazol-1-yl)azetidine-1-carboxylate (5.6 g) as a solid was obtained.

A 4 N hydrochloric acid-dioxane solution (38 mL) was added to a mixture containing tert-butyl 3-(4-nitro-1H-pyrazol-1-yl)azetidine-1-carboxylate (4.0 g) and methanol (80 mL), and the mixture was stirred at room temperature overnight. The reaction mixture was concentrated under a reduced pressure, the obtained residue was washed with ethyl acetate, and thereby 1-(azetidin-3-yl)-4-nitro-1H-pyrazole hydrochloride (1.62 g) as a colorless solid was obtained.

A mixture containing 1-(azetidin-3-yl)-4-nitro-1H-pyrazole hydrochloride (200 mg), 2,2-dimethyloxirane (2.6 mL), N,N-diisopropylethylamine (569 mg), and methanol (0.5 mL) was stirred at 70° C. overnight. The reaction mixture was concentrated under a reduced pressure, the obtained residue was purified through silica gel column chromatography (elution solvent: dichloromethane-methanol), and thereby 2-methyl-1-(3-(4-nitro-1H-pyrazol-1-yl)azetidin-1-yl)propan-2-ol (310 mg) as a light yellow oily substance was obtained.

Production Example 30

A mixture containing 1,2-phenylenebis(ethane-2,1-diyl) dimethanesulfonate (Synthesis literature 7, 0.525 g), and cyclopropylamine (0.57 mL) was stirred at room temperature overnight. The reaction solution was concentrated under a reduced pressure, dichloromethane was added to the obtained residue, and the mixture was then washed with water. The organic layer was concentrated under a reduced pressure, the obtained residue was purified through silica gel column chromatography (elution solvent: dichloromethane-methanol), and thereby 3-cyclopropyl-2,3,4,5-tetrahydro-1H-benzo[d]azepine (0.16 g) was obtained.

Production Example 31

Sulfuric acid (0.018 mL) and 60% nitric acid (0.039 mL) were added to a mixture containing 3-cyclopropyl-2,3,4,5-tetrahydro-1H-benzo[d]azepine (Production Example 30, 160 mg), trifluoroacetic acid (0.52 mL), and acetic acid (0.040 mL) under ice cooling while maintaining the internal temperature at 10° C. or lower. The reaction mixture was stirred at room temperature for 2 hours, and ice water was then added thereto, a 4 N sodium hydroxide aqueous solution was added dropwise thereto, and a pH was adjusted to 9. The product was extracted using diethyl ether, the organic layer was dried with anhydrous sodium sulfate and then concentrated under a reduced pressure, and thereby 3-cyclopropyl-7-nitro-2,3,4,5-tetrahydro-1H-benzo[d]azepine (149 mg) was obtained.

Production Example 32

2-Picoline borane (78 mg) was gradually added at 80° C. to a mixture containing 5-nitroisoindoline (Synthesis literature 8, 100 mg), 3-oxetanone (44 mg), acetic acid (0.2 mL) and 1,2-dichloroethane (1.8 mL) and the reaction mixture was then stirred at 80° C. for 10 minutes. The product was extracted using dichloromethane, and an organic layer was washed with water, and then concentrated under a reduced pressure. The obtained residue was purified by silica gel thin layer chromatography (developing solvent: dichloromethane-methanol), and thereby 5-nitro-2-(oxetan-3-yl)isoindoline (26 mg) was obtained.

Production Example 33

In the same manner as in Production Example 32, 4-(4-nitrophenyl)-1-(oxetan-3-yl)piperidine was obtained using 4-(4-nitrophenyl)piperidine (Synthesis literature 37) in place of 5-nitroisoindoline.

Production Example 34

A mixture containing N-(4-methyl-1-(4-nitrophenyl)piperidin-4-yl)acetamide (Production Example 21, 389 mg), 5% Pd/C (100 mg), ethanol (8 mL) and THF (4 mL) was stirred at room temperature for 4 hours under a hydrogen atmosphere. Insoluble substances in the reaction mixture were filtered off. Then, the filtrate was concentrated under a reduced pressure, and thereby N-(1-(4-aminophenyl)-4-methylpiperidin-4-yl)acetamide (379 mg) as a purple oily substance was obtained.

Production Example 47

A mixture containing tert-butyl 3-oxo-8-azabicyclo[3.2.1]octane-8-carboxylate (commercially available from Tokyo Chemical Industry Co., Ltd., 2.25 g), a 30% methylamine aqueous solution (2.5 mL), 10% Pd/C (400 mg) and methanol (30 mL) was stirred at 55° C. for 17 hours under a hydrogen atmosphere. Insoluble substances in the reaction mixture were filtered off. Then, the filtrate was concentrated under a reduced pressure, and thereby tert-butyl 3-(methylamino)-8-azabicyclo[3.2.1]octane-8-carboxylate (2.38 g) as a colorless oily substance was obtained.

A mixture containing tert-butyl 3-(methylamino)-8-azabicyclo[3.2.1]octane-8-carboxylate (422 mg), 4-nitrobenzoyl chloride (372 mg), triethylamine (1.0 g) and dichloromethane (20 mL) was stirred at room temperature for 1 hour. The reaction mixture was concentrated under a reduced pressure, the obtained residue was purified through silica gel column chromatography (elution solvent: dichloromethane-ethyl acetate), and trifluoroacetic acid (1.5 mL) was then added thereto, and the mixture was stirred at room temperature for 30 minutes. The reaction mixture was concentrated under a reduced pressure, and acetone (0.7 mL), sodium triacetoxyborohydride (440 mg) and 1,2-dichloroethane (10 mL) were added to the obtained residue, and the mixture was stirred at 70° C. for 1 hour. A saturated sodium bicarbonate aqueous solution was added to the reaction mixture, and extraction was performed using dichloromethane. The organic layer was dried with anhydrous sodium sulfate and then concentrated under a reduced pressure, and methanol (20 mL) and 10% Pd/C (100 mg) were added to the obtained residue, and the mixture was then stirred at room temperature for 4 hours under a hydrogen atmosphere. Insoluble substances in the reaction mixture were filtered off. Then, the filtrate was concentrated under a reduced pressure, and thereby 4-amino-N-(8-isopropyl-8-azabicyclo[3.2.1]octan-3-yl)-N-methylbenzamide (133 mg) as a colorless solid was obtained.

Production Example 48

Cyanomethylene tributylphosphorane (0.407 mL) was added to a mixture containing 2-chloro-4-(3-(pyridin-3-yl)-1H-pyrazol-4-yl)pyrimidine (Production Example 2, 200 mg), tetrahydrofuran-3-ol (0.074 mL), and toluene (4 mL) under a nitrogen atmosphere, and the mixture was stirred at room temperature for 3 days, and then at 80° C. for 5 hours. The reaction mixture was concentrated under a reduced pressure, the obtained residue was purified through silica gel column chromatography (elution solvent: chloroform-methanol), and thereby 2-chloro-4-(3-(pyridin-3-yl)-1-(tetrahydrofuran-3-yl)-1H-pyrazol-4-yl)pyrimidine (164 mg) as a brown oily substance was obtained.

Production Example 49

A mixture containing 2-chloro-4-(1-ethyl-3-(pyridin-3-yl)-1H-pyrazol-4-yl)pyrimidine (Production Example 3, 571 mg), tert-butyl (1-(4-(aminophenyl)piperidin-4-yl)carbamate (Synthesis literature 9, 947 mg) and methanol (1.5 mL) was stirred at 100° C. for 2 hours under a nitrogen atmosphere, and the solidified reaction mixture was suspended in dichloromethane, and then purified through aminopropyl silica gel column chromatography (elution solvent: dichloromethane-ethyl acetate), and thereby tert-butyl (1-(4-((4-(1-ethyl-3-(pyridin-3-yl)-1H-pyrazol-4-yl)pyrimidin-2-yl)amino)phenyl)piperidin-4-yl)carbamate (595 mg) as a yellow solid was obtained.

Production Example 50

A mixture containing tert-butyl 3-(4-nitrophenoxy)-8-azabicyclo[3.2.1]octane-8-carboxylate (Synthesis literature 10, 310 mg), 5% Pd/C (62 mg) and methanol was stirred at room temperature for 3 hours under a hydrogen atmosphere. Insoluble substances in the reaction mixture were filtered off. Then, the filtrate was concentrated under a reduced pressure, the obtained residue was purified through silica gel column chromatography, and thereby tert-butyl 3-(4-aminophenoxy)-8-azabicyclo[3.2.1]octane-8-carboxylate (260 mg) as a light red white solid was obtained.

A mixture containing tert-butyl 3-(4-aminophenoxy)-8-azabicyclo[3.2.1]octane-8-carboxylate (150 mg), 2-chloro-4-(1-ethyl-3-(pyridin-3-yl)-1H-pyrazol-4-yl)pyrimidine (Production Example 3, 86 mg) and methanol (1.5 mL) was stirred at 100° C. for 1 hour under a nitrogen atmosphere. The solidified reaction mixture was purified in the same manner as in Production Example 49, and thereby tert-butyl 3-(4-((4-(1-ethyl-3-(pyridin-3-yl)-1H-pyrazol-4-yl)pyrimidin-2-yl)amino)phenoxy)-8-azabicyclo[3.2.1]octane-8-carboxylate (102 mg) as a yellow solid was obtained.

Production Example 51

In the same manner as in Production Example 49, tert-butyl 3-(4-((4-(1-ethyl-3-(pyridin-3-yl)-1H-pyrazol-4-yl)

pyrimidin-2-yl)amino)phenoxy)azetidine-1-carboxylate as a yellow-brown solid was obtained using tert-butyl 3-(4-aminophenoxy)azetidine-1-carboxylate (Synthesis literature 11) in place of tert-butyl (1-(4-(aminophenyl)piperidin-4-yl)carbamate.

Production Example 53

In the same manner as in Production Example 49, tert-butyl 4-(4-((4-(3-(pyridin-3-yl)-1H-pyrazol-4-yl)pyrimidin-2-yl)amino)phenyl)piperidine-1-carboxylate was obtained using tert-butyl 4-(4-aminophenyl)piperidine-1-carboxylate (Synthesis literature 12) in place of tert-butyl (1-(4-(aminophenyl)piperidin-4-yl)carbamate.

Production Example 54

In the same manner as in Production Example 49, tert-butyl 6-((4-(3-(pyridin-3-yl)-1H-pyrazol-4-yl)pyrimidin-2-yl)amino)-3,4-dihydroisoquinoline-2(1H)-carboxylate was obtained using tert-butyl 6-amino-3,4-dihydroisoquinoline-2(1H)-carboxylate (Synthesis literature 13) in place of tert-butyl (1-(4-(aminophenyl)piperidin-4-yl)carbamate.

Production Example 57

In the same manner as in Production Example 49, tert-butyl 4-(4-((4-(1-(pyridin-2-ylmethyl)-3-(pyridin-3-yl)-1H-pyrazol-4-yl)pyrimidin-2-yl)amino)phenyl)piperazine-1-carboxylate was obtained using tert-butyl 4-(4-aminophenyl)piperazine-1-carboxylate (Synthesis literature 14) in place of tert-butyl (1-(4-(aminophenyl)piperidin-4-yl)carbamate.

Production Example 58

A mixture containing 2-chloro-4-(3-(pyridin-3-yl)-1H-pyrazol-4-yl)pyrimidine (Production Example 2, 1.0 g), 1,4-dioxane (10 mL) and tert-butyl 4-(4-aminophenyl)piperazine-1-carboxylate (Synthesis literature 14, 1.13 g) was stirred at 150° C. for 4 hours under microwave radiation. The reaction mixture was concentrated under a reduced pressure, the obtained residue was purified through silica gel column chromatography (elution solvent: dichloromethane-methanol), and thereby tert-butyl 4-(4-((4-(3-(pyridin-3-yl)-1H-pyrazol-4-yl)pyrimidin-2-yl)amino)phenyl)piperazine-1-carboxylate (772 mg) as a light brown foamy substance was obtained.

Production Example 60

In the same manner as in Production Example 58, tert-butyl 4-(4-((4-(1-ethyl-3-(pyridin-3-yl)-1H-pyrazol-4-yl)pyrimidin-2-yl)amino)phenyl)-1,4-diazepane-1-carboxylate was obtained using tert-butyl 4-(4-aminophenyl)-1,4-diazepane-1-carboxylate (Synthesis literature 15) in place of tert-butyl 4-(4-aminophenyl)piperazine-1-carboxylate.

Production Example 65

In the same manner as in Production Example 58, benzyl 4-(4-((4-(1-ethyl-3-(pyridin-3-yl)-1H-pyrazol-4-yl)pyrimidin-2-yl)amino)phenyl)piperazine-1-carboxylate was obtained using benzyl 4-(4-aminophenyl)piperazine-1-carboxylate (Synthesis literature 16) in place of tert-butyl 4-(4-aminophenyl)piperazine-1-carboxylate.

Production Example 67

In the same manner as in Production Example 58, tert-butyl 3-(4-((4-(1-ethyl-3-(pyridin-3-yl)-1H-pyrazol-4-yl)pyrimidin-2-yl)amino)phenyl)-8-azabicyclo[3.2.1]octane-8-carboxylate was obtained using tert-butyl 3-(4-aminophenyl)-8-azabicyclo[3.2.1]octane-8-carboxylate (Synthesis literature 17) in place of tert-butyl 4-(4-aminophenyl)piperazine-1-carboxylate.

Production Example 68 tert-Butyl 4-(4-amino-1H-pyrazol-1-yl)piperidine-1-carboxylate (commercially available from Ark Pharm, Inc, 98 mg) was added to a mixture containing 2-chloro-4-(1-ethyl-3-(pyridin-3-yl)-1H-pyrazol-4-yl)pyrimidine (Production Example 3, 100 mg) and ethanol (4 mL). The mixture was stirred at 150° C. for 3 hours under microwave radiation. A solvent was distilled off, the residue was purified through aminopropyl silica gel column chromatography (elution solvent: dichloromethane-methanol), and thereby 4-(1-ethyl-3-(pyridin-3-yl)-1H-pyrazol-4-yl)-N-(1-(piperidin-4-yl)-1H-pyrazol-4-yl)pyrimidin-2-amine (78 mg) as a light yellow solid was obtained.

Production Example 69

A mixture containing 8-nitro-2,3,4,5-tetrahydrobenzo[f][1,4]oxazepine (Synthesis literature 18, 162 mg), 30% di-tert-butyl dicarbonate-THF solution (1.4 mL), N,N-dimethylpyridin-4-amine (13.2 mg) and triethylamine (0.116 mL) was stirred at room temperature for 4 hours. The reaction mixture was concentrated under a reduced pressure, the obtained residue was purified through silica gel column chromatography (elution solvent: dichloromethane-methanol), and thereby tert-butyl 8-nitro-2,3-dihydrobenzo[f][1,4]oxazepine-4(5H)-carboxylate (233 mg) was obtained.

Ethanol and 10% Pd/C (150 mg) were sequentially added thereto, and the mixture was stirred at room temperature for 18 hours under a hydrogen atmosphere. Insoluble substances in the reaction mixture were filtered off. Then, the filtrate was concentrated under a reduced pressure, and thereby tert-butyl 8-amino-2,3-dihydrobenzo[f][1,4]oxazepine-4(5H)-carboxylate (193 mg) as a light yellow amorphous solid was obtained.

A mixture containing tert-butyl 8-amino-2,3-dihydrobenzo[f][1,4]oxazepine-4(5H)-carboxylate (93 mg), 2-chloro-4-(1-ethyl-3-(pyridin-3-yl)-1H-pyrazol-4-yl)pyrimidine (Production Example 3, 100 mg) and ethanol (2 mL) was stirred at 150° C. for 2 hours under microwave radiation. A solvent was distilled off, dichloromethane was then added to the residue, and washing with a 1 N sodium hydroxide aqueous solution was performed. An organic layer was dried with anhydrous sodium sulfate. Then, the obtained residue was purified through silica gel column chromatography (elution solvent: dichloromethane-methanol), and thereby N-(4-(1-ethyl-3-(pyridin-3-yl)-1H-pyrazol-4-yl)pyrimidin-2-yl)-2,3,4,5-tetrahydrobenzo[f][1,4]oxazepin-8-amine (18.4 mg) was obtained.

Production Example 71

In the same manner as in Production Example 68, 4-(1-ethyl-3-(3-(pyridin-3-yl)-1H-pyrazol-4-yl)-N-(3-(piperidin-4-yl)phenyl)pyrimidin-2-amine was obtained using tert-butyl 4-(3-aminophenyl)piperidine-1-carboxylate (commercially available from Ark Pharm, Inc) in place of tert-butyl 4-(4-amino-1H-pyrazol-1-yl)piperidine-1-carboxylate.

Production Example 72

A mixture containing 2-chloro-4-(1-ethyl-3-iodo-1H-pyrazol-4-yl)pyrimidine (Synthesis literature 1, 1.65 g) and tert-butyl 4-(4-aminophenyl)piperazine-1-carboxylate (Synthesis literature 14, 3.61 g) was stirred at 80° C. for 1 hour, and then at 100° C. overnight. The reaction mixture was purified through silica gel column chromatography (elution solvent: dichloromethane-ethyl acetate), and thereby tert-butyl 4-(4-((4-(1-ethyl-3-iodo-1H-pyrazol-4-yl)pyrimidin-2-yl)amino)phenyl)piperazine-1-carboxylate (2.305 g) as a brown powder was obtained.

Production Example 73

A mixture containing tert-butyl 4-(4-((4-(1-ethyl-3-iodo-1H-pyrazol-4-yl)pyrimidin-2-yl)amino)phenyl)piperazine-1-carboxylate (Production Example 72, 253 mg), (5-fluoropyridine-3-yl)boronic acid (70 mg), potassium phosphate (191 mg), 1,2-dimethoxyethane (12 mL) and water (2.5 mL) was bubbled under a nitrogen atmosphere for 10 minutes, (1,1'-bis(diphenylphosphino)ferrocene)palladium(II) dichloride (32 mg) was then added thereto, and the mixture was stirred at 83° C. for 2.5 hours. The reaction mixture was concentrated under a reduced pressure, the obtained residue was purified through aminopropyl silica gel column chromatography (elution solvent: hexane-ethyl acetate), and thereby tert-butyl 4-(4-((4-(1-ethyl-3-(5-fluoropyridin-3-yl)-1H-pyrazol-4-yl)pyrimidin-2-yl)amino)phenyl)piperazine-1-carboxylate (225 mg) as a light yellow powder was obtained.

Production Example 74

A mixture containing 2-chloro-4-(1-ethyl-3-(pyridin-3-yl)-1H-pyrazol-4-yl)pyrimidine (Production Example 3, 200 mg), 28% ammonia water (2 mL) and a 7 N ammonia-methanol solution (2 mL) was stirred in a sealed tube at 50° C. overnight, and then at 80° C. for 24 hours. The reaction mixture was concentrated under a reduced pressure, the obtained residue was purified by silica gel thin layer chromatography (developing solvent: dichloromethane-methanol), and thereby 4-(1-ethyl-3-(pyridin-3-yl)-1H-pyrazol-4-yl)pyrimidin-2-amine (65 mg) was obtained.

Production Example 75

A mixture containing tert-butyl 4-(4-((4-(3-(pyridin-3-yl)-1H-pyrazol-4-yl)pyrimidin-2-yl)amino)phenyl)piperazine-1-carboxylate (Production Example 58, 209 mg), 4-fluorobenzyl bromide (95 mg), potassium carbonate (207 mg) and DMF (8 mL) was stirred at 70° C. for 1 hour. The reaction mixture was filtered off, and the filtrate was concentrated under a reduced pressure. Then, the obtained residue was purified through silica gel column chromatography (elution solvent: dichloromethane-ethyl acetate), and thereby tert-butyl 4-(4-((4-(1-(4-fluorobenzyl)-3-(pyridin-3-yl)-1H-pyrazol-4-yl)pyrimidin-2-yl)amino)phenyl)piperazine-1-carboxylate (145 mg) as a yellow solid was obtained.

Production Example 79

In the same manner as in Production Example 75, benzyl 4-(4-((4-(1-(3-methyloxetan-3-yl)methyl-3-(pyridin-3-yl))-1H-pyrazol-4-yl)pyrimidin-2-yl)amino)phenyl)piperazine-1-carboxylate was obtained using benzyl 4-(4-((4-(1-ethyl-3-(pyridin-3-yl)-1H-pyrazol-4-yl)pyrimidin-2-yl)amino)phenyl)piperazine-1-carboxylate (Production Example 65) and (3-methyloxetan-3-yl)methyl 4-methylbenzenesulfonate (commercially available from Ark Pharm, Inc).

Production Example 80

A mixture containing 2-chloro-4-(3-(pyridin-3-yl)-1H-pyrazol-4-yl)pyrimidine (Production Example 2, 618 mg), 3-(bromomethyl)pyridine hydrobromide (600 mg), potassium carbonate (1.0 g) and DMF (7 mL) was stirred at 70° C. for 2 hours. The reaction mixture was poured into water and extraction was performed with dichloromethane-methanol (9:1). The organic layer was dried with anhydrous sodium sulfate and then concentrated under a reduced pressure. The obtained residue was purified through aminopropyl silica gel column chromatography (elution solvent: dichloromethane-ethyl acetate) and thereby a black-brown oily substance (240 mg) was obtained. Tert-butyl 4-(4-aminophenyl)piperazine-1-carboxylate (Synthesis literature 14, 382 mg) and methanol (2 mL) were added thereto and the mixture was stirred at 110° C. for 2 hours under a nitrogen atmosphere. The solidified reaction mixture was suspended in dichloromethane and then purified through aminopropyl silica gel column chromatography (elution solvent: dichloromethane-ethyl acetate), and thereby tert-butyl 4-(4-((4-(3-(pyridin-3-yl)-1-(pyridin-3-ylmethyl)-1H-pyrazol-4-yl)pyrimidin-2-yl)amino)phenyl)piperazine-1-carboxylate (199 mg) as a black-brown oily substance was obtained.

Production Example 81

A mixture containing tert-butyl 6-((4-(3-(pyridin-3-yl)-1H-pyrazol-4-yl)pyrimidin-2-yl)amino)-3,4-dihydroisoquinoline-2(1H)-carboxylate (Production Example 54, 300 mg), 2,2-dimethyloxirane (0.19 mL) and DMF (1 mL) was stirred at 70° C. for 20 hours, and 2,2-dimethyloxirane (0.2 mL) was then added to the reaction solution, and the mixture was stirred at 70° C. for 20 hours. The reaction mixture was concentrated under a reduced pressure, the obtained residue was purified through silica gel column chromatography (elution solvent: dichloromethane-methanol), and thereby tert-butyl 6-((4-(1-(2-hydroxy-2-methylpropyl)-3-(pyridin-3-yl)-1H-pyrazol-4-yl)pyrimidin-2-yl)amino)-3,4-dihydroisoquinoline-2(1H)-carboxylate (155 mg) was obtained.

Production Example 82

A mixture containing tert-butyl 4-(4-((4-(3-(pyridin-3-yl)-1H-pyrazol-4-yl)pyrimidin-2-yl)amino)phenyl)piperidine-1-carboxylate (Production Example 53, 0.20 g) and 2,2-dimethyloxirane (0.36 mL) was stirred at 70° C. overnight, 2,2-dimethyloxirane (0.36 mL) was then added to the reaction solution, and the mixture was stirred at 70° C. After disappearance of the raw material was confirmed with LC/MS, dichloromethane was added to the reaction mixture, washing with water was performed, and an organic layer was concentrated under a reduced pressure. The obtained residue was purified by silica gel thin layer chromatography (developing solvent: dichloromethane-methanol), and tert-butyl 4-(4-((4-(1-(2-hydroxy-2-methylpropyl)-3-(pyridin-3-yl)-1H-pyrazol-4-yl)pyrimidin-2-yl)amino)phenyl)piperidine-1-carboxylate (52 mg) was obtained.

Dichloromethane (2 mL), and trifluoroacetic acid (3 mL) were added thereto, and the mixture was stirred at room temperature for 1 hour. The reaction solution was concentrated under a reduced pressure, the obtained residue was purified through silica gel column chromatography (elution solvent: dichloromethane-methanol-ammonia water), and thereby 2-methyl-1-(4-(2-((4-(piperidin-4-yl)phenyl)amino)pyrimidin-4-yl)-3-(pyridin-3-yl)-1H-pyrazol-1-yl)propan-2-ol (18 mg) was obtained.

Production Example 83

A mixture containing 2-chloro-4-(1-ethyl-3-(pyridin-3-yl)-1H-pyrazol-4-yl)pyrimidine (Production Example 3, 257 mg), tert-butyl 4-(4-aminobenzoyl)piperazine-1-carboxylate (commercially available from Ark Pharm, Inc, 310 mg) and 1,4-dioxane was degassed by repeating depressurization and nitrogen substitution, tris(dibenzylideneacetone)dipalladium(O) (82 mg) and 4,5-bis(diphenylphosphino)-9,9-dimethylxanthene (156 mg) were then added thereto, and the mixture was stirred at 100° C. for 14 hours. The reaction mixture was filtered off, the filtrate was then concentrated under a reduced pressure, the obtained residue was purified through aminopropyl silica gel column chromatography (elution solvent: dichloromethane-ethyl acetate), and thereby tert-butyl 4-(4-((1-ethyl-4-(3-(pyridin-3-yl)-1H-pyrazol-4-yl)pyrimidin-2-yl)amino)benzoyl)piperazine-1-carboxylate (215 mg) as a yellow solid obtained.

Production Example 84

In the same manner as in Production Example 83, tert-butyl 4-(3-((1-ethyl-4-(3-(pyridin-3-yl)-1H-pyrazol-4-yl)pyrimidin-2-yl)amino)benzoyl)piperazine-1-carboxylate was obtained using tert-butyl 4-(3-aminobenzoyl)piperazine-1-carboxylate (commercially available from Fluorochem Ltd) in place of tert-butyl 4-(4-aminobenzoyl)piperazine-1-carboxylate.

Production Example 89

In the same manner as in Production Example 83, tert-butyl 3-(4-((4-(1-ethyl-3-(pyridin-3-yl)-1H-pyrazol-4-yl)pyrimidin-2-yl)amino)benzoyl)-3,8-diazabicyclo[3.2.1]octane-8-carboxylate was obtained using tert-butyl 3-(4-aminobenzoyl)-3,8-diazabicyclo[3.2.1]octane-8-carboxylate (Synthesis literature 19) in place of tert-butyl 4-(4-aminobenzoyl)piperazine-1-carboxylate.

Production Example 90

A mixture containing tert-butyl 4-(4-((1-ethyl-4-(3-(pyridine-3-yl)-1H-pyrazol-4-yl)pyrimidin-2-yl)amino)benzoyl)piperazine-1-carboxylate (Production Example 83, 212 mg) and trifluoroacetic acid (1.5 mL) was stirred at room temperature for 30 minutes. A sodium hydrogen carbonate aqueous solution was added to the reaction mixture, the mixture was made basic, and then extraction using chloroform-methanol (9:1) was performed. The organic layer was dried with anhydrous sodium sulfate and then concentrated under a reduced pressure, the obtained residue was purified through silica gel column chromatography (elution solvent: dichloromethane-methanol-ammonia water), and thereby (4-((4-(1-ethyl-3-(pyridin-3-yl)-1H-pyrazol-4-yl)pyrimidin-2-yl)amino)phenyl) (piperazin-1-yl)methanone (148 mg) as a colorless solid was obtained.

Production Example 104

5% Pd/C (50 mg) was added to a mixture containing benzyl 4-(4-((4-(1-(3-methyloxetan-3-yl)methyl-3-(pyridin-3-yl)-1H-pyrazol-4-yl)pyrimidin-2-yl)amino)phenyl)piperazine-1-carboxylate (Production Example 79, 153 mg), ethanol (1.5 mL) and THF (1.5 mL) under a nitrogen atmosphere, and the mixture was stirred at room temperature overnight under a hydrogen atmosphere. Insoluble substances in the reaction mixture were filtered off. Then, the filtrate was concentrated under a reduced pressure. Ethanol (1 mL), THF (1 mL), and 5% Pd/C (150 mg) were sequentially added to the obtained residue, and the mixture was then stirred at room temperature overnight under a hydrogen atmosphere. Insoluble substances in the reaction mixture were filtered off. Then, the filtrate was concentrated under a reduced pressure. The obtained residue was purified through aminopropyl silica gel column chromatography (elution solvent: chloroform-methanol), and thereby 4-(1-((3-methyloxetan-3-yl)methyl)-3-(pyridin-3-yl)-1H-pyrazol-4-yl)-N-(4-(piperazin-1-yl)phenyl)pyrimidin-2-amine (66 mg) as a light yellow oily substance was obtained.

Production Example 105

A mixture containing N-(4-(1-ethyl-3-(pyridin-3-yl)-1H-pyrazol-4-yl)pyrimidin-2-yl)-1,2,3,4-tetrahydroisoquinolin-6-amine (Example 168, 35 mg), tert-butyl 2-bromoacetate (17 mg), N,N-diisopropylethylamine (11 mg), acetonitrile (0.5 mL) and DMF (1 mL) was stirred at room temperature overnight. Dichloromethane and water were added to the reaction mixture, and an aqueous layer was adjusted to a pH of 9 with a sodium hydroxide aqueous solution. The organic layer was concentrated under a reduced pressure. Then, the obtained residue was sequentially purified by silica gel thin layer chromatography (developing solvent: dichloromethane-methanol-ammonia water), and then gel permeation chromatography (elution solvent: chloroform), and thereby tert-butyl 2-(6-((4-(1-ethyl-3-(pyridin-3-yl)-1H-pyrazol-4-yl)pyrimidin-2-yl)amino)-3,4-dihydroisoquinolin-2(1H)-yl)acetate (12.3 mg) was obtained.

Production Example 107

2-((tert-Butyldimethylsilyl)oxy)acetaldehyde and sodium triacetoxyborohydride were added to a mixture containing N-(4-(1-ethyl-3-(pyridin-3-yl)-1H-pyrazol-4-yl)pyrimidin-2-yl)-1,2,3,4-tetrahydroisoquinolin-7-amine (Example 169), 1,2-dichloroethane, and acetic acid, and the mixture was stirred at room temperature for 3 hours. The reaction mixture was neutralized by adding potassium carbonate, and extraction was then performed using dichloromethane-methanol (9:1). The organic layer was washed with a saturated saline solution, and dried with anhydrous sodium sulfate, and then concentrated under a reduced pressure. The obtained residue was purified through silica gel column chromatography (elution solvent: dichloromethane-methanol-ammonia water), and thereby 2-(2-((tert-butyldimethylsilyl)oxy)ethyl)-N-(4-(1-ethyl-3-(pyridin-3-yl)-1H-pyrazol-4-yl)pyrimidin-2-yl)-1,2,3,4-tetrahydroisoquinolin-7-amine was obtained.

Production Example 108

A mixture containing a mixture (Production Example 15, 2.21 g) containing 4-(1-ethyl-5-iodo-1H-pyrazol-4-yl)-2-(methylthio)pyrimidine and 4-(1-ethyl-3-iodo-1H-pyrazol- 4-yl)-2-(methylthio)pyrimidine, tetrakis(triphenylphosphine)palladium(O) (0.24 g), 3-pyridylboronic acid (1.55 g), potassium phosphate (6.25 g), 1,4-dioxane (12 mL) and water (12 mL) was degassed under an argon atmosphere, and then heated to reflux, and stirred for 3 hours. The reaction mixture was cooled to room temperature, and an insoluble substance was then filtered off, and the filtrate was concentrated under a reduced pressure. The obtained residue was purified through silica gel column chromatography (elution solvent: dichloromethane-methanol), and a mixture (1.78 g) containing 4-(1-ethyl-5-(pyridin-3-yl)-1H-pyrazol-4-yl)-2-(methylthio)pyrimidine and 4-(1-ethyl-3-(pyridin-3-yl)-1H-pyrazol-4-yl)-2-(methylthio)pyrimidine as a yellow oily substance was obtained.

Production Example 110

75% Metachloroperbenzoic acid (2.62 g) was added little by little to a THF (30 mL) solution of a mixture (Production Example 108, 1.36 g) containing 4-(1-ethyl-5-(pyridine-3-yl)-1H-pyrazol-4-yl)-2-(methylthio)pyrimidine and 4-(1-ethyl-3-(pyridin-3-yl)-1H-pyrazol-4-yl)-2-(methylthio)pyrimidine under ice cooling, and the mixture was then stirred at room temperature for 4 hours. The reaction mixture was concentrated under a reduced pressure, the residue was then purified through silica gel column chromatography (elution solvent: dichloromethane-methanol), and thereby 4-(1-ethyl-3-(pyridin-3-yl)-1H-pyrazol-4-yl)-2-(methylsulfonyl)pyrimidine (0.94 g) as a colorless foamy substance was obtained.

Production Example 112

N-bromosuccinimide (1.84 g) was added little by little to a mixture containing 3-(1-ethyl-1H-pyrazol-3-yl)pyridine (Synthesis literature 20, 1.63 g) and DMF (16 mL) at room temperature, and the mixture was stirred at room temperature for 1 hour. Ice water and NaCl were added to the reaction mixture, and extraction was performed using ethyl acetate. The organic layer was dried with anhydrous sodium sulfate, and then concentrated under a reduced pressure. The obtained residue was purified through silica gel column chromatography (elution solvent: dichloromethane-methanol), and 3-(4-bromo-1-ethyl-1H-pyrazol-3-yl)pyridine (0.94 g) as a yellow oily substance was obtained.

Production Example 113

A mixture containing 3-(4-bromo-1-ethyl-1H-pyrazol-3-yl)pyridine (Production Example 112, 1.33 g), 4,4,4',4',5,5,5',5'-octamethyl-2,2'-bi(1,3,2-dioxaborolane) (1.61 g), potassium acetate (1.55 g), [1,1-bis(diphenylphosphino)ferrocene]-palladium(II) dichloride dichloromethane adduct (0.15 g) and DMF (5 mL) was degassed under an argon atmosphere and stirred at 100° C. overnight. Insoluble substances in the reaction mixture were filtered off, the filtrate was concentrated under a reduced pressure, the obtained residue was purified through silica gel column chromatography (elution solvent: hexane-ethyl acetate, and then dichloromethane-methanol), and thereby 3-(1-ethyl-4-(4,4,5,5-tetramethyl-1,3,2-dioxaborolan-2-yl)-1H-pyrazol-3-yl)pyridine (0.50 g) as a colorless oily substance was obtained.

Production Example 114

A mixture containing 3-(1-ethyl-4-(4,4,5,5-tetramethyl-1,3,2-dioxaborolan-2-yl)-1H-pyrazol-3-yl)pyridine (Production Example 113, 491 mg), 5-fluoro-2,4-dichloropyrimidine (712.4 mg), bis(triphenylphosphine)palladium(II) dichloride (76.5 mg), 2 N sodium carbonate aqueous solution (1.4 mL), 1,2-dimethoxyethane (3 mL) and ethanol (18 mL) was degassed under an argon atmosphere and then heated to reflux, and stirred overnight. The reaction mixture was cooled to room temperature, water was then added thereto, and extraction was performed using ethyl acetate. The organic layer was dried with anhydrous sodium sulfate and then concentrated under a reduced pressure, the obtained residue was purified through silica gel column chromatography (elution solvent: dichloromethane-methanol), and then aminopropyl silica gel chromatography (elution solvent: dichloromethane), and thereby 2-chloro-4-(1-ethyl-3-(pyridin-3-yl)-1H-pyrazol-4-yl)-5-fluoropyrimidine (0.41 g) as a yellow oily substance was obtained.

Production Example 115

A mixture containing 4-fluoronitrobenzene (0.67 g), tert-butyl (S)-piperidin-3-ylcarbamate (commercially available from Tokyo Chemical Industry Co., Ltd., 1.09 g), N,N-diisopropylethylamine (0.65 g) and acetonitrile (10 mL) was heated to reflux and stirred overnight. The reaction mixture was concentrated under a reduced pressure, the residue was purified through silica gel column chromatography (elution solvent: dichloromethane-methanol), and thereby tert-butyl (S)-(1-(4-nitrophenyl)piperidin-3-yl)carbamate (0.32 g) as a yellow solid was obtained.

Production Example 117

A mixture containing tert-butyl (S)-(1-(4-nitrophenyl)piperidin-3-yl)carbamate (Production Example 115, 0.32 g), methanol (7.5 mL) and 10% Pd/C (32 mg) was stirred at room temperature overnight under a hydrogen atmosphere. Insoluble substances in the reaction mixture were filtered off. Then, the filtrate was concentrated under a reduced pressure, and thereby tert-butyl (S)-(1-(4-aminophenyl)piperidin-3-yl)carbamate (0.28 g) as a brown solid was obtained.

Production Example 119

A mixture containing 4-fluoronitrobenzene (0.30 g), 2-(piperazin-1-yl)-1-(piperidin-1-yl)ethan-1-one (commercially available from Apollo Scientific Ltd., 0.45 g), potassium carbonate (0.61 g) and DMF (8 mL) was stirred at 80° C. overnight. The reaction mixture was cooled to room temperature, ethyl acetate was then added thereto, and washing with water was performed. The organic layer was dried with anhydrous sodium sulfate and then concentrated under a reduced pressure. Ethanol (20 mL) and 10% Pd/C (66 mg) were added to the obtained residue (0.66 g), and the mixture was stirred at room temperature overnight under a hydrogen atmosphere. An insoluble substance in the reaction mixture was removed. Then, the filtrate was concentrated under a reduced pressure, and thereby 2-(4-(4-aminophenyl)piperazin-1-yl)-1-(piperidin-1-yl)ethan-1-one (0.61 g) as a brown solid was obtained.

Production Example 120

Potassium tert-butoxide (202 mg) was added to a mixture containing 4-fluoronitrobenzene (141 mg), tert-butyl 3-fluoro-4-hydroxypiperidine-1-carboxylate (commercially available from Ark Pharm, Inc, 219 mg) and THF (10 mL)

under ice cooling, and the mixture was heated to reflux and stirred overnight. The reaction mixture was cooled to room temperature, ethyl acetate was then added thereto, and washing with a saturated sodium bicarbonate aqueous solution was performed. The organic layer was dried with anhydrous sodium sulfate and then concentrated under a reduced pressure, and thereby a yellow solid (214 mg) containing tert-butyl 3-fluoro-4-(4-nitrophenoxy)piperidine-1-carboxylate was obtained.

Ethanol (10 mL) and 10% Pd/C (21 mg) were added thereto, and the mixture was stirred at room temperature overnight under a hydrogen atmosphere. Insoluble substances in the reaction mixture were filtered off. Then, the filtrate was concentrated under a reduced pressure, and thereby a brown solid (180 mg) containing tert-butyl 4-(4-aminophenoxy)-3-fluoropiperidine-1-carboxylate was obtained.

2-Chloro-4-(1-ethyl-3-(pyridin-3-yl)-1H-pyrazol-4-yl) pyrimidine (Production Example 3, 165 mg) and methanol (2 mL) were added thereto and the mixture was stirred at 100° C. overnight, and then concentrated under a reduced pressure. The obtained residue was purified through aminopropyl silica gel column chromatography (elution solvent: dichloromethane-methanol), and thereby tert-butyl 4-(4-((4-(1-ethyl-3-(pyridin-3-yl)-1H-pyrazol-4-yl)pyrimidin-2-yl)amino)phenoxy)-3-fluoropiperidine-1-carboxylate (131 mg) as a yellow oily substance was obtained.

Production Example 121

A mixture containing 2-chloro-4-(1-ethyl-3-(pyridin-3-yl)-1H-pyrazol-4-yl)pyrimidine (Production Example 3, 1.02 g), tert-butyl 4-(4-aminophenyl)piperazine-1-carboxylate (Synthesis literature 14, 1.30 g) and THF (10 mL) was stirred at 80° C. overnight. The reaction mixture was concentrated under a reduced pressure, the obtained residue was purified through aminopropyl silica gel column chromatography (elution solvent: dichloromethane-methanol), and thereby tert-butyl 4-(4-((4-(1-ethyl-3-(pyridin-3-yl)-1H-pyrazol-4-yl)pyrimidin-2-yl)amino)phenyl)piperazine-1-carboxylate (0.77 g) as a yellow solid was obtained.

Production Example 122

In the same manner as in Production Example 121, tert-butyl 4-(3-((4-(1-ethyl-3-(pyridin-3-yl)-1H-pyrazol-4-yl)pyrimidin-2-yl)amino)phenoxy)piperidine-1-carboxylate was obtained using tert-butyl 4-(3-aminophenoxy)piperidine-1-carboxylate (Synthesis literature 21) in place of tert-butyl 4-(4-aminophenyl)piperazine-1-carboxylate.

Production Example 123

In the same manner as in Production Example 121, tert-butyl 4-(4-((4-(1-ethyl-3-(pyridin-3-yl)-1H-pyrazol-4-yl)pyrimidin-2-yl)amino)-2-fluorophenyl)piperazine-1-carboxylate was obtained using tert-butyl 4-(4-amino-2-fluorophenyl)piperazine-1-carboxylate (Synthesis literature 22) in place of tert-butyl 4-(4-aminophenyl)piperazine-1-carboxylate.

Production Example 124

In the same manner as in Production Example 121, tert-butyl 7-((4-(1-ethyl-3-(pyridin-3-yl)-1H-pyrazol-4-yl)pyrimidin-2-yl)amino)-3,4-dihydroquinolin-1 (2H)-carboxylate was obtained using tert-butyl 7-amino-3,4-dihydroquinoline-1(2H)-carboxylate (commercially available from Ark Pharm, Inc.) in place of tert-butyl 4-(4-aminophenyl)piperazine-1-carboxylate.

Production Example 126

In the same manner as in Production Example 121, tert-butyl 7-((4-(1-ethyl-3-(pyridin-3-yl)-1H-pyrazol-4-yl)pyrimidin-2-yl)amino)-3,4-dihydroisoquinoline-2 (1H)-carboxylate was obtained using tert-butyl 7-amino-3,4-dihydroisoquinoline-2(1H)-carboxylate (commercially available from Ark Pharm, Inc.) in place of tert-butyl 4-(4-aminophenyl)piperazine-1-carboxylate.

Production Example 127

In the same manner as in Production Example 121, tert-butyl 7-((4-(1-ethyl-3-(pyridin-3-yl)-1H-pyrazol-4-yl)pyrimidin-2-yl)amino)-1,2,4,5-tetrahydro-3H-benzo[d] azepine-3-carboxylate was obtained using tert-butyl 7-amino-1,2,4,5-tetrahydro-3H-benzo[d]azepine-3-carboxylate (Synthesis literature 23) in place of tert-butyl 4-(4-aminophenyl)piperazine-1-carboxylate.

Production Example 130

In the same manner as in Production Example 121, tert-butyl 4-(5-((4-(1-(2,2-difluoroethyl)-3-(pyridin-3-yl)-1H-pyrazol-4-yl)pyrimidin-2-yl)amino)pyridin-2-yl)piperazine-1-carboxylate was obtained using tert-butyl 4-(5-aminopyridin-2-yl)piperazine-1-carboxylate (commercially available from Enamine) in place of tert-butyl 4-(4-aminophenyl)piperazine-1-carboxylate.

Production Example 132

In the same manner as in Production Example 121, tert-butyl 4-(4-((4-(1-ethyl-3-(pyridin-3-yl)-1H-pyrazol-4-yl)pyrimidin-2-yl)amino)-2,6-difluorophenyl)piperazine-1-carboxylate was obtained using tert-butyl 4-(4-amino-2,6-difluorophenyl)piperazine-1-carboxylate (Synthesis literature 24) in place of tert-butyl 4-(4-aminophenyl)piperazine-1-carboxylate.

Production Example 134

Di-tert-butyl azodicarboxylate (158 mg) was added to a mixture containing 4-(4-nitrophenyl)-1H-pyrazole (commercially available from Combi-Brocks, 98 mg), tert-butyl 4-hydroxypiperidine-1-carboxylate (112 mg), triphenyl phosphine (190 mg), and THF (2 mL), and the mixture was stirred at room temperature overnight. The reaction mixture was concentrated under a reduced pressure, the obtained residue was purified through silica gel column chromatography (elution solvent: dichloromethane-methanol), and thereby tert-butyl 4-(4-(4-nitrophenyl)-1H-pyrazol-1-yl)piperidine-1-carboxylate (163 mg) as a yellow oily substance was obtained.

Methanol (7.5 mL) and 10% Pd/C (16 mg) were sequentially added thereto, and the mixture was stirred at room temperature overnight under a hydrogen atmosphere. Then, Insoluble substances in the reaction mixture were filtered off. The filtrate was concentrated under a reduced pressure, and thereby tert-butyl 4-(4-(4-aminophenyl)-1H-pyrazol-1-yl)piperidine-1-carboxylate (104 mg) as a brown solid was obtained.

2-Chloro-4-(1-ethyl-3-(pyridin-3-yl)-1H-pyrazol-4-yl)pyrimidine (Production Example 3, 72 mg) and methanol (0.5 mL) were added thereto, and the mixture was stirred at 90° C. overnight. The reaction mixture was concentrated under a reduced pressure, the obtained residue was purified through silica gel column chromatography (elution solvent: dichloromethane-methanol), and thereby tert-butyl 4-(4-(4-((4-(1-ethyl-3-(pyridin-3-yl)-1H-pyrazol-4-yl)pyrimidin-2-yl)amino)phenyl)-1H-pyrazol-1-yl)piperidine-1-carboxylate (40 mg) as a colorless solid was obtained.

Production Example 135

In the same manner as in Production Example 121, N-(4-(4-(oxetan-3-yl)piperazin-1-yl)phenyl)-4-(3-(pyridin-3-yl)-1H-pyrazol-4-yl)pyrimidin-2-amine was obtained using 4-(4-(oxetan-3-yl)piperazin-1-yl)aniline (Synthesis literature 25) in place of tert-butyl 4-(4-aminophenyl)piperazine-1-carboxylate.

Production Example 138

In the same manner as in Production Example 121, tert-butyl 3-(4-((4-(1-ethyl-3-(pyridin-3-yl)-1H-pyrazol-4-yl)pyrimidin-2-yl)amino)phenyl)piperidine-1-carboxylate was obtained using tert-butyl 3-(4-aminophenyl)piperidine-1-carboxylate (Synthesis literature 26) in place of tert-butyl 4-(4-aminophenyl)piperazine-1-carboxylate.

Production Example 139

In the same manner as in Production Example 121, N-(4-(4-(2-methoxyethyl)piperazin-1-yl)phenyl)-4-(3-(pyridin-3-yl)-1H-pyrazol-4-yl)pyrimidin-2-amine was obtained using 44442-methoxyethyl)piperazin-1-yl)aniline (commercially available from OTAVA chemicals) in place of tert-butyl 4-(4-aminophenyl)piperazine-1-carboxylate.

Production Example 140

In the same manner as in Production Example 121, tert-butyl 4-(2-cyano-4-((4-(1-ethyl-3-(pyridin-3-yl)-1H-pyrazol-4-yl)pyrimidin-2-yl)amino)phenyl)piperazine-1-carboxylate was obtained using tert-butyl 4-(4-amino-2-cyanophenyl)piperazine-1-carboxylate (Synthesis literature 27) in place of tert-butyl 4-(4-aminophenyl)piperazine-1-carboxylate.

Production Example 142

In the same manner as in Production Example 121, tert-butyl 4-(3-((4-(1-ethyl-3-(pyridin-3-yl)-1H-pyrazol-4-yl)pyrimidin-2-yl)amino)phenyl)piperazine-1-carboxylate was obtained using tert-butyl 4-(3-aminophenyl)piperazine-1-carboxylate (Synthesis literature 28) in place of tert-butyl 4-(4-aminophenyl)piperazine-1-carboxylate.

Production Example 143

In the same manner as in Production Example 121, tert-butyl 4-(4-((4-(1-ethyl-3-(pyridin-3-yl)-1H-pyrazol-4-yl)pyrimidin-2-yl)amino)phenethyl)piperazine-1-carboxylate was obtained using tert-butyl 4-(4-aminophenethyl)piperazine-1-carboxylate (Synthesis literature 29) in place of tert-butyl 4-(4-aminophenyl)piperazine-1-carboxylate.

Production Example 144

In the same manner as in Production Example 121, N-(4-(4-(cyclopropylmethyl)piperazin-1-yl)phenyl)-4-(3-(pyridin-3-yl)-1H-pyrazol-4-yl)pyrimidin-2-amine was obtained using 4-(4-(cyclopropylmethyl)piperazin-1-yl)aniline (Synthesis literature 30) in place of tert-butyl 4-(4-aminophenyl)piperazine-1-carboxylate.

Production Example 146

In the same manner as in Production Example 121, N-(4-(3-bromo-1H-1,2,4-triazol-1-yl)phenyl)-4-(1-ethyl-3-(pyridin-3-yl)-1H-pyrazole-4-yl)pyrimidin-2-amine was obtained using 4-(3-bromo-1H-1,2,4-triazol-1-yl)aniline (Synthesis literature 31) in place of tert-butyl 4-(4-aminophenyl)piperazine-1-carboxylate.

Production Example 148

A mixture containing N-(4-(1-ethyl-3-(pyridin-3-yl)-1H-pyrazol-4-yl)pyrimidin-2-yl)-1,2,3,4-tetrahydroisoquinolin-6-amine (Example 168, 34 mg), N,N-diisopropylethylamine (9.8 mg), 2,5-dioxopyrrolidin-1-yl 2-acetoxyacetate (Synthesis literature 50, 19.6 mg) and chloroform (0.7 mL) was stirred at room temperature for 45 minutes. The reaction mixture was concentrated under a reduced pressure, the obtained residue was sequentially purified through silica gel column chromatography (elution solvent: dichloromethane-methanol) and aminopropyl silica gel column chromatography (elution solvent: dichloromethane-methanol), and thereby 2-(6-((4-(1-ethyl-3-(pyridin-3-yl)-1H-pyrazol-4-yl)pyrimidin-2-yl)amino)-3,4-dihydroisoquinolin-2(1H)-yl)-2-oxoethyl acetate (4.4 mg) as a colorless oily substance was obtained.

In Production Examples 4 to 14, 16, 23, 27, 35 to 46, 52, 55, 56, 59, 61 to 64, 66, 70, 76 to 78, 85 to 88, 91 to 103, 106, 109, 111, 116, 118, 125, 128, 129, 131, 133, 136, 137, 141, 145, 147 and 149, compounds were synthesized according to the above methods or methods equivalent thereto. Compound names, structural formulae, synthesis method description examples, raw material compounds, MS molecular ion peaks, and $^1$H NMR chemical shift values of production example compounds are shown in the following table.

Here, unless otherwise specified, NMR was measured using deuterated chloroform.

TABLE 1

| Production example number | Compound name | Structural formula | Synthesis method description example | Raw material | MS | Ion | 1HNMR chemical shift value |
|---|---|---|---|---|---|---|---|
| 1 | 2-(2-Chloropyrimidin-4-yl)-1-(pyridin-3-yl)ethan-1-one | 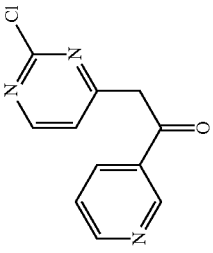 | | | 234.03 | [M + H]+ | |
| 2 | 2-Chloro-4-(3-(pyridin-3-yl)-1H-pyrazol-4-yl)pyrimidine | 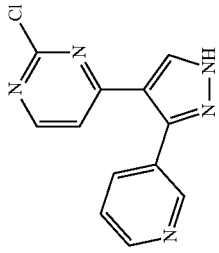 | | Production Example 1 | 258.12 | [M + H]+ | 8.82 (1 H, d, J = 2.3 Hz), 8.72 (1 H, dd, J = 4.6, 1.6 Hz), 8.42 (1 H, d, J = 5.3 Hz), 8.33 (1 H, s), 7.90-7.98 (1 H, m), 7.39-7.48 (1 H, m), 7.07 (1 H, d, J = 5.3 Hz) |
| 3 | 2-Chloro-4-(1-ethyl-3-(pyridin-3-yl)-1H-pyrazol-4-yl)pyrimidine | 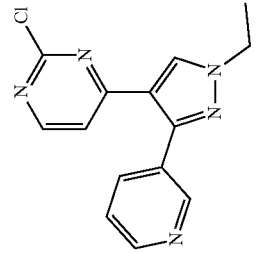 | | Production Example 2 | 286.26 | [M + H]+ | 8.79 (1 H, dd, J = 2.1, 0.8 Hz), 8.68 (1 H, dd, J = 4.9, 1.6 Hz), 8.36 (1 H, d, J = 5.3 Hz), 8.22 (1 H, s), 7.89 (1 H, dt, J = 7.7, 2.1 Hz), 7.39 (1 H, ddd, J = 7.8, 4.9, 0.8 Hz), 6.96 (1 H, d, J = 5.3 Hz), 4.28 (2 H, q, J = 7.3 Hz), 1.56-1.64 (3 H, m) |

TABLE 1-continued

| Production example number | Compound name | Structural formula | Synthesis method description example | Raw material | MS | Ion | 1HNMR chemical shift value |
|---|---|---|---|---|---|---|---|
| 4 | 2-Chloro-4-(1-(pyridin-2-ylmethyl)-3-(pyridin-3-yl)-1H-pyrazol-4-yl)pyrimidine | | Production Example 3 | Production Example 2 | | | 8.79-8.82 (1 H, m), 8.66-8.70 (1 H, m), 8.61-8.65 (1 H, m), 8.37 (1 H, d, J = 5.3 Hz), 8.33 (1 H, s), 7.90 (1 H, dt, J = 7.7, 1.9 Hz), 7.72 (1 H, td, J = 7.9, 1.0 Hz), 7.35-7.41 (1 H, m), 7.24-7.32 (2 H, m), 6.99 (1 H, d, J = 5.3 Hz), 5.52 (2 H, s) |
| 5 | 2-Chloro-4-(1-(2-methoxyethyl)-3-(pyridin-3-yl)-1H-pyrazol-4-yl)pyrimidine | | Production Example 3 | Production Example 2 | | | 8.79-8.82 (1 H, m), 8.67-8.70 (1 H, m), 8.37 (1 H, d, J = 5.3 Hz), 8.26 (1 H, s), 7.89 (1 H, m), 7.36-7.42 (1 H, m), 6.98 (1 H, d, J = 5.3 Hz), 4.38 (2 H, t, J = 5.1 Hz), 3.83 (2 H, t, J = 5.1 Hz), 3.39 (3 H, s) |
| 6 | 4-(1-Benzyl-3-(pyridin-3-yl)-1H-pyrazol-4-yl)-2-chloropyrimidine | | Production Example 3 | Production Example 2 | 348.14 | [M + H]+ | |

TABLE 1-continued

| Production example number | Compound name | Structural formula | Synthesis method description | Raw material | MS | Ion | 1HNMR chemical shift value |
|---|---|---|---|---|---|---|---|
| 7 | 2-Chloro-4-(1-(4-fluorobenzyl)-3-(pyridin-3-yl)-1H-pyrazol-4-yl)pyrimidine | | Production Example 3 | Production Example 2 | 366.27 | [M + H]+ | 8.78-8.83 (1 H, m), 8.64-8.71 (1 H, m), 8.30-8.38 (1 H, m), 7.85-7.93 (1 H, m), 7.31-7.43 (4 H, m), 7.05-7.14 (2 H, m), 6.94-7.00 (1 H, m), 5.36 (2 H, s) |
| 8 | 3-((4-(2-Chloropyrimidin-4-yl)-3-(pyridin-3-yl)-1H-pyrazol-1-yl)methyl)benzonitrile | | Production Example 3 | Production Example 2 | 373.25 | [M + H]+ | 8.78-8.80 (1 H, m), 8.70 (1 H, dd, J = 4.9, 1.6 Hz), 8.39 (1 H, d, J = 5.3 Hz), 8.23 (1 H, s), 7.89 (1 H, dt, J = 7.9, 2.0 Hz), 7.65-7.70 (1 H, m), 7.52-7.63 (3 H, m), 7.38-7.44 (1 H, m), 6.98 (1 H, d, J = 5.3 Hz), 5.43 (2 H, s) |
| 9 | 2-((4-(2-Chloropyrimidin-4-yl)-3-(pyridin-3-yl)-1H-pyrazol-1-yl)methyl)benzonitrile | | Production Example 3 | Production Example 2 | 373.31 | [M + H]+ | 8.79 (1 H, d, J = 2.3 Hz), 8.68 (1 H, dd, J = 4.8, 1.5 Hz), 8.39 (1 H, d, J = 5.3 Hz), 8.28 (1 H, s), 7.90 (1 H, dt, J = 7.9, 2.0 Hz), 7.73-7.77 (1 H, m), 7.60-7.68 (1 H, m), 7.35-7.53 (3 H, m), 7.00 (1 H, d, J = 5.3 Hz), 5.62 (2 H, s) |

TABLE 1-continued

| Production example number | Compound name | Structural formula | Synthesis method description example | Raw material | MS | Ion | 1HNMR chemical shift value |
|---|---|---|---|---|---|---|---|
| 10 | 2-Chloro-4-(3-(pyridin-3-yl)-1-(2-(trifluoromethoxy)ethyl)-1H-pyrazol-4-yl)pyrimidine | | Production Example 3 | Production Example 2 | 370.25 | [M + H]+ | 8.78-8.80 (1 H, m), 8.69-8.72 (1 H, m), 8.39 (1 H, d, J = 5.3 Hz), 8.25 (1 H, s), 7.89 (1 H, dt, J = 7.9, 2.0 Hz), 7.38-7.43 (1 H, m), 6.99 (1 H, d, J = 5.3 Hz), 4.42-4.53 (4 H, m) |
| 11 | 2-Chloro-4-(1-(2,2-difluoroethyl)-3-(pyridin-3-yl)-1H-pyrazol-4-yl)pyrimidine | | Production Example 3 | Production Example 2 | 322 | [M + H]+ | 8.78-8.79 (1 H, m), 8.71 (1 H, dd, J = 4.9, 1.6 Hz), 8.41 (1 H, d, J = 5.4 Hz), 8.27 (1 H, s), 7.86-7.90 (1 H, m), 7.38-7.43 (1 H, m), 6.99 (1 H, d, J = 4.9 Hz), 5.99-6.43 (1 H, m), 4.51-4.63 (2 H, m) |
| 12 | 2-Chloro-4-(1-(oxetan-3-yl)-3-(pyridin-3-yl)-1H-pyrazol-4-yl)pyrimidine | | Production Example 3 | Production Example 2 | 314.27 | [M + H]+ | 8.80-8.83 (1 H, m), 8.70-8.72 (1 H, m), 8.37-8.40 (1 H, m), 8.17 (1 H, s), 7.91 (1 H, dt, J = 7.8, 1.9 Hz), 7.39-7.43 (1 H, m), 6.99 (1 H, d, J = 5.4 Hz), 5.50-5.60 (1 H, m), 5.07-5.20 (4 H, m) |

TABLE 1-continued

| Production example number | Compound name | Structural formula | Synthesis method description example | Raw material | MS | Ion | 1HNMR chemical shift value |
|---|---|---|---|---|---|---|---|
| 13 | 2-Chloro-4-(1-phenethyl-3-(pyridin-3-yl)-1H-pyrazol-4-yl)pyrimidine | | Production Example 3 | Production Example 2 | 362.29 | [M + H]+ | 8.79-8.82 (1 H, m), 8.68-8.72 (1 H, m), 8.35 (1 H, d, J = 5.3 Hz), 8.04 (1 H, s), 7.90 (1 H, dt, J = 7.9, 2.0 Hz), 7.38-7.45 (1 H, m), 7.28-7.36 (3 H, m), 7.14-7.23 (2 H, m), 6.94 (1 H, d, J = 5.3 Hz), 4.38-4.49 (2 H, m), 3.24-3.31 (2 H, m) |
| 14 | 2-Chloro-4-(3-(pyridin-3-yl)-1-((tetrahydrofuran-3-yl)methyl)-1H-pyrazol-4-yl)pyrimidine | | Production Example 3 | Production Example 2 | 342.34 | [M + H]+ | 8.78-8.80 (1 H, m), 8.69 (1 H, dd, J = 4.9, 1.6 Hz), 8.38 (1 H, d, J = 5.3 Hz), 8.21 (1 H, s), 7.89 (1 H, dt, J = 7.8, 1.9 Hz), 7.36-7.44 (1 H, m), 6.98 (1 H, d, J = 5.3 Hz), 4.20 (2 H, d, J = 7.6 Hz), 3.96 (1 H, td, J = 8.3, 5.4 Hz), 3.74-3.90 (2 H, m), 3.67 (1 H, dd, J = 9.2, 4.9 Hz), 2.84-3.06 (1 H, m), 2.05-2.19 (1 H, m), 1.68-1.81 (1 H, m) |
| 15 | 4-(1-Ethyl-5-iodo-1H-pyrazol-4-yl)-2-(methylthio)pyrimidine 4-(1-ethyl-3-iodo-1H-pyrazol-4-yl)-2-(methylthio)pyrimidine | | Synthesis literature 1 | | 347 | [M + H]+ | 4-(1-Ethyl-5-iodo-1H-pyrazol-4-yl)-2-(methylthio)pyrimidine 8.48 (1 H, d, J = 5.1 Hz), 8.09 (1 H, s), 7.35 (1 H, d, J = 5.4 Hz), 4.33-4.41 (2 H, m), 2.67 (3 H, s), 1.45-1.50 (3 H, m) 4-(1-Ethyl-3-iodo-1H-pyrazol-4-yl)-2-(methylthio)pyrimidine 8.51 (1 H, d, J = 5.1 Hz), 8.00 (1 H, s), 7.68 (1 H, d, J = 5.4 Hz), 4.20-4.28 (2 H, m), 2.62 (3 H, s), 1.54 (3 H, t, J = 7.3 Hz) |

TABLE 1-continued

| Production example number | Compound name | Structural formula | Synthesis method description example | Raw material | MS | Ion | 1HNMR chemical shift value |
|---|---|---|---|---|---|---|---|
| 16 | 4-(1-(2,2-Difluoroethyl)-5-iodo-1H-pyrazol-4-yl)-2-(methylthio)pyrimidine 4-(1-(2,2-Difluoroethyl)-3-iodo-1H-pyrazol-4-yl)-2-(methylthio)pyrimidine | | Production Example 15 | Synthesis literature 1 | 383 | [M + H]+ | 4-(1-(2,2-Difluoroethyl)-5-iodo-1H-pyrazol-4-yl)-2-(methylthio)pyrimidine 8.53 (1 H, d, J = 5.1 Hz), 8.05 (1 H, s), 7.64 (1 H, d, J = 5.4 Hz), 5.93-6.37 (1 H, m), 4.46-4.57 (2 H, m), 2.62 (3 H, s) 4-(1-(2,2-Difluoroethyl)-3-iodo-1H-pyrazol-4-yl)-2-(methylthio)pyrimidine 8.51 (1 H, d, J = 5.7 Hz), 8.16 (1 H, s), 7.36 (1 H, d, J = 5.1 Hz), 5.99-6.43 (1 H, m), 4.64-4.75 (2 H, m), 2.66 (3 H, s) |
| 17 | 1-(4-(2-Chloropyrimidin-4-yl)-3-(pyridin-3-yl)-1H-pyrazol-1-yl)-2-methylpropan-2-ol | | | Production Example 2 | 330.21 | [M + H]+ | 8.78-8.81 (1 H, m), 8.70 (1 H, dd, J = 4.9, 1.6 Hz), 8.39 (1 H, d, J = 5.3 Hz), 8.25 (1 H, s), 7.89 (1 H, dt, J = 7.9, 2.0 Hz), 7.37-7.43 (1 H, m), 7.00 (1 H, d, J = 5.3 Hz), 4.18 (2 H, s), 3.24 (1 H, s), 1.28 (6 H, s) |
| 18 | tert-Butyl 3-(5-nitropyridin-2-yl)-3,8-diazabicyclo[3.2.1]octane-8-carboxylate | | | | 335.14 | [M + H]+ | 9.05 (1 H, d, J = 2.6 Hz), 8.23 (1 H, dd, J = 9.4, 2.8 Hz), 6.53 (1 H, d, J = 9.6 Hz), 4.29-4.47 (2 H, m), 3.93-4.26 (2 H, m), 3.16-3.34 (2 H, m), 1.90-2.04 (2 H, m), 1.65-1.74 (2 H, m), 1.49 (9 H, s) |
| 19 | N-(2-(1-benzylpiperidin-4-yl)propan-2-yl)acetamide | | | Synthesis literature 2 | 275.27 | [M + H]+ | 7.27-7.33 (4 H, s), 7.20-7.26 (1 H, m), 5.14 (1 H, br s), 3.49 (2 H, s), 2.90-2.98 (2 H, m), 1.87-2.08 (5 H, m), 1.54-1.69 (3 H, m), 1.22-1.45 (8 H, m) |

TABLE 1-continued

| Production example number | Compound name | Structural formula | Synthesis method description example | Raw material | MS | Ion | 1HNMR chemical shift value |
|---|---|---|---|---|---|---|---|
| 20 | N-(2-(piperidin-4-yl)propan-2-yl)acetamide | (structure) | | Production Example 19 | 185.18 | [M + H]+ | 5.16 (1 H, br s), 3.07-3.16 (2 H, m), 2.60 (2 H, td, J = 12.0, 2.3 Hz), 2.15 (1 H, tt, J = 12.2, 3.3 Hz), 1.92 (3 H, s), 1.58-1.68 (2 H, m), 1.12-1.33 (8 H, m) |
| 21 | N-(4-methyl-1-(4-nitrophenyl)piperidin-4-yl)acetamide | (structure) | Synthesis literature 3 | | 278.18 | [M + H]+ | 8.09-8.15 (2 H, m), 6.79-6.86 (2 H, m), 5.20 (1 H, br s), 3.57 (2 H, dt, J = 13.4, 4.8 Hz), 3.29 (2 H, ddd, J = 13.4, 10.1, 3.3 Hz), 2.24 (2. H, dt, J = 14.0, 3.7 Hz), 1.98 (3 H, s), 1.76 (2 H, ddd, J = 13.8, 9.9, 4.0 Hz), 1.46 (3 H, s) |
| 22 | N-(4-ethyl-1-(4-nitrophenyl)piperidin-4-yl)acetamide | (structure) | Synthesis literature 4 | | 292.19 | [M + H]+ | 8.09-8.15 (2 H, m), 6.79-6.86 (2 H, m), 5.03 (1 H, s), 3.66 (2 H, dt, J = 13.8, 4.2 Hz), 3.14-3.26 (2 H, m), 2.22-2.32 (2 H, m), 2.01 (3 H, s), 1.86 (2 H, q, J = 7.5 Hz), 1.60-1.76 (2 H, m), 0.86 (3 H, t, J = 7.4 Hz) |
| 23 | N-(2-(1-(4-nitrophenyl)piperidin-2-yl)propan-2-yl)acetamide | (structure) | Production Example 21 | Production Example 20 | 306.26 | [M + H]+ | 8.07-8.14 (2 H, m), 6.76-6.83 (2 H, m), 5.17 (1 H, s), 3.96-4.06 (2 H, m), 2.94 (2 H, td, J = 12.7, 2.3 Hz), 2.52 (1 H, tt, J = 12.2, 3.4 Hz), 1.95 (3 H, s), 1.71-1.82 (2 H, m), 1.22-1.43 (8 H, m) |

TABLE 1-continued

| Production example number | Compound name | Structural formula | Synthesis method description example | Raw material | MS | Ion | 1HNMR chemical shift value |
|---|---|---|---|---|---|---|---|
| 24 | N,N,4-trimethyl-1-(4-nitrophenyl)piperidin-4-amine | | | | 264.30 | [M + H]+ | 8.35-8.41 (2 H, m), 7.97-8.05 (2 H, m), 4.08-4.27 (2 H, m), 3.90-4.08 (1 H, m), 2.80 (3 H, s), 2.63-2.78 (2 H, m), 1.45-1.63 (4 H, m), 1.44 (9 H, s) |
| 25 | tert-Butyl 4-((N-methyl-4-nitrophenyl)sulfonamido)piperidine-1-carboxylate | | | Synthesis literature 5 | | | |
| 26 | 1-(2-(2,2-Difluoroethoxy)ethyl)-4-(4-nitrophenyl)piperazine | | Production Example 26 | Synthesis literature 5 | 316.36 | [M + H]+ | 8.09-8.18 (2 H, m), 6.82 (2 H, d, J = 9.6 Hz), 5.66-6.12 (1 H, m), 3.64-3.78 (4 H, m), 3.41-3.48 (4 H, m), 2.63-2.72 (6 H, m) |
| 27 | 1-(2-(Cyclopropylmethoxy)ethyl)-4-(4-nitrophenyl)piperazine | | | | 306.35 | [M + H]+ | 8.09-8.16 (2 H, m), 6.79-6.85 (2 H, m), 3.64 (2 H, t, J = 5.8 Hz), 3.41-3.48 (4 H, m), 3.31 (2 H, d, J = 6.9 Hz), 2.64-2.71 (6 H, m), 1.01-1.10 (1 H, m), 0.51-0.58 (2 H, m), 0.18-0.24 (2 H, m) |

TABLE 1-continued

| Production example number | Compound name | Structural formula | Synthesis method description example | Raw material | MS | Ion | 1HNMR chemical shift value |
|---|---|---|---|---|---|---|---|
| 28 | 2-Methyl-1-(4-(4-nitro-1H-pyrazol-1-yl)piperidin-1-yl)propan-2-ol | 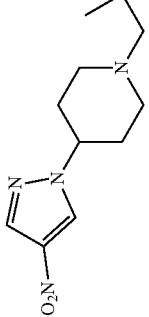 | | Synthesis literature 6 | 269.32 | [M + H]+ | 8.17 (1 H, s), 8.08 (1 H, s), 4.07-4.22 (1 H, m), 3.03-3.13 (2 H, m), 2.47-2.59 (2 H, m), 2.38 (2 H, s), 2.03-2.20 (4 H, m), 1.10 (6 H, s) |
| 29 | 2-Methyl-1-(3-(4-nitro-1H-pyrazol-1-yl)azetidin-1-yl)propan-2-ol | 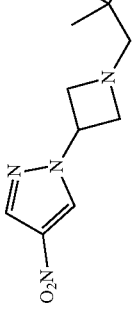 | | | 241.25 | [M + H]+ | 8.32 (1 H, s), 8.11 (1 H, s), 4.90-5.06 (1 H, m), 3.90-3.98 (2 H, m), 3.66-3.74 (2 H, m), 2.58 (2 H, s), 1.17 (6 H, s) |
| 30 | 3-Cyclopropyl-2,3,4,5-tetrahydro-1H-benzo[d]azepine | 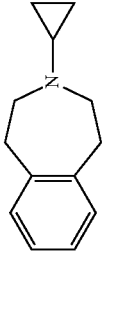 | | Synthesis literature 7 | 188.23 | [M + H]+ | |
| 31 | 3-Cyclopropyl-7-nitro-2,3,4,5-tetrahydro-1H-benzo[d]azepine | 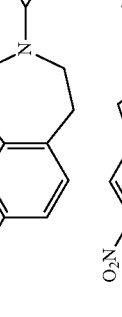 | | Production Example 30 | 233.25 | [M + H]+ | |
| 32 | 5-Nitro-2-(oxetan-3-yl)isoindoline | 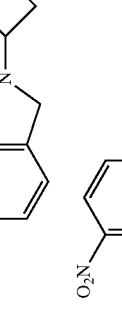 | | Synthesis literature 8 | 221.23 | [M + H]+ | 8.07-8.19 (2 H, m), 7.36 (1 H, d, J = 8.1 Hz), 4.69-4.85 (4 H, m), 4.00-4.21 (5 H, m) |
| 33 | 4-(4-Nitrophenyl)-1-(oxetan-3-yl)piperidine | 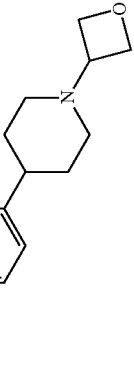 | Production Example 32 | Synthesis literature 37 | 263.33 | [M + H]+ | 8.15-8.21 (2 H, m), 7.36-7.42 (2 H, m), 4.62-4.73 (4 H, m), 3.49-3.58 (1 H, m), 2.84-2.96 (2 H, m), 2.53-2.73 (1 H, m), 1.76-2.04 (6 H, m) |

TABLE 1-continued

| Production example number | Compound name | Structural formula | Synthesis method description example | Raw material | MS | Ion | 1HNMR chemical shift value |
|---|---|---|---|---|---|---|---|
| 34 | N-(1-(4-aminophenyl)-4-methylpiperidin-4-yl)acetamide | | | Production Example 21 | 248.19 | [M + H]+ | 6.79-6.85 (2 H, m), 6.62-6.68 (2 H, m), 5.14 (1 H, br s), 3.42 (2 H, br s), 3.16 (2 H, dt, J = 12.4, 4.7 Hz), 2.80-2.91 (2 H, m), 2.17 (2 H, br d, J = 13.5 Hz), 1.96 (3 H, s), 1.81 (2 H, ddd, J = 13.8, 10.1, 4.1 Hz), 1.45 (3 H, s) |
| 35 | N-(1-(4-aminophenyl)-4-ethylpiperidin-4-yl)acetamide | | Production Example 34 | Production Example 22 | 262.23 | [M + H]+ | 6.80-6.86 (2 H, m), 6.62-6.68 (2 H, m), 4.97 (1 H, s), 3.43 (2 H, br s), 3.23 (2 H, dt, J = 12.6, 3.9 Hz), 2.78 (2 H, td, J = 11.9, 2.6 Hz), 2.15-2.26 (2 H, m), 1.98 (3 H, s), 1.68-1.95 (4 H, m), 0.84 (3 H, t, J = 7.4 Hz) |
| 36 | N-(2-(1-(4-aminophenyl)piperidin-4-yl)propan-2-yl)acetamide | | Production Example 34 | Production Example 23 | 276.27 | [M + H]+ | 6.79-6.86 (2 H, m), 6.61-6.68 (2 H, m), 5.19 (1 H, s), 3.46-3.54 (2 H, m), 2.57 (2 H, td, J = 12.0, 2.3 Hz), 2.09-2.21 (1 H, m), 1.94 (3 H, s), 1.69-1.79 (2 H, m), 1.44-1.56 (2 H, m), 1.31 (6 H, s) |
| 37 | tert-Butyl 3-(5-aminopyridin-2-yl)-3,8-diazabicyclo[3.2.1]octane-8-carboxylate | | Production Example 34 | Production Example 18 | | | 7.78 (1 H, d, J = 3.0 Hz), 6.99 (1 H, dd, J = 8.9, 3.0 Hz), 6.47 (1 H, d, J = 8.9 Hz), 4.24-4.42 (2 H, m), 3.57-3.81 (2 H, m), 2.86-3.39 (4 H, m), 1.76-1.97 (4 H, m), 1.47 (9 H, s) |

TABLE 1-continued

| Production example number | Compound name | Structural formula | Synthesis method description | Raw material | MS | Ion | 1HNMR chemical shift value |
|---|---|---|---|---|---|---|---|
| 38 | 1-(4-Aminophenyl)-N,N,4-trimethylpiperidin-4-amine | | Production Example 34 | Production Example 24 | 234.28 | [M + H]+ | 6.80-6.88 (2 H, m), 6.57-6.67 (2 H, m), 3.10-3.30 (2 H, m), 2.80-2.99 (2 H, m), 2.23 (6 H, s), 1.80-1.94 (2 H, m), 1.53-1.73 (2 H, m), 0.94 (3 H, s) |
| 39 | tert-Butyl 4-((4-amino-N-methylphenyl)sulfonamido)piperidine-1-carboxylate | | Production Example 34 | Production Example 25 | 392.16 | [M + Na]+ | 7.55-7.61 (2 H, m), 6.65-6.71 (2 H, m), 4.04-4.22 (4 H, m), 3.82-4.01 (1 H, m), 2.68-2.70 (3 H, m), 1.44-1.52 (4 H, m), 1.42-1.44 (9 H, m) |
| 40 | 4-(4-(2-(2,2-Difluoroethoxy)ethyl)piperazin-1-yl)aniline | | Production Example 34 | Production Example 26 | 286.31 | [M + H]+ | 6.82 (2 H, d, J = 8.9 Hz), 6.65 (2 H, d, J = 8.9 Hz), 5.66-6.13 (1 H, m), 3.79-3.89 (2 H, m), 3.64-3.78 (2 H, m), 3.11-3.22 (4 H, m), 2.74-2.93 (6 H, m) |
| 41 | 4-(4-(2-(Cyclopropylmethoxy)ethyl)piperazin-1-yl)aniline | | Production Example 34 | Production Example 27 | 276.36 | [M + H]+ | |

TABLE 1-continued

| Production example number | Compound name | Structural formula | Synthesis method description example | Raw material | MS | Ion | 1HNMR chemical shift value |
|---|---|---|---|---|---|---|---|
| 42 | 1-(4-(4-Amino-1H-pyrazol-1-yl)piperidin-1-yl)-2-methylpropan-2-ol | | Production Example 34 | Production Example 28 | 239.30 | [M + H]+ | 7.15 (1 H, s), 7.05 (1 H, s), 3.90-4.07 (1 H, m), 2.95-3.07 (2 H, m), 2.41-2.56 (2 H, m), 2.35 (2 H, s), 1.91-2.12 (4 H, m), 1.16 (6 H, s) |
| 43 | 1-(3-(4-Amino-1H-pyrazol-1-yl)azetidin-1-yl)-2-methylpropan-2-ol | | Production Example 34 | Production Example 29 | 211.27 | [M + H]+ | 7.20 (1 H, s), 7.16 (1 H, s), 4.77-4.89 (1 H, m), 3.84-3.93 (2 H, m), 3.58-3.66 (2 H, m), 2.54 (2 H, s), 1.14 (6 H, s) |
| 44 | 3-Cyclopropyl-2,3,4,5-tetrahydro-1H-benzo[d]azepin-7-amine | | Production Example 34 | Production Example 31 | 203.19 | [M + H]+ | |
| 45 | 2-(Oxetan-3-yl)isoindolin-5-amine | | Production Example 34 | Production Example 32 | 191.23 | [M + H]+ | 6.99 (1 H, d, J = 8.4 Hz), 6.53-6.61 (2 H, m), 4.69-4.82 (4 H, m), 3.93-4.11 (1 H, m), 3.85-3.91 (4 H, m) |
| 46 | 4-(1-(Oxetan-3-yl)piperidin-4-yl)aniline | | Production Example 34 | Production Example 33 | 233.30 | [M + H]+ | |
| 47 | 4-Amino-N-(8-isopropyl-8-azabicyclo[3.2.1]octan-3-yl)-N-methylbenzamide | | | | | | 7.19-7.25 (2 H, m), 6.62-6.68 (2 H, m), 3.82 (2 H, s), 3.43-3.53 (2 H, m), 2.86 (3 H, s), 2.14-2.39 (2 H, m), 1.93-2.01 (2 H, m), 1.44-1.53 (2 H, m), 1.26-1.38 (2 H, m), 0.97 (6 H, d, J = 5.9 Hz) |

TABLE 1-continued

| Production example number | Compound name | Structural formula | Synthesis method description example | Raw material | MS | Ion | 1HNMR chemical shift value |
|---|---|---|---|---|---|---|---|
| 48 | 2-Chloro-4-(3-(pyridin-3-yl)-1-(tetrahydrofuran-3-yl)-1H-pyrazol-4-yl)pyrimidine | | | Production Example 2 | 328.27 | [M + H]+ | 8.78-8.80 (1 H, m), 8.67-8.71 (1 H, m), 8.37 (1 H, d, J = 5.3 Hz), 8.27 (1 H, s), 7.85-7.91 (1 H, m), 7.36-7.42 (1 H, m), 6.97 (1 H, d, J = 5.3 Hz), 5.02-5.12 (1 H, m), 3.94-4.25 (4 H, m), 2.40-2.61 (2 H, m) |
| 49 | tert-Butyl (1-(4-((4-(1-ethyl-3-(pyridin-3-yl)-1H-pyrazol-4-yl)pyrimidin-2-yl)amino)phenyl)piperidin-4-yl)carbamate | | | Production Example 3 Synthesis literature 9 | 541.63 | [M + H]+ | |
| 50 | tert-Butyl 3-(4-((4-(1-ethyl-3-(pyridin-3-yl)-1H-pyrazol-4-yl)pyrimidin-2-yl)amino)phenoxy)-8-azabicyclo[3.2.1]octane-8-carboxylate | | | Production Example 3 Synthesis literature 10 | 568.54 | [M + H]+ | 8.84-8.86 (1 H, m), 8.62 (1 H, dd, J = 4.8, 1.8 Hz), 8.22 (1 H, d, J = 5.3 Hz), 7.98 (1 H, s), 7.90 (1 H, dt, J = 7.7, 1.9 Hz), 7.30-7.38 (3 H, m), 6.80-6.91 (3 H, m), 6.54 (1 H, d, J = 5.3 Hz), 4.51-4.64 (1 H, m), 4.28 (4 H, q, J = 7.5 Hz), 1.97-2.14 (4 H, m), 1.59-1.73 (7 H, m), 1.49 (9 H, s) |

TABLE 1-continued

| Production example number | Compound name | Structural formula | Synthesis method description example | Raw material | Synthesis literature | MS | Ion | 1HNMR chemical shift value |
|---|---|---|---|---|---|---|---|---|
| 51 | tert-Butyl 3-(4-((4-(1-ethyl-3-(pyridin-3-yl)-1H-pyrazol-4-yl)pyrimidin-2-yl)amino)phenoxy)azetidine-1-carboxylate | | Production Example 49 | Production Example 3 | Synthesis literature 11 | | | 8.83-8.86 (1 H, m), 8.62 (1 H, dd, J = 4.8, 1.8 Hz), 8.23 (1 H, d, J = 5.3 Hz), 7.98 (1 H, s), 7.90 (1 H, dt, J = 7.9, 2.0 Hz), 7.28-7.39 (3 H, m), 6.93 (1 H, s), 6.62-6.69 (2 H, m), 6.56 (1 H, d, J = 4.9 Hz), 4.81-4.89 (1 H, m), 4.24-4.33 (4 H, m), 4.00 (2 H, dd, J = 10.2, 4.3 Hz), 1.55-1.64 (3 H, m), 1.45 (9 H, s) |
| 52 | tert-Butyl 3-(4-((4-(1-(2-methoxyethyl)-3-(pyridin-3-yl)-1H-pyrazol-4-yl)pyrimidin-2-yl)amino)phenoxy)azetidine-1-carboxylate | | Production Example 49 | Production Example 5 | Synthesis literature 11 | 544.58 | [M + H]+ | 8.80-8.85 (1 H, m), 8.55-8.60 (1 H, m), 8.20 (1 H, d, J = 5.3 Hz), 8.01 (1 H, s), 7.87 (1 H, dt, J = 8.2, 1.7 Hz), 7.31 (2 H, d, J = 9.0 Hz), 6.90 (1 H, s), 6.22-6.36 (3 H, m), 4.77-4.87 (1 H, m), 4.35 (2 H, t, J = 4.8 Hz), 4.19-4.31 (2 H, m), 3.91-4.01 (2 H, m), 3.80 (2 H, t, J = 4.8 Hz), 3.37 (3 H, s), 1.43 (9 H, s) |
| 53 | tert-Butyl 4-(4-((4-(3-(pyridin-3-yl)-1H-pyrazol-4-yl)pyrimidin-2-yl)amino)phenyl)piperidine-1-carboxylate | | Production Example 49 | Production Example 2 | Synthesis literature 12 | 498.51 | [M + H]+ | |

TABLE 1-continued

| Production example number | Compound name | Structural formula | Synthesis method description example | Raw material | MS | Ion | 1HNMR chemical shift value |
|---|---|---|---|---|---|---|---|
| 54 | tert-Butyl 6-((4-(3-(pyridin-3-yl)-1H-pyrazol-4-yl)pyrimidin-2-yl)amino)-3,4-dihydroisoquinoline-2(1H)-carboxylate | | Production Example 49 | Production Example 2 Synthesis literature 13 | 470.59 | [M + H]+ | 8.85-8.88 (1 H, m), 8.64-8.67 (1 H, m), 8.28 (1 H, d, J = 4.9 Hz), 8.17 (1 H, s), 7.87-7.94 (1 H, m), 7.22-7.37 (3 H, m), 6.95-7.02 (2 H, m), 6.63 (1 H, d, J = 5.4 Hz), 4.53 (2 H, s), 3.58-3.69 (2 H, m), 2.73-2.82 (2 H, m), 1.48 (9 H, s) |
| 55 | tert-Butyl 3-(4-((4-(1-ethyl-3-(pyridin-3-yl)-1H-pyrazol-4-yl)pyrimidin-2-yl)amino)phenyl)-3,8-diazabicyclo[3.2.1]octane-8-carboxylate | | Production Example 49 | Production Example 3 Synthesis literature 12 | 553.23 | [M + H]+ | 8.84-8.86 (1 H, m), 8.61 (1 H, dd, J = 4.9, 1.6 Hz), 8.20 (1 H, d, J = 5.3 Hz), 7.99 (1 H, s), 7.89 (1 H, dt, J = 7.9, 2.0 Hz), 7.28-7.36 (3 H, m), 6.73-6.84 (3 H, m), 6.51 (1 H, d, J = 5.3 Hz), 4.22-4.42 (4 H, m), 3.32-3.39 (2 H, m), 2.89-3.06 (2 H, m), 1.83-2.00 (4 H, m), 1.58-1.62 (3 H, m), 1.48 (9 H, s) |
| 56 | tert-Butyl 3-(5-((4-(1-ethyl-3-(pyridin-3-yl)-1H-pyrazol-4-yl)pyrimidin-2-yl)amino)pyridin-2-yl)-3,8-diazabicyclo[3.2.1]octane-8-carboxylate | | Production Example 49 | Production Example 3 Synthesis literature 37 | 554.20 | [M + H]+ | 8.83 (1 H, d, J = 1.6 Hz), 8.61 (1 H, dd, J = 4.9, 1.6 Hz), 8.22 (1 H, d, J = 2.9 Hz), 8.19 (1 H, d, J = 5.2 Hz), 7.98 (1 H, s), 7.88 (1 H, dt, J = 7.9, 2.0 Hz), 7.62-7.68 (1 H, m), 7.28-7.33 (1 H, m), 6.78 (1 H, s), 6.53 (1 H, d, J = 5.1 Hz), 6.49 (1 H, d, J = 9.2 Hz), 4.21-4.50 (4 H, m), 3.72-3.93 (2 H, m), 2.97-3.16 (2 H, m), 1.88-2.00 (2 H, m), 1.72-1.87 (2 H, m), 1.59 (3 H, t, J = 7.3 Hz), 1.47-1.49 (9 H, m) |

TABLE 1-continued

| Production example number | Compound name | Structural formula | Synthesis method description example | Raw material | MS | Ion | 1HNMR chemical shift value |
|---|---|---|---|---|---|---|---|
| 57 | tert-Butyl 4-(4-((4-(1-(pyridin-2-ylmethyl)-3-(pyridin-3-yl)-1H-pyrazol-4-yl)pyrimidin-2-yl)amino)phenyl)piperazine-1-carboxylate | | Production Example 49 | Production Example 4 Synthesis literature 14 | | | 8.87 (1 H, dd, J = 2.1, 0.8 Hz), 8.59-8.65 (2 H, m), 8.21-8.26 (1 H, m), 8.12 (1 H, s), 7.90 (1 H, dt, J = 7.9, 2.0 Hz), 7.67-7.75 (1 H, m), 7.24-7.36 (5 H, m), 6.93 (1 H, s), 6.80-6.88 (2 H, m), 6.56 (1 H, d, J = 5.3 Hz), 5.53 (2 H, s), 3.56-3.61 (4 H, m), 3.03-3.09 (4 H, m), 1.49 (9 H, s) |
| 58 | tert-Butyl 4-(4-((4-(3-(pyridin-3-yl)-1H-pyrazol-4-yl)pyrimidin-2-yl)amino)phenyl)piperazine-1-carboxylate | | Production Example 58 | Production Example 2 Synthesis literature 14 | 499.38 | [M + H]+ | 8.86 (1 H, d, J = 1.6 Hz), 8.65 (1 H, dd, J = 4.6, 1.6 Hz), 8.26 (1 H, d, J = 4.9 Hz), 8.15 (1 H, s), 7.89 (1 H, dt, J = 7.9, 2.0 Hz), 7.29-7.37 (3 H, m), 6.97 (1 H, s), 6.84 (2 H, d, J = 8.9 Hz), 6.61 (1 H, d, J = 5.3 Hz), 3.54-3.62 (4 H, m), 3.01-3.10 (4 H, m), 1.49 (9 H, s) |
| 59 | N-(1-(4-(4-(1-ethyl-3-(pyridin-3-yl)-1H-pyrazol-4-yl)pyrimidin-2-yl)amino)phenyl)-4-methyl)piperidin-4-yl)acetamide | | Production Example 58 | Production Example 3 Production Example 34 | 497.49 | [M + H]+ | 8.85 (1 H, dd, J = 4.9, 1.6 Hz), 8.61 (1 H, dd, J = 2.1, 0.8 Hz), 8.21 (1 H, d, J = 5.3 Hz), 7.98 (1 H, s), 7.86-7.92 (1 H, m), 7.27-7.38 (3 H, m), 6.84-6.92 (3 H, m), 6.52 (1 H, d, J = 5.3 Hz), 5.16 (1 H, s), 4.27 (2 H, q, J = 7.4 Hz), 3.22-3.34 (2 H, m), 2.89-3.01 (2 H, m), 2.14-2.25 (2 H, m), 1.97 (3 H, s), 1.75-1.88 (2 H, m), 1.59 (3 H, t, J = 7.3 Hz), 1.46 (3 H, s) |

TABLE 1-continued

| Production example number | Compound name | Structural formula | Synthesis method description example | Raw material | MS | Ion | 1HNMR chemical shift value |
|---|---|---|---|---|---|---|---|
| 60 | tert-Butyl 4-(4-((4-(1-ethyl-3-(pyridin-3-yl)-1H-pyrazol-4-yl)pyrimidin-2-yl)amino)phenyl)-1,4-diazepane-1-carboxylate | | Production Example 58 | Production Example 3 Synthesis literature 15 | 541.46 | [M + H]+ | 8.86 (1 H, dd, J = 2.3, 1.0 Hz), 8.61 (1 H, dd, J = 4.9, 1.6 Hz), 8.19 (1 H, d, J = 4.9 Hz), 7.98 (1 H, s), 7.90 (1 H, dt, J = 7.8, 1.9 Hz), 7.27-7.33 (3 H, m), 6.94-7.00 (1 H, m), 6.63 (2 H, d, J = 8.9 Hz), 6.48 (1 H, d, J = 5.3 Hz), 4.27 (2 H, q, J = 7.4 Hz), 3.49-3.62 (6 H, m), 3.16-3.36 (2 H, m), 1.82-2.04 (2 H, m), 1.58 (3 H, t, J = 7.4 Hz), 1.39-1.50 (9 H, m) |
| 61 | N-(4-ethyl-1-(4-((4-(1-ethyl-3-(pyridin-3-yl)-1H-pyrazol-4-yl)pyrimidin-2-yl)amino)phenyl)piperidin-4-yl)acetamide | | Production Example 58 | Production Example 3 Production Example 35 | 511.51 | [M + H]+ | |
| 62 | tert-Butyl 4-(4-((4-(1-(3-cyanobenzyl)-3-(pyridin-3-yl)-1H-pyrazol-4-yl)pyrimidin-2-yl)amino)phenyl)piperazine-1-carboxylate | | Production Example 58 | Production Example 8 Synthesis literature 14 | 614.60 | [M + H]+ | 8.84-8.87 (1 H, m), 8.61-8.65 (1 H, m), 8.24 (1 H, d, J = 5.3 Hz), 7.99 (1 H, s), 7.86-7.92 (1 H, m), 7.49-7.68 (4 H, m), 7.31-7.36 (3 H, m), 6.82-6.90 (3 H, m), 6.54 (1 H, d, J = 4.9 Hz), 5.43 (2 H, s), 3.55-3.62 (4 H, m), 3.03-3.10 (4 H, m), 1.48-1.50 (9 H, m) |

TABLE 1-continued

| Production example number | Compound name | Structural formula | Synthesis method description example | Raw material | MS | Ion | 1HNMR chemical shift value |
|---|---|---|---|---|---|---|---|
| 63 | N-(2-(1-(4-(4-(1-ethyl-3-(pyridin-3-yl)-1H-pyrazol-4-yl)pyrimidin-2-yl)amino)phenyl)piperidin-4-yl)propan-2-yl)acetamide | | Production Example 58 | Production Example 3 Production Example 36 | 525.56 | [M + H]+ | |
| 64 | tert-Butyl 4-(4-((4-(1-(2-cyanobenzyl)-3-(pyridin-3-yl)-1H-pyrazol-4-yl)pyrimidin-2-yl)amino)phenyl)piperazine-1-carboxylate | | Production Example 58 | Production Example 9 Synthesis literature 14 | 614.75 | [M + H]+ | 8.85 (1 H, d, J = 1.3 Hz), 8.61 (1 H, dd, J = 4.9, 1.6 Hz), 8.23 (1 H, d, J = 5.3 Hz), 8.14 (1 H, s), 7.88 (1 H, dt, J = 7.8, 1.9 Hz), 7.70-7.75 (1 H, m), 7.58-7.66 (1 H, m), 7.42-7.52 (2 H, m), 7.28-7.37 (3 H, m), 7.17 (1 H, s), 6.84 (2 H, d, J = 8.9 Hz), 6.55 (1 H, d, J = 5.3 Hz), 5.59 (2 H, s), 3.52-3.65 (4 H, m), 3.01-3.11 (4 H, m), 1.49 (9 H, s) |
| 65 | Benzyl 4-(4-((4-(1-ethyl-3-(pyridin-3-yl)-1H-pyrazol-4-yl)pyrimidin-2-yl)amino)phenyl)piperazine-1-carboxylate | | Production Example 58 | Production Example 2 Synthesis literature 16 | 533.31 | [M + H]+ | 8.85-8.88 (1 H, m), 8.64 (1 H, dd, J = 4.9, 1.6 Hz), 8.26 (1 H, d, J = 4.9 Hz), 8.14 (1 H, s), 7.89 (1 H, dt, J = 7.8, 1.9 Hz), 7.30-7.41 (8 H, m), 7.03 (1 H, s), 6.83 (2 H, d, J = 8.9 Hz), 6.61 (1 H, d, J = 5.3 Hz), 5.17 (2 H, s), 3.63-3.71 (4 H, m), 3.01-3.15 (4 H, m) |

TABLE 1-continued

| Production example number | Compound name | Structural formula | Synthesis method description example | Raw material | MS | Ion | 1HNMR chemical shift value |
|---|---|---|---|---|---|---|---|
| 66 | tert-Butyl 4-(4-((4-(1-(2-hydroxy-2-methylpropyl)-3-(pyridin-3-yl)-1H-pyrazol-4-yl)pyrimidin-2-yl)amino)phenyl)piperazine-1-carboxylate | | Production Example 58 | Production Example 17 Synthesis literature 14 | 571.52 | [M + H]+ | 8.84-8.87 (1 H, m), 8.62 (1 H, dd, J = 4.9, 1.6 Hz), 8.24 (1 H, d, J = 5.3 Hz), 8.02 (1 H, s), 7.89 (1 H, dt, J = 7.9, 2.0 Hz), 7.28-7.38 (3 H, m), 6.92 (1 H, s), 6.85 (2 H, d, J = 8.9 Hz), 6.57 (1 H, d, J = 5.3 Hz), 4.17 (2 H, s), 3.56-3.62 (4 H, m), 3.44 (1 H, s), 3.03-3.10 (4 H, m), 1.49 (9 H, s), 1.28 (6 H, s) |
| 67 | tert-Butyl 3-(4-((4-(1-ethyl-3-(pyridin-3-yl)-1H-pyrazol-4-yl)pyrimidin-2-yl)amino)phenyl)-8-azabicyclo[3.2.1]octane-8-carboxylate | | Production Example 58 | Production Example 17 Synthesis literature 17 | 552.54 | [M + H]+ | 8.83-8.86 (1 H, m), 8.60 (1 H, dd, J = 4.9, 1.6 Hz), 8.24 (1 H, d, J = 5.3 Hz), 8.00 (1 H, s), 7.84-7.93 (1 H, m), 7.28-7.42 (4 H, m), 7.05-7.14 (2 H, m), 6.55 (1 H, d, J = 5.3 Hz), 4.19-4.37 (4 H, m), 2.34-3.12 (2 H, m), 1.54-2.14 (10 H, m), 1.51 (9 H, s) |
| 68 | 4-(1-Ethyl-3-(pyridin-3-yl)-1H-pyrazol-4-yl)-N-(1-(piperidin-4-yl)-1H-pyrazol-4-yl)pyrimidin-2-amine | | Production Example 3 | Production Example 3 | 416.20 | [M + H]+ | DMSO-$d_6$ 9.31 (1 H, s), 8.70-8.74 (1 H, m), 8.53 (1 H, dd, J = 4.9, 1.6 Hz), 8.39 (1 H, s), 8.33 (1 H, s), 8.31 (1 H, s), 7.94 (1 H, d, J = 8.2 Hz), 7.19-7.46 (2 H, m), 6.60-6.70 (1 H, m), 4.26 (2 H, q, J = 7.2 Hz), 3.71-4.08 (1 H, m), 2.96-3.06 (2 H, m), 2.53-2.61 (2 H, m), 1.52-1.89 (4 H, m), 1.47 (3 H, t, J = 7.2 Hz) |

TABLE 1-continued

| Production example number | Compound name | Structural formula | Synthesis method description example | Raw material | MS | Ion | 1HNMR chemical shift value |
|---|---|---|---|---|---|---|---|
| 69 | N-(4-(1-ethyl-3-(pyridin-3-yl)-1H-pyrazol-4-yl)pyrimidin-2-yl)-2,3,4,5-tetrahydrobenzo[f][1,4]oxazepin-8-amine | | Production Example 3 | Production Example 69 Synthesis literature 18 | 414.35 | [M + H]+ | 8.81-8.87 (1 H, m), 8.61-8.64 (1 H, m), 8.24 (1 H, d, J = 5.1 Hz), 8.03 (1 H, s), 7.90 (1 H, dt, J = 7.8, 1.9 Hz), 7.33-7.36 (2 H, m), 7.00-7.16 (3 H, m), 6.56 (1 H, d, J = 5.4 Hz), 4.28 (2 H, q, J = 7.3 Hz), 4.06-4.09 (2 H, m), 3.96 (2 H, s), 3.24-3.27 (2 H, m), 1.60 (3 H, t, J = 7.3 Hz) |
| 70 | N-(4-(piperazin-1-yl)phenyl)-4-(3-(pyridin-3-yl)-1-(tetrahydrofuran-3-yl)-1H-pyrazol-4-yl)pyrimidin-2-amine | | Production Example 68 | Production Example 48 Synthesis literature 14 | 469.46 | [M + H]+ | 8.85 (1 H, dd, J = 4.9, 1.6 Hz), 8.61 (1 H, dd, J = 2.1, 0.8 Hz), 8.23 (1 H, d, J = 5.3 Hz), 8.05 (1 H, s), 7.88 (1 H, dt, J = 7.9, 2.0 Hz), 7.28-7.37 (3 H, m), 7.22-7.27 (1 H, m), 6.78-6.90 (2 H, m), 6.53 (1 H, d, J = 5.3 Hz), 5.01-5.10 (1 H, m), 3.93-4.24 (4 H, m), 3.00-3.12 (8 H, m), 2.27-2.60 (2 H, m) |
| 71 | 4-(1-Ethyl-3-(3-(pyridin-3-yl)-1H-pyrazol-4-yl)-N-(3-(piperidin-4-yl)phenyl)pyrimidin-2-amine | | Production Example 68 | Production Example 3 | 426.46 | [M + H]+ | |

TABLE 1-continued

| Production example number | Compound name | Structural formula | Synthesis method description example | Raw material | MS | Ion | 1HNMR chemical shift value |
|---|---|---|---|---|---|---|---|
| 72 | tert-Butyl 4-(4-((4-(1-ethyl-3-iodo-1H-pyrazol-4-yl)pyrimidin-2-yl)amino)phenyl)piperazine-1-carboxylate | | | Synthesis literature 1 Synthesis literature 14 | 576.32 | [M + H]+ | |
| 73 | tert-Butyl 4-(4-((4-(1-ethyl-3-(5-fluoropyridin-3-yl)-1H-pyrazol-4-yl)pyrimidin-2-yl)amino)phenyl)piperazine-1-carboxylate | | | Production Example 72 | 545.47 | [M + H]+ | 8.66 (1 H, t, J = 1.6 Hz), 8.44 (1 H, d, J = 2.6 Hz), 8.27 (1 H, d, J = 5.3 Hz), 7.95 (1 H, s), 7.64-7.70 (1 H, m), 7.29-7.36 (2 H, m), 7.02 (1 H, s), 6.80-6.88 (2 H, m), 6.58 (1 H, d, J = 4.9 Hz), 4.27 (2 H, q, J = 7.3 Hz), 3.54-3.64 (4 H, m), 3.01-3.13 (4 H, m), 1.59 (3 H, t, J = 7.6 Hz), 1.49 (9 H, s) |
| 74 | 4-(1-Ethyl-3-(pyridin-3-yl)-1H-pyrazol-4-yl)pyrimidin-2-amine | | | Production Example 3 | 267.30 | [M + H]+ | 8.81-8.87 (1 H, m), 8.61 (1 H, dd, J = 4.9, 1.6 Hz), 8.11 (1 H, d, J = 5.4 Hz), 7.99 (1 H, s), 7.90 (1 H, dt, J = 7.8, 1.9 Hz), 7.31-7.36 (1 H, m), 6.44 (1 H, d, J = 5.1 Hz), 5.01 (2 H, br s), 4.25 (2 H, q, J = 7.3 Hz), 1.58 (3 H, t, J = 7.3 Hz) |

TABLE 1-continued

| Production example number | Compound name | Structural formula | Synthesis method description example | Raw material | MS | Ion | 1HNMR chemical shift value |
|---|---|---|---|---|---|---|---|
| 75 | tert-Butyl 4-(4-((4-(1-(4-fluorobenzyl)-3-(pyridin-3-yl)-1H-pyrazol-4-yl)pyrimidin-2-yl)amino)phenyl)piperazine-1-carboxylate | | Production Example 58 | Production Example 58 | 607.58 | [M + H]+ | 8.86 (1 H, dd, J = 2.1, 0.8 Hz), 8.62 (1 H, dd, J = 4.8, 1.8 Hz), 8.21 (1 H, d, J = 5.3 Hz), 7.87-7.92 (2 H, m), 7.29-7.38 (5 H, m), 7.06-7.15 (2 H, m), 6.80-6.89 (3 H, m), 6.52 (1 H, d, J = 5.3 Hz), 5.37 (2 H, s), 3.55-3.63 (4 H, m), 3.02-3.11 (4 H, m), 1.49 (9 H, s) |
| 76 | tert-Butyl 4-(4-((4-(3-(pyridin-3-yl)-1-(2,2,2-trifluoroethyl)-1H-pyrazol-4-yl)pyrimidin-2-yl)amino)phenyl)piperazine-1-carboxylate | | Production Example 75 | Production Example 58 | 581.48 | [M + H]+ | 8.83-8.88 (1 H, m), 8.64 (1 H, dd, J = 4.8, 1.5 Hz), 8.26 (1 H, d, J = 5.3 Hz), 8.08 (1 H, s), 7.89 (1 H, dt, J = 7.7, 2.1 Hz), 7.28-7.38 (3 H, m), 6.79-6.93 (3 H, m), 6.56 (1 H, d, J = 5.3 Hz), 4.81 (2 H, q, J = 8.2 Hz), 3.54-3.63 (4 H, m), 3.02-3.12 (4 H, m), 1.49 (9 H, s) |
| 77 | tert-Butyl 4-(4-((4-(1-(oxetan-3-yl)-3-(pyridin-3-yl)-1H-pyrazol-4-yl)pyrimidin-2-yl)amino)phenyl)piperazine-1-carboxylate | | Production Example 75 | Production Example 58 | | | 8.85-8.89 (1 H, m), 8.63 (1 H, dd, J = 4.9, 1.6 Hz), 8.24 (1 H, d, J = 5.1 Hz), 8.15 (1 H, s), 7.88-7.94 (1 H, m), 7.29-7.40 (3 H, m), 6.95 (1 H, s), 6.82-6.90 (2 H, m), 6.55 (1 H, d, J = 5.1 Hz), 5.48-5.61 (1 H, m), 5.07-5.20 (4 H, m), 3.55-3.63 (4 H, m), 3.03-3.11 (4 H, m), 1.49 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 78 | tert-Butyl 4-(4-((4-(1-phenethyl-3-(pyridin-3-yl)-1H-pyrazol-4-yl)pyrimidin-2-yl)amino)phenyl)piperazine-1-carboxylate | | Production Example 75 | Production Example 58 | 603.58 | [M + H]+ | 8.87 (1 H, dd, J = 2.1, 0.8 Hz), 8.61-8.65 (1 H, m), 8.21 (1 H, d, J = 4.9 Hz), 7.87-7.93 (1 H, m), 7.77 (1 H, s), 7.28-7.37 (6 H, m), 7.16-7.21 (2 H, m), 6.82-6.90 (3 H, m), 6.49 (1 H, d, J = 5.3 Hz), 4.43 (2 H, t, J = 7.4 Hz), 3.55-3.63 (4 H, m), 3.27 (2 H, t, J = 7.3 Hz), 3.03-3.11 (4 H, m), 1.45-1.51 (9 H, m) |
| 79 | Benzyl 4-(4-(1-(3-methyloxetan-3-yl)methyl)-3-(pyridin-3-yl)-1H-pyrazol-4-yl)pyrimidin-2-yl)amino)phenyl)piperazine-1-carboxylate | | Production Example 75 | Production Example 65 | 617.35 | [M + H]+ | |
| 80 | tert-Butyl 4-(4-((4-(3-(pyridin-3-yl)-1-(pyridin-3-ylmethyl)-1H-pyrazol-4-yl)pyrimidin-2-yl)amino)phenyl)piperazine-1-carboxylate | | Production Example 2 Synthesis literature 14 | | 590.73 | [M + H]+ | 8.85-8.87 (1 H, m), 8.66-8.68 (1 H, m), 8.61-8.65 (2 H, m), 8.23 (1 H, d, J = 5.3 Hz), 7.97 (1 H, s), 7.86-7.91 (1 H, m), 7.67-7.72 (1 H, m), 7.29-7.37 (4 H, m), 6.80-6.92 (3 H, m), 6.53 (1 H, d, J = 5.3 Hz), 5.42 (2 H, s), 3.53-3.62 (4 H, m), 3.01-3.10 (4 H, m), 1.49 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 81 | tert-Butyl 6-(4-(1-(2-hydroxy-2-methylpropyl)-3-(pyridin-3-yl)-1H-pyrazol-4-yl)pyrimidin-2-yl)amino)-3,4-dihydroisoquinoline-2(1H)-carboxylate | | | Production Example 54 | 542.68 | [M + H]+ | 8.83-8.89 (1 H, m), 8.60-8.64 (1 H, m), 8.24-8.29 (1 H, m), 8.04 (1 H, s), 7.88-7.92 (1 H, m), 7.29-7.35 (3 H, m), 6.96-7.05 (2 H, m), 6.58 (1 H, d, J = 5.1 Hz), 4.52 (2 H, br s), 4.18 (2 H, s), 3.57-3.70 (2 H, m), 2.73-2.83 (2 H, m), 1.59 (9 H, s), 1.50 (6 H, s) |
| 82 | 2-Methyl-1-(4-(2-(4-(piperidin-4-yl)phenyl)amino)pyrimidin-4-yl)-3-(pyridin-4-yl)-1H-pyrazol-1-yl)propan-2-ol | | | Production Example 53 | 470.41 | [M + H]+ | 8.83-8.87 (1 H, m), 8.60-8.66 (1 H, m), 8.26 (1 H, d, J = 5.1 Hz), 8.04 (1 H, s), 7.91 (1 H, dt, J = 8.1, 1.6 Hz), 7.29-7.43 (3 H, m), 7.10-7.13 (2 H, m), 7.00 (1 H, s), 6.58 (1 H, d, J = 5.4 Hz), 4.18 (2 H, s), 3.15-3.24 (2 H, m), 2.69-2.83 (2 H, m), 2.68-2.72 (1 H, m), 1.52-1.91 (4 H, m), 1.26 (6 H, s) |
| 83 | tert-Butyl 4-(4-((1-ethyl-4-(3-(pyridin-3-yl)-1H-pyrazol-4-yl)pyrimidin-2-yl)amino)benzoyl)piperazine-1-carboxylate | | | Production Example 3 | 555.51 | [M + H]+ | 8.83-8.86 (1 H, m), 8.62 (1 H, dd, J = 4.8, 1.8 Hz), 8.30 (1 H, d, J = 4.9 Hz), 8.01 (1 H, s), 7.88-7.94 (1 H, m), 7.50-7.57 (2 H, m), 7.30-7.38 (3 H, m), 7.20 (1 H, s), 6.65 (1 H, d, J = 5.3 Hz), 4.30 (2 H, q, J = 7.5 Hz), 3.40-3.70 (8 H, m), 1.61 (3 H, t, J = 7.6 Hz), 1.48 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 84 | tert-Butyl 4-(3-((1-ethyl-4-(3-(pyridin-3-yl)-1H-pyrazol-4-yl)pyrimidin-2-yl)amino)benzoyl)piperazine-1-carboxylate | | Production Example 83 | Production Example 3 | 555.34 | [M + H]+ | 8.83-8.86 (1 H, m), 8.63 (1 H, dd, J = 4.6, 1.6 Hz), 8.26 (1 H, d, J = 5.3 Hz), 8.10 (1 H, s), 7.88-7.93 (1 H, m), 7.79-7.82 (1 H, m), 7.49-7.55 (1 H, m), 7.28-7.39 (2 H, m), 7.15 (1 H, s), 6.99-7.05 (1 H, m), 6.60 (1 H, d, J = 5.3 Hz), 4.29 (2 H, q, J = 7.3 Hz), 3.34-3.86 (8 H, m), 1.61 (4 H, m), 1.47 (9 H, s) |
| 85 | tert-Butyl 4-((4-((1-ethyl-4-(3-pyridin-3-yl)-1H-pyrazol-4-yl)pyrimidin-2-yl)amino)-N-methylphenyl)sulfonamido)piperidine-1-carboxylate | | Production Example 83 | Production Example 3 Production Example 39 | 619.21 | [M + H]+ | 8.82 (1 H, dd, J = 2.1, 0.8 Hz), 8.62 (1 H, dd, J = 4.8, 1.8 Hz), 8.32 (1 H, d, J = 5.3 Hz), 8.02 (1 H, s), 7.92 (1 H, dt, J = 7.9, 2.0 Hz), 7.62-7.71 (4 H, m), 7.33-7.39 (2 H, m), 6.71 (1 H, d, J = 5.3 Hz), 4.31 (2 H, q, J = 7.3 Hz), 4.06-4.21 (2 H, m), 3.87-4.03 (1 H, m), 2.60-2.79 (5 H, m), 1.62 (3 H, t, J = 7.3 Hz), 1.44-1.54 (4 H, m), 1.42-1.44 (9 H, m) |
| 86 | tert-Butyl 4-(4-((4-(1-benzyl-3-(pyridin-3-yl)-1H-pyrazol-4-yl)pyrimidin-2-yl)amino)benzoyl)piperazine-1-carboxylate | | Production Example 83 | Production Example 6 | 617.27 | [M + H]+ | |

TABLE 1-continued

| Production example number | Compound name | Structural formula | Synthesis method description example | Raw material | MS | Ion | 1HNMR chemical shift value |
|---|---|---|---|---|---|---|---|
| 87 | tert-Butyl 4-(4-((4-(1-phenethyl-3-(pyridin-3-yl)-1H-pyrazol-4-yl)pyrimidin-2-yl)amino)benzoyl)piperazine-1-carboxylate | | Production Example 83 | Production Example 13 | 631.52 | [M + H]+ | 8.84-8.87 (1 H, m), 8.63 (1 H, dd, J = 4.9, 1.6 Hz), 8.28 (1 H, d, J = 5.3 Hz), 7.92 (1 H, dt, J = 7.9, 2.0 Hz), 7.79 (1 H, s), 7.47-7.53 (2 H, m), 7.28-7.39 (6 H, m), 7.16-7.21 (3 H, m), 6.60 (1 H, d, J = 5.3 Hz), 4.45 (2 H, t, J = 7.3 Hz), 3.42-3.67 (8 H, m), 3.28 (2 H, t, J = 7.3 Hz), 1.48 (9 H, s) |
| 88 | tert-Butyl 4-(4-((4-(1-(4-fluorobenzyl)-3-(pyridin-3-yl)-1H-pyrazol-4-yl)pyrimidin-2-yl)amino)benzoyl)piperazine-1-carboxylate | | Production Example 83 | Production Example 7 | 635.51 | [M + H]+ | 8.85 (1 H, dd, J = 2.1, 0.8 Hz), 8.63 (1 H, dd, J = 4.8, 1.8 Hz), 8.29 (1 H, d, J = 5.3 Hz), 7.89-7.94 (2 H, m), 7.46-7.52 (2 H, m), 7.28-7.40 (5 H, m), 7.07-7.17 (3 H, m), 6.64 (1 H, d, J = 4.9 Hz), 5.38 (2 H, s), 3.38-3.70 (8 H, m), 1.48 (9 H, s) |
| 89 | tert-Butyl 3-(4-((4-(1-ethyl-3-(pyridin-3-yl)-1H-pyrazol-4-yl)pyrimidin-2-yl)amino)benzoyl)-3,8-diazabicyclo[3.2.1]octane-8-carboxylate | | Production Example 83 | Production Example 3 Synthesis literature 19 | 581.51 | [M + H]+ | 8.84 (1 H, dd, J = 2.1, 0.8 Hz), 8.62 (1 H, dd, J = 4.8, 1.8 Hz), 8.29 (1 H, d, J = 5.3 Hz), 8.01 (1 H, s), 7.91 (1 H, dt, J = 7.9, 2.0 Hz), 7.50-7.56 (2 H, m), 7.28-7.37 (3 H, m), 7.21 (1 H, s), 6.64 (1 H, d, J = 5.3 Hz), 4.41-4.64 (2 H, m), 4.30 (2 H, d, J = 7.6 Hz), 2.89-3.71 (4 H, m), 1.78-2.01 (4 H, m), 1.61 (3 H, t, J = 7.3 Hz), 1.49 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 90 | (4-((4-(1-Ethyl-3-(pyridin-3-yl)-1H-pyrazol-4-yl)pyrimidin-2-yl)amino)phenyl)(piperazin-1-yl)methanone | | Production Example 90 | Production Example 83 | 455.42 | [M + H]+ | 8.83-8.85 (1 H, m), 8.61 (1 H, dd, J = 4.6, 1.6 Hz), 8.29 (1 H, d, J = 5.3 Hz), 8.01 (1 H, s), 7.88-7.93 (1 H, m), 7.50-7.55 (2 H, m), 7.29-7.37 (3 H, m), 7.23 (1 H, s), 6.64 (1 H, d, J = 5.3 Hz), 4.29 (2 H, q, J = 7.5 Hz), 3.46-3.76 (4 H, m), 2.79-2.95 (4 H, m), 1.60 (3 H, t, J = 7.3 Hz) |
| 91 | (3-((4-(1-Ethyl-3-(pyridin-3-yl)-1H-pyrazol-4-yl)pyrimidin-2-yl)amino)phenyl)(piperazine-1-yl)methanone | | Production Example 90 | Production Example 84 | 455.25 | [M + H]+ | 8.82-8.86 (1 H, m), 8.63 (1 H, dd, J = 4.8, 1.5 Hz), 8.25 (1 H, d, J = 5.3 Hz), 8.10 (1 H, s), 7.91 (1 H, dt, J = 7.9, 1.8 Hz), 7.74-7.78 (1 H, m), 7.51-7.57 (1 H, m), 7.28-7.38 (2 H, m), 7.17 (1 H, s), 6.99-7.05 (1 H, m), 6.59 (1 H, d, J = 5.3 Hz), 4.29 (2 H, q, J = 7.4 Hz), 3.38-3.86 (4 H, m), 2.74-3.03 (4 H, m), 1.61 (3 H, t, J = 7.3 Hz) |
| 92 | 4-((4-(1-Ethyl-3-(pyridin-3-yl)-1H-pyrazol-4-yl)pyrimidin-2-yl)amino)-N-methyl-N-(piperidin-4-yl)benzene-sulfonamide | | Production Example 90 | Production Example 85 | 519.23 | [M + H]+ | 8.78-8.83 (1 H, m), 8.61 (1 H, dd, J = 4.9, 1.6 Hz), 8.29-8.35 (1 H, m), 8.02 (1 H, s), 7.93 (1 H, dt, J = 7.9, 2.0 Hz), 7.58-7.69 (5 H, m), 7.32-7.39 (1 H, m), 6.69-6.74 (1 H, m), 4.30 (2 H, q, J = 7.3 Hz), 3.83-3.99 (1 H, m), 3.17-3.29 (2 H, m), 2.67-2.83 (5 H, m), 1.69-1.85 (2 H, m), 1.49-1.64 (5 H, m) |

TABLE 1-continued

| Production example number | Compound name | Structural formula | Synthesis method description example | Raw material | MS | Ion | 1HNMR chemical shift value |
|---|---|---|---|---|---|---|---|
| 93 | (4-(4-(1-Phenethyl-3-(pyridin-3-yl)-1H-pyrazol-4-yl)pyrimidin-2-yl)amino)phenyl)(piperazin-1-yl)methanone | | Production Example 90 | Production Example 87 | 531.46 | [M + H]+ | 8.85 (1 H, dd, J = 2.1, 0.8 Hz), 8.63 (1 H, d, J = 4.7 Hz), 8.27 (1 H, d, J = 5.3 Hz), 7.92 (1 H, dt, J = 7.7, 1.9 Hz), 7.79 (1 H, s), 7.45-7.52 (2 H, m), 7.28-7.39 (6 H, m), 7.16-7.21 (3 H, m), 6.59 (1 H, d, J = 4.9 Hz), 4.45 (2 H, t, J = 7.4 Hz), 3.67 (4 H, m, J = 19.5 Hz), 3.27 (2 H, t, J = 7.4 Hz), 2.80-3.01 (4 H, m) |
| 94 | (4-(4-(1-(4-Fluorobenzyl)-3-(pyridin-3-yl)-1H-pyrazol-4-yl)pyrimidin-2-yl)amino)phenyl)(piperazin-1-yl)methanone | | Production Example 90 | Production Example 88 | 535.43 | [M + H]+ | 8.85 (1 H, dd, J = 2.3, 0.7 Hz), 8.62 (1 H, dd, J = 4.8, 1.8 Hz), 8.28 (1 H, d, J = 5.3 Hz), 7.89-7.96 (2 H, m), 7.46-7.51 (2 H, m), 7.27-7.39 (5 H, m), 7.21 (1 H, s), 7.07-7.15 (2 H, m), 6.63 (1 H, d, J = 5.3 Hz), 5.38 (2 H, s), 3.44-3.82 (4 H, m), 2.82-3.01 (4 H, m) |
| 95 | (3,8-Diazabicyclo[3.2.1]octan-3-yl)(4-((4-(1-ethyl-3-(pyridin-3-yl)-1H-pyrazol-4-yl)pyrimidin-2-yl)amino)phenyl)methanone | | Production Example 90 | Production Example 89 | 481.44 | [M + H]+ | 8.82-8.85 (1 H, m), 8.62 (1 H, dd, J = 4.9, 1.6 Hz), 8.29 (1 H, d, J = 5.3 Hz), 8.01 (1 H, s), 7.91 (1 H, dt, J = 7.9, 2.0 Hz), 7.49-7.55 (2 H, m), 7.28-7.38 (4 H, m), 6.64 (1 H, d, J = 4.9 Hz), 4.29 (2 H, q, J = 7.3 Hz), 2.78-3.72 (6 H, m), 1.64-2.15 (4 H, m), 1.60 (3 H, t, J = 7.3 Hz) |

TABLE 1-continued

| Production example number | Compound name | Structural formula | Synthesis method description example | Raw material | MS | Ion | 1HNMR chemical shift value |
|---|---|---|---|---|---|---|---|
| 96 | N-(4-(1,4-diazepan-1-yl)phenyl)-4-(1-ethyl-3-(pyridin-3-yl)-1H-pyrazol-4-yl)pyrimidin-2-amine | | Production Example 90 | Production Example 60 | 441.33 | [M + H]+ | 8.86 (1 H, dd, J = 2.1, 0.8 Hz), 8.61 (1 H, dd, J = 4.9, 1.6 Hz), 8.19 (1 H, d, J = 5.3 Hz), 7.98 (1 H, s), 7.87-7.95 (1 H, m), 7.27-7.34 (3 H, m), 6.78 (1 H, s), 6.61-6.67 (2 H, m), 6.47 (1 H, d, J = 5.3 Hz), 4.27 (2 H, q, J = 7.4 Hz), 3.50-3.61 (4 H, m), 3.01-3.07 (2 H, m), 2.81-2.87 (2 H, m), 1.85-1.95 (2 H, m), 1.59 (3 H, t, J = 7.3 Hz) |
| 97 | 2-Methyl-1-(4-(2-((4-(piperazin-1-yl)phenyl)amino)pyrimidin-4-yl)-3-(pyridin-3-yl)-1H-pyrazol-1-yl)propan-2-ol | | Production Example 90 | Production Example 66 | 471.42 | [M + H]+ | 8.84-8.87 (1 H, m), 8.62 (1 H, dd, J = 4.6, 1.6 Hz), 8.23 (1 H, d, J = 5.3 Hz), 8.02 (1 H, s), 7.89 (1 H, dt, J = 7.9, 2.0 Hz), 7.28-7.37 (3 H, m), 6.94 (1 H, s), 6.83-6.89 (2 H, m), 6.55 (1 H, d, J = 5.3 Hz), 4.17 (2 H, s), 3.02-3.13 (8 H, m), 1.28 (6 H, s) |
| 98 | N-(4-(8-azabicyclo[3.2.1]octan-3-yl)phenyl)-4-(1-ethyl-3-(pyridin-3-yl)-1H-pyrazol-4-yl)pyrimidin-2-amine | | Production Example 90 | Production Example 67 | 452.49 | [M + H]+ | 8.83-8.87 (1 H, m), 8.58-8.62 (1 H, m), 8.21-8.28 (1 H, m), 7.98-8.02 (1 H, m), 7.86-7.93 (1 H, m), 7.29-7.46 (4 H, m), 7.15-7.25 (2 H, m), 6.55-6.61 (1 H, m), 4.21-4.35 (2 H, m), 3.94-4.09 (2 H, m), 2.89-3.27 (1 H, m), 2.48-2.64 (1 H, m), 1.95-2.31 (5 H, m), 1.68-1.86 (2 H, m), 1.54-1.62 (3 H, m) |

TABLE 1-continued

| Production example number | Compound name | Structural formula | Synthesis method description example | Raw material | MS | Ion | 1HNMR chemical shift value |
|---|---|---|---|---|---|---|---|
| 99 | N-(4-(azetidin-3-yloxy)phenyl)-4-(1-(2-methoxyethyl)-3-(pyridin-3-yl)-1H-pyrazol-4-yl)pyrimidin-2-amine | | Production Example 90 | Production Example 52 | 444.56 | [M + H]+ | 8.82-8.86 (1 H, m), 8.60 (1 H, dd, J = 4.6, 1.5 Hz), 8.22 (1 H, d, J = 5.2 Hz), 8.04 (1 H, s), 7.89 (1 H, dt, J = 7.9, 1.9 Hz), 7.32 (2 H, d, J = 9.0 Hz), 6.90 (1 H, s), 6.65 (2 H, d, J = 9.0 Hz), 6.57 (2 H, d, J = 5.1 Hz), 4.90-5.02 (1 H, m), 4.37 (2 H, t, J = 5.3 Hz), 3.75-3.98 (6 H, m), 3.39 (3 H, s) |
| 100 | 2-Methyl-1-(3-(pyridin-3-yl)-4-(2-((1,2,3,4-tetrahydroisoquinolin-6-yl)amino)pyrimidin-4-yl)-1H-pyrazol-1-yl)propan-2-ol | | Production Example 90 | Production Example 81 | 442.53 | [M + H]+ | 8.83-8.89 (1 H, m), 8.60-8.66 (1 H, m), 8.25 (1 H, d, J = 5.1 Hz), 8.04 (1 H, s), 7.90 (1 H, dt, J = 8.4, 1.6 Hz), 7.19-7.30 (3 H, m), 6.87-6.97 (2 H, m), 6.58 (1 H, d, J = 5.4 Hz), 4.17 (2 H, s), 3.98 (2 H, s), 3.13 (2 H, t, J = 6.2 Hz), 2.76 (2 H, t, J = 6.2 Hz), 1.28 (6 H, s) |
| 101 | N-(4-(piperazin-1-yl)phenyl)-4-(3-(pyridin-3-yl)-1H-pyrazol-4-yl)pyrimidin-2-amine | | Production Example 90 | Production Example 58 | 399.42 | [M + H]+ CD3OD | 8.71-8.73 (1 H, m), 8.49 (1 H, dd, J = 5.1, 1.5 Hz), 8.24-8.28 (2 H, m), 8.01 (1 H, dt, J = 8.2, 1.9 Hz), 7.39-7.44 (1 H, m), 7.23 (2 H, d, J = 9.2 Hz), 6.73-6.83 (3 H, m), 3.04-3.10 (4 H, m), 2.97-3.02 (4 H, m) |

TABLE 1-continued

| Production example number | Compound name | Structural formula | Synthesis method description example | Raw material | MS | Ion | 1HNMR chemical shift value |
|---|---|---|---|---|---|---|---|
| 102 | 4-(1-Ethyl-3-(pyridin-3-yl)-1H-pyrazol-4-yl)-N-(4-(piperidin-3-yl)phenyl)pyrimidin-2-amine | | Production Example 90 | Production Example 138 | 426 | [M + H]+ | 8.84-8.85 (1 H, m), 8.60-8.62 (1 H, m), 8.24 (1 H, d, J = 5.1 Hz), 8.00 (1 H, s), 7.87-7.91 (1 H, m), 7.40-7.43 (2 H, m), 7.29-7.35 (1 H, m), 7.10 (2 H, d, J = 8.6 Hz), 7.06 (1 H, s), 6.56 (1 H, d, J = 5.4 Hz), 4.28 (2 H, q, J = 7.3 Hz), 3.24-3.26 (2 H, m), 3.00-3.03 (1 H, m), 2.66-2.76 (3 H, m), 2.00-2.02 (1 H, m), 1.63-1.83 (2 H, m), 1.60 (3 H, t, J = 7.3 Hz) |
| 103 | 5-((4-(1-Ethyl-3-(pyridin-3-yl)-1H-pyrazol-4-yl)pyrimidin-2-yl)amino)-2-(piperazin-1-yl)benzonitrile | | Production Example 90 | Production Example 140 | 452 | [M + H]+ | 8.60-8.61 (1 H, m), 8.35-8.38 (1 H, m), 8.18 (1 H, s), 8.14 (1 H, d, J = 5.1 Hz), 7.88-7.92 (1 H, m), 7.27-7.31 (1 H, m), 7.09-7.14 (2 H, m), 6.64-6.68 (3 H, m), 4.20 (2 H, q, J = 7.3 Hz), 3.04-3.08 (4 H, m), 2.60-2.64 (4 H, m), 1.46 (3 H, t, J = 7.3 Hz) |
| 104 | 4-(1-((3-Methyloxetan-3-yl)methyl)-3-(pyridin-3-yl)-1H-pyrazol-4-yl)-N-(4-(piperazin-1-yl)phenyl)pyrimidin-2-amine | | | Production Example 79 | 483 | [M + H]+ | 8.84 (1 H, dd, J = 2.1, 0.8 Hz), 8.60-8.63 (1 H, m), 8.23 (1 H, d, J = 5.3 Hz), 7.94 (1 H, s), 7.87 (1 H, dt, J = 7.8, 1.9 Hz), 7.28-7.38 (3 H, m), 7.06 (1 H, s), 6.82-6.90 (2 H, m), 6.53 (1 H, d, J = 5.3 Hz), 4.76 (2 H, d, J = 6.3 Hz), 4.46 (2 H, d, J = 6.3 Hz), 4.42 (2 H, s), 3.01-3.12 (8 H, m), 1.36 (3 H, s) |

TABLE 1-continued

| Production example number | Compound name | Structural formula | Synthesis method description example | Raw material | MS | Ion | 1HNMR chemical shift value |
|---|---|---|---|---|---|---|---|
| 105 | tert-Butyl 2-(6-((4-(1-ethyl-3-(pyridin-3-yl)-1H-pyrazol-4-yl)pyrimidin-2-yl)amino)-3,4-dihydroisoquinolin-2(1H)-yl)acetate | | | Example 168 | 512.40 | [M + H]+ | 8.84-8.88 (1 H, m), 8.63-8.60 (1 H, m), 8.22 (1 H, d, J = 4.9 Hz), 8.00 (1 H, s), 7.89 (1 H, dt, J = 8.1, 1.6), 7.21-7.34 (3 H, m), 6.90-6.94 (2 H, m), 6.53 (1 H, d, J = 5.4 Hz), 4.29 (2 H, q, J = 7.3 Hz), 3.76 (2 H, s), 3.32 (2 H, s), 2.84-2.93 (4 H, m), 1.52-1.62 (3 H, m), 1.50 (9 H, s) |
| 106 | tert-Butyl 2-(4-(4-((4-(1-ethyl-3-(pyridin-3-yl)-1H-pyrazol-4-yl)pyrimidin-2-yl)amino)phenyl)piperazin-1-yl)acetate | | Production Example 105 | Example 151 | 541.51 | [M + H]+ | 8.84-8.88 (1 H, m), 8.61 (1 H, dd, J = 4.8, 1.8 Hz), 8.21 (1 H, d, J = 4.9 Hz), 7.99 (1 H, s), 7.89 (1 H, dt, J = 7.9, 2.0 Hz), 7.28-7.39 (3 H, m), 6.84-6.94 (3 H, m), 6.52 (1 H, d, J = 5.3 Hz), 4.28 (2 H, q, J = 7.4 Hz), 3.16-3.25 (6 H, m), 2.73-2.83 (4 H, m), 1.59 (3 H, t, J = 7.3 Hz), 1.49 (9 H, s). |
| 107 | 2-(2-((tert-Butyldimethylsilyl)oxy)ethyl)-N-(4-(1-ethyl-3-(pyridin-3-yl)-1H-pyrazol-4-yl)pyrimidin-2-yl)-1,2,3,4-tetrahydroisoquinolin-7-amine | | | Example 169 | 556.26 | [M + H]+ | 8.69-8.85 (1 H, m), 8.44-8.60 (1 H, m), 8.14 (1 H, d, J = 4.9 Hz), 7.91 (1 H, s), 7.74-7.87 (1 H, m), 7.06-7.29 (4 H, m), 6.79-6.97 (1 H, m), 6.45 (1 H, d, J = 4.9 Hz), 4.18 (2 H, q, J = 7.3 Hz), 3.77 (2 H, t, J = 6.4 Hz), 3.58 (2 H, s), 2.69-2.81 (4 H, m), 2.62 (2 H, t, J = 6.3 Hz), 1.50 (3 H, t, J = 7.3 Hz), 0.83 (9 H, s), 0.00 (6 H, s) |

TABLE 1-continued

| Production example number | Compound name | Structural formula | Synthesis method description example | Raw material | MS | Ion | 1HNMR chemical shift value |
|---|---|---|---|---|---|---|---|
| 108 | 4-(1-Ethyl-5-(pyridin-3-yl)-1H-pyrazol-4-yl)-2-(methylthio)pyrimidine 4-(1-ethyl-3-(pyridin-3-yl)-1H-pyrazol-4-yl)-2-(methylthio)pyrimidine | | | Production Example 15 | 298 | [M + H]+ | 4-(1-Ethyl-5-(pyridin-3-yl)-1H-pyrazol-4-yl)-2-(methylthio)pyrimidine 8.75-8.77 (1 H, m), 8.65-8.66 (1 H, m), 8.29 (1 H, d, J = 5.1 Hz), 8.13 (1 H, s), 7.69-7.73 (1 H, m), 7.45-7.50 (1 H, m), 6.77 (1 H, d, J = 5.4 Hz), 4.03 (2 H, q, J = 7.3 Hz), 2.10 (3 H, s), 1.39-1.41 (3 H, m) 4-(1-Ethyl-3-(pyridin-3-yl)-1H-pyrazol-4-yl)-2-(methylthio)pyrimidine 8.79-8.81 (1 H, m), 8.63-8.66 (1 H, m), 8.31 (1 H, d, J = 5.4 Hz), 8.08 (1 H, s), 7.85-7.89 (1 H, m), 7.33-7.38 (1 H, m), 6.77 (1 H, d, J = 5.4 Hz), 4.28 (2 H, q, J = 7.3 Hz), 2.42 (3 H, s), 1.57-1.63 (3 H, m) |
| 109 | 4-(1-(2,2-Difluoroethyl)-3-(pyridin-3-yl)-1H-pyrazol-4-yl)-2-(methylthio)pyrimidine | | Production Example 108 | Production Example 16 | 334 | [M + H]+ | 8.80 (1 H, d, J = 2.2 Hz), 8.66 (1 H, dd, J = 4.6, 1.6 Hz), 8.35 (1 H, d, J = 5.4 Hz) 8.14 (1 H, s), 7.84-7.88 (1 H, m), 7.35-7.39 (1 H, m), 6.79 (1 H, d, J = 5.4 Hz), 5.99-6.43 (1 H, m), 4.51-4.62 (2 H, m), 2.40 (3 H, s) |
| 110 | 4-(1-Ethyl-3-(pyridin-3-yl)-1H-pyrazol-4-yl)-2-(methylsulfonyl)pyrimidine | | | Production Example 108 | 330 | [M + H]+ | 8.78 (1 H, d, J = 2.4 Hz), 8.68-8.70 (1 H, m), 8.63 (1 H, d, J = 5.4 Hz), 8.28 (1 H, s), 7.88-7.92 (1 H, m), 7.42 (1 H, dd, J = 7.8, 4.9 Hz), 7.27 (1 H, s), 4.30 (2 H, q, J = 7.3 Hz), 3.24 (3 H, s), 1.61 (3 H, t, J = 7.3 Hz) |

TABLE 1-continued

| Production example number | Compound name | Structural formula | Synthesis method description example | Raw material | MS | Ion | 1HNMR chemical shift value |
|---|---|---|---|---|---|---|---|
| 111 | 4-(1-(2,2-Difluoroethyl)-3-(pyridin-3-yl)-1H-pyrazol-4-yl)-2-(methylsulfonyl)pyrimidine | | Production Example 110 | Production Example 109 | 366 | [M + H]+ | 8.79 (1 H, d, J = 5.4 Hz), 8.44-8.46 (1 H, m), 8.25-8.28 (2 H, m), 7.55-7.58 (1 H, m), 7.36-7.43 (2 H, m), 5.99-6.43 (1 H, m), 4.54-4.65 (2 H, m), 3.29 (3 H, s) |
| 112 | 3-(4-Bromo-1-ethyl-1H-pyrazol-3-yl)pyridine | | | Synthesis literature 20 | 252 | [M + H]+ | 9.14 (1 H, dd, J = 2.4, 1.1 Hz), 8.59 (1 H, dd, J = 4.9, 1.9 Hz), 8.17-8.21 (1 H, m), 7.53 (1 H, s), 7.33-7.38 (1 H, m), 4.17-4.25 (2 H, m), 1.51-1.56 (3 H, m) |
| 113 | 3-(1-Ethyl-4-(4,4,5,5-tetramethyl-1,3,2-dioxaborolan-2-yl)-1H-pyrazol-3-yl)pyridine | | | Production Example 112 | 300 | [M + H]+ | 9.17 (1 H, dd, J = 2.4, 1.1 Hz), 8.55 (1 H, dd, J = 4.9, 1.6 Hz), 8.22-8.26 (1 H, m), 7.81 (1 H, s), 7.27-7.32 (1 H, m), 4.18-4.27 (2 H, m), 1.32 (12 H, s), 1.51-1.57 (3 H, m) |

TABLE 1-continued

| Production example number | Compound name | Structural formula | Synthesis method description example | Raw material | MS | Ion | 1HNMR chemical shift value |
|---|---|---|---|---|---|---|---|
| 114 | 2-Chloro-4-(1-ethyl-3-(pyridin-3-yl)-1H-pyrazol-4-yl)-5-fluoropyrimidine | | | Production Example 113 | 304 | [M + H]+ | 8.79-8.80 (1 H, m), 8.60-8.64 (1 H, m), 8.38 (1 H, d, J = 2.2 Hz), 8.08-8.14 (1 H, m), 7.93-7.98 (1 H, m), 7.34-7.37 (1 H, m), 4.28-4.36 (2 H, m), 1.61 (3 H, t, J = 7.3 Hz) |
| 115 | tert-Butyl (S)-(1-(4-nitrophenyl)piperidin-3-yl)carbamate | | | | 322 | [M + H]+ | 8.08-8.14 (2 H, m), 6.82-6.88 (2 H, m), 4.57-4.59 (1 H, m), 3.55-3.85 (3 H, m), 3.14-3.27 (2 H, m), 1.93-2.02 (1 H, m), 1.60-1.88 (3 H, m), 1.46 (9 H, s) |
| 116 | tert-Butyl (R)-(1-(4-nitrophenyl)piperidin-3-yl)carbamate | | Production Example 115 | | 322 | [M + H]+ | 8.08-8.14 (2 H, m), 6.82-6.88 (2 H, m), 4.58-4.60 (1 H, m), 3.55-3.85 (3 H, m), 3.10-3.27 (2 H, m), 1.95-2.05 (1 H, m), 1.63-1.88 (3 H, m), 1.46 (9 H, s) |
| 117 | tert-Butyl (S)-(1-(4-aminophenyl)piperidin-3-yl)carbamate | | Production Example 117 | Production Example 115 | 292 | [M + H]+ | 6.77-6.83 (2 H, m), 6.61-6.66 (2 H, m), 5.02-5.04 (1 H, m), 3.86-3.88 (1 H, m), 3.42-3.44 (2 H, m), 2.86-3.14 (4 H, m), 1.64-1.86 (4 H, m), 1.46 (9 H, s) |
| 118 | tert-Butyl (R)-(1-(4-aminophenyl)piperidin-3-yl)carbamate | | Production Example 117 | Production Example 116 | 292 | [M + H]+ | 6.78-6.83 (2 H, m), 6.61-6.67 (2 H, m), 5.02-5.04 (1 H, m), 3.86-3.88 (1 H, m), 3.42-3.44 (2 H, m), 2.86-3.14 (4 H, m), 1.50-1.87 (4 H, m), 1.46 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 119 | 2-(4-(4-Aminophenyl) piperazin-1-yl)-1-(piperidin-1-yl)ethan-1-one | | | | 303 | [M + H]+ | 6.78-6.82 (2 H, m), 6.63-6.67 (2 H, m), 3.41-3.53 (5 H, m), 3.22 (2 H, s), 3.05-3.08 (4 H, m), 2.64-2.68 (4 H, m), 1.57-1.64 (7 H, m) |
| 120 | tert-Butyl 4-(4-((4-(1-ethyl-3-(pyridin-3-yl)-1H-pyrazol-4-yl)pyrimidin-2-yl)amino)phenoxy)-3-fluoropiperidine-1-carboxylate | | | Production Example 3 | 560 | [M + H]+ | 8.84 (1 H, d, J = 2.4 Hz), 8.60-8.62 (1 H, m), 8.23 (1 H, d, J = 4.9 Hz), 7.98 (1 H, s), 7.87-7.91 (1 H, m), 7.34-7.40 (2 H, m), 7.29-7.34 (1 H, m), 6.93 (1 H, s), 6.87-6.90 (2 H, m), 6.56 (1 H, d, J = 4.9 Hz), 4.83-4.86 (0.5 H, m), 4.66-4.69 (0.5 H, m), 4.34-4.45 (1 H, m), 4.28 (2 H, q, J = 7.3 Hz), 4.01-4.11 (1 H, m), 3.77-3.83 (1 H, m), 3.37-3.51 (1 H, m), 3.19-3.23 (1 H, m), 2.01-2.09 (1 H, m), 1.79-1.86 (1 H, m), 1.57-1.62 (3 H, m), 1.48 (9 H, s) |
| 121 | tert-Butyl 4-(4-((4-(1-ethyl-3-(pyridin-3-yl)-1H-pyrazol-4-yl)pyrimidin-2-yl)amino)phenyl)piperazine-1-carboxylate | | | Production Example 3 Synthesis literature 14 | 527 | [M + H]+ | 8.85-8.86 (1 H, m), 8.22 (1 H, d, J = 5.4 Hz), 7.98 (1 H, s), 7.87-8.91 (1 H, m), 7.28-7.38 (3 H, m), 6.90 (1 H, s), 6.84-6.90 (2 H, m), 6.54 (1 H, d, J = 5.1 Hz), 4.24-4.32 (2 H, m), 3.57-3.61 (4 H, m), 3.57-3.61 (4 H, m), 1.59 (3 H, t, J = 7.3 Hz), 1.49 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 122 | tert-Butyl 4-(3-((4-(1-ethyl-3-(pyridin-3-yl)-1H-pyrazol-4-yl)pyrimidin-2-yl)amino)phenoxy)piperidine-1-carboxylate | | Production Example 121 | Production Example 3 Synthesis literature 21 | 542 | [M + H]+ | 8.84-8.85 (1 H, m), 8.62 (1 H, dd, J = 4.6, 1.6 Hz), 8.25 (1 H, d, J = 5.1 Hz), 8.03 (1 H, s), 7.88-7.93 (1 H, m), 7.31-7.36 (2 H, m), 7.14-7.20 (1 H, m), 7.02-7.06 (2 H, m), 6.55-6.60 (2 H, m), 4.43-4.50 (1 H, m), 4.24-4.32 (2 H, m), 3.66-3.75 (2 H, m), 3.30-3.39 (2 H, m), 1.90-1.93 (2 H, m), 1.79-1.80 (2 H, m), 1.60 (3 H, t, J = 7.3 Hz), 1.47 (9 H, s) |
| 123 | tert-Butyl 4-(4-((4-(1-ethyl-3-(pyridin-3-yl)-1H-pyrazol-4-yl)pyrimidin-2-yl)amino)-2-fluorophenyl)piperazine-1-carboxylate | | Production Example 121 | Production Example 3 Synthesis literature 22 | 545 | [M + H]+ | 8.82-8.83 (1 H, m), 8.61 (1 H, d, J = 4.9, 1.6 Hz), 8.24 (1 H, d, J = 5.1 Hz), 8.01 (1 H, s), 7.88-7.92 (1 H, m), 7.48-7.54 (1 H, m), 7.31-7.36 (1 H, m), 7.00-7.04 (1 H, m), 6.95 (1 H, s), 6.81-6.87 (1 H, m), 6.58 (1 H, d, J = 8.1 Hz), 4.25-4.33 (2 H, m), 3.60 (4 H, t, J = 5.1 Hz), 2.96-3.00 (4 H, m), 1.57-1.63 (3 H, m), 1.49 (9 H, s) |
| 124 | tert-Butyl 7-((4-(1-ethyl-3-(pyridin-3-yl)-1H-pyrazol-4-yl)pyrimidin-2-yl)amino)-3,4-dihydroquinoline-1(2H)-carboxylate | | Production Example 121 | Production Example 3 | 498 | [M + H]+ | 8.83-8.41 (1 H, m), 8.61 (1 H, dd, J = 1.6, 4.9 Hz), 8.21 (1 H, d, J = 5.4 Hz), 8.11 (1 H, s), 7.94 (1 H, d, J = 4.9 Hz), 7.86-7.91 (1 H, m), 7.30-7.35 (1 H, m), 7.18 (1 H, dd, J = 1.9, 8.4 Hz), 7.00 (1 H, s), 6.97 (1 H, d, J = 8.4 Hz), 6.50 (1 H, d, J = 5.1 Hz), 4.24-4.32 (2 H, m), 3.68-3.73 (2 H, m), 2.71-2.76 (2 H, m), 1.89-1.94 (2 H, m), 1.56-1.62 (3 H, m), 1.52 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 125 | tert-Butyl 6-((4-(1-ethyl-3-(pyridin-3-yl)-1H-pyrazol-4-yl)pyrimidin-2-yl)amino)-3,4-dihydroisoquinoline-2(1H)-carboxylate | | Production Example 121 | Production Example 3 Synthesis literature 13 | 498 | [M + H]+ | 8.85-8.86 (1 H, m), 8.60-8.62 (1 H, m), 8.24 (1 H, d, J = 5.1 Hz), 8.00 (1 H, s), 7.88-7.92 (1 H, m), 7.28-7.34 (3 H, m), 6.97-7.02 (2 H, m), 6.57 (1 H, d, J = 5.1 Hz), 4.53 (2 H, s), 4.24-4.33 (2 H, m), 3.62-3.64 (2 H, m), 2.77-2.79 (2 H, m), 1.58-1.63 (3 H, m), 1.50 (9 H, s) |
| 126 | tert-Butyl 7-((4-(1-ethyl-3-(pyridin-3-yl)-1H-pyrazol-4-yl)pyrimidin-2-yl)amino)-3,4-dihydroisoquinoline-2(1H)-carboxylate | | Production Example 121 | Production Example 3 Synthesis literature 23 | 498 | [M + H]+ | 8.84 (1 H, d, J = 2.2 Hz), 8.61 (1 H, dd, J = 4.9, 2.2 Hz), 8.24 (1 H, d, J = 5.4 Hz), 8.01 (1 H, s), 7.88-7.92 (1 H, m), 7.30-7.35 (2 H, m), 7.24-7.25 (1 H, m), 7.03 (1 H, d, J = 8.4 Hz), 6.96 (1 H, s), 6.56 (1 H, d, J = 5.1 Hz), 4.55 (2 H, s), 4.25-4.33 (2 H, m), 3.62-3.66 (2 H, m), 2.77-2.81 (2 H, m), 1.60 (3 H, t, J = 7.3 Hz), 1.50 (9 H, s) |
| 127 | tert-Butyl 7-((4-(1-ethyl-3-(pyridin-3-yl)-1H-pyrazol-4-yl)pyrimidin-2-yl)amino)-1,2,4,5-tetrahydro-3H-benzo[d]azepine-3-carboxylate | | Production Example 121 | Production Example 3 Synthesis literature 23 | 512 | [M + H]+ | 8.84-8.85 (1 H, m), 8.61-8.63 (1 H, m), 8.24 (1 H, d, J = 4.9 Hz), 8.01 (1 H, s), 7.88-7.93 (1 H, m), 7.29-7.36 (3 H, m), 7.02 (1 H, d, J = 8.4 Hz), 6.96 (1 H, s), 6.55 (1 H, d, J = 5.1 Hz), 4.24-4.33 (2 H, m), 3.54-3.56 (4 H, m), 2.85-2.87 (4 H, m), 1.60 (3 H, t, J = 7.3 Hz), 1.50 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 128 | tert-Butyl 3-(4-((4-(1-ethyl-3-(pyridin-3-yl)-1H-pyrazol-4-yl)pyrimidin-2-yl)amino)phenyl)-8-azabicyclo[3.2.1]octane-8-carboxylate | | Production Example 121 | Production Example 3 Synthesis literature 17 | 552 | [M + H]+ | 8.84-8.86 (1 H, m), 8.60-8.61 (1 H, m), 8.23 (1 H, d, J = 4.9 Hz), 8.00 (1 H, s), 7.88-7.92 (1 H, m), 7.39-7.42 (2 H, m), 7.30-7.35 (1 H, m), 7.07-7.14 (3 H, m), 6.55 (1 H, d, J = 5.1 Hz), 4.24-4.32 (4 H, m), 3.00-3.07 (1 H, m), 2.57-2.67 (1 H, m), 2.46-2.50 (1 H, m), 2.00-2.02 (2 H, m), 1.74-1.81 (4 H, m), 1.54-1.60 (3 H, m), 1.48 (9 H, s) |
| 129 | tert-Butyl 4-(4-((4-(1-(2,2-difluoroethyl)-3-(pyridin-3-yl)-1H-pyrazol-4-yl)pyrimidin-2-yl)amino)phenyl)piperazine-1-carboxylate | | Production Example 121 | Production Example 11 Synthesis literature 14 | 563 | [M + H]+ | 8.85 (1 H, d, J = 1.4 Hz), 8.62-8.64 (1 H, m), 8.25 (1 H, d, J = 4.9 Hz), 8.04 (1 H, s), 7.86-7.90 (1 H, m), 7.30-7.35 (4 H, m), 6.90 (1 H, s), 6.85 (2 H, d, J = 8.9 Hz), 5.99-6.54 (1 H, m), 4.56 (2 H, m), 3.57-3.61 (4 H, m), 3.05-3.09 (4 H, m), 1.49 (9 H, s) |
| 130 | tert-Butyl 4-(5-((4-(1-(2,2-difluoroethyl)-3-(pyridin-3-yl)-1H-pyrazol-4-yl)pyrimidin-2-yl)amino)pyridin-2-yl)piperazine-1-carboxylate | | Production Example 121 | Production Example 11 | 564 | [M + H]+ | 8.82-8.83 (1 H, m), 8.61-8.63 (1 H, m), 8.23-8.25 (2 H, m), 8.04 (1 H, s), 7.85-7.89 (1 H, m), 7.65-7.69 (1 H, m), 7.28-7.33 (1 H, m), 6.90 (1 H, s), 6.57 (2 H, d, J = 5.4 Hz), 5.99-6.43 (1 H, m), 4.50-4.62 (2 H, m), 3.45-3.58 (8 H, m), 1.49 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 131 | tert-Butyl 4-(4-((4-(1-ethyl-3-(pyridin-3-yl)-1H-pyrazol-4-yl)-5-fluoropyrimidin-2-yl)amino)phenyl)piperazine-1-carboxylate | | Production Example 121 | Production Example 114 Synthesis literature 14 | 545 | [M + H]+ | 8.87-8.88 (1 H, m), 8.54 (1 H, d, J = 4.9, 1.6 Hz), 8.22 (1 H, d, J = 3.0 Hz), 8.03 (1 H, d, J = 3.0 Hz), 7.85-7.89 (1 H, m), 7.20-7.25 (1 H, m), 7.07-7.12 (2 H, m), 6.71-6.75 (3 H, m), 4.26-4.34 (2 H, m), 3.56-3.60 (4 H, m), 3.02-3.06 (4 H, m), 1.57-1.63 (3 H, m), 1.49 (9 H, s) |
| 132 | tert-Butyl 4-(4-((4-(1-ethyl-3-(pyridin-3-yl)-1H-pyrazol-4-yl)pyrimidin-2-yl)amino)-2,6-difluorophenyl)piperazine-1-carboxylate | | Production Example 121 | Production Example 3 Synthesis literature 24 | 563 | [M + H]+ | |
| 133 | tert-Butyl 4-(5-((4-(1-ethyl-3-(pyridin-3-yl)-1H-pyrazol-4-yl)pyrimidin-2-yl)amino)pyridin-2-yl)piperazine-1-carboxylate | | Production Example 121 | Production Example 3 | 528 | [M + H]+ | 8.84 (1 H, d, J = 1.9 Hz), 8.59-8.61 (1 H, m), 8.26 (1 H, d, J = 2.7 Hz), 8.20 (1 H, d, J = 5.1 Hz), 7.98 (1 H, s), 7.86-7.90 (1 H, m), 7.69 (1 H, dd, J = 8.9, 2.7 Hz), 7.27-7.32 (1 H, m), 6.82 (1 H, s), 6.54-6.59 (2 H, m), 4.23-4.31 (2 H, m), 3.54-3.57 (4 H, m), 3.44-3.48 (4 H, m), 1.56-1.62 (3 H, m), 1.49 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 134 | tert-Butyl 4-(4-(4-(((4-(1-ethyl-3-(pyridin-3-yl)-1H-pyrazol-4-yl)pyrimidin-2-yl)amino)phenyl)-1H-pyrazol-1-yl)piperidine-1-carboxylate | | | Production Example 3 | 592 | [M + H]+ | 8.85-8.87 (1 H, m), 8.59-8.62 (1 H, m), 8.24 (1 H, d, J = 4.9 Hz), 8.00 (1 H, s), 7.87-7.92 (1 H, m), 7.75 (1 H, s), 7.63 (1 H, s), 7.48 (2 H, d, J = 8.4 Hz), 7.34 (2 H, d, J = 8.9 Hz), 7.29-7.32 (1 H, m), 7.10 (1 H, s), 6.59 (1 H, d, J = 5.1 Hz), 4.25-4.33 (5 H, m), 2.86-2.96 (2 H, m), 2.16-2.19 (1 H, m), 1.93-2.04 (2 H, m), 1.58-1.63 (3 H, m), 1.49 (9 H, s) |
| 135 | N-(4-(4-(oxetan-3-yl)piperazin-1-yl)phenyl)-4-(3-(pyridin-3-yl)-1H-pyrazol-4-yl)pyrimidin-2-amine | | Production Example 121 | Production Example 2 Synthesis literature 25 | 455 | [M + H]+ | 8.85-8.87 (1 H, m), 8.64-8.66 (1 H, m), 8.26 (1 H, d, J = 5.4 Hz), 8.15 (1 H, s), 7.87-7.91 (1 H, m), 7.31-7.35 (3 H, m), 6.83-6.91 (3 H, m), 6.60 (1 H, d, J = 4.9 Hz), 4.65-4.74 (4 H, m), 3.52-3.62 (1 H, m), 3.17-3.21 (4 H, m), 2.50-2.54 (4 H, m) |
| 136 | tert-Butyl (S)-(1-(4-(((4-(1-ethyl-3-(pyridin-3-yl)-1H-pyrazol-4-yl)pyrimidin-2-yl)amino)phenyl)piperidin-3-yl)carbamate | | Production Example 121 | Production Example 3 Production Example 117 | 541 | [M + H]+ | 8.84-8.85 (1 H, m), 8.60-8.63 (1 H, m), 8.21 (1 H, d, J = 5.1 Hz), 7.99 (1 H, s), 7.87-7.91 (1 H, m), 7.29-7.37 (3 H, m), 6.85-6.89 (3 H, m), 6.51 (1 H, d, J = 4.9 Hz), 4.31-4.33 (1 H, m), 4.24-4.32 (2 H, m), 3.90-3.92 (1 H, m), 3.25-3.27 (1 H, m), 2.96-3.07 (3 H, m), 1.72-1.80 (3 H, m), 1.57-1.62 (4 H, m), 1.47 (9 H, s) |
| 137 | tert-Butyl (R)-(1-(4-(((4-(1-ethyl-3-(pyridin-3-yl)-1H-pyrazol-4-yl)pyrimidin-2-yl)amino)phenyl)piperidin-3-yl)carbamate | | Production Example 121 | Production Example 3 Production Example 118 | 541 | [M + H]+ | 8.84-8.85 (1 H, m), 8.60-8.63 (1 H, m), 8.21 (1 H, d, J = 5.1 Hz), 7.99 (1 H, s), 7.87-7.99 (1 H, m), 7.34-7.37 (2 H, m), 7.29-7.33 (1 H, m), 6.90 (1 H, s), 6.87 (2 H, d, J = 8.9 Hz), 6.51 (1 H, d, J = 5.1 Hz), 4.95-4.97 (1 H, m), 4.24-4.32 (2 H, m), 3.87-3.89 (1 H, m), 3.26-3.28 (1 H, m), 2.92-3.07 (3 H, m), 1.72-1.85 (3 H, m), 1.53-1.60 (3 H, m), 1.47 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 138 | tert-Butyl 3-(4-((4-(1-ethyl-3-(pyridin-3-yl)-1H-pyrazol-4-yl)pyrimidin-2-yl)amino)phenyl)piperidine-1-carboxylate | | Production Example 121 | Production Example 3 Synthesis literature 26 | 526 | [M + H]+ | 8.84-8.86 (1 H, m), 8.60-8.63 (1 H, m), 8.24 (1 H, d, J = 5.4 Hz), 8.00 (1 H, s), 7.87-7.91 (1 H, m), 7.42 (2 H, d, J = 8.6 Hz), 7.30-7.35 (2 H, m), 7.13 (2 H, d, J = 8.6 Hz), 7.00 (1 H, s), 6.56 (1 H, d, J = 5.4 Hz), 4.25-4.33 (2 H, m), 4.13-4.17 (2 H, m), 3.44-3.51 (1 H, m), 2.63-2.73 (3 H, m), 1.64-1.99 (3 H, m), 1.57-1.63 (3 H, m), 1.47 (9 H, m) |
| 139 | N-(4-(4-(2-methoxyethyl)piperazin-1-yl)phenyl)-4-(1-ethyl-3-(pyridin-3-yl)-1H-pyrazol-4-yl)pyrimidin-2-amine | | Production Example 121 | Production Example 2 | | | 8.85-8.86 (1 H, m), 8.64-8.66 (1 H, m), 8.25 (1 H, d, J = 5.1 Hz), 8.15 (1 H, s), 7.87-7.91 (1 H, m), 7.29-7.35 (3 H, m), 6.87 (1 H, s), 6.84 (2 H, d, J = 9.2 Hz), 6.59 (1 H, d, J = 5.4 Hz), 3.57 (2 H, t, J = 5.7 Hz), 3.38 (3 H, s), 3.16-3.20 (4 H, m), 2.64-2.70 (6 H, m) |
| 140 | tert-Butyl 4-(2-cyano-4-((4-(1-ethyl-3-(pyridin-3-yl)-1H-pyrazol-4-yl)pyrimidin-2-yl)amino)phenyl)piperazine-1-carboxylate | | Production Example 121 | Production Example 3 Synthesis literature 27 | 552 | [M + H]+ | |

TABLE 1-continued

| Production example number | Compound name | Structural formula | Synthesis method description example | Raw material | MS | Ion | 1HNMR chemical shift value |
|---|---|---|---|---|---|---|---|
| 141 | tert-Butyl 4-(4-((4-((1-ethyl-3-(pyridin-3-yl)-1H-pyrazol-4-yl)pyrimidin-2-yl)amino)-2-methylphenyl)piperazine-1-carboxylate | | Production Example 121 | Production Example 3 Synthesis literature 12 | 541 | [M + H]+ | 8.85 (1 H, d, J = 1.1 Hz), 8.60-8.62 (1 H, m), 8.22 (1 H, d, J = 4.9 Hz), 8.00 (1 H, s), 7.87-7.92 (1 H, m), 7.29-7.36 (3 H, m), 6.91 (2 H, d, J = 4.9 Hz), 6.53 (1 H, d, J = 4.9 Hz), 4.24-4.32 (2 H, m), 3.56 (4 H, t, J = 4.9 Hz), 2.80-2.83 (4 H, m), 2.29 (3 H, s), 1.60 (3 H, t, J = 7.3 Hz), 1.49 (9 H, s) |
| 142 | tert-Butyl 4-(3-((4-(1-ethyl-3-(pyridin-3-yl)-1H-pyrazol-4-yl)pyrimidin-2-yl)amino)phenyl)piperazine-1-carboxylate | | Production Example 121 | Production Example 3 Synthesis literature 28 | 527 | [M + H]+ | 8.85-8.86 (1 H, m), 8.60-8.63 (1 H, m), 8.23 (1 H, d, J = 5.4 Hz), 8.03 (1 H, s), 7.88-7.92 (1 H, m), 7.30-7.35 (1 H, m), 7.25-7.26 (1 H, d, J = 2.2 Hz), 7.14-7.20 (1 H, m), 7.10 (1H, s), 7.00-7.03 (1 H, m), 6.60-6.63 (1 H, m), 6.53 (1 H, d, J = 4.9 Hz), 4.23-4.31 (2 H, m), 3.14-3.18 (4 H, m), 3.01-3.06 (4 H, m), 1.59 (3 H, t, J = 7.3 Hz), 1.80 (9 H, s) |
| 143 | tert-Butyl 4-(4-((4-(1-ethyl-3-(pyridin-3-yl)-1H-pyrazol-4-yl)pyrimidin-2-yl)amino)phenethyl)piperazine-1-carboxylate | | Production Example 121 | Production Example 3 Synthesis literature 29 | 555 | [M + H]+ | 8.84-8.52 (1 H, m), 8.24 (1 H, d, J = 4.9 Hz), 8.00 (1 H, s), 7.87-7.92 (1 H, m), 7.39 (2 H, J = 8.6 Hz), 7.29-7.35 (1 H, m), 7.10 (2 H, d, J = 8.6 Hz), 7.01 (1 H, s), 6.56 (1 H, d, J = 5.1 Hz), 4.27-4.32 (2 H, m), 3.45-3.49 (4 H, m), 2.74-2.77 (2 H, m), 2.58-2.62 (2 H, m), 2.45-2.49 (4 H, m), 1.47-1.60 (3 H, m), 1.46 (9 H, s) |

TABLE 1-continued

| Production example number | Compound name | Structural formula | Synthesis method description example | Raw material | MS | Ion | 1HNMR chemical shift value |
|---|---|---|---|---|---|---|---|
| 144 | N-(4-(4-(cyclopropylmethyl)piperazin-1-yl)phenyl)-4-(3-(pyridin-3-yl)-1H-pyrazol-4-yl)pyrimidin-2-amine | | Production Example 121 | Production Example 3 Synthesis literature 30 | 453 | [M + H]+ | |
| 145 | N-(4-bromophenyl)-4-(1-ethyl-3-(pyridin-3-yl)-1H-pyrazol-4-yl)pyrimidin-2-amine | | Production Example 121 | Production Example 3 | 421 | [M + H]+ | 8.85-8.86 (1 H, m), 8.59-8.62 (1 H, m), 8.43 (1 H, s), 8.18 (1 H, d, J = 5.1 Hz), 7.98 (1 H, s), 7.88-7.92 (1 H, m), 7.28-7.40 (5 H, m), 6.61 (1 H, d, J = 5.1 Hz), 4.24-4.32 (2 H, m), 1.57-1.62 (3 H, m) |
| 146 | N-(4-(3-bromo-1H-1,2,4-triazol-1-yl)phenyl)-4-(1-ethyl-3-(pyridin-3-yl)-1H-pyrazole-4-yl)pyrimidin-2-amine | | Production Example 121 | Production Example 3 Synthesis literature 31 | 488 | [M + H]+ | 8.43-8.50 (1 H, m), 8.60-8.62 (1 H, m), 8.36 (1 H, s), 8.30 (1 H, d, J = 5.4 Hz), 8.00 (1 H, s), 7.89-7.92 (1 H, m), 7.63 (2 H, d, J = 8.9 Hz), 7.48 (2 H, d, J = 8.9 Hz), 7.29-7.36 (1 H, m), 7.16 (1 H, s), 6.68 (1 H, d, J 5.1 Hz), 4.26-4.34 (2 H, m), 1.59-1.64 (3 H, m) |

TABLE 1-continued

| Production example number | Compound name | Structural formula | Synthesis method description example | Raw material | MS | Ion | 1HNMR chemical shift value |
|---|---|---|---|---|---|---|---|
| 147 | tert-Butyl 4-(4-((4-(1-ethyl-3-(pyridin-3-yl)-1H-pyrazol-4-yl)pyrimidin-2-yl)amino)phenyl)piperidine-1-carboxylate | | Production Example 121 | Production Example 3 Synthesis literature 12 | 426 | [M + H]+ | 8.85 (1 H, dd, J = 2.2, 0.8 Hz), 8.60-8.63 (1 H, m), 8.24 (1 H, d, J = 5.4 Hz), 8.00 (1 H, s), 7.87-7.91 (1 H, m), 7.41 (2 H, d, J = 8.6 Hz), 7.30-7.34 (1 H, m), 7.10 (2 H, d, J = 8.6 Hz), 6.97 (1 H, s), 6.57 (1 H, d, J = 5.1 Hz), 4.25-4.33 (4 H, m), 2.75-2.84 (2 H, m), 2.57-2.65 (1 H, m), 1.79-1.83 (2 H, m), 1.58-1.63 (5 H, m), 1.49 (9 H, s) |
| 148 | 2-(6-((4-(1-Ethyl-3-(pyridin-3-yl)-1H-pyrazol-4-yl)pyrimidin-2-yl)amino)-3,4-dihydroisoquinolin-2(1H)-yl)-2-oxoethyl acetate | | Example 168 | Synthesis literature 50 | 498 | [M + H]+ | 8.86 (1 H, s), 8.61 (1 H, d, J = 4.6 Hz), 8.26 (1 H, d, J = 5.1 Hz), 7.99 (1 H, s), 7.90 (1 H, d, J = 8.1 Hz), 7.36 (1 H, s), 7.29-7.33 (2 H, m), 6.96-7.06 (2 H, m), 6.60 (1 H, d, J = 5.4 Hz), 4.81 (2 H, s), 4.68 (1 H, s), 4.50 (1 H, s), 4.28 (2 H, q, J = 7.3 Hz), 3.80-3.84 (1 H, m), 3.59 (1 H, t, J = 7.3 Hz), 2.80-2.87 (2 H, m), 2.20 (3 H, s), 1.60 (3 H, t, J = 7.0 Hz) |
| 149 | 2-(4-(4-((4-(1-Ethyl-3-(pyridin-3-yl)-1H-pyrazol-4-yl)pyrimidin-2-yl)amino)phenyl)piperazin-1-yl)-2-oxoethyl acetate | | Production Example 148 | Example 151 Synthesis literature 50 | 527 | [M + H]+ | 8.84-8.86 (1 H, m), 8.23 (1 H, d, J = 5.1 Hz), 7.98 (1 H, s), 7.86-7.91 (1 H, m), 7.37 (2 H, d, J = 8.9 Hz), 7.26-7.33 (1 H, m), 6.83-6.90 (3 H, m), 6.55 (1 H, d, J = 5.4 Hz), 4.78 (2 H, s), 4.24-4.32 (2 H, m), 3.78-3.80 (2 H, m), 3.55-3.57 (2 H, m), 3.12-3.14 (4 H, m), 2.20 (3 H, s), 1.58-1.62 (3 H, m) |

Example 1

A mixture containing 4-nitrobenzoyl chloride (167 mg), 1-(tert-butyl)piperazine (142 mg), triethylamine (1.0 mL) and dichloromethane (10 mL) was stirred at room temperature for 1 hour, and then concentrated under a reduced pressure, the obtained residue was purified through silica gel column chromatography (elution solvent: dichloromethane-ethyl acetate), and thereby 4-(tert-butyl)piperazin-1-yl)(4-nitrophenyl)methanone (246 mg) as a colorless powder was obtained.

A mixture containing (4-(tert-butyl)piperazin-1-yl)(4-nitrophenyl)methanone (240 mg), 5% Pd/C (40 mg), and methanol (15 mL) was stirred at room temperature for 3 hours under a hydrogen atmosphere. Insoluble substances in the reaction mixture were filtered off. Then, the filtrate was concentrated under a reduced pressure, the obtained residue was purified through aminopropyl silica gel column chromatography (elution solvent: dichloromethane-ethyl acetate), and thereby (4-aminophenyl) (4-(tert-butyl)piperazin-1-yl)methanone (205 mg) as a colorless powder was obtained.

A mixture containing (4-aminophenyl)(4-(tert-butyl)piperazin-1-yl)methanone (157 mg), 2-chloro-4-(1-ethyl-3-(pyridin-3-yl)-1H-pyrazol-4-yl)pyrimidine (Production Example 3, 143 mg), potassium phosphate (318 mg) and 1,4-dioxane (5 mL) was degassed by repeating depressurization and nitrogen substitution, and tris(dibenzylideneacetone)dipalladium(O)(46 mg) and 4,5-bis(diphenylphosphino)-9,9-dimethylxanthene (87 mg) were then added thereto, and the mixture was stirred at 100° C. for 16 hours. Insoluble substances in the reaction mixture were filtered off. Then, the filtrate was concentrated under a reduced pressure, the obtained residue was purified through silica gel column chromatography (elution solvent: dichloromethane-methanol-ammonia water), and thereby (4-(tert-butyl)piperazin-1-yl)(4-((4-(1-ethyl-3-(pyridin-3-yl)-1H-pyrazol-4-yl)pyrimidin-2-yl)amino)phenyl)methanone (152 mg) as a colorless solid was obtained.

Example 2

A mixture containing 2-chloro-4-(1-ethyl-3-(pyridin-3-yl)-1H-pyrazol-4-yl)pyrimidine (Production Example 3, 71 mg), (4-aminophenyl) (piperidin-1-yl)methanone (Synthesis literature 32, 61 mg), potassium phosphate (106 mg) and 1,4-dioxane was degassed by repeating depressurization and nitrogen substitution, and tris(dibenzylideneacetone)dipalladium(O) (23 mg) and 4,5-bis(diphenylphosphino)-9,9-dimethylxanthene (43 mg) were then added thereto, and the mixture was stirred at 100° C. for 14 hours. Insoluble substances in the reaction mixture were filtered off. Then, the filtrate was concentrated under a reduced pressure, the obtained residue was purified through aminopropyl silica gel column chromatography (elution solvent: dichloromethane-ethyl acetate), and thereby (4-((4-(1-ethyl-3-(pyridin-3-yl)-1H-pyrazol-4-yl)pyrimidin-2-yl)amino)phenyl)(piperidin-1-yl)methanone (35 mg) as a colorless solid was obtained.

Example 3

In the same manner as in Example 2, (4-((4-(1-ethyl-3-(pyridin-3-yl)-1H-pyrazol-4-yl)pyrimidin-2-yl)amino)phenyl)(4-(4-fluorophenyl)piperazin-1-yl)methanone was obtained using (4-aminophenyl)(4-(4-fluorophenyl)piperazin-1-yl)methanone (Synthesis literature 33) in place of (4-aminophenyl)(piperidin-1-yl)methanone.

Example 4

In the same manner as in Example 2, 4-((4-(1-ethyl-3-(pyridin-3-yl)-1H-pyrazol-4-yl)pyrimidin-2-yl)amino)-N-methyl-N-(1-methylpiperidin-4-yl)benzamide was obtained using 4-amino-N-methyl-N-(1-methylpiperidin-4-yl)benzamide (Synthesis literature 34) in place of (4-aminophenyl)(piperidin-1-yl)methanone.

Example 7

In the same manner as in Example 2, N-(4-(1-ethyl-3-(pyridin-3-yl)-1H-pyrazol-4-yl)pyrimidin-2-yl)-6-methyl-5,6,7,8-tetrahydro-1,6-naphthyridin-2-amine was obtained using 4-(1-ethyl-3-(pyridin-3-yl)-1H-pyrazol-4-yl)pyrimidin-2-amine (Production Example 74) and 2-chloro-6-methyl-5,6,7,8-tetrahydro-1,6-naphthyridine (Synthesis literature 35).

Example 8

A mixture containing 2-chloro-4-(1-(oxetan-3-yl)-3-(pyridin-3-yl)-1H-pyrazol-4-yl)pyrimidine (Production Example 12, 43 mg), 2-methyl-1,2,3,4-tetrahydroisoquinolin-6-amine (Synthesis literature 36, 22 mg), 4,5-bis(diphenylphosphino)-9,9-dimethylxanthene (3.3 mg), sodium tert-butoxide (21 mg), tris(dibenzylideneacetone)dipalladium (O) (2.5 mg) and 1,4-dioxane (0.8 mL) was stirred at 100° C. for 4 hours under an argon atmosphere. The reaction mixture was concentrated under a reduced pressure, and the residue was then purified by silica gel thin layer chromatography (developing solvent: dichloromethane-methanol), and thereby 2-methyl-N-(4-(1-(oxetan-3-yl)-3-(pyridin-3-yl)-1H-pyrazol-4-yl)pyrimidin-2-yl)-1,2,3,4-tetrahydroisoquinolin-6-amine (7.3 mg) was obtained.

Example 12

A mixture containing 4-(4-nitrophenyl)piperidine (Synthesis literature 37, 156 mg), 1-bromo-2-methoxyethane (158 mg), N,N-diisopropylethylamine (108 mg) and acetonitrile (4 mL) was stirred at room temperature overnight and then at 100° C. for 15 minutes under microwave radiation. The reaction mixture was concentrated under a reduced pressure, the obtained residue was purified through silica gel column chromatography (elution solvent: dichloromethane-methanol), and thereby 1-(2-methoxyethyl)-4-(4-nitrophenyl)piperidine (140 mg) was obtained.

10% Pd/C (56 mg) was added to a mixture containing 1-(2-methoxyethyl)-4-(4-nitrophenyl)piperidine (140 mg) and ethanol (8 mL) and the mixture was stirred at room temperature overnight under a hydrogen atmosphere. Insoluble substances in the reaction mixture were filtered off. Then, the filtrate was concentrated under a reduced pressure, and thereby 4-(1-(2-methoxyethyl)piperidin-4-yl)aniline (129 mg) was obtained.

A mixture containing 4-(1-(2-methoxyethyl)piperidin-4-yl)aniline (9.0 mg), 2-chloro-4-(1-(oxetan-3-yl)-3-(pyridin-3-yl)-1H-pyrazol-4-yl)pyrimidine (Production Example 12, 12 mg), 4,5-bis(diphenylphosphino)-9,9-dimethylxanthene (0.93 mg), sodium tert-butoxide (5.8 mg), tris(dibenzylideneacetone)dipalladium (O) (0.7 mg) and 1,4-dioxane (0.8 mL) was stirred at 100° C. for 4 hours under an argon atmosphere. The reaction mixture was concentrated under a reduced pressure, the obtained residue was purified by silica gel thin layer chromatography (developing solvent: dichloromethane-methanol-ammonia water), and thereby N-(4-(1-(2-methoxyethyl)piperidin-4-yl)phenyl)-4-(1-(oxetan-3-yl)-3-(pyridin-3-yl)-1H-pyrazol-4-yl)pyrimidin-2-amine (3.94 mg) was obtained.

Example 14

In the same manner as in Example 8, 4-(1-ethyl-3-(pyridin-3-yl)-1H-pyrazol-4-yl)-N-(4-(imidazo[1,2-a]pyridin-2-yl)phenyl)pyrimidin-2-amine was obtained using 2-chloro-4-(1-ethyl-3-(pyridin-3-yl)-1H-pyrazol-4-yl)pyrimidine (Production Example 3) and 4-(imidazo[1,2-a]pyridin-2-yl)aniline (Synthesis literature 38).

Example 15

A mixture containing 2-chloro-4-(1-ethyl-3-(pyridin-3-yl)-1H-pyrazol-4-yl)pyrimidine (Production Example 3, 109 mg), 4-(4-(oxetan-3-yl)piperazin-1-yl)aniline (Synthesis literature 25, 103 mg) and methanol (1 mL) was stirred in a sealed tube at 100° C. overnight. The reaction mixture was concentrated under a reduced pressure, the residue was purified through aminopropyl silica gel column chromatography (elution solvent: dichloromethane-methanol), and thereby 4-(1-ethyl-3-(pyridin-3-yl)-1H-pyrazol-4-yl)-N-(4-(4-(oxetan-3-yl)piperazin-1-yl)phenyl)pyrimidin-2-amine (82 mg) as a yellow solid was obtained.

Example 16

In the same manner as in Example 15, 4-(1-ethyl-3-(pyridin-3-yl)-1H-pyrazol-4-yl)-N-(4-(4-isopropylpiperazin-1-yl)phenyl)pyrimidin-2-amine was obtained using 4-(4-isopropylpiperazin-1-yl)aniline (commercially available from OTAVA chemicals) in place of 4-(4-(oxetan-3-yl)piperazin-1-yl)aniline.

Example 17

In the same manner as in Example 15, 4-(1-ethyl-3-(pyridin-3-yl)-1H-pyrazol-4-yl)-N-(4-(4-(2-methoxyethyl)piperazin-1-yl)phenyl)pyrimidin-2-amine was obtained using 4-(4-(2-methoxyethyl)piperazin-1-yl)aniline (commercially available from OTAVA chemicals) in place of 4-(4-(oxetan-3-yl)piperazin-1-yl)aniline.

Example 19

In the same manner as in Example 15, N-(4-(4-benzylpiperazin-1-yl)phenyl)-4-(1-ethyl-3-(pyridin-3-yl)-1H-pyrazol-4-yl)pyrimidin-2-amine was obtained using 4-(4-benzylpiperazin-1-yl)aniline (commercially available from BePharm Ltd.) in place of 4-(4-(oxetan-3-yl)piperazin-1-yl)aniline.

Example 20

In the same manner as in Example 15, 4-(1-ethyl-3-(pyridin-3-yl)-1H-pyrazol-4-yl)-N-(4-(4-(4-methylpiperazin-1-yl)pyrimidin-1-yl)phenyl)pyrimidin-2-amine was obtained using 4-(4-(4-methylpiperazin-1-yl)piperidin-1-yl)aniline (Synthesis literature 39) in place of 4-(4-(oxetan-3-yl)piperazin-1-yl)aniline.

Example 21

A mixture containing 1-fluoro-4-nitrobenzene (109 mg), tert-butyl 2,7-diazaspiro[3.5]nonane-2-carboxylate (commercially available from BePharm Ltd., 175 mg), potassium carbonate (214 mg) and DMF (4 mL) was stirred at 80° C. overnight. The reaction mixture was cooled to room temperature and ethyl acetate was then added thereto, and washing with water was performed. The organic layer was dried with anhydrous sodium sulfate and then concentrated under a reduced pressure, and thereby tert-butyl 7-(4-nitrophenyl)-2,7-diazaspiro[3.5]nonane-2-carboxylate (226 mg) was obtained.

Trifluoroacetic acid (370 mg) was added to a mixture containing tert-butyl 7-(4-nitrophenyl)-2,7-diazaspiro[3.5]nonane-2-carboxylate (226 mg) and dichloromethane (5 mL) under ice cooling, the mixture was stirred at room temperature overnight, and a saturated sodium bicarbonate aqueous solution was then added to the reaction mixture, and extraction was performed using dichloromethane. The organic layer was washed with a saturated saline solution, and dried over anhydrous sodium sulfate and then concentrated under a reduced pressure. The obtained residue was purified through aminopropyl silica gel column chromatography (elution solvent: dichloromethane-methanol-ammonia water), and thereby 7-(4-nitrophenyl)-2,7-diazaspiro[3.5]nonane (147 mg) as a yellow solid was obtained.

Acetyl chloride (16 mg) was added to a mixture containing 7-(4-nitrophenyl)-2,7-diazaspiro[3.5]nonane (50 mg), triethylamine (23 mg) and dichloromethane (1 mL), and the mixture was stirred at room temperature for 3.5 hours. Dichloromethane was added to the reaction mixture, and washing with water was performed. The organic layer was dried over anhydrous sodium sulfate and then concentrated under a reduced pressure, and thereby 1-(7-(4-nitrophenyl)-2,7-diazaspiro[3.5]nonan-2-yl)ethan-1-one (35 mg) was obtained.

Ethanol (3 mL) and 5% Pd/C (4 mg) were sequentially added thereto, and the mixture was stirred at room temperature overnight under a hydrogen atmosphere. Insoluble substances in the reaction mixture were filtered off. Then, the filtrate was concentrated under a reduced pressure, and thereby a brown solid (30 mg) containing 1-(7-(4-aminophenyl)-2,7-diazaspiro[3.5]nonan-2-yl)ethan-1-one was obtained.

2-Chloro-4-(1-ethyl-3-(pyridin-3-yl)-1H-pyrazol-4-yl)pyrimidine (Production Example 3, 30 mg) and methanol (1.0 mL) were added thereto and the mixture was stirred at 100° C. overnight. The reaction mixture was concentrated under a reduced pressure, the obtained residue was sequentially purified through aminopropyl silica gel column chromatography (elution solvent: dichloromethane-methanol) and silica gel column chromatography (elution solvent: dichloromethane-methanol), and thereby 1-(7-(4-((4-(1-ethyl-3-(pyridin-3-yl)-1H-pyrazol-4-yl)pyrimidin-2-yl)amino)phenyl)-2,7-diazaspiro[3.5]nonan-2-yl)ethan-1-one (27 mg) as a yellow solid was obtained.

Example 22

In the same manner as in Example 15, 4-(1-ethyl-3-(pyridin-3-yl)-1H-pyrazol-4-yl)-N-(4-morpholinophenyl)pyrimidin-2-amine was obtained using 4-morpholino aniline (commercially available from Tokyo Chemical Industry Co., Ltd.) in place of 4-(4-(oxetan-3-yl)piperazin-1-yl)aniline.

Example 24

In the same manner as in Example 15, N-(3-(2-(dimethylamino)ethoxy)phenyl)-4-(1-ethyl-3-(pyridin-3-yl)-1H-pyrazol-4-yl)pyrimidin-2-amine was obtained using 3-(2-

(dimethylamino)ethoxy)aniline (commercially available from Enamine) in place of 4-(4-(oxetan-3-yl)piperazin-1-yl)aniline.

Example 25

In the same manner as in Example 15, N-(4-(2-morpholinoethoxy)phenyl)-4-(3-(pyridin-3-yl)-1H-pyrazol-4-yl)pyrimidin-2-amine was obtained using 4-(2-morpholinoethoxy)aniline (commercially available from Maybridge) in place of 4-(4-(oxetan-3-yl)piperazin-1-yl)aniline.

Example 26

In the same manner as in Example 15, 4-(1-ethyl-3-(pyridin-3-yl)-1H-pyrazol-4-yl)-N-(4-(3-methyl-1H-1,2,4-triazol-1-yl)phenyl)pyrimidin-2-amine was obtained using 4-(3-methyl-1H-1,2,4-triazol-1-yl)aniline (Synthesis literature 40) in place of 4-(4-(oxetan-3-yl)piperazin-1-yl)aniline.

Example 27

A mixture containing 4-(4-nitrophenyl)-1H-pyrazole (commercially available from Combi-Blocks, 963 mg), iodoethane (0.532 mL), potassium carbonate (1.41 g) and DMF (10 mL) was stirred at 60° C. for 9 hours. Water was added to the reaction mixture, and extraction was performed using ethyl acetate. Then, the organic layer was washed with a saturated saline solution, and dried over anhydrous sodium sulfate. A solvent was distilled off, the obtained residue was purified through silica gel column chromatography (elution solvent: hexane-ethyl acetate), and thereby 1-ethyl-4-(4-nitrophenyl)-1H-pyrazole (752 mg) as a red-brown solid was obtained.

5% Pd/C (200 mg) was added to a mixture containing 1-ethyl-4-(4-nitrophenyl)-1H-pyrazole (750 mg), ethanol (5 mL) and THF (5 mL), and the mixture was stirred at room temperature overnight under a hydrogen atmosphere. Insoluble substances in the reaction mixture were filtered off. Then, the filtrate was concentrated under a reduced pressure, and thereby 4-(1-ethyl-1H-pyrazol-4-yl)aniline (637 mg) was obtained.

A mixture containing 2-chloro-4-(1-ethyl-3-(pyridin-3-yl)-1H-pyrazol-4-yl)pyrimidine (Production Example 3, 136 mg), 4-(1-ethyl-1H-pyrazol-4-yl)aniline (107 mg) and methanol (1 mL) was stirred in a sealed tube at 90° C. overnight. The reaction mixture was concentrated under a reduced pressure, the obtained residue was purified through silica gel chromatography (elution solvent: dichloromethane-methanol), and thereby N-(4-(1-ethyl-1H-pyrazol-4-yl)phenyl)-4-(1-ethyl-3-(pyridin-3-yl)-1H-pyrazol-4-yl)pyrimidin-2-amine (66 mg) as a pale red solid was obtained.

Example 30

A mixture containing 4-(4-nitrophenyl)-1H-pyrazole (commercially available from Combi-Blocks, 110 mg), 10% Pd/C (11 mg) and methanol (5 mL) was stirred at room temperature for 4 hours under a hydrogen atmosphere. Insoluble substances in the reaction mixture were filtered off. Then, the filtrate was concentrated under a reduced pressure, and thereby 4-(1H-pyrazol-4-yl)aniline (90 mg) as a brown solid was obtained.

A mixture containing 4-(1H-pyrazol-4-yl)aniline (77 mg), 2-chloro-4-(1-ethyl-3-(pyridin-3-yl)-1H-pyrazol-4-yl)pyrimidine (Production Example 3, 115 mg) and methanol (0.5 mL) was stirred at 90° C. overnight. The reaction mixture was concentrated under a reduced pressure, the obtained residue was purified through silica gel column chromatography (elution solvent: dichloromethane-methanol), and thereby N-(4-(1H-pyrazol-4-yl)phenyl)-4-(1-ethyl-3-(pyridin-3-yl)-1H-pyrazol-4-yl)pyrimidin-2-amine (61 mg) as a yellow solid was obtained.

Example 32

In the same manner as in Example 15, N-(4-(4-cyclopropylpiperazin-1-yl)phenyl)-4-(1-ethyl-3-(pyridin-3-yl)-1H-pyrazol-4-yl)pyrimidin-2-amine was obtained using 4-(4-cyclopropylpiperazin-1-yl)aniline (Synthesis literature 41) in place of 4-(4-(oxetan-3-yl)piperazin-1-yl)aniline.

Example 34

In the same manner as in Example 15, 4-(1-ethyl-3-(pyridin-3-yl)-1H-pyrazol-4-yl)-N-(3-(4-methylpiperazin-1-yl)phenyl)pyrimidin-2-amine was obtained using 3-(4-methylpiperazin-1-yl)aniline (commercially available from Apollo Scientific) in place of 4-(4-(oxetan-3-yl)piperazin-1-yl)aniline.

Example 35

In the same manner as in Example 15, 4-(1-(2-methoxyethyl)-3-(pyridin-3-yl)-1H-pyrazol-4-yl)-N-(4-(4-methylpiperazin-1-yl)phenyl)pyrimidin-2-amine was obtained using 2-chloro-4-(1-(2-methoxyethyl)-3-(pyridin-3-yl)-1H-pyrazol-4-yl)pyrimidine (Production Example 5) and 4-(4-methylpiperazin-1-yl)aniline (commercially available from Apollo Scientific).

Example 38

In the same manner as in Example 15, N-(4-(1H-1,2,4-triazol-1-yl)phenyl)-4-(1-ethyl-3-(pyridin-3-yl)-1H-pyrazol-4-yl)pyrimidin-2-amine was obtained using 4-(1H-1,2,4-triazol-1-yl)aniline (commercially available from Ark Pharm, Inc) in place of 4-(4-(oxetan-3-yl)piperazin-1-yl)aniline.

Example 39

A mixture containing 1-fluoro-4-nitrobenzene (282 mg), 3,5-dimethyl-1H-1,2,4-triazole (194 mg), potassium carbonate (552 mg) and DMF (6 mL) was stirred at 80° C. overnight. The reaction mixture was cooled to room temperature and ethyl acetate was then added thereto, and washing with water was performed. The organic layer was dried over anhydrous sodium sulfate and concentrated under a reduced pressure, and thereby 3,5-dimethyl-1-(4-nitrophenyl)-1H-1,2,4-triazole (330 mg) was obtained.

Ethanol (8 mL) and 5% Pd/C (60 mg) were sequentially added thereto, and the mixture was stirred at room temperature for 5 hours under a hydrogen atmosphere. Insoluble substances in the reaction mixture were filtered off. Then, the filtrate was concentrated under a reduced pressure, and thereby 4-(3,5-dimethyl-1H-1,2,4-triazol-1-yl)aniline (273 mg) as a colorless solid was obtained.

A mixture containing 4-(3,5-dimethyl-1H-1,2,4-triazol-1-yl)aniline (109 mg), 2-chloro-4-(1-ethyl-3-(pyridin-3-yl)-1H-pyrazol-4-yl)pyrimidine (Production Example 3, 150 mg) and acetic acid (1.0 mL) was stirred at 100° C. overnight. The reaction mixture was concentrated under a reduced pressure, the obtained residue was purified through aminopropyl silica gel column chromatography (elution solvent: dichloromethane-methanol), and thereby N-(4-(3,5-dimethyl-1H-1,2,4-triazol-1-yl)phenyl)-4-(1-ethyl-3-(pyridin-3-yl)-1H-pyrazol-4-yl)pyrimidin-2-amine (34 mg) as a yellow solid was obtained.

Example 40

In the same manner as in Example 15, N-(3-((dimethylamino)methyl)phenyl)-4-(1-ethyl-3-(pyridin-3-yl)-1H-pyrazol-4-yl)pyrimidin-2-amine was obtained using 3-((dimethylamino)methyl)aniline (commercially available from Enamine) in place of 4-(4-(oxetan-3-yl)piperazin-1-yl)aniline.

Example 41

In the same manner as in Example 15, 4-(1-ethyl-3-(pyridin-3-yl)-1H-pyrazol-4-yl)-N-(3-(morpholinomethyl)phenyl)pyrimidin-2-amine was obtained using 3-(morpholinomethyl)aniline (commercially available from Matrix Scientific) in place of 4-(4-(oxetan-3-yl)piperazin-1-yl)aniline.

Example 43

A mixture containing 1-(2-bromoethyl)-4-nitrobenzene (commercially available from Alfa Aesar, 310 mg), 1-(2-methoxyethyl)piperazine (225 mg), potassium carbonate (227 mg) and DMF (1.5 mL) was stirred at 90° C. overnight. The reaction mixture was cooled to room temperature, ethyl acetate was then added thereto, and washing with water was performed. The organic layer was dried over anhydrous sodium sulfate and then concentrated under a reduced pressure, and thereby 1-(2-methoxyethyl)-4-(4-nitrophenethyl)piperazine (387 mg) was obtained.

Methanol (5 mL) and 10% Pd/C (40 mg) were sequentially added thereto and the mixture was stirred at room temperature overnight under a hydrogen atmosphere. Insoluble substances in the reaction mixture were filtered off. Then, the filtrate was concentrated under a reduced pressure, and thereby 4-(2-(4-(2-methoxyethyl)piperazin-1-yl)ethyl)aniline (341 mg) as a brown solid was obtained.

A mixture containing 4-(2-(4-(2-methoxyethyl)piperazin-1-yl)ethyl)aniline (111 mg), 2-chloro-4-(1-ethyl-3-(pyridin-3-yl)-1H-pyrazol-4-yl)pyrimidine (Production Example 3, 100 mg) and acetic acid (1.0 mL) was stirred at 90° C. overnight. The reaction mixture was concentrated under a reduced pressure, the obtained residue was purified through aminopropyl silica gel column chromatography (elution solvent: dichloromethane-methanol), and thereby 4-(1-ethyl-3-(pyridin-3-yl)-1H-pyrazol-4-yl)-N-(4-(2-(4-(2-methoxyethyl)piperazin-1-yl)ethyl)phenyl)pyrimidin-2-amine (23 mg) as a yellow oily substance was obtained.

Example 45

In the same manner as in Example 15, 4-(1-ethyl-3-(pyridin-3-yl)-1H-pyrazol-4-yl)-N-(3-fluoro-4-(1-methylpiperidin-4-yl)phenyl)pyrimidin-2-amine was obtained using 3-fluoro-4-(1-methylpiperidin-4-yl)aniline (Synthesis literature 42) in place of 4-(4-(oxetan-3-yl)piperazin-1-yl)aniline.

Example 47

In the same manner as in Example 15, 4-(1-ethyl-3-(pyridin-3-yl)-1H-pyrazol-4-yl)-N-(3-methoxy-4-(4-methylpiperazin-1-yl)phenyl)pyrimidin-2-amine was obtained using 3-methoxy-4-(4-methylpiperazin-1-yl)aniline (Synthesis literature 43) in place of 4-(4-(oxetan-3-yl)piperazin-1-yl)aniline.

Example 49

A mixture containing 2-chloro-4-(1-ethyl-3-(pyridin-3-yl)-1H-pyrazol-4-yl)pyrimidine (Production Example 3, 103 mg), and 4-(piperidin-1-yl)aniline (86 mg) was stirred at 100° C. overnight. The reaction mixture was purified through aminopropyl silica gel column chromatography (elution solvent: dichloromethane-methanol), and thereby 4-(1-ethyl-3-(pyridin-3-yl)-1H-pyrazol-4-yl)-N-(4-(piperidin-1-yl)phenyl)pyrimidin-2-amine (66 mg) as a brown oily substance was obtained.

Example 50

A mixture containing 3-phenylpyrrolidine (commercially available from Apollo Scientific, 300 mg), 1-bromo-2-methoxyethane (0.230 mL), N,N-diisopropylethylamine (0.532 mL) and acetonitrile (3 mL) was stirred at room temperature overnight. The reaction mixture was concentrated under a reduced pressure, ethyl acetate was added to the obtained residue, and the mixture was then sequentially washed with water and a saturated saline solution. The organic layer was dried over anhydrous sodium sulfate and then concentrated under a reduced pressure, the obtained residue was purified through silica gel column chromatography (elution solvent: dichloromethane-methanol), and thereby 1-(2-methoxyethyl)-3-phenylpyrrolidine (135 mg) as a light brown oily substance was obtained.

Concentrated sulfuric acid (1 mL) and concentrated nitric acid (73 mg) were sequentially added dropwise thereto under ice cooling, and the mixture was stirred on an ice bath for 15 minutes, and then at room temperature overnight. The reaction mixture was poured onto ice water, and the whole was made basic with a 25% sodium hydroxide aqueous solution, and then extraction was performed using diethyl ether. The organic layer was dried over anhydrous sodium sulfate and then concentrated under a reduced pressure, and THF (1.5 mL), ethanol (1.5 mL) and 5% Pd/C were sequentially added to the obtained residue, and the mixture was stirred at room temperature for 4.5 hours under a hydrogen atmosphere. Insoluble substances in the reaction mixture were filtered off. Then, the filtrate was concentrated under a reduced pressure, and thereby 4-(1-(2-methoxyethyl)pyrrolidin-3-yl)aniline (158 mg) as a light brown oily substance was obtained.

A mixture containing 4-(1-(2-methoxyethyl)pyrrolidin-3-yl)aniline (72 mg), 2-chloro-4-(1-ethyl-3-(pyridin-3-yl)-1H-pyrazol-4-yl)pyrimidine (Production Example 3, 50 mg) and ethanol (0.5 mL) was stirred at 150° C. for 4 hours under microwave radiation. The reaction mixture was dried under a nitrogen stream, the obtained residue was purified through silica gel column chromatography (elution solvent: dichloromethane-methanol), and thereby 4-(1-ethyl-3-(pyridin-3-yl)-1H-pyrazol-4-yl)-N-(4-(1-(2-methoxyethyl)pyrrolidin-3-yl)phenyl)pyrimidin-2-amine (35 mg) as a light yellow oily substance was obtained.

Example 51

A mixture containing 2-chloro-4-(1-ethyl-3-(pyridin-3-yl)-1H-pyrazol-4-yl)pyrimidine (Production Example 3, 175 mg), 4-(4-(2-(2,2-difluoroethoxy)ethyl)piperazin-1-yl)aniline (Production Example 40, 175 mg) and ethanol (1.7 mL) was stirred at 150° C. for 4 hours under microwave radiation. The reaction mixture was concentrated under a reduced pressure, the obtained residue was purified through aminopropyl silica gel column chromatography (elution solvent: hexane-dichloromethane), and thereby N-(4-(4-(2-(2,2-difluoroethoxy)ethyl)piperazin-1-yl)phenyl)-4-(1-ethyl-3-(pyridin-3-yl)-1H-pyrazol-4-yl)pyrimidin-2-amine (86 mg) as a brown oily substance was obtained.

Example 53

In the same manner as in Example 51, 4-(1-ethyl-3-(pyridin-3-yl)-1H-pyrazol-4-yl)-N-(1-(tetrahydro-2H-pyran-4-yl)-1H-pyrazol-4-yl)pyrimidin-2-amine was obtained using 1-(tetrahydro-2H-pyran-4-yl)-1H-pyrazol-4-amine (Synthesis literature 44) in place of 4-(4-(2-(2,2-difluoroethoxy)ethyl)piperazin-1-yl)aniline.

Example 55

1-Bromo-2-methoxyethane (156 mg) and N,N-diisopropylethylamine (263 mg) were added to acetonitrile solution (4 mL) of a 4-(4-nitro-1H-pyrazol-1-yl)piperidine (Synthesis literature 6, 200 mg), and the mixture was stirred at 60° C. for 6 hours. The mixture was poured onto a solution in which water and ethyl acetate were mixed, and the aqueous layer was separated off. The organic layer was washed with water and a saturated saline solution, and dried over anhydrous magnesium sulfate. A solvent was distilled off under a reduced pressure, and thereby 1-(2-methoxyethyl)-4-(4-nitro-1H-pyrazol-1-yl)piperidine (250 mg) as a yellow oily substance was obtained.

Methanol (8 mL) and 5% Pd/C (105 mg) were sequentially added thereto, and the mixture was stirred overnight under a hydrogen atmosphere. Insoluble substances in the reaction mixture were filtered off, and the filtrate was concentrated under a reduced pressure. The residue was purified through amino silica gel column chromatography (elution solvent: dichloromethane-methanol), and thereby 1-(1-(2-methoxyethyl)piperidin-4-yl)-1H-pyrazol-4-amine (109 mg) as a pink solid was obtained.

In the same manner as in Example 51, 4-(1-ethyl-3-(pyridin-3-yl)-1H-pyrazol-4-yl)-N-(1-(1-(2-methoxyethyl)piperidin-4-yl)-1H-pyrazol-4-yl)pyrimidin-2-amine (102 mg) was obtained using 1-(1-(2-methoxyethyl)piperidin-4-yl)-1H-pyrazol-4-amine (100 mg) in place of 4-(4-(2-(2,2-difluoroethoxy)ethyl)piperazin-1-yl)aniline.

An ethanol solution (1 mL) containing oxalic acid dihydrate (19 mg) was added to an ethanol solution (1 mL) containing 1-(1-(2-methoxyethyl)piperidin-4-yl)-1H-pyrazol-4-amine (76 mg), and the mixture was stirred at room temperature for 20 minutes. The precipitated solid was collected by filtration, washed with ethanol, and then dried under a reduced pressure, and thereby 4-(1-ethyl-3-(pyridin-3-yl)-1H-pyrazol-4-yl)-N-(1-(1-(2-methoxyethyl)piperidin-4-yl)-1H-pyrazol-4-yl)pyrimidin-2-amine oxalate (25 mg) as a colorless solid was obtained.

Example 56

4-Nitrobenzoyl chloride (1.86 g) was added to a mixture containing acetohydrazide (810 mg), N,N-diisopropylethylamine (2.62 mL) and DMF (25 mL) under ice cooling, and the mixture was stirred at room temperature for 30 minutes. Water (25 mL) was added to the reaction mixture, the precipitated solid was collected by filtration, and thereby N'-acetyl-4-nitrobenzohydrazide (1.71 g) was obtained.

A mixture containing N'-acetyl-4-nitrobenzohydrazide (10.0 g), 2,4-bis(4-methoxyphenyl)-1,3,2,4-dithiadiphosphetane 2,4-disulfide (Lawesson's reagent, 19.3 g) and THF (110 mL) was stirred at 70° C. for 30 minutes. Ethyl acetate (250 mL) and a sodium hydrogen carbonate aqueous solution (100 mL) were added to the reaction mixture, the precipitated solid was collected by filtration, and then washed with chloroform, and thereby 2-methyl-5-(4-nitrophenyl)-1,3,4-thiadiazole (4.61 g) was obtained.

A mixture containing 2-methyl-5-(4-nitrophenyl)-1,3,4-thiadiazole (2.63 g), iron powder (6.64 g), ammonium chloride (6.4 g), methanol (96 mL) and water (20 mL) was stirred at 60° C. for 1 hour. Insoluble substances in the reaction mixture were filtered off. Then, the filtrate was concentrated under a reduced pressure, the precipitated solid was collected by filtration, washed with water, and then recrystallized from methanol, and thereby 4-(5-methyl-1,3,4-thiadiazol-2-yl)aniline (1.52 g) was obtained.

A mixture containing 4-(5-methyl-1,3,4-thiadiazol-2-yl)aniline (66.3 mg), 2-chloro-4-(1-ethyl-3-(pyridin-3-yl)-1H-pyrazol-4-yl)pyrimidine (Production Example 3, 93 mg), a 4 N hydrochloric acid-dioxane solution (4 drops) and ethanol (2 mL) was stirred at 160° C. for 10 minutes under microwave radiation. The reaction mixture was concentrated under a reduced pressure, the obtained residue was purified by silica gel thin layer chromatography (developing solvent: dichloromethane-methanol), and thereby 4-(1-ethyl-3-(pyridin-3-yl)-1H-pyrazol-4-yl)-N-(4-(5-methyl-1,3,4-thiadiazol-2-yl)phenyl)pyrimidin-2-amine (40.8 mg) as a colorless solid was obtained.

Example 57

In the same manner as in Example 51, 4-(1-(2-methoxyethyl)-3-(pyridin-3-yl)-1H-pyrazol-4-yl)-N-(4-(1-(2-methoxyethyl)piperidin-4-yl)phenyl)pyrimidin-2-amine was obtained using 4-(1-(2-methoxyethyl)piperidin-4-yl)aniline synthesized by the method described in Example 12 and 2-chloro-4-(1-(2-methoxyethyl)-3-(pyridin-3-yl)-1H-pyrazol-4-yl)pyrimidine (Production Example 5).

Example 58

In the same manner as in Example 51, 4-(1-ethyl-3-(pyridin-3-yl)-1H-pyrazol-4-yl)-N-(4-(1-(2-methoxyethyl)piperidin-4-yl)phenyl)pyrimidin-2-amine was obtained using 4-(1-(2-methoxyethyl)piperidin-4-yl)aniline synthesized by the method described in Example 12 and 2-chloro-4-(1-ethyl-3-(pyridin-3-yl)-1H-pyrazol-4-yl)pyrimidine (Production Example 3).

Example 59

A mixture containing 4-(4-nitrophenyl)piperidine (Synthesis literature 37, 170 mg), 2-hydroxyacetic acid (188 mg), 1-ethyl-3-(3-dimethylaminopropyl)carbodiimide hydrochloride (474 mg), 1-hydroxybenzotriazole (122 mg), N-methyl morpholine (183 mg) and dichloromethane (15 mL) was stirred at room temperature for 2 hours. The reaction mixture was diluted with dichloromethane and then washed with water, and the organic layer was concentrated under a reduced pressure. The obtained residue was purified by silica gel thin layer chromatography (developing solvent:

dichloromethane-methanol), and thereby 2-hydroxy-1-(4-(4-nitrophenyl)piperidin-1-yl)ethan-1-one (187 mg) was obtained.

Ethanol (5 mL) and 10% Pd/C (75.3 mg) were sequentially added thereto, and the mixture was stirred at room temperature overnight under a hydrogen atmosphere. Insoluble substances in the reaction mixture were filtered off. Then, the filtrate was concentrated under a reduced pressure, the obtained residue was purified through aminopropyl silica gel column chromatography (elution solvent: dichloromethane-methanol), and thereby 1-(4-(4-aminophenyl)piperidin-1-yl)-2-hydroxyethan-1-one (120 mg) was obtained.

A mixture containing 2-chloro-4-(1-ethyl-3-(pyridin-3-yl)-1H-pyrazol-4-yl)pyrimidine (Production Example 3, 110 mg), 1-(4-(4-aminophenyl)piperidin-1-yl)-2-hydroxyethan-1-one (90.9 mg), a 4 N hydrochloric acid-dioxane solution (4 drops), and ethanol (2 mL) was stirred at 160° C. for 10 minutes under microwave radiation. The reaction mixture was concentrated under a reduced pressure, the obtained residue was diluted with dichloromethane, and then washed with a 2 N sodium hydroxide aqueous solution. The organic layer was concentrated under a reduced pressure, the obtained residue was purified by silica gel thin layer chromatography (developing solvent: dichloromethane-methanol), and thereby 1-(4-(4-((4-(1-ethyl-3-(pyridin-3-yl)-1H-pyrazol-4-yl)pyrimidin-2-yl)amino)phenyl)piperidin-1-yl)-2-hydroxyethan-1-one (5.8 mg) was obtained.

Example 60

In the same manner as in Example 51, N-(4-(1-(2-methoxyethyl)-3-(pyridin-3-yl)-1H-pyrazol-4-yl)pyrimidin-2-yl)-2-methylisoindolin-5-amine was obtained using 2-chloro-4-(1-(2-methoxyethyl)-3-(pyridin-3-yl)-1H-pyrazol-4-yl)pyrimidine (Production Example 5) and 2-methylisoindolin-5-amine (commercially available from Enamine).

Example 61

In the same manner as in Example 51, N-(4-(1-ethyl-3-(pyridin-3-yl)-1H-pyrazol-4-yl)pyrimidin-2-yl)-2-(2-methoxyethyl)isoindolin-5-amine was obtained using 2-(2-methoxyethyl)isoindolin-5-amine (Synthesis literature 5) in place of 4-(4-(2-(2,2-difluoroethoxy)ethyl)piperazin-1-yl)aniline.

Example 67

2-Picoline borane (45.6 mg) was added to a mixture containing 8-nitro-2,3,4,5-tetrahydrobenzo[f][1,4]oxazepine (Synthesis literature 18, 69 mg), paraformaldehyde (21.5 mg), acetic acid (0.3 mL) and 1,2-dichloroethane (2.7 mL) at 50° C., and the reaction mixture was then stirred at 50° C. for 2 hours. The reaction mixture was concentrated under a reduced pressure, the obtained residue was purified by silica gel thin layer chromatography (developing solvent: dichloromethane-methanol), and thereby 4-methyl-8-nitro-2,3,4,5-tetrahydrobenzo[f][1,4]oxazepine (40.1 mg) was obtained.

Ethanol (4 mL) and 10% Pd/C (20.4 mg) were sequentially added thereto, and the mixture was stirred at room temperature overnight under a hydrogen atmosphere. Insoluble substances in the reaction mixture were filtered off. Then, the filtrate was concentrated under a reduced pressure, the obtained residue was purified by silica gel thin layer chromatography (developing solvent: dichloromethane-methanol), and thereby 4-methyl-2,3,4,5-tetrahydrobenzo[f][1,4]oxazepine-8-amine (13.3 mg) was obtained.

2-Chloro-4-(1-ethyl-3-(pyridin-3-yl)-1H-pyrazol-4-yl)pyrimidine (Production Example 3, 20.8 mg), a 4 N hydrochloric acid-dioxane solution (2 drops) and ethanol (2 mL) were added thereto, and the mixture was stirred at 160° C. for 15 minutes under microwave radiation. A 2 N sodium hydroxide aqueous solution was added to the reaction mixture and a pH was set to 9, and the mixture was then concentrated under a reduced pressure, the obtained residue was purified by silica gel thin layer chromatography (developing solvent: dichloromethane-methanol, and then dichloromethane-methanol-ammonia water), and thereby N-(4-(1-ethyl-3-(pyridin-3-yl)-1H-pyrazol-4-yl)pyrimidin-2-yl)-4-methyl-2,3,4,5-tetrahydrobenzo[f][1,4]oxazepin-8-amine (9.5 mg) was obtained.

Example 69

In the same manner as in Example 51, N-(4-(1,4-diazabicyclo[3.2.2]nonan-4-yl)phenyl)-4-(1-ethyl-3-(pyridin-3-yl)-1H-pyrazol-4-yl)pyrimidin-2-amine was obtained using 4-(1,4-diazabicyclo[3.2.2]nonan-4-yl)aniline (Synthesis literature 45) in place of 4-(4-(2-(2,2-difluoroethoxy)ethyl)piperazin-1-yl)aniline.

Example 70

In the same manner as in Example 51, 4-(1-ethyl-3-(pyridin-3-yl)-1H-pyrazol-4-yl)-N-(4-(oxazol-5-yl)phenyl)pyrimidin-2-amine was obtained using 4-(oxazol-5-yl)aniline (Synthesis literature 46) in place of 4-(4-(2-(2,2-difluoroethoxy)ethyl)piperazin-1-yl)aniline.

Example 71

A mixture containing 2-chloro-4-(1-(2-methoxyethyl)-3-(pyridin-3-yl)-1H-pyrazol-4-yl)pyrimidine (Production Example 5, 629 mg), tert-butyl 4-(4-aminophenyl)piperazine-1-carboxylate (Synthesis literature 14, 608 mg) and ethanol (5 mL) was stirred at 150° C. for 4 hours under microwave radiation. The reaction mixture was concentrated under a reduced pressure, the obtained residue was purified through aminopropyl silica gel column chromatography (elution solvent: dichloromethane-methanol), and thereby 4-(1-(2-methoxyethyl)-3-(pyridin-3-yl)-1H-pyrazol-4-yl)-N-(4-(piperazin-1-yl)phenyl)pyrimidin-2-amine (569 mg) as a light brown foamy substance was obtained.

Example 73

In the same manner as in Example 71, N-(4-(1-ethyl-3-(pyridin-3-yl)-1H-pyrazol-4-yl)pyrimidin-2-yl)isoindolin-5-amine was obtained using 2-chloro-4-(1-ethyl-3-(pyridin-3-yl)-1H-pyrazol-4-yl)pyrimidine (Production Example 3) and tert-butyl 5-aminoisoindoline-2-carboxylate (Synthesis literature 47).

Example 74

A mixture containing (4-((4-(1-phenethyl-3-(pyridin-3-yl)-1H-pyrazol-4-yl)pyrimidin-2-yl)amino)phenyl) (piperazin-1-yl)methanone (Production Example 93, 60 mg), 1,2-dichloroethane (3 mL), triethylamine (0.07 mL) and acetyl chloride (20 mg) was stirred at room temperature for 1 hour. Methanol was added to the reaction mixture and the mixture was then concentrated under a reduced pressure, the obtained residue was purified through silica gel column chromatography (elution solvent: dichloromethane-methanol-ammonia water), and thereby 1-(4-(4-((4-(1-phenethyl-3-(pyridin-3-yl)-1H-pyrazol-4-yl)pyrimidin-2-yl)amino)benzoyl)piperazin-1-yl)ethan-1-one (90 mg) as a colorless solid was obtained.

Example 76

A mixture containing N-(4-(piperazin-1-yl)phenyl)-4-(3-(pyridin-3-yl)-1-(tetrahydrofuran-3-yl)-1H-pyrazol-4-yl)pyrimidin-2-amine (Production Example 70, 90 mg), DMF (1 mL), N,N-diisopropylethylamine (0.067 mL) and 1-bromo-2-methoxyethane (0.027 mL) was stirred at room temperature for 5 days. Ethyl acetate was added to the reaction mixture, and the mixture was sequentially washed with water and a saturated saline solution. Then, the organic layer was dried over anhydrous magnesium sulfate, and concentrated under a reduced pressure. The obtained residue was purified through silica gel column chromatography (elution solvent: chloroform-methanol), and thereby N-(4-(4-(2-methoxyethyl)piperazin-1-yl)phenyl)-4-(3-(pyridin-3-yl)-1-(tetrahydrofuran-3-yl)-1H-pyrazol-4-yl)pyrimidin-2-amine (45 mg) was obtained.

Example 96

In the same method as in Example 76, N-(4-(4-((4,4-dimethyloxetan-2-yl)methyl)piperazin-1-yl)phenyl)-4-(1-ethyl-3-(pyridin-3-yl)-1H-pyrazol-4-yl)pyrimidin-2-amine was obtained using 4-(1-ethyl-3-(pyridin-3-yl)-1H-pyrazol-4-yl)-N-(4-(piperazin-1-yl)phenyl)pyrimidin-2-amine (Example 151) and 4-(iodomethyl)-2,2-dimethyl oxetane (Synthesis literature 48).

Example 98

In the same method as in Example 76, 4-(1-ethyl-3-(pyridin-3-yl)-1H-pyrazol-4-yl)-N-(4-(4-((3-methyloxetan-3-yl)methyl)piperazin-1-yl)phenyl)pyrimidin-2-amine was obtained using 4-(1-ethyl-3-(pyridin-3-yl)-1H-pyrazol-4-yl)-N-(4-(piperazin-1-yl)phenyl)pyrimidin-2-amine (Example 151) and (3-methyl oxetan-3-yl)methyl 4-methylbenzenesulfonate (Synthesis literature 49).

Example 101

A mixture containing N-(4-(4-(oxetan-3-yl)piperazin-1-yl)phenyl)-4-(3-(pyridin-3-yl)-1H-pyrazol-4-yl)pyrimidin-2-amine (Production Example 135, 78 mg), 3-iodooxetane (75.8 mg), cesium carbonate (112 mg) and DMF (1 mL) was stirred at room temperature overnight. Water was added to the reaction mixture, and extraction was performed using dichloromethane-methanol (9:1). The extract was washed with a saturated saline solution, and then dried over anhydrous sodium sulfate, and concentrated under a reduced pressure. The obtained residue was sequentially purified through aminopropyl silica gel column chromatography (elution solvent: dichloromethane-methanol) and silica gel column chromatography (elution solvent: dichloromethane-methanol), and thereby 4-(1-(oxetan-3-yl)-3-(pyridin-3-yl)-1H-pyrazol-4-yl)-N-(4-(4-(oxetan-3-yl)piperazin-1-yl)phenyl)pyrimidin-2-amine (42 mg) as a yellow solid was obtained.

Example 104

A mixture containing 4-(1-ethyl-3-(pyridin-3-yl)-1H-pyrazol-4-yl)-N-(4-(piperazin-1-yl)phenyl)pyrimidin-2-amine (Example 151, 50 mg) and 2,2-dimethyloxirane (0.1 mL) was stirred at 50° C. for 3.5 hours, and 2,2-dimethyloxirane (0.5 mL) was then added thereto, and the mixture was additionally stirred at 50° C. for 18 hours. Methanol was added to the reaction mixture, and the mixture was stirred at room temperature for 5 minutes and then concentrated under a reduced pressure. The obtained residue was purified through silica gel column chromatography (elution solvent: chloroform-methanol), and thereby 1-(4-(4-((4-(1-ethyl-3-(pyridin-3-yl)-1H-pyrazol-4-yl)pyrimidin-2-yl)amino)phenyl)piperazin-1-yl)-2-methylpropan-2-ol (44 mg) as a light yellow oily substance was obtained.

Example 112

A mixture containing 4-(1-ethyl-3-(pyridin-3-yl)-1H-pyrazol-4-yl)-N-(4-(2-(piperazin-1-yl)ethyl)phenyl)pyrimidin-2-amine (Example 159, 26 mg), 37% formaldehyde aqueous solution (0.64 mL), formic acid (0.64 mL) and ethanol (0.2 mL) was stirred at 80° C. for 4 hours. The reaction mixture was concentrated under a reduced pressure, the residue was purified through silica gel column chromatography (elution solvent: dichloromethane-methanol), and thereby 4-(1-ethyl-3-(pyridin-3-yl)-1H-pyrazol-4-yl)-N-(4-(2-(4-methylpiperazin-1-yl)ethyl)phenyl)pyrimidin-2-amine (4.1 mg) as a colorless oily substance was obtained.

Example 133

A mixture containing N-(4-bromophenyl)-4-(1-ethyl-3-(pyridin-3-yl)-1H-pyrazol-4-yl)pyrimidin-2-amine (Production Example 145, 82 mg), tetrakis(triphenylphosphine)palladium(O) (21 mg), 3-pyridylboronic acid (43 mg), potassium carbonate (83 mg) and DMF (1.5 mL) was degassed under an argon atmosphere and then heated to reflux, and stirred overnight. Insoluble substances in the reaction mixture were filtered off, the filtrate was concentrated under a reduced pressure, the obtained residue was purified through aminopropyl silica gel column chromatography (elution solvent: dichloromethane-methanol), and thereby 4-(1-ethyl-3-(pyridin-3-yl)-1H-pyrazol-4-yl)-N-(4-(pyridin-3-yl)phenyl)pyrimidin-2-amine (30.5 mg) as a light yellow solid was obtained.

Example 135

A mixture containing tert-butyl 4-(4-((4-(3-(pyridin-3-yl)-1H-pyrazol-4-yl)pyrimidin-2-yl)amino)phenyl)piperazine-1-carboxylate (Production Example 58, 0.24 g), 2-bromo-2-methylpropane (0.84 g), potassium carbonate (1.00 g) and DMF (3 mL) was stirred at 80° C. overnight. Insoluble substances in the reaction mixture were filtered off, the filtrate was then concentrated under a reduced pressure, the obtained residue was purified through aminopropyl silica gel column chromatography (elution solvent: dichloromethane-methanol), and thereby 4-(1-tert-butyl)-3-(pyridin-3-yl)-1H-pyrazol-4-yl)-N-(4-(piperazin-1-yl)phenyl)pyrimidin-2-amine (30 mg) as a light yellow solid was obtained.

Example 136

A mixture containing tert-butyl 4-(4-((4-(3-(pyridin-3-yl)-1-(2,2,2-trifluoroethyl)-1H-pyrazol-4-yl)pyrimidin-2-yl)amino)phenyl)piperazine-1-carboxylate (Production Example 76, 200 mg) and trifluoroacetic acid (1.5 mL) was stirred at room temperature for 30 minutes. A potassium carbonate aqueous solution was added to the reaction solution, and extraction was then performed using chloroform-methanol (9:1). The organic layer was dried over anhydrous sodium sulfate and then concentrated under a reduced pressure, and thereby N-(4-(piperazin-1-yl)phenyl)-4-(3-(pyridin-3-yl)-1-(2,2,2-trifluoroethyl)-1H-pyrazol-4-yl)pyrimidin-2-amine (134 mg) as a yellow powder was obtained.

Example 172

A mixture containing tert-butyl 2-(6-((4-(1-ethyl-3-(pyridin-3-yl)-1H-pyrazol-4-yl)pyrimidin-2-yl)amino)-3,4-dihydroisoquinolin-2(1H)-yl)acetate (Production Example 105, 12 mg), 1 N hydrochloric acid (0.12 mL) and methanol (0.1 mL) was stirred at room temperature for 2 hours, a 4 N hydrochloric acid-dioxane solution (0.1 mL) was then added thereto, and the mixture was stirred at room temperature overnight. The reaction solution was neutralized with a sodium hydroxide aqueous solution and then concentrated under a reduced pressure. Ethanol (1 mL) was added to the obtained residue, an insoluble substance was filtered off, and the filtrate was then concentrated under a reduced pressure. This operation was additionally repeated twice, chloroform was added to the obtained residue, the resulting solid was collected by filtration, and thereby 2-(6-((4-(1-ethyl-3-(pyridin-3-yl)-1H-pyrazol-4-yl)pyrimidin-2-yl)amino)-3,4-dihydroisoquinolin-2(1H)-yl)acetic acid (8.1 mg) was obtained.

Example 174

A 0.5 M sodium methoxide-methanol solution (0.034 mL) was added to a mixture containing 2-(4-(4-((4-(1-ethyl-3-(pyridin-3-yl)-1H-pyrazol-4-yl)pyrimidin-2-yl)amino)phenyl)piperazin-1-yl)-2-oxoethyl acetate (Production Example 149, 55 mg), dichloromethane (0.16 mL) and methanol (0.04 mL), and the mixture was stirred at room temperature for 1 hour. The reaction mixture was concentrated under a reduced pressure, the residue was purified through silica gel column chromatography (elution solvent: dichloromethane-methanol), and thereby 1-(4-(4-((4-(1-ethyl-3-(pyridin-3-yl)-1H-pyrazol-4-yl)pyrimidin-2-yl)amino)phenyl)piperazin-1-yl)-2-hydroxyethan-1-one (47.8 mg) as a yellow oily substance was obtained.

Example 176

A mixture containing N-(1-(4-((4-(1-ethyl-3-(pyridin-3-yl)-1H-pyrazol-4-yl)pyrimidin-2-yl)amino)phenyl)-4-methylpiperidin-4-yl)acetamide (Production Example 59, 265 mg) and 6 N hydrochloric acid (5 mL) was stirred at 130° C. for 3 days. The reaction mixture was cooled to room temperature, and ice water, sodium carbonate and sodium chloride were sequentially added thereto, and extraction was then performed using chloroform. The organic layer was dried over anhydrous sodium sulfate and then concentrated under a reduced pressure, the obtained residue was purified through aminopropyl silica gel column chromatography (elution solvent: hexane-chloroform), and thereby N-(4-(4-amino-4-methylpiperidin-1-yl)phenyl)-4-(1-ethyl-3-(pyridin-3-yl)-1H-pyrazol-4-yl)pyrimidin-2-amine (54 mg) as a brown foamy substance was obtained.

Example 179

A mixture containing 2-(2-((tert-butyldimethylsilyl)oxy)ethyl)-N-(4-(1-ethyl-3-(pyridin-3-yl)-1H-pyrazol-4-yl)pyrimidin-2-yl)-1,2,3,4-tetrahydroisoquinolin-7-amine (Production Example 107, 77.8 mg), a 1 M tetrabutylammonium fluoride-THF solution (0.28 mL) and THF (2 mL) was stirred at room temperature for 16 hours. The reaction mixture was concentrated under a reduced pressure, the obtained residue was purified through silica gel column chromatography (elution solvent: dichloromethane-methanol-ammonia water), and thereby 2-(7-((4-(1-ethyl-3-(pyridin-3-yl)-1H-pyrazol-4-yl)pyrimidin-2-yl)amino)-3,4-dihydroisoquinolin-2(1H)-yl)ethan-1-ol (40.6 mg) as a brown solid was obtained.

Example 180

A mixture containing N-(4-(3-bromo-1H-1,2,4-triazol-1-yl)phenyl)-4-(1-ethyl-3-(pyridin-3-yl)-1H-pyrazol-4-yl)pyrimidin-2-amine (Production Example 146, 40 mg), 1-methyl piperazine (164.3 mg) and DMF (0.2 mL) was stirred at 120° C. overnight. Water was added to the reaction mixture, the precipitated solid was collected by filtration, and then purified through aminopropyl silica gel column chromatography (elution solvent: dichloromethane-methanol), and thereby 4-(1-ethyl-3-(pyridin-3-yl)-1H-pyrazol-4-yl)-N-(4-(3-(4-methylpiperazin-1-yl)-1H-1,2,4-triazol-1-yl)phenyl)pyrimidin-2-amine (23 mg) as a colorless solid was obtained.

Here, in Examples 5, 6, 9 to 11, 13, 18, 23, 28, 29, 31, 33, 36, 37, 42, 44, 46, 48, 52, 54, 62 to 66, 68, 72, 75, 77 to 95, 97, 99, 100, 102, 103, 105 to 111, 113 to 132, 134, 137 to 171, 173, 175, 177 and 178, compounds were synthesized according to the above methods or methods equivalent thereto. Compound names, structural formulae, synthesis method description examples, raw material compounds, MS molecular ion peaks, $^1$H NMR chemical shift values of compounds of examples are shown in the following table.

Unless otherwise specified, a solvent for NMR indicates deuterated chloroform.

TABLE 2

| Example number | Compound name | Structural formula |
|---|---|---|
| 1 | (4-(tert-Butyl)piperazin-1-yl)(4-((4-(1-ethyl-3-(pyridin-3-yl)-1H-pyrazol-4-yl)pyrimidin-2-yl)amino)phenyl)methanone | |

TABLE 2-continued

| | | |
|---|---|---|
| 2 | (4-((4-(1-Ethyl-3-(pyridin-3-yl)-1H-pyrazol-4-yl)pyrimidin-2-yl)amino)phenyl)(piperidin-1-yl)methanone | |
| 3 | (4-((4-(1-Ethyl-3-(pyridin-3-yl)-1H-pyrazol-4-yl)pyrimidin-2-yl)amino)phenyl)(4-(4-fluorophenyl)piperazin-1-yl)methanone | |
| 4 | 4-((4-(1-Ethyl-3-(pyridin-3-yl)-1H-pyrazol-4-yl)pyrimidin-2-yl)amino)-N-methyl-N-(1-methylpiperidin-4-yl)benzamide | |
| 5 | 4-((4-(1-Ethyl-3-(pyridin-3-yl)-1H-pyrazol-4-yl)pyrimidin-2-yl)amino)-N-(8-isopropyl-8-azabicyclo[3.2.1]octan-3-yl)-N-methylbenzamide | |
| 6 | 1-(4-((4-(1-Ethyl-3-(pyridin-3-yl)-1H-pyrazol-4-yl)pyrimidin-2-yl)amino)phenyl)ethan-1-one | |
| 7 | N-(4-(1-Ethyl-3-(pyridin-3-yl)-1H-pyrazol-4-yl)pyrimidin-2-yl)-6-methyl-5,6,7,8-tetrahydro-1,6-naphthyridin-2-amine | |

TABLE 2-continued

| | | |
|---|---|---|
| 8 | 2-Methyl-N-(4-(1-(oxetan-3-yl)-3-(pyridin-3-yl)-1H-pyrazol-4-yl)pyrimidin-2-yl)-1,2,3,4-tetrahydroisoquinolin-6-amine | |
| 9 | N-(4-(1-Ethyl-3-(pyridin-3-yl)-1H-pyrazol-4-yl)pyrimidin-2-yl)-2-(oxetan-3-yl)isoindolin-5-amine | |
| 10 | 2-Methyl-N-(4-(3-(pyridin-3-yl)-1-((tetrahydrofuran-3-yl) methyl)-1H-pyrazol-4-yl)pyrimidin-2-yl)-1,2,3,4-tetrahydroisoquinolin-6-amine | |
| 11 | 4-(1-Ethyl-3-(pyridin-3-yl)-1H-pyrazol-4-yl)-N-(4-(1-(oxetan-3-yl)piperidin-4-yl)phenyl)pyrimidin-2-amine | |
| 12 | N-(4-(1-(2-Methoxyethyl)piperidin-4-yl)phenyl)-4-(1-(oxetan-3-yl)-3-(pyridin-3-yl)-1H-pyrazol-4-yl)pyrimidin-2-amine | |
| 13 | 4-(1-(2-Methoxyethyl)-3-(pyridin-3-yl-1H-pyrazol-4-yl)-N-(4-(1-(oxetan-3-yl) piperidin-4-yl)phenyl)pyrimidin-2-amine | |

TABLE 2-continued

| | | |
|---|---|---|
| 14 | 4-(1-Ethyl-3-(pyridin-3-yl)-1H-pyrazol-4-yl)-N-(4-(imidazo[1,2-a]pyridin-2-yl)phenyl)pyrimidin-2-amine | |
| 15 | 4-(1-Ethyl-3-(pyridin-3-yl)-1H-pyrazol-4-yl)-N-(4-(4-(oxetan-3-yl)piperazin-1-yl)phenyl)pyrimidin-2-amine | |
| 16 | 4-(1-Ethyl-3-(pyridin-3-yl)-1H-pyrazol-4-yl)-N-(4-(4-isopropylpiperazin-1-yl)phenyl)pyrimidin-2-amine | |
| 17 | 4-(1-Ethyl-3-(pyridin-3-yl)-1H-pyrazol-4-yl)-N-(4-(4-(2-methoxyethyl)piperazin-1-yl)phenyl)pyrimidin-2-amine | |
| 18 | 4-(1-Ethyl-3-(pyridin-3-yl)-1H-pyrazol-4-yl)-N-(3-fluoro-4-(4-(2-methoxyethyl)piperazin-1-yl)phenyl)pyrimidin-2-amine | |
| 19 | N-(4-(4-Benzylpiperazin-1-yl)phenyl)-4-(1-ethyl-3-(pyridin-3-yl)-1H-pyrazol-4-yl)pyrimidin-2-amine | |

TABLE 2-continued

| | | |
|---|---|---|
| 20 | 4-(1-Ethyl-3-(pyridin-3-yl)-1H-pyrazol-4-yl)-N-(4-(4-(4-methylpiperazin-1-yl)piperidin-1-yl)phenyl)pyrimidin-2-amine | |
| 21 | 1-(7-(4-((4-(1-Ethyl-3-(pyridin-3-yl)-1H-pyrazol-4-yl)pyrimidin-2-yl)amino)phenyl)-2,7-diazaspiro[3.5]nonan-2-yl)ethan-1-one | |
| 22 | 4-(1-Ethyl-3-(pyridin-3-yl)-1H-pyrazol-4-yl)-N-(4-morpholinophenyl)pyrimidin-2-amine | |
| 23 | 4-((4-(1-Ethyl-3-(pyridin-3-yl)-1H-pyrazol-4-yl)pyrimidin-2-yl)amino)benzamide | |
| 24 | N-(3-(2-(Dimethylamino)ethoxy)phenyl)-4-(1-ethyl-3-(pyridin-3-yl)-1H-pyrazol-4-yl)pyrimidin-2-amine | |
| 25 | N-(4-(2-Morpholinoethoxy)phenyl)-4-(-3-(pyridin-3-yl)-1H-pyrazol-4-yl)pyrimidin-2-amine | |

TABLE 2-continued

| | | |
|---|---|---|
| 26 | 4-(1-Ethyl-3-(pyridin-3-yl)-1H-pyrazol-4-yl)-N-(4-(3-methyl-1H-1,2,4-triazol-1-yl)phenyl)pyrimidin-2-amine | |
| 27 | N-(4-(1-Ethyl-1H-pyrazol-4-yl)phenyl)-4-(1-ethyl-3-(pyridin-3-yl)-1H-pyrazol-4-yl)pyrimidin-2-amine | |
| 28 | 4-(1-Ethyl-3-(pyridin-3-yl)-1H-pyrazol-4-yl)-N-(4-(1-(2-methoxyethyl)-1H-pyrazol-4-yl)phenyl)pyrimidin-2-amine | |
| 29 | N-(4-(1-(2,2-Difluoroethyl)-1H-pyrazol-4-yl)phenyl)-4-(1-ethyl-3-(pyridin-3-yl)-1H-pyrazol-4-yl)pyrimidin-2-amine | |
| 30 | N-(4-(1H-Pyrazol-4-yl)phenyl)-4-(1-ethyl-3-(pyridin-3-yl)-1H-pyrazol-4-yl)pyrimidin-2-amine | |
| 31 | 2-(4-(4-((4-(1-Ethyl-3-(pyridin-3-yl)-1H-pyrazol-4-yl)pyrimidin-2-yl)amino)phenyl)piperazin-1-yl)-1-(piperidin-1-yl)ethan-1-one | |

TABLE 2-continued

| | | |
|---|---|---|
| 32 | N-(4-(4-Cyclopropylpiperazin-1-yl)phenyl)-4-(1-ethyl-3-(pyridin-3-yl)-1H-pyrazol-4-yl)pyrimidin-2-amine | |
| 33 | N-(4-(4-(Cyclopropylmethyl)piperazin-1-yl)phenyl)-4-(1-ethyl-3-(pyridin-3-yl)-1H-pyrazol-4-yl)pyrimidin-2-amine | |
| 34 | 4-(1-Ethyl-3-(pyridin-3-yl)-1H-pyrazol-4-yl)-N-(3-(4-methylpiperazin-1-yl)phenyl)pyrimidin-2-amine | |
| 35 | 4-(1-(2-Methoxyethyl)-3-(pyridin-3-yl)-1H-pyrazol-4-yl)-N-(4-(4-methylpiperazin-1-yl)phenyl)pyrimidin-2-amine | |
| 36 | N-(4-(4-(Cyclopropylmethyl)piperazin-1-yl)phenyl)-4-(1-(2-methoxyethyl)-3-(pyridin-3-yl)-1H-pyrazole-4-yl)pyrimidin-2-amine | |
| 37 | 4-(1-(2-Methoxyethyl)-3-(pyridin-3-yl)-1H-pyrazol-4-yl)-N-(4-(4-(2-methoxyethyl)-piperazin-1-yl)phenyl)pyrimidin-2-amine | |

TABLE 2-continued

| 38 | N-(4-(1H-1,2,4-Triazol-1-yl)phenyl)-4-(1-ethyl-3-(pyridin-3-yl)-1H-pyrazol-4-yl)pyrimidin-2-amine |
| 39 | N-(4-(3,5-Dimethyl-1H-1,2,4-triazol-1-yl)phenyl)-4-(1-ethyl-3-(pyridin-3-yl)-1H-pyrazol-4-yl)pyrimidin-2-amine |
| 40 | N-(3-((Dimethylamino)methyl)phenyl)-4-(1-ethyl-3-(pyridin-3-yl)-1H-pyrazol-4-yl)pyrimidin-2-amine |
| 41 | 4-(1-Ethyl-3-(pyridin-3-yl)-1H-pyrazol-4-yl)-N-(3-(morpholinomethyl)phenyl)pyrimidin-2-amine |
| 42 | N-(4-((1H-1,2,4-Triazol-1-yl)methyl)phenyl)-4-(1-ethyl-3-(pyridin-3-yl)-1H-pyrazol-4-yl)pyrimidin-2-amine |
| 43 | 4-(1-Ethyl-3-(pyridin-3-yl)-1H-pyrazol-4-yl)-N-(4-(2-(4-(2-methoxyethyl)piperazin-1-yl)ethyl)phenyl)pyrimidin-2-amine |

TABLE 2-continued

| 44 | N-(4-(1H-Imidazol-1-yl)phenyl)-4-(1-ethyl-3-(pyridin-3-yl)-1H-pyrazol-4-yl)pyrimidin-2-amine | |
| 45 | 4-(1-Ethyl-3-(pyridin-3-yl)-1H-pyrazol-4-yl)-N-(3-fluoro-4-(1-methylpiperidin-4-yl)phenyl)pyrimidin-2-amine | |
| 46 | 4-(1-Ethyl-3-(pyridin-3-yl)-1H-pyrazol-4-yl)-N-(4-(4-methylpiperazin-1-yl)phenyl)pyrimidin-2-amine | |
| 47 | 4-(1-Ethyl-3-(pyridin-3-yl)-1H-pyrazol-4-yl)-N-(3-methoxy-4-(4-methyl-1-yl)phenyl)pyrimidin-2-amine | |
| 48 | 1-(3-(4-((4-(1-Ethyl-3-(pyridin-3-yl)-1H-pyrazol-4-yl)pyrimidin-2-yl)amino)-1H-pyrazol-1-yl)azetidin-1-yl)-2-methylpropan-2-ol | |
| 49 | 4-(1-Ethyl-3-(pyridin-3-yl)-1H-pyrazol-4-yl)-N-(4-(piperidin-1-yl)phenyl)pyrimidin-2-amine | |

TABLE 2-continued

| | | |
|---|---|---|
| 50 | 4-(1-Ethyl-3-(pyridin-3-yl)-1H-pyrazol-4-yl)-N-(4-(1-(2-methoxyethyl)pyrrolidin-3-yl)phenyl)pyrimidin-2-amine | 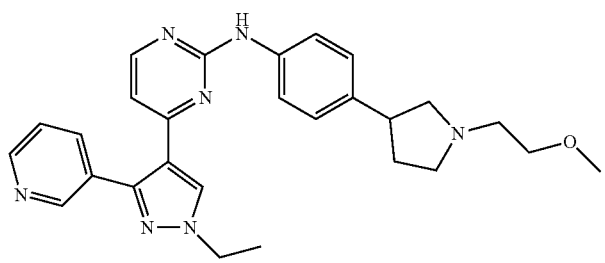 [SMILES: CCn1cc(-c2ccnc(Nc3ccc(C4CCN(CCOC)C4)cc3)n2)c(-c2cccnc2)n1] |
| 51 | N-(4-(4-(2-(2,2-Difluoroethoxy)ethyl)piperazin-1-yl)phenyl)-4-(1-ethyl-3-(pyridin-3-yl)-1H-pyrazol-4-yl)pyrimidin-2-amine | 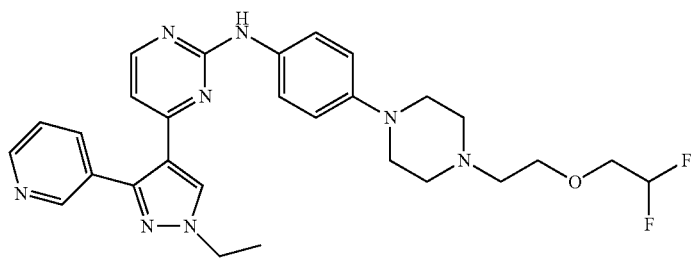 [SMILES: CCn1cc(-c2ccnc(Nc3ccc(N4CCN(CCOCC(F)F)CC4)cc3)n2)c(-c2cccnc2)n1] |
| 52 | N-(4-(4-(2-(Cyclopropylmethoxy)ethyl)piperazin-1-yl)phenyl)-4-(1-ethyl-3-(pyridin-3-yl)-1H-pyrazol-4-yl)Pyrimidin-2-amine | 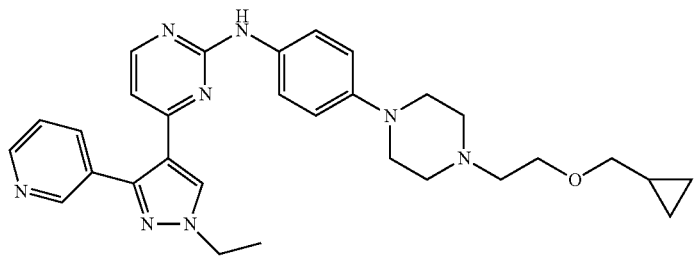 [SMILES: CCn1cc(-c2ccnc(Nc3ccc(N4CCN(CCOCC5CC5)CC4)cc3)n2)c(-c2cccnc2)n1] |
| 53 | 4-(1-Ethyl-3-(pyridin-3-yl)-1H-pyrazol-4-yl)-N-(1-(tetrahydro-2H-pyran-4-yl)-1H-pyrazol-4-yl)pyrimidin-2-amine | 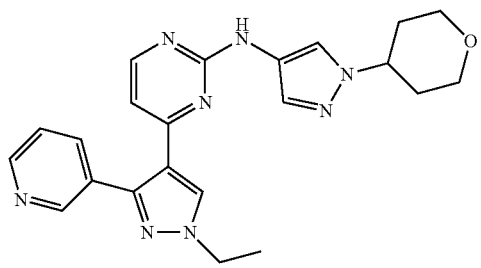 [SMILES: CCn1cc(-c2ccnc(Nc3cnn(C4CCOCC4)c3)n2)c(-c2cccnc2)n1] |
| 54 | 1-(4-(4-((4-(1-Ethyl-3-(pyridin-3-yl)-1H-pyrazol-4-yl)pyrimidin-2-yl)amino)-1H-pyrazol-1-yl)piperidin-1-yl)-2-methylpropan-2-ol | 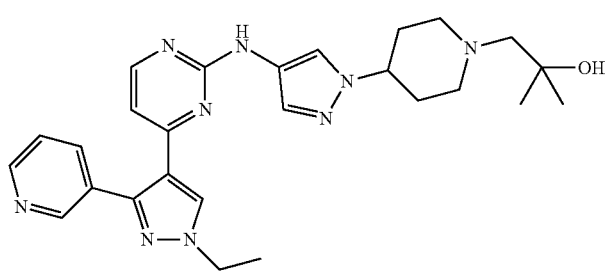 [SMILES: CCn1cc(-c2ccnc(Nc3cnn(C4CCN(CC(C)(C)O)CC4)c3)n2)c(-c2cccnc2)n1] |
| 55 | 4-(1-Ethyl-3-(pyridin-3-yl)-1H-pyrazol-4-yl)-N-(1-(1-(2-methoxyethyl)piperidin-4-yl)-1H-pyrazol-4-yl)pyrimidin-2-amine oxalate | 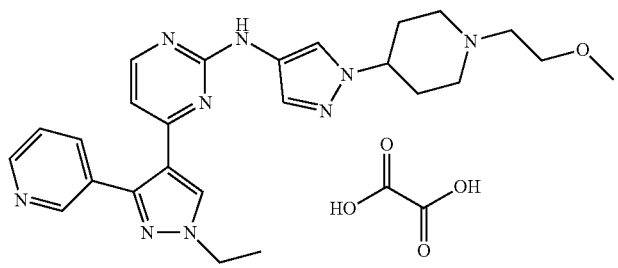 |

TABLE 2-continued
| | | |
|---|---|---|
| 56 | 4-(1-Ethyl-3-(pyridin-3-yl)-1H-pyrazol-4-yl)-N-(4-(5-methyl-1,3,4-thiadiazol-2-yl)phenyl)pyrimidin-2-amine | 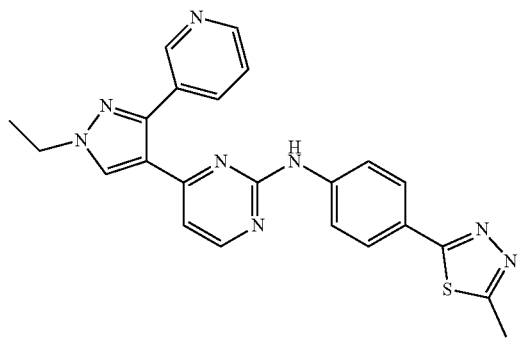 [SMILES: CCn1cc(-c2ccnc(Nc3ccc(-c4nnc(C)s4)cc3)n2)c(-c2cccnc2)n1] |
| 57 | 4-(1-(2-Methoxyethyl)-3-(pyridin-3-yl)-1H-pyrazol-4-yl)-N-(4-(1-(2-methoxyethyl)-piperidin-4-yl)phenyl)-pyrimidin-2-amine | 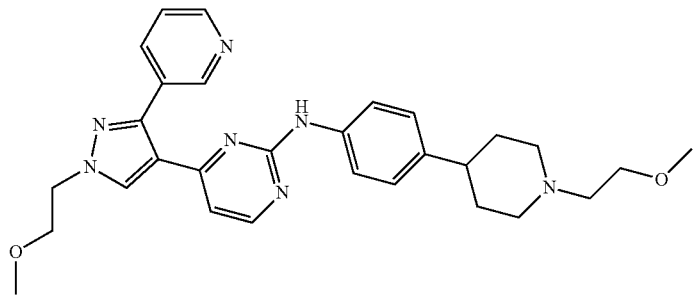 [SMILES: COCCN1CCC(c2ccc(Nc3nccc(-c4cn(CCOC)nc4-c4cccnc4)n3)cc2)CC1] |
| 58 | 4-(1-Ethyl-3-(pyridin-3-yl)-1H-pyrazol-4-yl)-N-(4-(1-(2-methoxyethyl)piperidin-4-yl)phenyl)pyrimidin-2-amine | 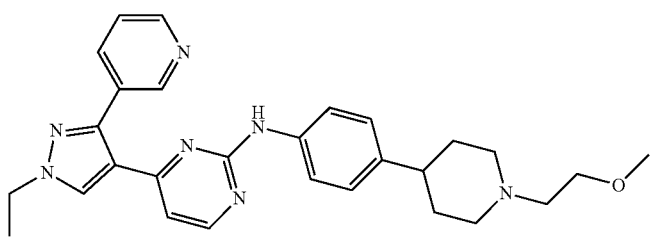 [SMILES: CCn1cc(-c2ccnc(Nc3ccc(C4CCN(CCOC)CC4)cc3)n2)c(-c2cccnc2)n1] |
| 59 | 1-(4-(4-((4-(1-Ethyl-3-(pyridin-3-yl)-1H-pyrazol-4-yl)pyrimidin-2-yl)amino)phenyl)piperidin-1-yl)-2-hydroxyethan-1-one | 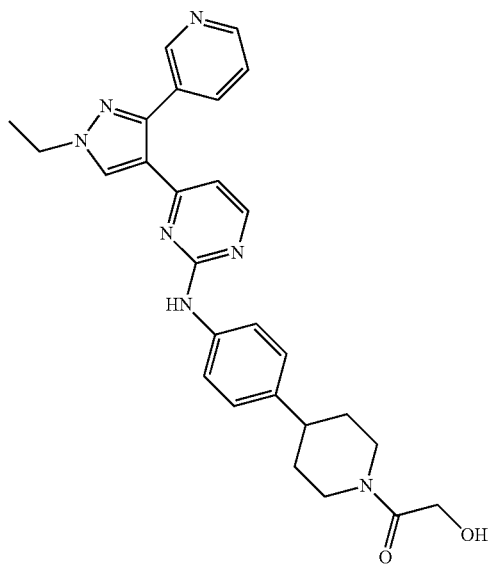 [SMILES: CCn1cc(-c2ccnc(Nc3ccc(C4CCN(C(=O)CO)CC4)cc3)n2)c(-c2cccnc2)n1] |

TABLE 2-continued

| | | |
|---|---|---|
| 60 | N-(4-(1-(2-Methoxyethyl)-3-(pyridin-3-yl)-1H-pyrazol-4-yl)pyrimidin-2-yl)-2-methylisoindolin-5-amine | 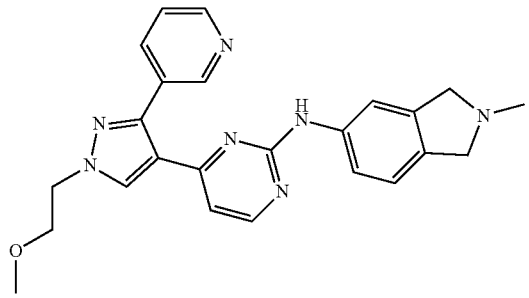 [SMILES: COCCn1cc(-c2ccnc(Nc3ccc4c(c3)CN(C)C4)n2)c(-c2cccnc2)n1] |
| 61 | N-(4-(1-Ethyl-3-(pyridin-3-yl)-1H-pyrazol-4-yl)pyrimidin-2-yl)-2-(2-methoxyethyl)-isoindolin-5-amine | 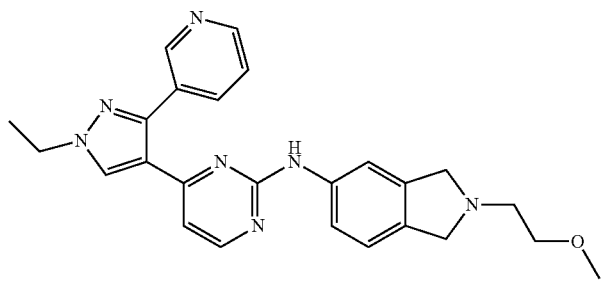 [SMILES: CCn1cc(-c2ccnc(Nc3ccc4c(c3)CN(CCOC)C4)n2)c(-c2cccnc2)n1] |
| 62 | 2-(2-Methoxyethyl)-N-(4-(1-(2-methoxyethyl)-3-(pyridin-3-yl)-1H-pyrazol-4-yl)pyrimidin-2-yl)isoindolin-5-amine | 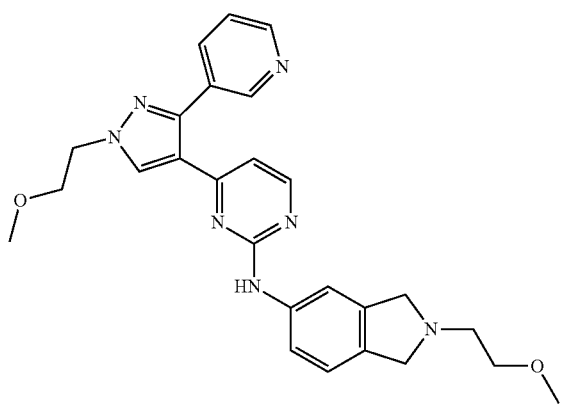 |
| 63 | 2-Methyl-1-(4-(2-((2-methylisoindolin-5-yl)amino)pyrimidin-4-yl)-3-(pyridin-3-yl)-1H-pyrazol-1-yl)propan-2-ol | 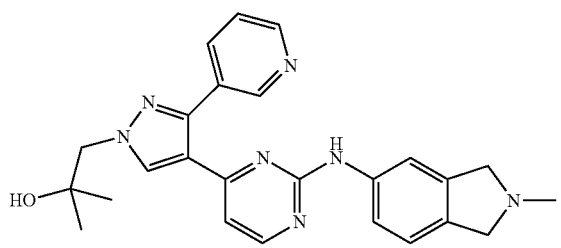 [SMILES: CN1Cc2ccc(Nc3nccc(-c4cn(CC(C)(C)O)nc4-c4cccnc4)n3)cc2C1] |
| 64 | N-(4-(1-(2-Methoxyethyl)-3-(pyridin-3-yl)-1H-pyrazol-4-yl)pyrimidin-2-yl)-2-methyl-1,2,3,4-tetrahydroisoquinolin-6-amine | 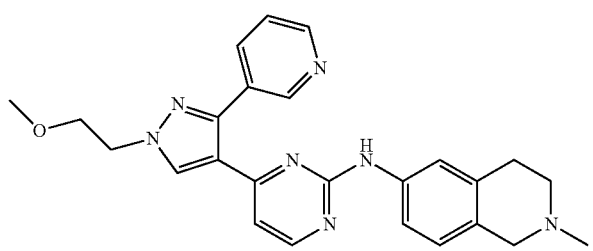 |

TABLE 2-continued

| | | |
|---|---|---|
| 65 | 2-Methyl-1-(4-(2-((2-methyl-1,2,3,4-tetrahydroisoquinolin-6-yl)amino)pyrimidin-4-yl)-3-(pyridin-3-yl)-1H-pyrazol-1-yl)propan-2-ol | |
| 66 | 3-Cyclopropyl-N-(4-(1-ethyl-3-(pyridin-3-yl)-1H-pyrazol-4-yl)pyrimidin-2-yl)-2,3,4,5-tetrahydro-1H-benzo[d]azepin-7-amine | |
| 67 | N-(4-(1-Ethyl-3-(pyridin-3-yl)-1H-pyrazol-4-yl)pyrimidin-2-yl)-4-methyl-2,3,4,5-tetrahydrobenzo[f][1,4]oxazepin-8-amine | |
| 68 | N-(4-(4-(Dimethylamino)-4-methylpiperidin-1-yl)phenyl)-4-(1-ethyl-3-(pyridin-3-yl)-1H-pyrazol-4-yl)pyrimidin-2-amine | |
| 69 | N-(4-(1,4-Diazabicyclo[3.2.2]nonan-4-yl)phenyl)-4-(1-ethyl-3-(pyridin-3-yl)-1H-pyrazol-4-yl)pyrimidin-2-amine | |
| 70 | 4-(1-Ethyl-3-(pyridin-3-yl)-1H-pyrazol-4-yl)-N-(4-(oxazol-5-yl)phenyl)pyrimidin-2-amine | |

TABLE 2-continued

| | | |
|---|---|---|
| 71 | 4-(1-(2-Methoxyethyl)-3-(pyridin-3-yl)-1H-pyrazol-4-yl)-N-(4-(piperazin-1-yl)phenyl)pyrimidin-2-amine | |
| 72 | N-(4-(Piperazin-1-yl)phenyl)-4-(3-(pyridin-3-yl)-1-(2-(trifluoromethoxy)ethyl)-1H-pyrazol-4-yl)pyrimidin-2-amine | |
| 73 | N-(4-(1-Ethyl-3-(pyridin-3-yl)-1H-pyrazol-4-yl)pyrimidin-2-yl)isoindolin-5-amine | |
| 74 | 1-(4-(4-((4-(1-Phenethyl-3-(pyridin-3-yl)-1H-pyrazol-4-yl)pyrimidin-2-yl)amino)benzoyl)piperazin-1-yl)ethan-1-one | |
| 75 | 1-(6-((4-(1-Ethyl-3-(pyridin-3-yl)-1H-pyrazol-4-yl)pyrimidin-2-yl)amino)-3,4-dihydroisoquinolin-2(1H)-yl)ethan-1-one | |

TABLE 2-continued

| | | |
|---|---|---|
| 76 | N-(4-(4-(2-Methoxyethyl)piperazin-1-yl)phenyl)-4-(3-(pyridin-3-yl)-1-(tetrahydrofuran-3-yl)-1H-pyrazol-4-yl)pyrimidin-2-amine | |
| 77 | N-(4-(4-(2-Methoxyethyl)piperazin-1-yl)phenyl)-4-(1-((3-methyloxetan-3-yl)methyl)-3-(pyridin-3-yl))-1H-pyrazol-4-yl)pyrimidin-2-amine | |
| 78 | 4-(1-Ethyl-3-(pyridin-3-yl)-1H-pyrazol-4-yl)-N-(4-(4-((1-methylpyrrolidin-2-yl)methyl)piperazin-1-yl)phenyl)pyrimidin-2-amine | |
| 79 | N-(4-(4-((1-Methylpyrrolidin-2-yl)methyl)piperazin-1-yl)phenyl)-4-(1-(oxetan-3-yl)-3-(pyridin-3-yl)-1H-pyrazol-4-yl)pyrimidin-2-amine | |
| 80 | 4-(1-(2-Methoxyethyl)-3-(pyridin-3-yl)-1H-pyrazol-4-yl)-N-(4-(4-((1-methylpyrrolidin-2-yl)methyl)piperazin-1-yl)phenyl)pyrimidin-2-amine | |

| | | |
|---|---|---|
| 81 | 1-(4-(2-((4-(4-(2-Methoxyethyl)piperazin-1-yl)phenyl)amino)pyrimidin-4-yl)-3-(pyridin-3-yl)-1H-pyrazol-1-yl)-2-methylpropan-2-ol | 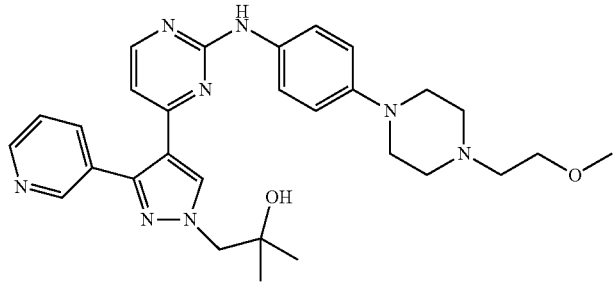 [SMILES: COCCN1CCN(c2ccc(Nc3nccc(-c4cn(CC(C)(C)O)nc4-c4cccnc4)n3)cc2)CC1] |
| 82 | 2-((4-(2-((4-(4-(2-Methoxyethyl)piperazin-1-yl)phenyl)amino)pyrimidin-4-yl)-3-(pyridin-3-yl-1H-pyrazol-1-yl)methyl)benzonitrile | 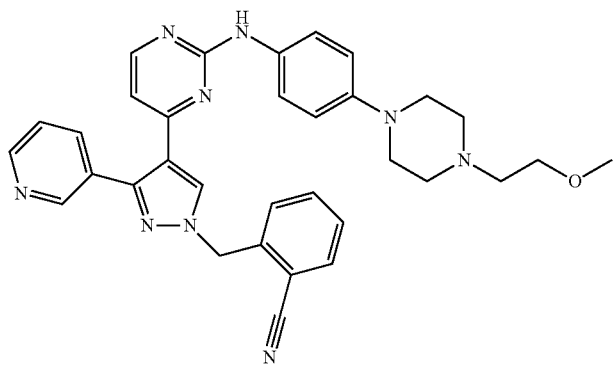 [SMILES: COCCN1CCN(c2ccc(Nc3nccc(-c4cn(Cc5ccccc5C#N)nc4-c4cccnc4)n3)cc2)CC1] |
| 83 | 5-((4-(1-Ethyl-3-(pyridin-3-yl)-1H-pyrazol-4-yl)pyrimidin-2-yl)amino)-2-(4-(2-methoxyethyl)piperazin-1-yl)benzonitrile | 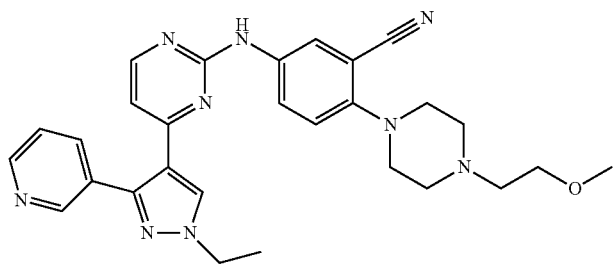 [SMILES: CCn1cc(-c2ccnc(Nc3ccc(N4CCN(CCOC)CC4)c(C#N)c3)n2)c(-c2cccnc2)n1] |
| 84 | 4-(1-Ethyl-3-(pyridin-3-yl)-1H-pyrazol-4-yl)-N-(6-(4-(2-methoxyethyl)piperazin-1-yl)pyridin-3-yl)pyrimidin-2-amine | 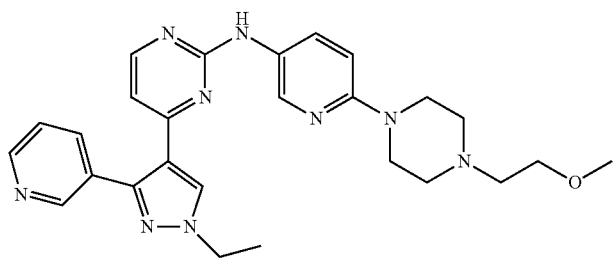 [SMILES: CCn1cc(-c2ccnc(Nc3ccc(N4CCN(CCOC)CC4)nc3)n2)c(-c2cccnc2)n1] |
| 85 | 4-(1-Ethyl-3-(pyridin-3-yl)-1H-pyrazol-4-yl)-N-(4-(8-(2-methoxyethyl)-8-azabicyclo[3.2.1]octan-3-yl)phenyl)pyrimidin-2-amine | 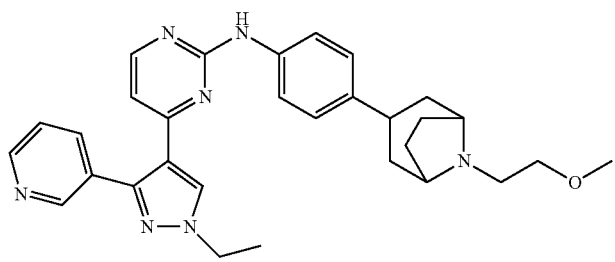 [SMILES: CCn1cc(-c2ccnc(Nc3ccc(N4CC5CCC(C4)N5CCOC)cc3)n2)c(-c2cccnc2)n1] |

TABLE 2-continued

| | | |
|---|---|---|
| 86 | 4-(1-Ethyl-3-(pyridin-3-yl)-1H-pyrazol-4-yl)-N-(4-(8-(2-methoxyethyl)-3,8-diazabicyclo[3.2.1]octan-3-yl)phenyl)pyrimidin-2-amine | |
| 87 | 2-(4-(4-((4-(1-Ethyl-3-(pyridin-3-yl)-1H-pyrazol-4-yl)pyrimidin-2-yl)amino)phenyl)piperazin-1-yl)acetamide | |
| 88 | N-(4-(1-Ethyl-3-(pyridin-3-yl)-1H-pyrazol-4-yl)pyrimidin-2-yl)-2-((tetrahydrofuran-2-yl)methyl)-1,2,3,4-tetrahydroisoquinolin-7-amine | |
| 89 | N-(4-(1-Ethyl-3-(pyridin-3-yl)-1H-pyrazol-4-yl)pyrimidin-2-yl)-2-((tetrahydrofuran-2-yl)methyl)-1,2,3,4-tetrahydroisoquinolin-6-amine | |
| 90 | 2-(6-((4-(1-Ethyl-3-(pyridin-3-yl)-1H-pyrazol-4-yl)pyrimidin-2-yl)amino)-3,4-dihydroisoquinolin-2(1H)-yl)acetamide | |

TABLE 2-continued

| | | |
|---|---|---|
| 91 | N-(4-(1-Ethyl-3-(pyridin-3-yl)-1H-pyrazol-4-yl)pyrimidin-2-yl)-4-(2-methoxyethyl)-2,3,4,5-tetrahydrobenzo[f][1,4]oxazepin-8-amine | |
| 92 | 4-(1-Ethyl-3-(pyridin-3-yl)-1H-pyrazol-4-yl)-N-(4-((1-(2-methoxyethyl)azetidin-3-yl)oxy)phenyl)pyrimidin-2-amine | |
| 93 | N-(4-(1-Ethyl-3-(pyridin-3-yl)-1H-pyrazol-4-yl)pyrimidin-2-yl)-3-(2-methoxyethyl)-2,3,4,5-tetrahydro-1H-benzo[d]azepin-7-amine | |
| 94 | 4-(1-Ethyl-3-(pyridin-3-yl)-1H-pyrazol-4-yl)-N-(4-(4-(2-methoxyethyl)-1,4-diazepan-1-yl)phenyl)pyrimidin-2-amine | |
| 95 | N-(4-(1-Ethyl-3-(pyridin-3-yl)-1H-pyrazol-4-yl)pyrimidin-2-yl)-2-(oxetan-3-yl)-1,2,3,4-tetrahydroisoquinolin-6-amine | |

TABLE 2-continued

| | | |
|---|---|---|
| 96 | N-(4-(4-((4,4-Dimethyloxetan-2-yl)methyl)piperazin-1-yl)phenyl)-4-(1-ethyl-3-(pyridin-3-yl)-1H-pyrazol-4-yl)pyrimidin-2-amine | |
| 97 | 4-(1-Ethyl-3-(pyridin-3-yl)-1H-pyrazol-4-yl)-N-(4-(4-((tetrahydrofuran-3-yl)methyl)piperazin-1-yl)phenyl)pyrimidin-2-amine | |
| 98 | 4-(1-Ethyl-3-(pyridin-3-yl)-1H-pyrazol-4-yl)-N-(4-(4-((3-methyloxetan-3-yl)methyl)piperazin-1-yl)phenyl)pyrimidin-2-amine | |
| 99 | 4-(1-Ethyl-3-(pyridin-3-yl)-1H-pyrazol-4-yl)-N-(4-(4-(oxetan-3-ylmethyl)piperazin-1-yl)phenyl)pyrimidin-2-amine | |
| 100 | 4-(1-Ethyl-3-(pyridin-3-yl)-1H-pyrazol-4-yl)-N-(4-(1-(2-methoxyethyl)piperidin-3-yl)phenyl)pyrimidin-2-amine | |
| 101 | 4-(1-(Oxetan-3-yl)-3-(pyridin-3-yl)-1H-pyrazol-4-yl)-N-(4-(4-(oxetan-3-yl)piperazin-1-yl)phenyl)pyrimidin-2-amine | |

TABLE 2-continued

| 102 | N-(4-(4-(2-Methoxyethyl)piperazin-1-yl)phenyl)-4-(1-(oxetan-3-ylmethyl)-3-(pyridin-3-yl)-1H-pyrazol-4-yl)pyrimidin-2-amine | 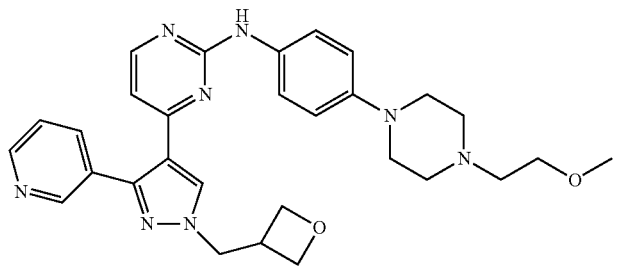 [SMILES: COCCN1CCN(c2ccc(Nc3nccc(-c4cn(CC5COC5)nc4-c4cccnc4)n3)cc2)CC1] |
| 103 | N-(4-(4-(Cyclopropylmethyl)piperazin-1-yl)phenyl)-4-(1-(oxetan-3-yl)-3-(pyridin-3-yl)-1H-pyrazol-4-yl)pyrimidin-2-amine | 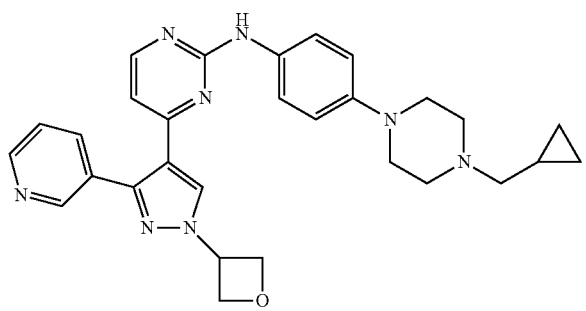 [SMILES: c1cncc(-c2nn(C3COC3)cc2-c2ccnc(Nc3ccc(N4CCN(CC5CC5)CC4)cc3)n2)c1] |
| 104 | 1-(4-(4-((4-(1-ethyl-3-(pyridin-3-yl)-1H-pyrazol-4-yl)pyrimidin-2-yl)amino)phenyl)piperazin-1-yl)-2-methylpropan-2-ol | 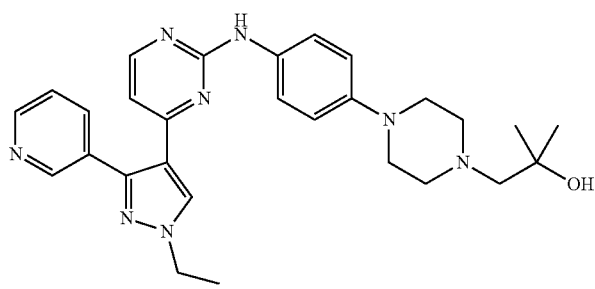 [SMILES: CCn1cc(-c2ccnc(Nc3ccc(N4CCN(CC(C)(C)O)CC4)cc3)n2)c(-c2cccnc2)n1] |
| 105 | 1-(4-(4-((4-(1-Ethyl-3-(pyridin-3-yl)-1H-pyrazol-4-yl)pyrimidin-2-yl)amino)phenyl)piperazin-1-yl)-3-methoxypropan-2-ol | 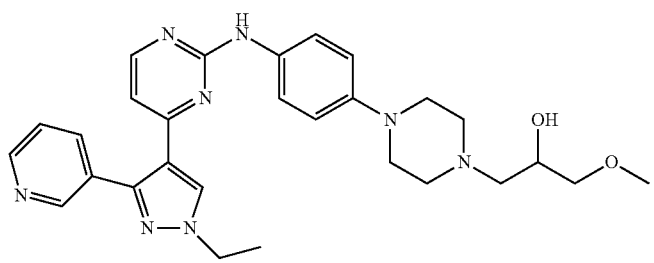 [SMILES: CCn1cc(-c2ccnc(Nc3ccc(N4CCN(CC(O)COC)CC4)cc3)n2)c(-c2cccnc2)n1] |
| 106 | 1-(7-((4-(1-Ethyl-3-(pyridin-3-yl)-1H-pyrazol-4-yl)pyrimidin-2-yl)amino)-3,4-dihydroisoquinolin-2(1H)-yl)-2-methylpropan-2-ol | 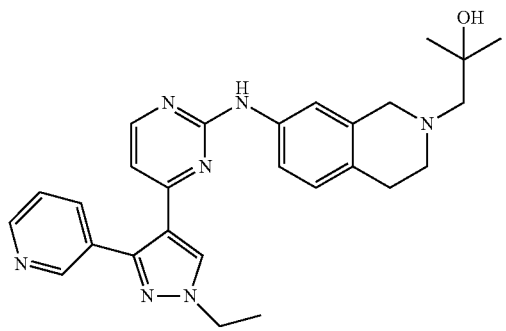 [SMILES: CCn1cc(-c2ccnc(Nc3ccc4c(c3)CN(CC(C)(C)O)CC4)n2)c(-c2cccnc2)n1] |

TABLE 2-continued

| 107 | 1-(3-(4-((4-(1-(2-Methoxyethyl)-3-(pyridin-3-yl)-1H-pyrazol-4-yl)pyrimidin-2-yl)amino)phenoxy)azetidin-1-yl)-2-methylpropan-2-ol | |
| --- | --- | --- |
| 108 | 1-(3-(4-((4-(1-Ethyl-3-(pyridin-3-yl)-1H-pyrazol-4-yl)pyrimidin-2-yl)amino)phenoxy)azetidin-1-yl)-2-methylpropan-2-ol | |
| 109 | 1-(6-((4-(1-Ethyl-3-(pyridin-3-yl)-1H-pyrazol-4-yl)pyrimidin-2-yl)amino)-3,4-dihydroisoquinolin-2(1H)-yl)-3-methoxypropan-2-ol | |
| 110 | 1-Methoxy-3-(4-(4-((4-(1-(oxetan-3-yl)-3-(pyridin-3-yl)-1H-pyrazol-4-yl)pyrimidin-2-yl)amino)phenyl)piperazin-1-yl)propan-2-ol | |
| 111 | 1-(4-(2-((4-(4-(2-Hydroxy-3-methoxypropyl)piperazin-1-yl)phenyl)amino)pyrimidin-4-yl)-3-(pyridin-3-yl)-1H-pyrazol-1-yl)-2-methylpropan-2-ol | |

TABLE 2-continued

| 112 | 4-(1-Ethyl-3-(pyridin-3-yl)-1H-pyrazol-4-yl)-N-(4-(2-(4-methylpiperazin-1-yl)ethyl)phenyl)pyrimidin-2-amine | 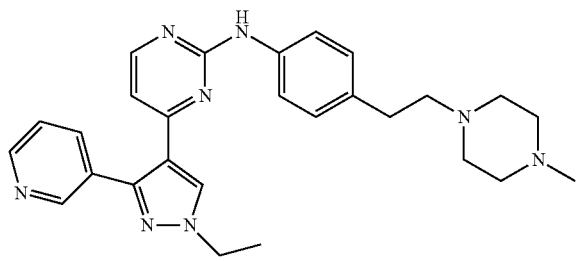 [SMILES: CCn1cc(-c2ccnc(Nc3ccc(CCN4CCN(C)CC4)cc3)n2)c(-c2cccnc2)n1] |
| 113 | 4-(1-Ethyl-3-(pyridin-3-yl)-1H-pyrazol-4-yl)-N-(4-(1-methylpiperidin-3-yl)phenyl)pyrimidin-2-amine | 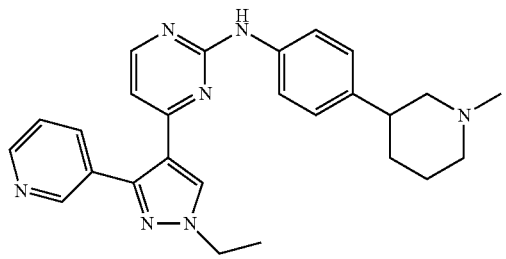 [SMILES: CCn1cc(-c2ccnc(Nc3ccc(C4CCCN(C)C4)cc3)n2)c(-c2cccnc2)n1] |
| 114 | 4-(1-Ethyl-3-(pyridin-3-yl)-1H-pyrazol-4-yl)-N-(3-(1-methylpiperidin-4-yl)phenyl)pyrimidin-2-amine | 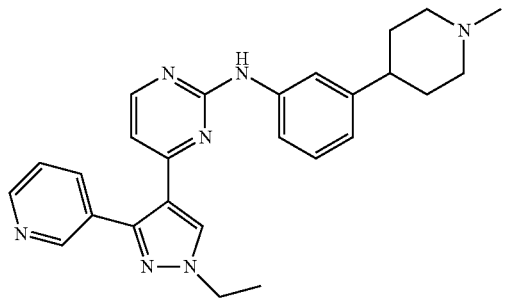 [SMILES: CCn1cc(-c2ccnc(Nc3cccc(C4CCN(C)CC4)c3)n2)c(-c2cccnc2)n1] |
| 115 | N-(4-(1-Ethyl-3-(pyridin-3-yl)-1H-pyrazol-4-yl)pyrimidin-2-yl)-3-methyl-2,3,4,5-tetrahydro-1H-benzo[d]azepin-7-amine | 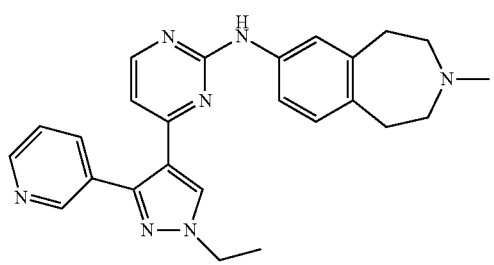 [SMILES: CCn1cc(-c2ccnc(Nc3ccc4c(c3)CCN(C)CC4)n2)c(-c2cccnc2)n1] |
| 116 | (4-((4-(1-Ethyl-3-(pyridin-3-yl)-1H-pyrazol-4-yl)pyrimidin-2-yl)amino)phenyl)(4-methylpiperazin-1-yl)methanone | 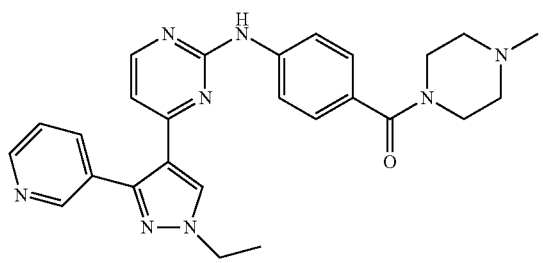 [SMILES: CCn1cc(-c2ccnc(Nc3ccc(C(=O)N4CCN(C)CC4)cc3)n2)c(-c2cccnc2)n1] |
| 117 | (4-((4-(1-Ethyl-3-(pyridin-3-yl)-1H-pyrazol-4-yl)pyrimidin-2-yl)amino)phenyl)(8-methyl-3,8-diazabicyclo[3.2.1]octan-3-yl)methanone | 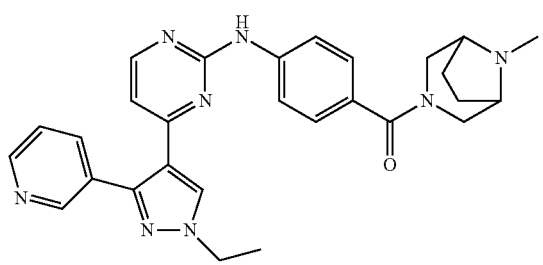 [SMILES: CCn1cc(-c2ccnc(Nc3ccc(C(=O)N4CC5CCC(C4)N5C)cc3)n2)c(-c2cccnc2)n1] |

TABLE 2-continued

| 118 | (8-Cyclopentyl-3,8-diazabicyclo [3.2.1]oct-3-yl) (4-((4-(1-ethyl-3-(pyridin-3-yl)-1H-pyrazol-4-yl)pyrimidin-2-yl)amino)phenyl)methanone | 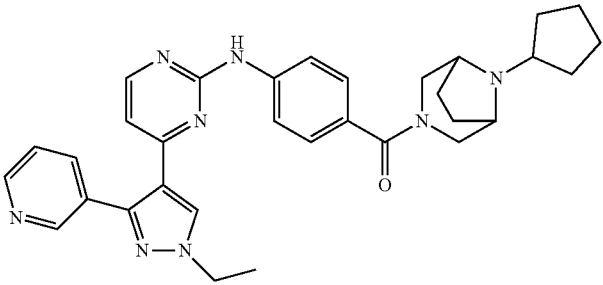 [SMILES: CCn1cc(-c2ccnc(Nc3ccc(C(=O)N4CC5CCC(C4)N5C4CCCC4)cc3)n2)c(-c2cccnc2)n1] |
|---|---|---|
| 119 | (4-((4-(1-Ethyl-3-(pyridin-3-yl)-1H-pyrazol-4-yl)pyrimidin-2-yl)amino)phenyl) (4-isopropylpiperazin-1-yl)methanone | 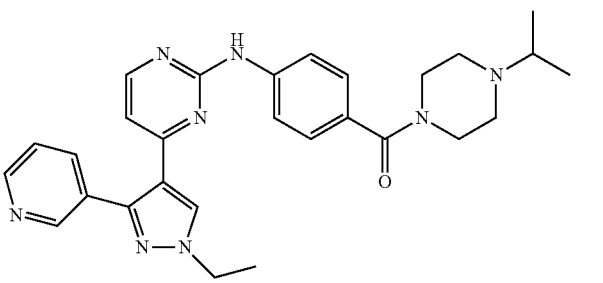 [SMILES: CCn1cc(-c2ccnc(Nc3ccc(C(=O)N4CCN(C(C)C)CC4)cc3)n2)c(-c2cccnc2)n1] |
| 120 | (4-Cyclohexylpiperazin-1-yl) (4-((4-(1-ethyl-3-(pyridin-3-yl)-1H-pyrazol-4-yl)pyrimidin-2-yl)amino)phenyl)methanone | 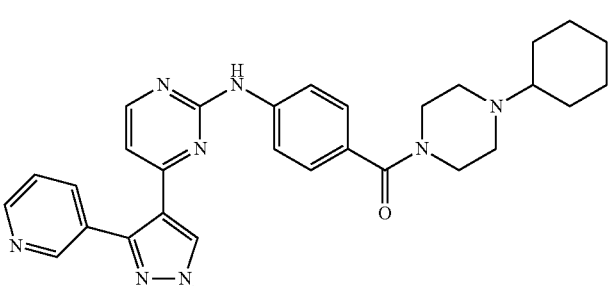 |
| 121 | (4-((4-(1-(4-Fluorobenzyl)-3-(pyridin-3-yl)-1H-pyrazol-4-yl)pyrimidin-2-yl)amino)phenyl)(4-isopropylpiperazin-1-yl)methanone | 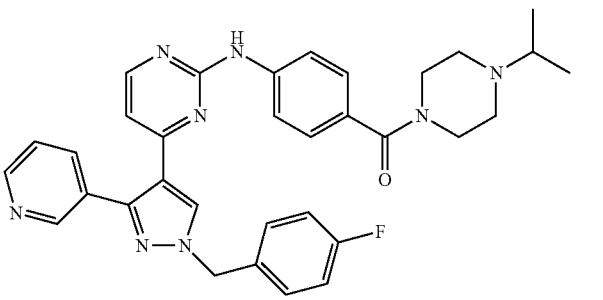 [SMILES: CC(C)N1CCN(C(=O)c2ccc(Nc3nccc(-c4cn(Cc5ccc(F)cc5)nc4-c4cccnc4)n3)cc2)CC1] |
| 122 | (3-((4-(1-Ethyl-3-(pyridin-3-yl)-1H-pyrazol-4-yl)pyrimidin-2-yl)amino)phenyl)(4-isopropylpiperazin-1-yl)methanone | 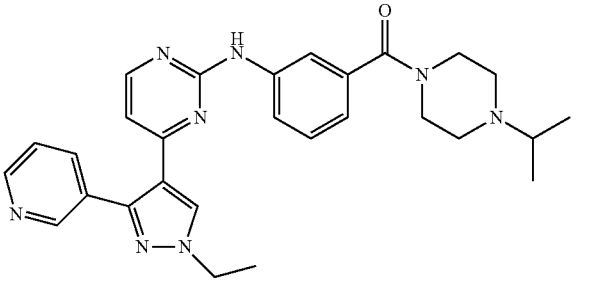 [SMILES: CCn1cc(-c2ccnc(Nc3cccc(C(=O)N4CCN(C(C)C)CC4)c3)n2)c(-c2cccnc2)n1] |

TABLE 2-continued

| | | |
|---|---|---|
| 123 | (4-Isopropylpiperazin-1-yl) (4-((4-(1-phenethyl-3-(pyridin-3-yl)-1H-pyrazol-4-yl)pyrimidin-2-yl)amino)phenyl)methanone | |
| 124 | (4-((4-(1-Ethyl-3-(pyridin-3-yl)-1H-pyrazol-4-yl)pyrimidin-2-yl)amino)-N-(1-isopropylpiperidin-4-yl)-N-methylbenzenesulfonamide | |
| 125 | N-(4-(1-Ethyl-3-(pyridin-3-yl)-1H-pyrazol-4-yl)pyrimidin-2-yl)-3-(oxetan-3-yl)-2,3,4,5-tetrahydro-1H-benzo[d]azepin-7-amine | |
| 126 | N-(4-(1-Ethyl-3-(pyridin-3-yl)-1H-pyrazol-4-yl)pyrimidin-2-yl)-2-(2-methoxyethyl)-1,2,3,4-tetrahydroisoquinolin-6-amine | |
| 127 | N-(4-(4-Methylpiperazin-1-yl)phenyl)-4-(3-(pyridin-3-yl)-1H-pyrazol-4-yl)pyrimidin-2-amine | |

TABLE 2-continued

| | | |
|---|---|---|
| 128 | 4-(1-Ethyl-3-(pyridin-3-yl)-1H-pyrazol-4-yl)-N-(1-(1-(oxetan-3-yl)piperidin-4-yl)-1H-pyrazol-4-yl)pyrimidin-2-amine | |
| 129 | N-(4-(1-Ethyl-3-(pyridin-3-yl)-1H-pyrazol-4-yl)pyrimidin-2-yl)-2-methyl-1,2,3,4-tetrahydroisoquinolin-6-amine | |
| 130 | 4-(1-Ethyl-3-(pyridin-3-yl)-1H-pyrazol-4-yl)-N-(4-(4-(tetrahydro-2H-pyran-4-yl)piperazin-1-yl)phenyl)pyrimidin-2-amine | |
| 131 | 2-Methyl-1-(4-(2-((2-(oxetan-3-yl)-1,2,3,4-tetrahydroisoquinolin-6-yl)amino)pyrimidin-4-yl)-3-(pyridin-3-yl)-1H-pyrazol-1-yl)propan-2-ol | |
| 132 | 2-Methyl-1-(4-(2-((4-(1-(oxetan-3-yl)piperidin-4-yl)phenyl)amino)pyrimidin-4-yl)-3-(pyridin-3)yl)-1H-pyrazol-1-yl)propan-2-ol | |

TABLE 2-continued

| | | |
|---|---|---|
| 133 | 4-(1-Ethyl-3-(pyridin-3-yl)-1H-pyrazol-4-yl)-N-(4-(pyridin-3-yl)phenyl)pyrimidin-2-amine | |
| 134 | 4-(1-Ethyl-3-(pyridin-3-yl)-1H-pyrazol-4-yl)-N-(4-(pyridin-4-yl)phenyl)pyrimidin-2-amine | |
| 135 | 4-(1-tert-Butyl)-3-(pyridin-3-yl)-1H-pyrazol-4-yl)-N-(4-(piperazin-1-yl)phenyl)pyrimidin-2-amine | |
| 136 | N-(4-(Piperazin-1-yl)phenyl)-4-(3-(pyridin-3-yl)-1-(2,2,2-trifluoroethyl)-1H-pyrazol-4-yl)pyrimidin-2-amine | |
| 137 | 4-(1-(Oxetan-3-yl)-3-(pyridin-3-yl)-1H-pyrazol-4-yl)-N-(4-(piperazin-1-yl)phenyl)pyrimidin-2-amine | |

TABLE 2-continued

| | | |
|---|---|---|
| 138 | (4-((4-(1-Benzyl-3-(pyridin-3-yl)-1H-pyrazol-4-yl)pyrimidin-2-yl)amino)phenyl)(piperazin-1-yl)methanone | 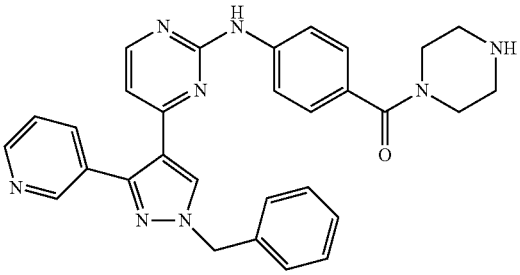 [SMILES: O=C(c1ccc(Nc2nccc(-c3cn(Cc4ccccc4)nc3-c3cccnc3)n2)cc1)N1CCNCC1] |
| 139 | 4-(1-(4-Fluorobenzyl)-3-(pyridin-3-yl)-1H-pyrazol-4-yl)-N-(4-(piperazin-1-yl)phenyl)pyrimidin-2-amine | 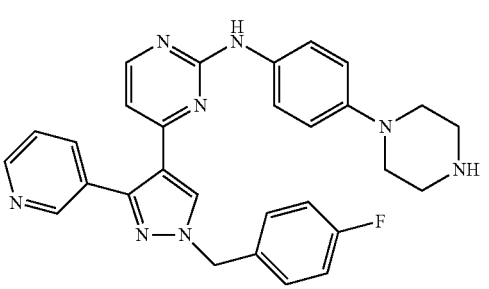 [SMILES: Fc1ccc(Cn2cc(-c3ccnc(Nc4ccc(N5CCNCC5)cc4)n3)c(-c3cccnc3)n2)cc1] |
| 140 | N-(4-(Piperazin-1-yl)phenyl)-4-(1-(pyridin-2-ylmethyl)-3-(pyridin-3-yl)-1H-pyrazol-4-yl)pyrimidin-2-amine | 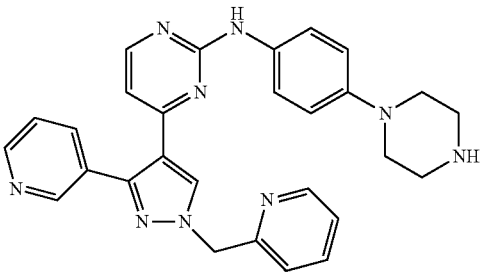 [SMILES: c1ccc(Cn2cc(-c3ccnc(Nc4ccc(N5CCNCC5)cc4)n3)c(-c3cccnc3)n2)nc1] |
| 141 | N-(4-(Piperazin-1-yl)phenyl)-4-(3-(pyr-3-yl)-1-(pyridin-3-ylmethyl)-1H-pyrazol-4-yl)pyrimidin-2-amine | 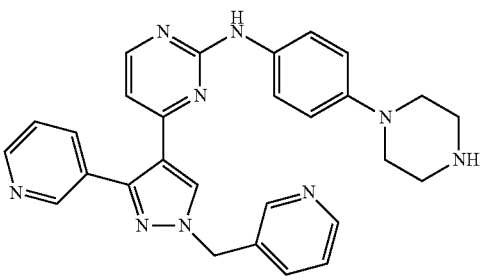 [SMILES: c1cncc(Cn2cc(-c3ccnc(Nc4ccc(N5CCNCC5)cc4)n3)c(-c3cccnc3)n2)c1] |
| 142 | 4-(1-Phenethyl-3-(pyridin-3-yl)-1H-pyrazol-4-yl)-N-(4-(piperazin-1-yl)phenyl)pyrimidin-2-amine | 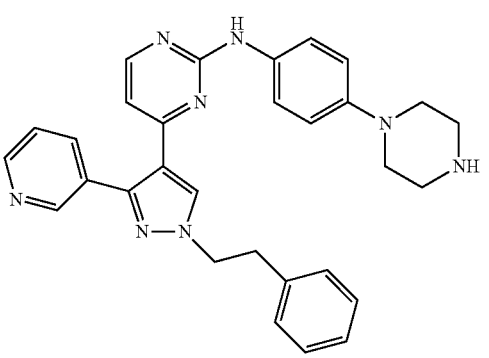 [SMILES: c1ccc(CCn2cc(-c3ccnc(Nc4ccc(N5CCNCC5)cc4)n3)c(-c3cccnc3)n2)cc1] |

TABLE 2-continued

| 143 | N-(4-(3,8-Diazabicyclo[3.2.1]octan-3-yl)phenyl)-4-(1-ethyl-3-(pyridin-3-yl)-1H-pyrazol-4-yl)pyrimidin-2-amine | 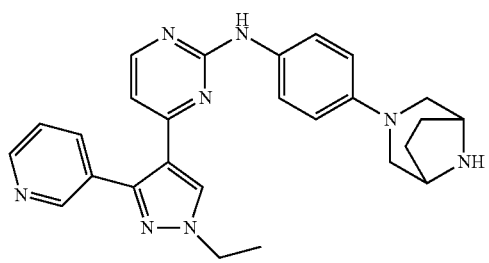 [SMILES: CCn1cc(-c2ccnc(Nc3ccc(N4CC5CCC(C4)N5)cc3)n2)c(-c2cccnc2)n1] |
| 144 | N-(6-(3,8-Diazabicyclo[3.2.1]octan-3-yl)pyridin-3-yl)-4-(1-ethyl-3-(pyridin-3-yl)-1H-pyrazol-4-yl)pyrimidin-2-amine | 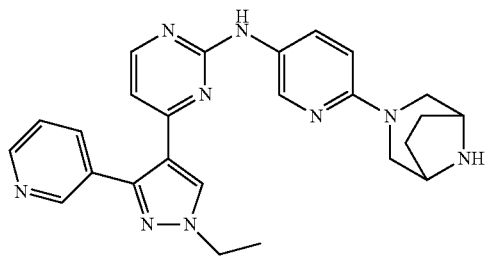 [SMILES: CCn1cc(-c2ccnc(Nc3ccc(N4CC5CCC(C4)N5)nc3)n2)c(-c2cccnc2)n1] |
| 145 | N-(4-(Azetidin-3-yloxy)phenyl)-4-(1-ethyl-3-(pyridin-3-yl)-1H-pyrazol-4-yl)pyrimidin-2-amine | 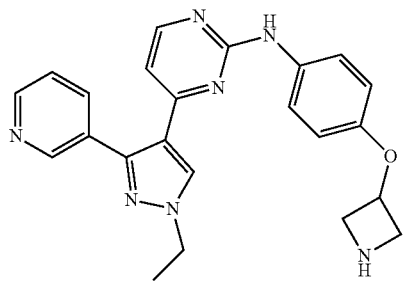 [SMILES: CCn1cc(-c2ccnc(Nc3ccc(OC4CNC4)cc3)n2)c(-c2cccnc2)n1] |
| 146 | N-(4-((8-Azabicyclo[3.2.1]octan-3-yl)oxy)phenyl)-4-(1-ethyl-3-(pyridin-3-yl)-1H-pyrazol-4-yl)pyrimidin-2-amine | 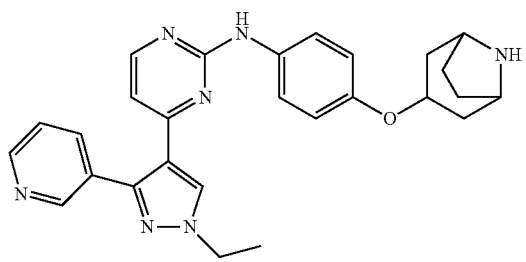 [SMILES: CCn1cc(-c2ccnc(Nc3ccc(OC4CC5CCC(C4)N5)cc3)n2)c(-c2cccnc2)n1] |
| 147 | N-(4-(4-Aminopiperidin-1-yl)phenyl)-4-(1-ethyl-3-(pyridin-3-yl)-1H-pyrazol-4-yl)pyrimidin-2-amine | 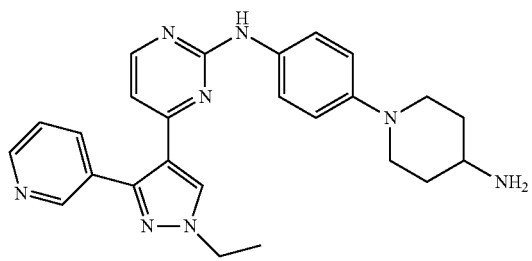 [SMILES: CCn1cc(-c2ccnc(Nc3ccc(N4CCC(N)CC4)cc3)n2)c(-c2cccnc2)n1] |
| 148 | 4-(1-Ethyl-3-(5-fluoropyridin-3-yl)-1H-pyrazol-4-yl)-N-(4-(piperazin-1-yl)phenyl)pyrimidin-2-amine | 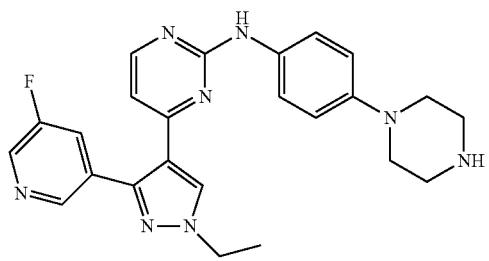 [SMILES: CCn1cc(-c2ccnc(Nc3ccc(N4CCNCC4)cc3)n2)c(-c2cncc(F)c2)n1] |

TABLE 2-continued

| | | |
|---|---|---|
| 149 | 4-(1-(2,2-Difluoroethyl)-3-(pyridin-3-yl)-1H-pyrazol-4-yl)-N-(4-(piperazin-1-yl)phenyl)pyrimidin-2-amine | |
| 150 | 4-(1-(2,2-Difluoroethyl)-3-(pyridin-3-yl)-1H-pyrazol-4-yl)-N-(6-(piperidin-1-yl)pyridin-3-yl)pyrimidin-2-amine | |
| 151 | 4-(1-Ethyl-3-(pyridin-3-yl)-1H-pyrazol-4-yl)-N-(4-(piperazin-1-yl)phenyl)pyrimidin-2-amine | |
| 152 | 4-(1-Ethyl-3-(pyridin-3-yl)-1H-pyrazol-4-yl)-N-(3-fluoro-4-(piperazin-1-yl)phenyl)pyrimidin-2-amine | |
| 153 | N-(3,5-Difluoro-4-(piperazin-1-yl)phenyl)-4-(1-ethyl-3-(pyridin-3-yl)-1H-pyrazol-4-yl)pyrimidin-2-amine | |
| 154 | 4-(1-Ethyl-3-(pyridin-3-yl)-1H-pyrazol-4-yl)-N-(3-methyl-4-(piperazin-1-yl)phenyl)pyrimidin-2-amine | |

TABLE 2-continued

| | | |
|---|---|---|
| 155 | 4-(1-Ethyl-3-(pyridin-3-yl)-1H-pyrazol-4-yl)-N-(6-(piperazin-1-yl)pyridin-3-yl)pyrimidin-2-amine | |
| 156 | 3-((4-(2-((4-(Piperazin-1-yl)phenyl)amino)pyrimidin-4-yl)-3-(pyridin-3-yl)-1H-pyrazol-1-yl)methyl)benzonitrile | |
| 157 | 2-((4-(2-((4-(Piperazin-1-yl)phenyl)amino)pyrimidin-4-yl)-3-(pyridin-3-yl)-1H-pyrazol-1-yl)methyl)benzonitrile | |
| 158 | 4-(1-Ethyl-3-(pyridin-3-yl)-1H-pyrazol-4-yl)-N-(3-(piperazin-1-yl)phenyl)pyrimidin-2-amine | |
| 159 | 4-(1-Ethyl-3-(pyridin-3-yl)-1H-pyrazol-4-yl)-N-(4-(2-(piperazin-1-yl)ethyl)phenyl)-pyrimidin-2-amine | |

TABLE 2-continued

| | | |
|---|---|---|
| 160 | (S)-N-(4-(3-Aminopiperidin-1-yl)phenyl)-4-(1-ethyl-3-(pyridin-3-yl)-1H-pyrazol-4-yl)pyrimidin-2-amine | |
| 161 | (R)-N-(4-(3-Aminopiperidin-1-yl)phenyl)-4-(1-ethyl-3-(pyridin-3-yl)-1H-pyrazol-4-yl)pyrimidin-2-amine | |
| 162 | 4-(1-Ethyl-3-(pyridin-3-yl)-1H-pyrazol-4-yl)-N-(4-(piperidin-4-yl)phenyl)pyrimidin-2-amine | |
| 163 | N-(4-(8-Azabicyclo[3.2.1]octan-3-yl)phenyl)-4-(1-ethyl-3-(pyridin-3-yl)-1H-pyrazol-4-yl)pyrimidin-2-amine | |
| 164 | 4-(1-Ethyl-3-(pyridin-3-yl)-1H-pyrazol-4-yl)-N-(4-((3-fluoropiperidin-4-yl)oxy)phenyl)pyrimidin-2-amine | |
| 165 | 4-(1-Ethyl-3-(pyridin-3-yl)-1H-pyrazol-4-yl)-N-(3-(piperidin-4-yloxy)phenyl)pyrimidin-2-amine | |

TABLE 2-continued

| | | |
|---|---|---|
| 166 | 4-(1-Ethyl-3-(pyridin-3-yl)-1H-pyrazol-4-yl)-5-fluoro-N-(4-(piperazin-1-yl)phenyl)pyrimidin-2-amine | 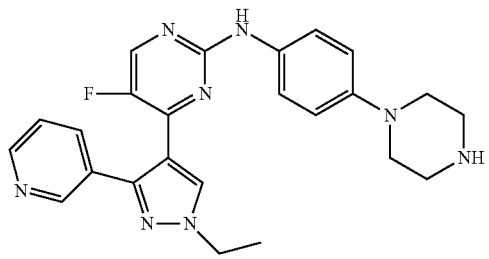 [SMILES: CCn1cc(-c2nc(Nc3ccc(N4CCNCC4)cc3)ncc2F)c(-c2cccnc2)n1] |
| 167 | 4-(1-Ethyl-3-(pyridin-3-yl)-1H-pyrazol-4-yl)-N-(4-(1-(piperidin-4-yl)-1H-pyrazol-4-yl)phenyl)pyrimidin-2-amine | 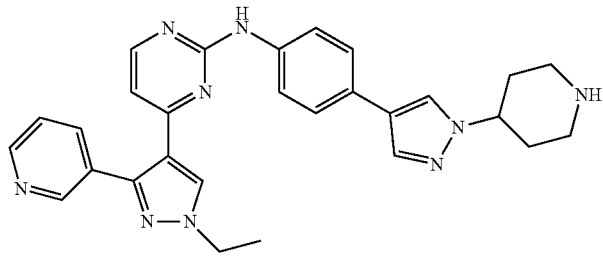 [SMILES: CCn1cc(-c2ccnc(Nc3ccc(-c4cnn(C5CCNCC5)c4)cc3)n2)c(-c2cccnc2)n1] |
| 168 | N-(4-(1-Ethyl-3-(pyridin-3-yl)-1H-pyrazol-4-yl)pyrimidin-2-yl)-1,2,3,4-tetrahydroisoquinolin-6-amine | 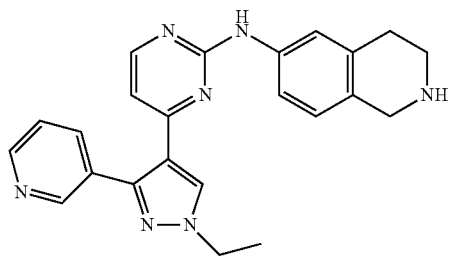 [SMILES: CCn1cc(-c2ccnc(Nc3ccc4c(c3)CCNC4)n2)c(-c2cccnc2)n1] |
| 169 | N-(4-(1-Ethyl-3-(pyridin-3-yl)-1H-pyrazol-4-yl)pyrimidin-2-yl)-1,2,3,4-tetrahydroisoquinolin-7-amine | 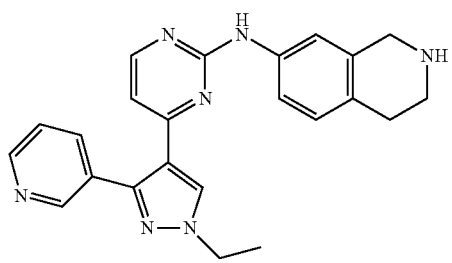 [SMILES: CCn1cc(-c2ccnc(Nc3ccc4c(c3)CNCC4)n2)c(-c2cccnc2)n1] |
| 170 | N-(4-(1-Ethyl-3-(pyridin-3-yl)-1H-pyrazol-4-yl)pyrimidin-2-yl)-1,2,3,4-tetrahydroquinolin-7-amine | 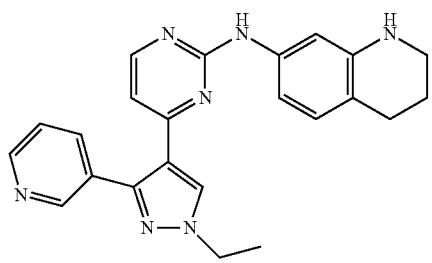 [SMILES: CCn1cc(-c2ccnc(Nc3ccc4c(c3)NCCC4)n2)c(-c2cccnc2)n1] |
| 171 | N-(4-(1-Ethyl-3-(pyridin-3-yl)-1H-pyrazol-4-yl)pyrimidin-2-yl)-2,3,4,5-tetrahydro-1H-benzo[d]azepin-7-amine | 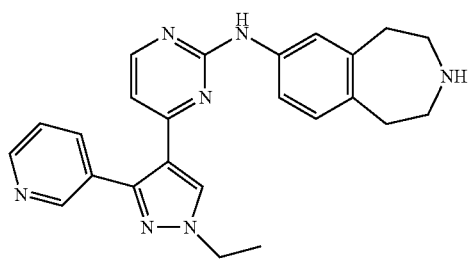 [SMILES: CCn1cc(-c2ccnc(Nc3ccc4c(c3)CCNCC4)n2)c(-c2cccnc2)n1] |

TABLE 2-continued

| | | |
|---|---|---|
| 172 | 2-(6-((4-(1-Ethyl-3-(pyridin-3-yl)-1H-pyrazol-4-yl)pyrimidin-2-yl)amino)-3,4-dihydroisoquinolin-2(1H)-yl)acetic acid | |
| 173 | 2-(4-(4-((4-(1-Ethyl-3-(pyridin-3-yl)-1H-pyrazol-4-yl)pyrimidin-2-yl)amino)phenyl)piperazin-1-yl)acetic acid | |
| 174 | 1-(4-(4-((4-(1-Ethyl-3-(pyridin-3-yl)-1H-pyrazol-4-yl)pyrimidin-2-yl)amino)phenyl)piperazin-1-yl)-2-hydroxyethan-1-one | |
| 175 | 1-(6-((4-(1-Ethyl-3-(pyridin-3-yl)-1H-pyrazol-4-yl)pyrimidin-2-yl)amino)-3,4-dihydroisoquinolin-2(1H)-yl)-2-hydroxyethan-1-one | |
| 176 | N-(4-(4-Amino-4-methylpiperidin-1-yl)phenyl)-4-(1-ethyl-3-(pyridin-3-yl)-1H-pyrazol-4-yl)pyrimidin-2-amine | |
| 177 | N-(4-(4-Amino-4-ethylpiperidin-1-yl)phenyl)-4-(1-ethyl-3-(pyridin-3-yl)-1H-pyrazol-4-yl)pyrimidin-2-amine | |

TABLE 2-continued

| | | |
|---|---|---|
| 178 | N-(4-(4-(2-Aminopropan-2-yl)piperidin-1-yl)phenyl)-4-(1-ethyl-3-pyridin-3-yl)-1H-pyrazol-4-yl)pyrimidin-2-amine | |
| 179 | 2-(7-((4-(1-Ethyl-3-(pyridin-3-yl)-1H-pyrazol-4-yl)pyrimidin-2-yl)amino)-3,4-dihydroisoquinolin-2(1H)-yl)ethan-1-ol | |
| 180 | 4-(1-Ethyl-3-(pyridin-3-yl)-1H-pyrazol-4-yl)-N-(4-(3-(4-methylpiperazin-1-yl)-1H-1,2,4-triazol-1-yl)phenyl)pyrimidin-2-amine | |

| Example number | Synthesis method | Raw material | MS | Ion | 1HNMR chemical shift value |
|---|---|---|---|---|---|
| 1 | | Production Example 3 | 511.34 | [M + H]+ | 8.81-8.86 (1 H, m), 8.62 (1 H, dd, J = 4.9, 1.6 Hz), 8.29 (1 H, d, J = 5.3 Hz), 8.02 (1 H, s), 7.92 (1 H, dt, J = 7.8, 1.9 Hz), 7.54 (2 H, d, J = 8.6 Hz), 7.32-7.39 (3 H, m), 7.23 (1 H, s), 6.63 (1 H, d, J = 5.3 Hz), 4.29 (2 H, q, J = 7.3 Hz), 3.41-3.90 (4 H, m), 2.48-2.67 (4 H, m), 1.61 (3 H, t, J = 7.4 Hz), 1.08 (9 H, s) |
| 2 | | Production Example 3 Synthesis literature 32 | 454.43 | [M + H]+ | 8.84 (1 H, dd, J = 2.1, 0.8 Hz), 8.62 (1 H, dd, J = 4.9, 1.6 Hz), 8.29 (1 H, d, J = 5.3 Hz), 8.02 (1 H, s), 7.91 (1 H, dt, J = 7.7, 1.9 Hz), 7.48-7.54 (2 H, m), 7.29-7.38 (3 H, m), 7.20 (1 H, s), 6.63 (1 H, d, J = 4.9 Hz), 4.29 (2 H, q, J = 7.4 Hz), 3.32-3.81 (4 H, m), 1.52-1.75 (9 H, m) |
| 3 | Example 2 | Production Example 3 Synthesis literature 33 | 549.42 | [M + H]+ | 8.83-8.86 (1 H, m), 8.62 (1 H, dd, J = 4.9, 1.6 Hz), 8.30 (1 H, d, J = 5.3 Hz), 8.02 (1 H, s), 7.91 (1 H, dt, J = 7.9, 2.0 Hz), 7.55 (2 H, d, J = 8.6 Hz), 7.31-7.42 (3 H, m), 7.22 (1 H, s), 6.87-7.03 (4 H, m), 6.65 (1 H, d, J = 5.3 Hz), 4.30 (2 H, q, J = 7.3 Hz), 3.63-3.96 (4 H, m), 3.03-3.21 (4 H, m), 1.61 (3 H, t, J = 7.6 Hz) |
| 4 | Example 2 | Production Example 3 Synthesis literature 34 | 497.28 | [M + H]+ | 8.83-8.85 (1 H, m), 8.62 (1 H, dd, J = 4.9, 1.6 Hz), 8.29 (1 H, d, J = 4.9 Hz), 8.02 (1 H, s), 7.91 (1 H, dt, J = 7.9, 2.0 Hz), 7.53 (2 H, d, J = 8.6 Hz), 7.28-7.38 (3 H, m), 7.17 (1 H, s), 6.64 (1 H, d, J = 4.9 Hz), 4.30 (2 H, q, J = 7.3 Hz), 2.83-2.98 (6 H, m), 2.27 (3 H, s), 1.79-2.01 (4 H, m), 1.67-1.74 (2 H, m), 1.61 (3 H, t, J = 7.4 Hz) |
| 5 | Example 2 | Production Example 3 Production Example 47 | 551.50 | [M + H]+ | 8.84-8.86 (1 H, m), 8.63 (1 H, dd, J = 4.9, 1.6 Hz), 8.28 (1 H, d, J = 5.3 Hz), 8.02 (1 H, s), 7.91 (1 H, dt, J = 7.9, 2.0 Hz), 7.51 (2 H, d, J = 8.6 Hz), 7.27-7.37 (3 H, m), 7.25 (1 H, s), 6.63 (1 H, d, J = 5.3 Hz), 4.29 (2 H, q, J = 7.3 Hz), 3.42-3.56 (2 H, m), 2.88 (3 H, s), 2.13-2.40 (3 H, m), 1.92-2.02 (2 H, m), 1.76-1.78 (1 H, m), 1.60 (3 H, t, J = 7.3 Hz), 1.29-1.55 (4 H, m), 0.83-1.07 (6 H, m) |

TABLE 2-continued

| 6 | Example 2 | Production Example 3 | | | 8.84 (1 H, dd, J = 2.3, 0.7 Hz), 8.62 (1 H, dd, J = 4.9, 1.6 Hz), 8.31 (1 H, d, J = 5.3 Hz), 8.03 (1 H, s), 7.85-7.94 (3 H, m), 7.56-7.63 (2 H, m), 7.32-7.39 (2 H, m), 6.68 (1 H, d, J = 5.3 Hz), 4.31 (2 H, q, J = 7.5 Hz), 2.58 (3 H, s), 1.62 (3 H, t, J = 7.3 Hz) |
|---|---|---|---|---|---|
| 7 | Example 2 | Production Example 74 Synthesis literature 35 | 413.48 | [M + H]+ | 8.83-8.88 (1 H, m), 8.60 (1 H, dd, J = 4.6, 1.7 Hz), 8.31 (1 H, d, J = 5.4 Hz), 7.98 (1 H, s), 7.87 (1 H, dt, J = 7.9, 1.6 Hz), 7.77-7.81 (2 H, m), 7.27-7.33 (1 H, m), 7.14-7.19 (1 H, m), 6.65 (1 H, d, J = 5.4 Hz), 4.30 (2 H, q, J = 7.3 Hz), 3.53 (2 H, s), 2.92-2.95 (2 H, m), 2.73-2.82 (2 H, m), 2.48 (3 H, s), 1.60 (3 H, t, J = 7.3 Hz) |
| 8 | | Production Example 12 Synthesis literature 36 | 440.50 | [M + H]+ | 8.86-8.89 (1 H, m), 8.64 (1 H, dd, J = 4.9, 1.6 Hz), 8.26 (1 H, d, J = 4.9 Hz), 8.17 (1 H, s), 7.91 (1 H, dt, J = 7.9, 2.0 Hz), 7.27-7.36 (3 H, m), 6.91-7.03 (2 H, m), 6.56 (1 H, d, J = 4.9 Hz), 5.50-5.60 (1 H, m), 5.09-5.20 (4 H, m), 3.59 (2 H, s), 2.90 (2 H, t, J = 5.7 Hz), 2.72 (2 H, t, J = 5.9 Hz), 2.46 (3 H, s) |
| 9 | Example 8 | Production Example 3 Production Example 45 | 440.49 | [M + H]+ | 8.85-8.87 (1 H, m), 8.59-8.63 (1 H, m), 8.25 (1 H, d, J = 4.9 Hz), 7.98 (1 H, s), 7.86-7.93 (1 H, m), 7.44-7.49 (1 H, m), 7.32-7.03 (4 H, m), 6.57 (1 H, d, J = 5.3 Hz), 4.70-4.83 (4 H, m), 4.27 (2 H, q, J = 7.3 Hz), 4.03-4.13 (1 H, m), 3.93 (4 H, br s), 1.58-1.63 (3 H, m). |
| 10 | Example 8 | Production Example 14 Synthesis literature 36 | 468.58 | [M + H]+ | 8.85-8.87 (1 H, m), 8.62 (1 H, dd, J = 4.8, 1.8 Hz), 8.24 (1 H, d, J = 5.4 Hz), 7.98 (1 H, s), 7.87-7.92 (1 H, m), 7.28-7.34 (3 H, m), 6.91-6.97 (2 H, m), 6.55 (1 H, d, J = 5.1), 4.20 (2 H, d, J = 7.6 Hz), 3.63-4.07 (4 H, m), 3.60 (2 H, s), 2.88-3.02 (5 H, m), 2.68-2.78 (2 H, m), 2.50 (3 H, s) |
| 11 | Example 8 | Production Example 3 Production Example 46 | 482.62 | [M + H]+ | 8.80-8.87 (1 H, m), 8.58-8.53 (1 H, m), 8.24 (1 H, d, J = 5.3 Hz), 8.00 (1 H, s), 7.86-7.93 (1 H, m), 7.28-7.43 (2 H, m), 7.08-7.24 (3 H, m), 7.02 (1 H, s), 6.53-6.58 (1 H, m), 4.64-4.73 (4 H, m), 4.22-4.33 (2 H, m), 3.48-3.58 (1 H, m), 2.80-2.96 (2 H, m), 2.43-2.57 (1 H, m), 1.63-2.07 (6 H, m), 1.56-1.62 (3 H, m). |
| 12 | | Production Example 12 Synthesis literature 37 | 256.95 | [M + 2H]2+ | 8.80-8.91 (1 H, m), 8.64 (1 H, dd, J = 4.8, 1.5 Hz), 8.26 (1 H, d, J = 5.3 Hz), 8.17 (1 H, s), 7.89-7.94 (1 H, m), 7.31-7.43 (3 H, m), 7.11-7.24 (2 H, m), 7.00 (1 H, s), 6.57 (1 H, d, J = 4.8 Hz), 5.51-5.59 (1 H, m), 5.09-5.20 (4 H, m), 3.62-3.76 (2 H, m), 3.07-3.40 (5 H, m), 2.66-3.04 (2 H, m), 2.41-2.65 (1 H, m), 1.73-1.94 (2 H, m), 1.47-1.64 (4 H, m). |
| 13 | Example 8 | Production Example 5 Production Example 46 | 512.64 | [M + H]+ | 8.82-8.88 (1 H, m), 8.57-8.63 (1 H, m), 8.25 (1 H, d, J = 5.3 Hz), 8.07 (1 H, s), 7.85-7.93 (1 H, m), 7.29-7.41 (3 H, m), 7.08-7.19 (2 H, m), 6.98 (1 H, s), 6.54-6.63 (1 H, m), 4.63-4.72 (4 H, m), 4.34-4.42 (2 H, m), 3.79-3.87 (2 H, m), 3.49-3.51 (1 H, m), 3.40 (3 H, s), 2.81-2.93 (2 H, m), 2.42-2.53 (1 H, m), 1.99-1.75 (6 H, m) |
| 14 | Example 8 | Production Example 3 Synthesis literature 38 | 459.54 | [M + H]+ | 8.87 (1 H, dd, J = 2.1, 0.8 Hz), 8.62 (1 H, dd, J = 4.8, 1.8 Hz), 8.27 (1 H, d, J = 4.9 Hz), 8.10-8.15 (1 H, m), 8.04 (1 H, s), 7.83-7.92 (4 H, m), 7.56-7.65 (3 H, m), 7.28-7.35 (1 H, m), 7.12-7.20 (2 H, m), 6.78 (1 H, td, J = 6.8, 1.0 Hz), 6.59 (1 H, d, J = 4.9 Hz), 4.30 (2 H, q, J = 7.4 Hz), 1.61 (3 H, t, J = 7.6 Hz) |
| 15 | | Production Example 3 Synthesis literature 25 | 483 | [M + H]+ | 8.85 (1 H, d, J = 2.4 Hz), 8.60-8.62 (1 H, m), 8.21 (1 H, d, J = 5.4 Hz), 7.98 (1 H, s), 7.86-7.91 (1 H, m), 7.35 (2 H, d, J = 8.9 Hz), 7.28-7.32 (1 H, m), 6.84-6.88 (3 H, m), 6.53 (1 H, d, J = 5.1 Hz), 4.65-4.73 (4 H, m), 4.13-4.23 (2 H, m), 3.52-3.62 (4 H, m), 3.17-3.20 (4 H, m), 2.50-2.53 (4 H, m), 1.56-1.62 (3 H, m) |
| 16 | Example 15 | Production Example 3 | 469 | [M + H]+ | 8.84-8.86 (1 H, m), 8.60-8.62 (1 H, dd, J = 1.6, 4.9 Hz), 8.21 (1 H, d, J = 5.4 Hz), 7.98 (1 H, s), 7.87-7.91 (1 H, m), 7.35 (2 H, d, J = 8.9 Hz), 7.28-7.32 (1 H, m), 6.86-6.89 (3 H, m), 6.51 (1 H, d, J = 5.4 Hz), 4.24-4.32 (2 H, m), 3.65-3.66 (1 H, m), 3.16-3.20 (4 H, m), 2.70-2.72 (4 H, m), 1.54-1.62 (3 H, m), 1.10-1.26 (6 H, m) |
| 17 | Example 15 | Production Example 3 | 485 | [M + H]+ | 8.85 (1 H, d, J = 1.4 Hz), 8.61 (1 H, dd, J = 4.6, 1.6 Hz), 8.21 (1 H, d, J = 5.4 Hz), 7.98 (1 H, s), 7.86-7.91 (1 H, m), 7.35 (2 H, d, J = 8.9 Hz), 7.28-7.32 (1 H, m), 6.85-6.88 (3 H, m), 6.52 (1 H, d, J = 4.9 Hz), 4.24-4.32 (2 H, m), 3.56-3.60 |

TABLE 2-continued

| | | | | | |
|---|---|---|---|---|---|
| | | | | | (2 H, m), 3.38 (3 H, s), 3.18-3.21 (4 H, m), 2.68-2.71 (6 H, m), 1.57-1.62 (3 H, m) |
| 18 | Example 15 | Production Example 3 Synthesis literature 5 | 503 | [M + H]+ | 8.82-8.83 (1 H, m), 8.60-8.62 (1 H, m), 8.23 (1 H, d, J = 5.4 Hz), 8.01 (1 H, s), 7.88-7.92 (1 H, m), 7.45-7.52 (1 H, m), 7.31-7.35 (1 H, m), 6.83-7.05 (3 H, m), 6.65 (1 H, d, J = 5.1 Hz), 4.24-4.33 (2 H, m), 3.51-3.58 (4 H, m), 3.34-3.38 (5 H, m), 3.09-3.12 (4 H, m), 2.48-2.53 (2 H, m), 1.56-1.62 (3 H, m) |
| 19 | Example 15 | Production Example 3 | 517 | [M + H]+ | 8.84-8.85 (1 H, m), 8.60-8.62 (1 H, m), 8.20 (1 H, d, J = 4.9 Hz), 7.98 (1 H, s), 7.86-7.91 (1 H, m), 7.28-7.36 (8 H, m), 6.86 (3 H, m), 6.51 (1 H, d, J = 4.9 Hz), 4.23-4.31 (2 H, m), 3.58 (2 H, s), 3.14-3.17 (4 H, m), 2.61-2.64 (4 H, m), 1.56-1.62 (3 H, m) |
| 20 | Example 15 | Production Example 3 Synthesis literature 39 | 524 | [M + H]+ | 8.84-8.85 (1 H, m), 8.60-8.62 (1 H, m), 8.21 (1 H, d, J = 5.1 Hz), 7.98 (1 H, s), 7.86-7.91 (1 H, m), 7.28-7.35 (3 H, m), 6.84-6.90 (3 H, m), 6.51 (1 H, d, J = 5.1 Hz), 4.23-4.31 (2 H, m), 3.64-3.69 (2 H, m), 2.34-2.72 (11 H, m), 2.30 (3 H, s), 1.92-1.96 (2 H, m), 1.67-1.75 (2 H, m), 1.59 (3 H, t, J = 7.3 Hz) |
| 21 | | Production Example 3 | 509 | [M + H]+ | 8.84-8.86 (1 H, m), 8.60-8.62 (1 H, m), 8.22 (1 H, d, J = 5.1 Hz), 7.98 (1 H, s), 7.86-7.98 (1 H, m), 7.28-7.36 (3 H, m), 6.84-6.88 (3 H, m), 6.53 (1 H, d, J = 4.9 Hz), 4.24-4.32 (2 H, m), 3.85 (2 H, s), 3.75 (2 H, s), 3.05-3.09 (4 H, m), 1.90-1.93 (7 H, m), 1.58-1.62 (3 H, m) |
| 22 | Example 15 | Production Example 3 | 428 | [M + H]+ | 8.85-8.86 (1 H, m), 8.61-8.62 (1 H, m), 8.22 (1 H, d, J = 4.9 Hz), 7.98 (1 H, s), 7.86-7.91 (1 H, m), 7.35-7.40 (2 H, m), 7.28-7.33 (1 H, m), 6.91 (1 H, s), 6.83-6.87 (2 H, m), 6.53 (1 H, d, J = 5.1 Hz), 4.24-4.32 (2 H, m), 3.85-3.89 (4 H, m), 3.09-3.13 (4 H, m), 1.57-1.62 (3 H, m) |
| 23 | Example 15 | Production Example 3 | 386 | [M + H]+ | 8.85 (1 H, dd, J = 2.2, 0.8 Hz), 8.60 (1 H, dd, J = 4.9, 1.6 Hz), 8.30 (1 H, d, J = 5.1 Hz), 8.01 (1 H, s), 7.86-7.91 (1 H, m), 7.69-7.72 (2 H, m), 7.55 (2 H, d, J = 8.6 Hz), 7.45 (1 H, s), 7.32 (1 H, m), 6.68 (1 H, d, J = 5.1 Hz), 4.26-4.34 (2 H, m), 1.58-1.64 (3 H, m) |
| 24 | Example 15 | Production Example 3 | 430 | [M + H]+ | 8.84-8.85 (1 H, m), 8.62 (1 H, dd, J = 5.1, 1.6 Hz), 8.24 (1 H, d, J = 5.4 Hz), 8.04 (1 H, s), 7.88-7.92 (1 H, m), 7.30-7.35 (2 H, m), 7.14-7.20 (1 H, m), 7.10 (1 H, s), 7.03-7.07 (1 H, m), 6.57-6.61 (1 H, m), 6.55 (1 H, d, J = 4.9 Hz), 4.24-4.32 (2 H, m), 4.06-4.10 (2 H, m), 2.75 (2 H, t, J = 5.9 Hz), 2.35 (6 H, s), 1.60 (3 H, t, J = 7.3 Hz) |
| 25 | Example 15 | Production Example 2 | 444.43 | [M + H]+ | 8.82-8.87 (1 H, m), 8.58 (1 H, dd, J = 4.9, 1.6 Hz), 8.23 (1 H, d, J = 4.9 Hz), 8.04 (1 H, s), 7.87 (1 H, dt, J = 7.9, 1.8 Hz), 7.68 (1 H, s), 7.22-7.34 (3 H, m), 6.69-6.78 (2 H, m), 6.58 (1 H, d, J = 4.9 Hz), 4.07 (2 H, t, J = 5.6 Hz), 3.71-3.77 (4 H, m), 2.78 (2 H, t, J = 5.6 Hz), 2.53-2.63 (4 H, m) |
| 26 | Example 15 | Production Example 3 Synthesis literature 40 | 424 | [M + H]+ | 8.84-8.85 (1 H, m), 8.60-8.62 (1 H, m), 8.36 (1 H, s), 8.29 (1 H, d, J = 5.4 Hz), 8.01 (1 H, s), 7.88-7.93 (1 H, m), 7.58-7.62 (2 H, m), 7.46-7.51 (2 H, m), 7.31-7.36 (1 H, m), 7.22 (1 H, s), 6.65 (1 H, d, J = 5.1 Hz), 4.25-4.34 (2 H, m), 2.50 (3 H, s), 1.58-1.64 (3 H, m) |
| 27 | | Production Example 3 | 437 | [M + H]+ | 8.86-8.87 (1 H, m), 8.60-8.62 (1 H, m), 8.26 (1 H, d, J = 5.4 Hz), 8.01 (1 H, s), 7.87-7.92 (1 H, m), 7.74 (1 H, s), 7.61 (1 H, s), 7.46-7.49 (2 H, m), 7.29-7.39 (3 H, m), 7.06 (1 H, s), 6.58 (1 H, d, J = 5.1 Hz), 4.17-4.33 (4 H, m), 1.51-1.63 (6 H, m) |
| 28 | Example 27 | Production Example 3 | 467 | [M + H]+ | 8.85-8.86 (1 H, m), 8.59-8.62 (1 H, m), 8.25 (1 H, d, J = 5.4 Hz), 8.01 (1 H, s), 7.88-7.91 (1 H, m), 7.76 (1 H, s), 7.69 (1 H, s), 7.46-7.50 (2 H, m), 7.36-7.39 (2 H, m), 7.29-7.34 (1 H, m), 7.10 (1 H, s), 6.58 (1 H, d, J = 5.1 Hz), 4.25-4.34 (4 H, m), 3.77-3.81 (2 H, m), 3.36 (3 H, s), 1.58-1.63 (3 H, m) |
| 29 | Example 27 | Production Example 3 | 473 | [M + H]+ | 8.86-8.87 (1 H, m), 8.59-8.62 (1 H, m), 8.26 (1 H, d, J = 5.4 Hz), 8.00 (1 H, s), 7.87-7.92 (1 H, m), 7.81 (1 H, s), 7.67 (1 H, s), 7.48-7.51 (2 H, m), 7.29-7.38 (3 H, m), 7.06 (1 H, s), 6.60 (1 H, d, J = 5.4 Hz), 5.90-6.35 (1 H, m), 4.46-4.56 (2 H, m), 4.28-4.44 (2 H, m), 1.58-1.63 (3 H, m) |
| 30 | | Production Example 3 | 409 | [M + H]+ | 8.86-8.88 (1 H, m), 8.59-8.62 (1 H, m), 8.27 (1 H, d, J = 4.9 Hz), 8.01 (1 H, s), 7.88-7.93 (1 H, |

TABLE 2-continued

| | | | | | |
|---|---|---|---|---|---|
| | | | | | m), 7.83 (2 H, s), 7.48-7.53 (2 H, m), 7.38-7.43 (2 H, m), 7.29-7.34 (1 H, m), 7.19 (1 H, s), 6.59 (1 H, d, J = 5.4 Hz), 4.25-4.33 (2 H, m), 1.58-1.63 (3 H, m) |
| 31 | Example 15 | Production Example 3 Production Example 119 | 552 | [M + H]+ | 8.84-8.86 (1 H, m), 8.59-8.62 (1 H, m), 8.21 (1 H, d, J = 5.1 Hz), 7.98 (1 H, s), 7.80-7.98 (1 H, m), 7.33-7.36 (2 H, m), 7.28-7.31 (1 H, m), 6.95 (1 H, s), 6.84-6.87 (2 H, m), 6.51 (1 H, d, J = 5.4 Hz), 4.22-4.31 (2 H, m), 3.54-3.58 (4 H, m), 3.24 (2 H, s), 3.15-3.18 (4 H, m), 2.67-2.70 (4 H, m), 1.56-1.62 (9 H, m) |
| 32 | Example 15 | Production Example 3 Synthesis literature 41 | 467 | [M + H]+ | 8.83-8.85 (1 H, m), 8.59-8.61 (1 H, m), 8.20 (1 H, d, J = 5.1 Hz), 7.97 (1 H, d, J = 3.8 Hz), 7.87-7.89 (1 H, m), 7.26-7.32 (3 H, m), 6.85-6.86 (3 H, m), 6.51 (1 H, d, J = 4.9 Hz), 4.26-4.29 (2 H, m), 3.10-3.13 (4 H, m), 2.78-2.80 (4 H, m), 1.56-1.68 (4 H, m), 0.45-0.48 (4 H, m) |
| 33 | Example 15 | Production Example 3 Synthesis literature 30 | 481 | [M + H]+ | 8.84-8.86 (1 H, m), 8.60-8.62 (1 H, m), 8.21 (1 H, d, J = 5.4 Hz), 7.98 (1 H, s), 7.87-7.90 (1 H, m), 7.31-7.37 (2 H, m), 7.28-7.31 (1 H, m), 6.85-6.91 (3 H, m), 6.51 (1 H, d, J = 5.4 Hz), 4.26-4.29 (2 H, m), 3.17-3.21 (4 H, m), 2.71 (4 H, t, J = 4.9 Hz), 2.33 (2 H, d, J = 6.8 Hz), 1.56-1.62 (3 H, m), 0.80-0.96 (1 H, m), 0.53-0.57 (2 H, m), 0.14 (2 H, d, J = 4.6 Hz) |
| 34 | Example 15 | Production Example 3 | 441 | [M + H]+ | 8.85-8.86 (1 H, m), 8.62 (1 H, dd, J = 4.6, 1.6 Hz), 8.23 (1 H, d, J = 5.1 Hz), 8.03 (1 H, s), 7.88-7.92 (1 H, m), 7.30-7.36 (1 H, m), 7.25 (1 H, d, J = 1.9 Hz), 7.14-7.20 (1 H, m), 6.99-7.04 (2 H, m), 6.61-6.64 (1 H, m), 6.53 (1 H, d, J = 4.9 Hz), 4.28 (2 H, q, J = 7.3 Hz), 3.22-3.26 (4 H, m), 2.57-2.60 (4 H, m), 2.36 (3 H, s), 1.58-1.62 (3 H, m) |
| 35 | Example 15 | Production Example 5 | 471 | [M + H]+ | 8.88 (1 H, d, J = 2.7 Hz), 8.59-8.61 (1 H, m), 8.21 (1 H, d, J = 2.7 Hz), 8.05 (1 H, s), 7.87-7.91 (1 H, m), 7.33 (2 H, d, J = 8.1 Hz), 7.27-7.31 (1 H, m), 7.09 (1 H, s), 6.82-6.86 (2 H, m), 6.55 (1 H, d, J = 5.4 Hz), 4.38 (2 H, t, J = 5.4 Hz), 3.83 (2 H, t, J = 5.4 Hz), 3.40 (3 H, s), 3.18-3.21 (4 H, m), 2.42-2.70 (4 H, m), 2.00 (3 H, s) |
| 36 | Example 15 | Production Example 5 Synthesis literature 30 | 256 | [M + 2H] 2+ | 8.85-8.60 (1 H, m), 8.59-8.62 (1 H, m), 8.22 (1 H, d, J = 5.1 Hz), 8.05 (1 H, s), 7.87-7.90 (1 H, m), 7.27-7.35 (3 H, m), 6.84-6.87 (3 H, m), 6.55 (1 H, d, J = 5.1 Hz), 4.36-4.40 (2 H, m), 3.81-3.85 (2 H, m), 3.40 (3 H, s), 3.17-3.19 (4 H, m), 2.71-2.74 (4 H, m), 2.34 (2 H, d, J = 6.2 Hz), 0.86-0.90 (1 H, m), 0.55-0.57 (2 H, m), 0.14-0.16 (2 H, m) |
| 37 | Example 15 | Production Example 5 | 258 | [M + 2H] 2+ | 8.86 (1 H, d, J = 2.4 Hz), 8.59-8.61 (1 H, m), 8.21 (1 H, d, J = 5.1 Hz), 8.05 (1 H, s), 7.86-7.91 (1 H, m), 7.29-7.34 (3 H, m), 6.91 (1 H, s), 6.84 (2 H, d, J = 8.9 Hz), 6.54 (1 H, d, J = 5.4 Hz), 4.37 (2 H, t, J = 5.1 Hz), 3.81-3.84 (2 H, m), 3.54-3.58 (2 H, m), 3.39 (3 H, s), 3.38 (3 H, s), 3.16-3.19 (4 H, m), 2.63-2.70 (6 H. m) |
| 38 | Example 15 | Production Example 3 | 410 | [M + H]+ | 8.85-8.86 (1 H, m), 8.60-8.62 (1 H, m), 8.50 (1 H, s), 8.30 (1 H, d, J = 5.4 Hz), 8.10 (1 H, s), 8.01 (1 H, s), 7.89-7.93 (1 H, m), 7.60-7.66 (2 H, m), 7.50-7.55 (2 H, m), 7.35-7.37 (1 H, m), 7.21 (1 H, s), 6.67 (1 H, d, J = 5.4 Hz), 4.26-4.32 (2 H, m), 1.58-1.64 (3 H, m) |
| 39 | | Production Example 3 | 438 | [M + H]+ | 8.84-8.85 (1 H, m), 8.60-8.63 (1 H, m), 8.30 (1 H, d, J = 5.1 Hz), 8.01 (1 H, s), 7.89-7.93 (1 H, m), 7.59-7.62 (2 H, m), 7.33-7.37 (1 H, m), 7.27-7.32 (2 H, m), 7.20 (1 H, s), 6.66 (1 H, d, J = 4.9 Hz), 4.25-4.34 (2 H, m), 2.46 (3 H, s), 2.42 (3 H, s), 1.56-1.63 (3 H, m) |
| 40 | Example 15 | Production Example 3 | 400 | [M + H]+ | 8.85 (1 H, dd, J = 2.4, 1.1 Hz), 8.62 (1 H, dd, J = 4.6, 1.6 Hz), 8.24 (1 H, d, J = 5.1 Hz), 8.07 (1 H, s), 7.88-7.92 (1 H, m), 7.47-7.50 (2 H, m), 7.31-7.36 (1 H, m), 7.19-7.25 (1 H, m), 7.04 (1 H, s), 6.96 (1 H, d, J = 7.6 Hz), 6.55 (1 H, d, J = 5.4 Hz), 4.24-4.33 (2 H, m), 3.41 (2 H, s), 2.27 (6 H, s), 1.58-1.63 (3 H, m) |
| 41 | Example 15 | Production Example 3 | 442 | [M + H]+ | 8.84-8.86 (1 H, m), 8.61-8.63 (1 H, m), 8.25 (1 H, d, J = 5.4 Hz), 8.02 (1 H, s), 7.88-7.93 (1 H, m), 7.51-7.54 (1 H, m), 7.43 (1 H, s), 7.30-7.33 (1 H, m), 7.22 (1 H, t, J = 7.8 Hz), 7.04 (1 H, s), 6.99 (1 H, d, J = 7.3 Hz), 6.57 (1 H, d, J = 5.1 Hz), 4.24-4.33 (2 H, m), 3.72 (4 H, t, J = 4.6 |

TABLE 2-continued

| | | | | | |
|---|---|---|---|---|---|
| | | | | | Hz), 3.48 (2 H, s), 2.45-2.48 (4 H, m), 1.58-1.63 (3 H, m) |
| 42 | Example 15 | Production Example 3 | 424 | [M + H]+ | 8.83-8.85 (1 H, m), 8.58-8.61 (1 H, m), 8.27 (1 H, d, J = 5.4 Hz), 8.03 (1 H, s), 8.00 (1 H, s), 7.98 (1 H, s), 7.87-7.91 (1 H, m), 7.49-7.52 (2 H, m), 7.30-7.34 (1 H, m), 7.18 (2 H, d, J = 8.6 Hz), 7.10 (1 H, s), 6.62 (1 H, d, J = 5.1 Hz), 5.29 (2 H, s), 4.25-4.33 (2 H, m), 1.58-1.65 (3 H, m) |
| 43 | | Production Example 3 | 513 | [M + H]+ | 8.84-8.85 (1 H, m), 8.60-8.62 (1 H, m), 8.23 (1 H, d, J = 5.1 Hz), 8.00 (1 H, s), 7.87-7.91 (1 H, m), 7.39 (2 H, d, J = 8.1 Hz), 7.29-7.34 (1 H, m), 7.08-7.11 (3 H, m), 6.55 (1 H, d, J = 5.1 Hz), 4.24-4.32 (2 H, m), 3.50-3.55 (2 H, m), 3.41 (3 H, s), 2.74-2.80 (2 H, m), 2.55-2.67 (12 H, m), 1.57-1.62 (3 H, m) |
| 44 | Example 15 | Production Example 3 | 409 | [M + H]+ | 8.84-8.85 (1 H, m), 8.60-8.62 (1 H, m), 8.30 (1 H, d, J = 5.4 Hz), 8.00 (1 H, s), 7.89-7.93 (1 H, m), 7.80-7.81 (1 H, m), 7.55-7.61 (2 H, m), 7.31-7.36 (1 H, m), 7.28 (1 H, s), 7.23-7.25 (2 H, m), 7.19-7.20 (2 H, m), 6.66 (1 H, d, J = 5.4 Hz), 4.26-4.33 (2 H, m), 1.58-1.64 (3 H, m) |
| 45 | Example 15 | Production Example 3 Synthesis literature 42 | 458 | [M + H]+ | 8.82-8.83 (1 H, m), 8.60-8.62 (1 H, m), 8.25 (1 H, d, J = 5.1 Hz), 8.02 (1 H, s), 7.88-7.92 (1 H, m), 7.47-7.53 (1 H, m), 7.31-7.36 (1 H, m), 7.02-7.15 (3 H, m), 6.58 (1 H, d, J = 5.1 Hz), 4.25-4.33 (2 H, m), 2.95-3.00 (2 H, m), 2.73-2.85 (1 H, m), 2.33 (3 H, s), 2.03-2.12 (2 H, m), 1.76-1.84 (4 H, m), 1.58-1.63 (3 H, m) |
| 46 | Example 15 | Production Example 110 | 441 | [M + H]+ | 8.85-8.86 (1 H, m), 8.61 (1 H, dd, J = 4.6, 1.6 Hz), 8.21 (1 H, d, J = 5.1 Hz), 7.98 (1 H, s), 7.91 (1 H, m), 7.35 (2 H, d, J = 9.2 Hz), 7.30-7.32 (1 H, m), 6.85-6.89 (3 H, m), 6.52 (1 H, d, J = 5.4 Hz), 4.24-4.32 (2 H, m), 3.16-3.19 (4 H, m), 2.58-2.63 (4 H, m), 2.37 (3 H, s) 1.56-1.62 (3 H, m) |
| 47 | Example 15 | Production Example 3 Synthesis literature 43 | 471.26 | [M + H]+ | DMSO-d$_6$<br>9.26 (1 H, s), 8.70 (1 H, d, J = 2.2 Hz), 8.52 (1 H, dd, J = 4.7, 1.2 Hz), 8.40 (1 H, s), 8.32 (1 H, d, J = 5.0 Hz), 7.93 (1 H, dt, J = 8.2, 2.0 Hz), 7.38 (1 H, dd, J = 7.6, 4.8 Hz), 7.27 (1 H, d, J = 2.3 Hz), 7.01-7.08 (1 H, m), 6.65 (1 H, d, J = 5.3 Hz), 6.60 (1 H, d, J = 8.6 Hz), 4.26 (2 H, q, J = 7.4 Hz), 3.68 (3 H, s), 2.82-2.94 (4 H, m), 2.37-2.51 (4 H, m), 2.22 (3 H, s), 1.46 (3 H, t, J = 7.4 Hz). |
| 48 | Example 15 | Production Example 3 Production Example 43 | 460.43 | [M + H]+ | DMSO-d$_6$<br>9.34 (1 H, s), 8.69-8.74 (1 H, m), 8.49-8.55 (1 H, m), 8.41 (1 H, s), 8.31 (1 H, d, J = 5.0 Hz), 7.84-7.97 (1 H, m), 7.32-7.47 (2 H, m), 6.58-6.72 (1 H, m), 4.54-4.75 (1 H, m), 4.27 (2 H, q, J = 7.8 Hz), 3.66-3.78 (2 H, m), 3.29-3.46 (4 H, m), 1.48 (3 H, t, J = 7.3 Hz), 1.06 (6 H, s). |
| 49 | | Production Example 3 | 426 | [M + H]+ | 8.85 (1 H, dd, J = 2.2, 1.1 Hz), 8.60-8.62 (1 H, m), 8.20 (1 H, d, J = 5.4 Hz), 7.98 (1 H, s), 7.87-7.91 (1 H, m), 7.28-7.35 (3 H, m), 6.86-6.91 (3 H, m), 6.50 (1 H, d, J = 5.1 Hz), 4.23-4.31 (2 H, m), 3.07-3.11 (4 H, m), 1.68-1.77 (4 H, m), 1.52-1.62 (5 H, m) |
| 50 | | Production Example 3 | 470.37 | [M + H]+ | 8.82-8.88 (1 H, m), 8.58-8.65 (1 H, m), 8.25 (1 H, d, J = 5.3 Hz), 8.01 (1 H, s), 7.87-7.94 (1 H, m), 7.45 (2 H, d, J = 8.2 Hz), 7.31-7.37 (1 H, m), 7.13-7.23 (2 H, m), 6.63-6.69 (1 H, m), 6.60 (1 H, d, J = 5.3 Hz), 4.25-4.35 (2 H, m), 3.79-3.94 (2 H, m), 3.47-3.77 (4 H, m), 3.39 (3 H, s), 3.18-3.27 (2 H, m), 2.35-2.58 (2 H, m), 2.01-2.28 (1 H, m), 1.60 (3 H, t, J = 7.4 Hz) |
| 51 | | Production Example 3 Production Example 40 | 535.66 | [M + H]+ | 8.85 (1 H, dd, J = 2.1, 0.8 Hz), 8.61 (1 H, dd, J = 4.6, 1.6 Hz), 8.21 (1 H, d, J = 5.3 Hz), 7.98 (1 H, s), 7.86-7.92 (1 H, m), 7.28-7.38 (3 H, m), 6.83-6.93 (3 H, m), 6.52 (1 H, d, J = 4.9 Hz), 5.89 (1 H, tt, J = 55.7, 4.3 Hz), 4.27 (2 H, q, J = 7.5 Hz), 3.65-3.78 (4 H, m), 3.14-3.21 (4 H, m), 2.65-2.72 (6 H, m), 1.59 (3 H, t, J = 7.3 Hz) |
| 52 | Example 51 | Production Example 3 Production Example 41 | 525.62 | [M + H]+ | 8.85 (1 H, dd, J = 2.1, 0.8 Hz), 8.61 (1 H, dd, J = 4.8, 1.8 Hz), 8.21 (1 H, d, J = 5.3 Hz), 7.98 (1 H, s), 7.89 (1 H, dt, J = 7.8, 1.9 Hz), 7.28-7.38 (3 H, m), 7.01-7.08 (1 H, m), 6.82-6.89 (2 H, m), 6.51 (1 H, d, J = 5.3 Hz), 4.27 (2 H, q, J = 7.3 Hz), 3.65 (2 H, t, J = 5.9 Hz), 3.31 (2 H, d, J = 6.9 Hz), 3.12-3.21 (4 H, m), 2.61-2.73 (6 H, m), |

TABLE 2-continued

| | | | | | |
|---|---|---|---|---|---|
| | | | | | 1.58 (3 H, t, J = 7.3 Hz), 1.00-1.15 (1 H, m), 0.50-0.58 (2 H, m), 0.17-0.25 (2 H, m) |
| 53 | Example 51 | Production Example 3 Synthesis literature 44 | 417.35 | [M + H]+ | DMSO-$d_6$ 9.32 (1 H, br s), 8.70-8.74 (1 H, m), 8.53 (1 H, d, J = 4.6 Hz), 8.40 (1 H, s), 8.32 (1 H, d, J = 5.2 Hz), 7.95 (1 H, d, J = 8.7 Hz), 7.25-7.47 (2 H, m), 6.16-6.72 (1 H, m), 4.26 (2 H, q, J = 7.4 Hz), 3.87-4.08 (3 H, m), 3.34-3.52 (2 H, m), 1.7-1.93 (4 H, m), 1.47 (3 H, t, J = 7.4 Hz) |
| 54 | Example 51 | Production Example 3 Production Example 42 | 488.45 | [M + H]+ | DMSO-$d_6$ 9.32 (1 H, br s), 8.70-8.74 (1 H, m), 8.53 (1 H, dd, J = 5.0, 1.6 Hz), 8.39 (1 H, s), 8.32 (1 H, d, J = 5.0 Hz), 7.86-8.01 (1 H, m), 7.17-7.49 (2 H, m), 6.60-6.75 (1 H, m), 4.26 (2 H, q, J = 7.3 Hz), 3.64-3.93 (1 H, m), 2.94-3.06 (2 H, m), 2.17-2.30 (4 H, m), 1.70-1.89 (4 H, m), 1.47 (3 H, t, J = 7.3 Hz), 1.10 (6 H, s) |
| 55 | | Production Example 3 Synthesis literature 6 | 474.45 | [M + H]+ | DMSO-$d_6$ 9.30 (1 H, br s), 8.71 (1 H, d, J = 1.9 Hz), 8.48-8.58 (1 H, m), 8.39 (1 H, s), 8.27-8.35 (2 H, m), 7.94 (1 H, d, J = 6.7 Hz), 7.22-7.47 (2 H, m), 6.60-6.71 (1 H, m), 4.26 (2 H, q, J = 7.5 Hz), 3.78-3.94 (1 H, m), 3.39-3.48 (2 H, m), 3.24 (3 H, s), 2.86-2.99 (2 H, m), 2.44-2.49 (2 H, m), 2.01-2.17 (2 H, m), 1.71-1.91 (4 H, m), 1.43 (3 H, t, J = 7.5 Hz) |
| 56 | | Production Example 3 | 441.47 | [M + H]+ | 8.83-8.87 (1 H, m), 8.59-8.63 (1 H, m), 8.30 (1 H, d, J = 4.9 Hz), 8.03 (1 H, s), 7.91 (1 H, dt, J = 8.0, 1.8 Hz), 7.79-8.85 (2 H, m), 7.58-7.65 (2 H, m), 7.21-7.38 (2 H, m), 6.66 (1 H, d, J = 5.3 Hz), 4.29 (2 H, q, J = 7.3 Hz), 2.81 (3 H, s), 1.52-1.64 (3 H, m). |
| 57 | Example 51 | Production Example 5 | 257.94 | [M + 2H] 2+ | 8.83-8.87 (1 H, m), 8.61 (1 H, dd, J = 4.8, 1.8 Hz), 8.24 (1 H, d, J = 5.3 Hz), 8.07 (1 H, s), 7.89 (1 H, dt, J = 8.1, 1.9 Hz), 7.28-7.42 (3 H, m), 7.09-7.13 (2 H, m), 6.97 (1 H, s), 6.58 (1 H, d, J = 5.0 Hz), 4.38 (2 H, t, J = 5.1 Hz), 3.83 (2 H, t, J = 5.1 Hz), 3.57 (2 H, t, J = 5.6 Hz), 3.40 (3 H, s), 3.38 (3 H, s), 3.06-3.18 (2 H, m), 2.62-2.66 (2 H, m), 2.36-2.54 (1 H, m), 2.07-2.21 (2 H, m), 1.72-1.92 (4 H, m) |
| 58 | Example 51 | Production Example 3 | 484.62 | [M + H]+ | 8.82-8.86 (1 H, m), 8.60-8.62 (1 H, m), 8.23 (1 H, d, J = 5.3 Hz), 8.00 (1 H, s), 7.89 (1 H, dt, J = 7.9 Hz), 7.29-7.43 (3 H, m), 7.16-7.25 (2 H, m), 6.99 (1 H, br s), 6.55 (1 H, d, J = 5.3 Hz), 4.21-4.33 (2 H, m), 3.51-3.61 (2 H, m), 3.38 (3 H, s), 3.02-3.16 (2 H, m), 2.62-2.66 (2 H, m), 2.39-2.54 (1 H, m), 2.05-2.19 (2 H, m), 1.73-1.89 (4 H, m), 1.58 (3 H, t, J = 7.3 Hz) |
| 59 | | Production Example 3 Synthesis literature 37 | 484.44 | [M + H]+ | 8.85-8.89 (1 H, m), 8.60-8.62 (1 H, m), 8.25 (1 H, d, J = 5.3 Hz), 7.99 (1 H, s), 7.90 (1 H, dt, J = 7.8, 2.1 Hz), 7.30-7.44 (3 H, m), 7.01-7.10 (3 H, m), 6.58 (1 H, d, J = 5.3 Hz), 4.71-4.79 (2 H, m), 4.19-4.33 (4 H, m), 3.56-3.78 (2 H, m), 3.01-3.68 (1 H, m), 2.68-2.85 (2 H, m), 1.86-1.98 (2 H, m), 1.60 (3 H, t, J = 7.3 Hz) |
| 60 | Example 51 | Production Example 5 | 428.58 | [M + H]+ | 8.85-8.89 (1 H, m), 8.61 (1 H, dd, J = 4.6, 1.6 Hz), 8.25 (1 H, d, J = 4.9 Hz), 8.05 (1 H, s), 7.90 (1 H, dt, J = 7.9, 2.0 Hz), 7.40-7.44 (1 H, m), 7.21-7.32 (2 H, m), 7.00-7.08 (2 H, m), 6.59 (1 H, d, J = 5.3 Hz), 4.39 (2 H, t, J = 5.1 Hz), 3.91 (4 H, s), 3.83 (2 H, t, J = 5.1 Hz), 3.40 (3 H, s), 2.62 (3 H, s) |
| 61 | Example 51 | Production Example 3 Synthesis literature 5 | 442.52 | [M + H]+ | 8.84-8.87 (1 H, m), 8.61 (1 H, dd, J = 4.6, 1.6 Hz m), 8.24 (1 H, d, J = 5.3 Hz), 7.99 (1 H, s), 7.90 (1 H, dt, J = 5.3 Hz), 7.42-7.45 (1 H, m), 7.24-7.34 (2 H, m), 6.95-7.11 (2 H, m), 6.56 (1 H, d, J = 5.3 Hz), 4.30 (2 H, q, J = 7.4 Hz), 4.01 (4 H, br s), 3.57-3.70 (2 H, m), 3.42 (3 H, s), 3.00 (2 H, t, J = 5.6 Hz), 1.57-1.63 (3 H, m). |
| 62 | Example 51 | Production Example 5 Synthesis literature 5 | 472.61 | [M + H]+ | 8.82-8.92 (1 H, m), 8.59-8.68 (1 H, m), 8.24 (1 H, d, J = 5.3 Hz), 8.05 (1 H, s), 7.87-7.93 (1 H, m), 7.21-7.41 (3 H, m), 7.01-7.07 (2 H, m), 6.55-6.63 (1 H, m), 4.38 (2 H, t, J = 4.9 Hz), 3.93-4.05 (4 H, m), 3.83 (2 H, t, J = 4.9 Hz), 3.60 (2 H, t, J = 5.4 Hz), 3.37-3.44 (6 H, m), 2.96 (2 H, t, J = 5.6 Hz). |
| 63 | Example 51 | Production Example 17 | 442.54 | [M + H]+ | 8.84-8.90 (1 H, m), 8.61 (1 H, dd, J = 4.8, 1.8 Hz), 8.26 (1 H, d, J = 5.3 Hz), 8.05 (1 H, s), 7.87-7.94 (1 H, m), 7.40-7.53 (1 H, m), 7.06- |

TABLE 2-continued

| | | | | | |
|---|---|---|---|---|---|
| 64 | Example 51 | Production Example 5 Synthesis literature 36 | 442.54 | [M + H]+ | 7.34 (4 H, m), 6.59 (1 H, d, J = 5.3 Hz), 4.17 (2 H, s), 3.97 (4 H, s), 2.66 (3 H, s), 1.28 (6 H, s). 8.84-8.88 (1 H, m), 8.61 (1 H, dd, J = 4.6, 1.6 Hz), 8.24 (1 H, d, J = 4.9 Hz), 8.07 (1 H, s), 7.89 (1 H, dt, J = 7.9, 2.0 Hz), 7.22-7.33 (3 H, m), 6.87-7.00 (2 H, m), 6.57 (1 H, d, J = 4.9 Hz), 4.38 (2 H, t, J = 5.1 Hz), 3.83 (2 H, t, J = 5.1 Hz), 3.58 (2 H, s), 3.40 (3 H, s), 2.84-2.94 (2 H, m), 2.68-2.76 (2 H, m), 2.48 (3 H, s). |
| 65 | Example 51 | Production Example 17 Synthesis literature 36 | 456.64 | [M + H]+ | 8.84-8.88 (1 H, m), 8.62 (1 H, d, J = 4.8, 1.8 Hz), 8.25 (1 H, d, J = 5.3 Hz), 8.03 (1 H, s), 7.91 (1 H, dt, J = 7.9, 2.0 Hz), 7.21-7.35 (3 H, m), 7.02 (1 H, s), 6.87-6.96 (1 H, m), 6.56 (1 H, d, J = 5.3 Hz), 4.17 (2 H, s), 3.54 (2 H, s), 2.87 (2 H, t, J = 5.9 Hz), 2.67 (2 H, t, J = 5.9 Hz), 2.45 (3 H, s), 1.28 (6 H, s). |
| 66 | Example 51 | Production Example 3 Production Example 44 | 452.41 | [M + H]+ | 8.82-8.88 (1 H, m), 8.62 (1 H, dd, J = 4.9, 1.6 Hz), 8.24 (1 H, d, J = 4.9 Hz), 8.01 (1 H, s), 7.87-7.94 (1 H, m), 7.36-7.24 (3 H, m), 6.99-7.02 (2 H, m), 6.54 (1 H, d, J = 5.3 Hz), 4.28 (2 H, q, J = 7.4 Hz), 2.72-2.86 (8 H, m), 1.73-1.84 (1 H, m), 1.60 (3 H, t, J = 7.4 Hz), 0.51-0.80 (4 H, m). |
| 67 | Example 51 | Production Example 3 Synthesis literature 18 | 428.50 | [M + H]+ | 8.83-8.87 (1 H, m), 8.62 (1 H, dd, J = 4.9, 1.6 Hz), 8.25 (1 H, d, J = 5.3 Hz), 8.03 (1 H, s), 7.89 (1 H, dt, J = 7.9, 2.0 Hz), 7.28-7.37 (2 H, m), 7.13-7.17 (1 H, m), 7.02-7.08 (2 H, m), 6.58 (1 H, d, J = 5.3 Hz), 4.27 (2 H, q, J = 7.3 Hz), 4.09-4.18 (2 H, m), 3.82 (2 H, s), 3.05-3.16 (2 H, m), 2.48 (3 H, s), 1.60 (3 H, t, J = 7.4 Hz). |
| 68 | Example 51 | Production Example 3 Production Example 38 | 483.52 | [M + H]+ | 8.84-8.87 (1 H, m), 8.62 (1 H, dd, J = 4.9, 1.6 Hz), 8.20 (1 H, d, J = 5.3 Hz), 7.99 (1 H, s), 7.89 (1 H, dt, J = 7.9, 2.0 Hz), 7.28-7.37 (3 H, m), 6.84-6.92 (3 H, m), 6.50 (1 H, d, J = 5.3 Hz), 4.28 (2 H, q, J = 7.3 Hz), 3.30 (2 H, ddd, J = 11.8, 7.7, 3.6 Hz), 3.01 (2 H, ddd, J = 11.8, 8.2, 3.5 Hz), 2.21-2.29 (6 H, m), 1.80-1.95 (2 H, m), 1.54-1.73 (5 H, m), 0.95 (3 H, s) |
| 69 | Example 51 | Production Example 3 Synthesis literature 45 | 467.57 | [M + H]+ | 8.86 (1 H, dd, J = 2.1, 0.8 Hz), 8.60 (1 H, dd, J = 4.9, 1.6 Hz), 8.20 (1 H, d, J = 5.3 Hz), 7.98 (1 H, s), 7.90 (1 H, dt, J = 7.9, 2.0 Hz), 7.28-7.38 (3 H, m), 6.91 (1 H, s), 6.68-6.77 (2 H, m), 6.50 (1 H, d, J = 5.3 Hz), 4.27 (2 H, q, J = 7.3 Hz), 3.95-4.04 (1 H, m), 3.42-3.54 (2 H, m), 2.90-3.21 (6 H, m), 2.06-2.22 (2 H, m), 1.75 (2 H, ddt, J = 14.3, 9.6, 4.8, 4.8 Hz), 1.53-1.62 (3 H, m) |
| 70 | Example 51 | Production Example 3 Synthesis literature 46 | 410.29 | [M + H]+ | 8.85-8.88 (1 H, m), 8.61 (1 H, dd, J = 4.6, 1.6 Hz), 8.29 (1 H, d, J = 5.3 Hz), 8.01 (1 H, s), 7.86-7.94 (2 H, m), 7.20-7.70 (7 H, m), 6.64 (1 H, d, J = 5.3 Hz), 4.28 (2 H, q, J = 7.3 Hz), 1.60 (3 H, t, J = 7.4 Hz) |
| 71 | | Production Example 5 Synthesis literature 14 | 457.42 | [M + H]+ | 8.86 (1 H, dd, J = 2.3, 0.7 Hz), 8.61 (1 H, dd, J = 4.8, 1.8 Hz), 8.22 (1 H, d, J = 5.3 Hz), 8.05 (1 H, s), 7.87-7.91 (1 H, m), 7.27-7.36 (3 H, m), 6.80-6.88 (3 H, m), 6.55 (1 H, d, J = 5.3 Hz), 4.38 (2 H, t, J = 5.1 Hz), 3.83 (2 H, t, J = 5.1 Hz), 3.40 (3 H, s), 3.00-3.13 (8 H, m) |
| 72 | Example 71 | Production Example 10 Synthesis literature 14 | 511.55 | [M + H]+ | 8.84-8.87 (1 H, m), 8.63 (1 H, dd, J = 4.9, 1.6 Hz), 8.23 (1 H, d, J = 5.3 Hz), 8.03 (1 H, s), 7.88 (1 H, dt, J = 7.9, 2.0 Hz), 7.28-7.41 (3 H, m), 6.80-6.95 (3 H, m), 6.54 (1 H, d, J = 4.9 Hz), 4.40-4.55 (4 H, m), 3.01-3.13 (8 H, m) |
| 73 | Example 71 | Production Example 3 Synthesis literature 47 | 384.47 | [M + H]+ | 8.83-8.87 (1 H, m), 8.58-8.63 (1 H, m), 8.22-8.27 (1 H, m), 7.99 (1 H, s), 7.87-7.92 (1 H, m), 7.46-7.49 (1 H, m), 7.28-7.34 (1 H, m), 6.99-7.22 (3 H, m), 6.58 (1 H, d, J = 4.6 Hz), 4.17-4.33 (6 H, m), 4.07 (1 H, br s), 1.60 (3 H, t, J = 7.3 Hz). |
| 74 | | Production Example 93 | 573.47 | [M + H]+ | 8.84-8.88 (1 H, m), 8.63 (1 H, dd, J = 4.6, 1.6 Hz), 8.29 (1 H, d, J = 5.3 Hz), 7.91 (1 H, dt, J = 7.7, 2.1 Hz), 7.78 (1 H, s), 7.51 (2 H, d, J = 8.6 Hz), 7.28-7.39 (6 H, m), 7.15-7.23 (3 H, m), 6.61 (1 H, d, J = 4.9 Hz), 4.45 (2 H, t, J = 7.3 Hz), 3.47-3.78 (8 H, m), 3.28 (2 H, t, J = 7.3 Hz), 2.15 (3 H, s) |
| 75 | Example 74 | Example 168 | | | 8.82-8.89 (1 H, m), 8.54-8.66 (1 H, m), 8.17-8.34 (1 H, m), 7.95-8.03 (1 H, m), 7.91 (1 H, dt, J = 7.8, 1.9 Hz), 7.24-7.36 (4 H, m), 6.94-7.08 (1 H, m), 6.59 (1 H, dd, J = 5.1, 1.2 Hz), 4.68, 4.57 (total H, both s), 4.28 (2 H, q, J = 7.5 Hz), 3.80, 3.65 (total 2 H, both t, J = 5.9 Hz), |

TABLE 2-continued

| | | | | | |
|---|---|---|---|---|---|
| | | | | | 2.73-2.88 (2 H, m), 2.18, 2.17 (total 3 H, both s), 1.59 (3 H, t, J = 7.3 Hz) |
| 76 | | Production Example 70 | 527.45 | [M + H]+ | 8.85 (1 H, dd, J = 2.1, 0.8 Hz), 8.61 (1 H, dd, J = 4.8, 1.8 Hz), 8.22 (1 H, d, J = 5.3 Hz), 8.05 (1 H, s), 7.88 (1 H, dt, J = 7.9, 2.0 Hz), 7.27-7.35 (3 H, m), 7.07 (1 H, s), 6.81-6.88 (2 H, m), 6.53 (1 H, d, J = 5.3 Hz), 5.02-5.10 (1 H, m), 3.94-4.24 (4 H, m), 3.56 (2 H, t, J = 5.6 Hz), 3.33-3.43 (3 H, m), 3.12-3.21 (4 H, m), 2.36-2.70 (8 H, m) |
| 77 | Example 76 | Production Example 104 | 541.50 | [M + H]+ | 8.84 (1 H, dd, J = 2.1, 0.8 Hz), 8.61 (1 H, dd, J = 4.6, 1.6 Hz), 8.22 (1 H, d, J = 4.9 Hz), 7.94 (1 H, s), 7.87 (1 H, dt, J = 7.9, 2.0 Hz), 7.28-7.37 (3 H, m), 7.16 (1 H, s), 6.81-6.89 (2 H, m), 6.52 (1 H, d, J = 5.3 Hz), 4.76 (2 H, d, J = 6.3 Hz), 4.46 (2 H, d, J = 6.3 Hz), 4.41 (2 H, s), 3.56 (2 H, t, J = 5.6 Hz), 3.38 (3 H, s), 3.11-3.22 (4 H, m), 2.62-2.72 (6 H, m), 1.35 (3 H, s) |
| 78 | Example 76 | Example 151 | 524.42 | [M + H]+ | 8.83-8.85 (1 H, m), 8.60 (1 H, dd, J = 4.8, 1.6 Hz), 8.20 (1 H, d, J = 5.1 Hz), 7.97 (1 H, s), 7.87 (1 H, dt, J = 7.8, 2.0 Hz), 7.27-7.37 (3 H, m), 7.04 (1 H, s), 6.84 (2 H, d, J = 9.0 Hz), 6.50 (1 H, d, J = 5.1 Hz), 4.25 (2 H, q, J = 7.3 Hz), 3.01-3.18 (5 H, m), 2.49-2.66 (5 H, m), 2.43 (3 H, s), 2.29-2.38 (2 H, m), 2.08-2.24 (1 H, m), 1.92-2.08 (2 H, m), 1.63-1.87 (2 H, m), 1.55-1.60 (3 H, m) |
| 79 | Example 76 | Example 137 | 552.70 | [M + H]+ | 8.87 (1 H, dd, J = 2.3, 1.0 Hz), 8.63 (1 H, dd, J = 4.9, 1.6 Hz), 8.21-8.26 (1 H, m), 8.15 (1 H, s), 7.91 (1 H, dt, J = 7.9, 2.0 Hz), 7.28-7.37 (3 H, m), 7.03 (1 H, s), 6.80-6.90 (2 H, m), 6.52 (1 H, d, J = 4.9 Hz), 5.54 (1 H, tt, J = 7.6, 6.2 Hz), 5.07-5.20 (4 H, m), 3.04-3.18 (6 H, m), 2.56-2.69 (5 H, m), 2.44 (3 H, s), 2.15-2.42 (3 H, m), 1.88-2.08 (1 H, m), 1.54-1.85 (2 H, m) |
| 80 | Example 76 | Example 71 | 554.60 | [M + H]+ | 8.86 (1 H, dd, J = 2.3, 1.0 Hz), 8.60 (1 H, dd, J = 4.9, 1.6 Hz), 8.21 (1 H, d, J = 5.0 Hz), 8.04 (1 H, s), 7.89 (1 H, dt, J = 7.8, 1.9 Hz), 7.25-7.35 (3 H, m), 7.08 (1 H, s), 6.76-6.89 (2 H, m), 6.54 (1 H, d, J = 5.3 Hz), 4.37 (2 H, t, J = 5.1 Hz), 3.82 (2 H, t, J = 5.1 Hz), 3.39 (3 H, s), 3.01-3.17 (6 H, m), 2.49-2.67 (5 H, m), 2.43 (3 H, s), 2.13-2.40 (3 H, m), 1.90-2.07 (1 H, m), 1.66-1.87 (2 H, m) |
| 81 | Example 76 | Production Example 97 | 529.41 | [M + H]+ | 8.82-8.86 (1 H, m), 8.59 (1 H, dd, J = 4.9, 1.6 Hz), 8.21 (1 H, d, J = 5.3 Hz), 8.02 (1 H, s), 7.88 (1 H, dt, J = 7.8, 1.9 Hz), 7.25-7.35 (4 H, m), 6.83 (2 H, d, J = 8.9 Hz), 6.52 (1 H, d, J = 4.9 Hz), 4.15 (2 H, s), 3.57 (2 H, t, J = 5.4 Hz), 3.38 (3 H, s), 3.07-3.26 (4 H, m), 2.61-2.77 (6 H, m), 1.27 (6 H, s) |
| 82 | Example 76 | Example 157 | 572.42 | [M + H]+ | 8.83-8.87 (1 H, m), 8.61 (1 H, dd, J = 4.6, 1.6 Hz), 8.22 (1 H, d, J = 5.3 Hz), 8.13 (1 H, s), 7.88 (1 H, dt, J = 8.1, 1.9 Hz), 7.70-7.77 (1 H, m), 7.57-7.66 (1 H, m), 7.40-7.51 (2 H, m), 7.26-7.34 (3 H, m), 7.15 (1 H, s), 6.80-6.89 (2 H, m), 6.53 (1 H, d, J = 5.3 Hz), 5.60 (2 H, s), 3.56 (2 H, t, J = 5.6 Hz), 3.38 (3 H, s), 3.11-3.24 (4 H, m), 2.62-2.72 (6 H, m) |
| 83 | Example 76 | Production Example 103 | 510 | [M + H]+ | 8.80-8.81 (1 H, m), 8.59-8.61 (1 H, m), 8.25 (1 H, d, J = 5.4 Hz), 8.02 (1 H, s), 7.98 (1 H, d, J = 2.4 Hz), 7.88-7.93 (1 H, m), 7.43-7.47 (1 H, m), 7.31-7.36 (1 H, m), 7.04 (1 H, s), 6.93 (1 H, d, J = 8.9 Hz), 6.61 (1 H, d, J = 5.4 Hz), 4.25-4.33 (2 H, m), 3.54-3.58 (2 H, m), 3.38 (3 H, s), 3.19-3.23 (4 H, m), 2.66-2.75 (6 H, m), 1.58-1.64 (3 H, m) |
| 84 | Example 76 | Example 155 | 486 | [M + H]+ | 8.83-8.84 (1 H, m), 8.59-8.61 (1 H, m), 8.24 (1 H, d, J = 5.1 Hz), 8.19 (1 H, d, J = 5.1 Hz), 7.98 (1 H, s), 7.86-7.89 (1 H, m), 7.76-7.78 (1 H, m), 7.29-7.32 (1 H, m), 7.00 (1 H, s), 6.51-6.59 (2 H, m), 4.27 (2 H, q, J = 4.6 Hz), 3.51-3.59 (6 H, m), 3.38 (3 H, s), 2.61-2.66 (6 H, m), 1.58-1.61 (3 H, m) |
| 85 | Example 76 | Production Example 98 | 510.57 | [M + H]+ | 8.85 (1 H, dd, J = 2.1, 0.8 Hz), 8.58-8.62 (1 H, m), 8.23 (1 H, dd, J = 5.1, 1.2 Hz), 7.99 (1 H, s), 7.86-7.93 (1 H, m), 7.26-7.43 (4 H, m), 7.09-7.21 (2 H, m), 6.54 (1 H, dd, J = 5.1, 0.8 Hz), 4.27 (2 H, q, J = 7.4 Hz), 3.54 (2 H, dt, J = 8.9, 6.3 Hz), 3.26-3.42 (5 H, m), 2.76-3.12 (1 H, |

TABLE 2-continued

| | | | | | |
|---|---|---|---|---|---|
| | | | | | m), 2.66 (1 H, t, J = 6.1 Hz), 2.51 (1 H, t, J = 6.1 Hz), 2.32-2.45 (1 H, m), 1.79-2.06 (3 H, m), 1.34-1.74 (7 H, m) |
| 86 | Example 76 | Example 143 | 511.39 | [M + H]+ | 8.83-8.88 (1 H, m), 8.60 (1 H, dd, J = 4.9, 1.6 Hz), 8.19 (1 H, d, J = 4.9 Hz), 7.97 (1 H, s), 7.88 (1 H, dt, J = 7.9, 2.0 Hz), 7.25-7.33 (3 H, m), 7.15-7.23 (1 H, m), 6.70 (2 H, d, J = 8.9 Hz), 6.48 (1 H, d, J = 5.3 Hz), 4.25 (2 H, q, J = 7.3 Hz), 3.58 (2 H, t, J = 5.9 Hz), 3.40-3.49 (2 H, m), 3.38 (3 H, s), 3.24-3.34 (2 H, m), 3.00-3.10 (2 H, m), 2.66 (2 H, t, J = 5.8 Hz), 1.92-2.03 (2 H, m), 1.74-1.85 (2 H, m), 1.57 (3 H, t, J = 7.3 Hz) |
| 87 | Example 76 | Example 151 | 484 | [M + H]+ | CD$_3$OD<br>8.60-8.61 (1 H, m), 8.35-8.38 (1 H, m), 8.18 (1 H, s), 8.14 (1 H, d, J = 5.1 Hz), 7.88-7.92 (1 H, m), 7.27-7.29 (1 H, m), 7.11-7.14 (2 H, m), 6.64-6.68 (3 H, m), 4.16-4.24 (2 H, m), 3.04-3.08 (4 H, m), 2.99 (2 H, s), 2.60-2.64 (4 H, m), 1.46 (3 H, t, J = 7.3 Hz) |
| 88 | Example 76 | Example 169 | 482.28 | [M + H]+ | 8.83-8.87 (1 H, m), 8.62 (1 H, dd, J = 4.9, 1.6 Hz), 8.22 (1 H, d, J = 5.3 Hz), 8.01 (1 H, s), 7.90 (1 H, dt, J = 7.9, 2.0 Hz), 7.20-7.35 (3 H, m), 6.86-7.03 (2 H, m), 6.53 (1 H, d, J = 5.3 Hz), 4.28 (2 H, q, J = 7.3 Hz), 4.11-4.22 (1 H, m), 3.64-3.95 (6 H, m), 2.77-2.92 (2 H, m), 2.62-2.69 (2 H, m), 1.81-2.10 (4 H, m), 1.60 (3 H, t, J = 7.4 Hz). |
| 89 | Example 76 | Example 168 | 482.25 | [M + H]+ | 8.84-8.89 (1 H, m), 8.62 (1 H, dd, J = 5.0, 1.7 Hz), 8.24 (1 H, d, J = 4.9 Hz), 8.00 (1 H, s), 7.89 (1 H, dt, J = 7.8, 1.9 Hz), 7.22-7.34 (3 H, m), 6.90-7.00 (2 H, m), 6.54 (1 H, d, J = 5.3 Hz), 4.28 (2 H, q, J = 7.4 Hz), 4.12-4.22 (1 H, m), 3.72-3.96 (4 H, m), 2.82-2.97 (4 H, m), 2.68 (2 H, d, J = 5.6 Hz), 1.79-2.13 (4 H, m) 1.60 (3 H, t, J = 7.3 Hz). |
| 90 | Example 76 | Example 168 | 455.51 | [M + H]+ | 8.84-8.88 (1 H, m), 8.61 (1 H, dd, J = 4.9, 1.6 Hz), 8.24 (1 H, d, J = 5.4 Hz), 8.00 (1 H, s), 7.89 (1 H, dt, J = 8.1, 1.9 Hz), 7.17-7.36 (3 H, m), 6.87-7.05 (2 H, m), 6.57 (1 H, d, J = 4.9 Hz), 5.44 (2 H, br s), 4.29 (2 H, q, J = 7.3 Hz), 3.70 (2 H, s), 3.20 (2 H, s), 2.79-2.97 (4 H, m), 1.60 (3 H, t, J = 7.4 Hz). |
| 91 | Example 76 | Production Example 69 | 472.58 | [M + H]+ | 8.82-8.88 (1 H, m), 8.61-8.63 (1 H, m), 8.25 (1 H, d, J = 4.9 Hz), 8.03 (1 H, s), 7.87-7.91 (1 H, m), 7.29-7.38 (2 H, m), 7.01-7.25 (3 H, m), 6.58 (1 H, d, J = 5.3 Hz), 4.28 (2 H, q, J = 7.5 Hz), 4.08-4.17 (2 H, m), 3.97-4.07 (2 H, m), 3.53-3.68 (2 H, m), 3.37 (3 H, s), 3.25-3.34 (2 H, m), 2.77-2.89 (2 H, m), 1.61 (3 H, t, J = 7.3 Hz). |
| 92 | Example 76 | Example 145 | 472.58 | [M + H]+ | 8.84 (1 H, d, J = 2.0 Hz), 8.61 (1 H, dd, J = 5.2, 1.5 Hz), 8.22 (1 H, d, J = 5.5 Hz), 7.98 (1 H, s), 7.90 (1 H, dt, J = 8.0, 2.2 Hz), 7.24-7.42 (3 H, m), 6.93 (1 H, s), 6.69 (2 H, d, J = 9.0 Hz), 6.54 (1 H, d, J = 5.2 Hz), 4.72-4.84 (1 H, m), 4.28 (2 H, q, J = 7.5 Hz), 3.86-3.95 (2 H, m), 3.42 (2 H, t, J = 5.3 Hz), 3.36 (3 H, s), 3.10-3.19 (2 H, m), 2.71 (2 H, t, J = 5.1 Hz), 1.60 (3 H, t, J = 7.5 Hz). |
| 93 | Example 76 | Example 171 | 470.36 | [M + H]+ | 8.83-8.88 (1 H, m), 8.62 (1 H, d, J = 4.9, 1.6 Hz), 8.24 (1 H, d, J = 5.3 Hz), 8.00 (1 H, s), 7.91 (1 H, dt, J = 7.8, 1.9 Hz), 7.25-7.37 (3 H, m), 6.93-7.04 (2 H, m), 6.55 (1 H, d, J = 4.9 Hz), 4.28 (2 H, q, J = 7.3 Hz), 3.54-3.72 (2 H, m), 3.37 (3 H, s), 2.77-3.10 (10 H, m), 1.60 (3 H, t, J = 7.4 Hz). |
| 94 | Example 76 | Production Example 96 | 499.58 | [M + H]+ | 8.84-8.87 (1 H, m), 8.59-8.63 (1 H, m), 8.18 (1 H, d, J = 5.6 Hz), 7.98 (1 H, s), 7.87-7.93 (1 H, m), 7.29-7.36 (3 H, m), 6.76 (1 H, s), 6.62 (2 H, d, J = 8.9 Hz), 6.47 (1 H, d, J = 4.9 Hz), 4.27 (2 H, q, J = 7.1 Hz), 3.40-3.61 (6 H, m), 3.36 (3 H, s), 2.80-2.93 (2 H, m), 2.65-2.80 (4 H, m), 1.93-2.06 (2 H, m), 1.59 (3 H, t, J = 7.6 Hz) |
| 95 | Example 76 | Example 168 | 454.37 | [M + H]+ | 8.85-8.90 (1 H, m), 8.59-8.65 (1 H, m), 8.24 (1 H, d, J = 5.3 Hz), 8.00 (1 H, s), 7.90 (1 H, dt, J = 7.9, 2.0 Hz), 7.25-7.34 (3 H, m), 7.02 (1 H, s), 6.92 (1 H, d, J = 8.2 Hz), 6.56 (1 H, d, J = 5.3 Hz), 4.72-4.80 (4 H, m), 4.28 (2 H, q, J = |

TABLE 2-continued

| | | | | | |
|---|---|---|---|---|---|
| | | | | | 7.4 Hz), 3.62-3.79 (1 H, m), 3.52 (2 H, s), 2.83-2.96 (2 H, m), 2.60-2.68 (2 H, m), 1.60 (3 H, t, J = 7.3 Hz). |
| 96 | Example 76 | Example 151 Synthesis literature 48 | 525.49 | [M + H]+ | 8.85 (1 H, dd, J = 2.3, 0.7 Hz), 8.61 (1 H, dd, J = 4.9, 1.6 Hz), 8.20 (1 H, d, J = 5.3 Hz), 7.98 (1 H, s), 7.89 (1 H, dt, J = 8.0, 1.8 Hz), 7.28-7.39 (3 H, m), 7.10 (1 H, s), 6.82-6.89 (2 H, m), 6.51 (1 H, d, J = 5.3 Hz), 4.78-4.88 (1 H, m), 4.27 (2 H, q, J = 7.3 Hz), 3.12-3.18 (4 H, m), 2.77 (1 H, dd, J = 13.5, 8.2 Hz), 2.64-2.71 (4 H, m), 2.61 (1 H, dd, J = 13.2, 4.0 Hz), 2.45 (1 H, dd, J = 10.7, 7.7 Hz), 2.14 (1 H, dd, J = 10.9, 7.3 Hz), 1.58 (3 H, t, J = 7.3 Hz), 1.47 (3 H, s), 1.41 (3 H, s) |
| 97 | Example 76 | Example 151 | 511.40 | [M + H]+ | 8.86 (1 H, dd, J = 2.1, 0.8 Hz), 8.61 (1 H, dd, J = 4.9, 1.6 Hz), 8.21 (1 H, d, J = 5.3 Hz), 7.98 (1 H, s), 7.89 (1 H, dt, J = 7.8, 1.9 Hz), 7.27-7.38 (3 H, m), 7.02 (1 H, s), 6.81-6.90 (2 H, m), 6.52 (1 H, d, J = 5.3 Hz), 4.27 (2 H, q, J = 7.5 Hz), 3.71-3.92 (3 H, m), 3.54 (1 H, dd, J = 8.6, 5.9 Hz), 3.14 (4 H, t, J = 4.9 Hz), 2.34-2.68 (7 H, m), 1.98-2.11 (1 H, m), 1.52-1.70 (4 H, m) |
| 98 | Example 76 | Example 151 Synthesis literature 49 | 511.47 | [M + H]+ | 8.85 (1 H, s), 8.61 (1 H, dd, J = 4.9, 1.7 Hz), 8.21 (1 H, d, J = 5.1 Hz), 7.98 (1 H, s), 7.88 (1 H, dt, J = 7.8, 2.0 Hz), 7.28-7.38 (3 H, m), 6.94 (1 H, s), 6.84 (2 H, d, J = 9.0 Hz), 6.52 (1 H, d, J = 5.1 Hz), 4.53 (2 H, d, J = 5.6 Hz), 4.36 (2 H, d, J = 5.6 Hz), 4.27 (2 H, q, J = 7.3 Hz), 3.04-3.19 (4 H, m), 2.62 (2 H, s), 2.47-2.56 (4 H, m), 1.59 (3 H, t, J = 7.3 Hz), 1.43 (3 H, s) |
| 99 | Example 76 | Example 151 | 497 | [M + H]+ | 8.84-8.85 (1 H, m), 8.59-8.62 (1 H, m), 8.21 (1 H, d, J = 5.1 Hz), 7.98 (1 H, s), 7.87-7.90 (1 H, m), 7.29-7.36 (3 H, m), 6.83-6.89 (3 H, m), 6.53 (1 H, d, J = 5.1 Hz), 4.81-4.86 (2 H, m), 4.43-4.48 (2 H, m), 4.23-4.31 (2 H, m), 3.24-3.34 (1 H, m), 3.11-3.15 (4 H, m), 2.78-2.80 (2 H, m), 2.55-2.59 (4 H, m), 1.56-1.62 (3 H, m) |
| 100 | Example 76 | Production Example 102 | 484 | [M + H]+ | 8.84-8.85 (1 H, m), 8.60-8.62 (1 H, m), 8.23 (1 H, d, J = 5.4 Hz), 8.00 (1 H, s), 7.88-7.92 (1 H, m), 7.41 (2 H, d, J = 8.6 Hz), 7.30-7.39 (1 H, m), 7.07-7.27 (3 H, m), 6.55 (1 H, d, J = 4.9 Hz), 4.24-4.32 (2 H, m), 3.53 (2 H, t, J = 5.7 Hz), 3.35 (3 H, s), 3.00-3.04 (2 H, m), 2.78-2.89 (1 H, m), 2.58-2.62 (2 H, m), 1.77-2.04 (5 H, m), 1.57-1.63 (3 H, m), 1.38-1.51 (1 H, m) |
| 101 | | Production Example 135 | 511 | [M + H]+ | 8.86-8.87 (1 H, m), 8.62-8.65 (1 H, m), 8.24 (1 H, d, J = 5.4 Hz), 8.15 (1 H, s), 7.89-7.93 (1 H, m), 7.30-7.37 (3 H, m), 6.85-6.89 (3 H, m), 6.54 (1 H, d, J = 5.4 Hz), 5.52-5.57 (1 H, m), 5.08-5.19 (4 H, m), 4.65-4.74 (4 H, m), 3.55-3.60 (1 H, m), 3,17-3.21 (4 H, m), 2.50-2.54 (4 H, m) |
| 102 | Example 101 | Production Example 139 | 527 | [M + H]+ | 8.82-8.83 (1 H, m), 8.60-8.63 (1 H, m), 8.22 (1 H, d, J = 4.9 Hz), 7.95 (1 H, s), 7.84-7.88 (1 H, m), 7.32-7.36 (2 H, m), 7.28-7.31 (1 H, m), 6.85-6.88 (3 H, m), 6.51 (1 H, d, J = 5.4 Hz), 4.87-4.92 (2 H, m), 4.52-4.60 (4 H, m), 3.60-3.67 (1 H, m), 3.57 (2 H, t, J = 5.7 Hz), 3.38 (3 H, s), 3.17-3.21 (4 H, m), 2.63-2.70 (6 H, m) |
| 103 | Example 101 | Production Example 144 | 509 | [M + H]+ | 8.86-8.87 (1 H, m), 8.62-8.64 (1 H, m), 8.24 (1 H, d, J = 5.4 Hz), 8.15 (1 H, s), 7.90-7.92 (1 H, m), 7.30-7.36 (3 H, m), 6.89 (1 H, s), 6.86-6.89 (2 H, m), 6.53 (1 H, d, J = 5.4 Hz), 5.53-5.55 (1 H, m), 5.08-5.19 (4 H, m), 3.19-3.22 (4 H, m), 2.72-2.75 (4 H, m), 2.35 (2 H, d, J = 5.4 Hz), 0.92 (1 H, m), 0.55-0.58 (2 H, m), 0.15-0.16 (2 H, m) |
| 104 | | Example 151 | 499.46 | [M + H]+ | 8.86 (1 H, dd, J = 2.3, 0.7 Hz), 8.61 (1 H, dd, J = 4.9, 1.6 Hz), 8.21 (1 H, d, J = 5.3 Hz), 7.98 (1 H, s), 7.89 (1 H, dt, J = 7.9, 2.0 Hz), 7.27-7.37 (3 H, m), 6.95-7.03 (1 H, m), 6.79-6.91 (2 H, m), 6.52 (1 H, d, J = 5.3 Hz), 4.27 (2 H, q, J = 7.3 Hz), 3.10-3.20 (4 H, m), 2.77-2.86 (4 H, m), 2.40 (2 H, s), 1.59 (3 H, t, J = 7.3 Hz), 1.20 (6 H, s) |
| 105 | Example 104 | Example 151 | 515.47 | [M + H]+ | 8.85 (1 H, d, J = 2.0 Hz), 8.61 (1 H, dd, J = 4.9, 1.5 Hz), 8.21 (1 H, d, J = 5.1 Hz), 7.98 (1 H, s), 7.88 (1 H, dt, J = 7.9, 1.8 Hz), 7.28-7.38 (3 H, m), 6.97-7.03 (1 H, m), 6.85 (2 H, d, J = 9.0 Hz), 6.52 (1 H, d, J = 5.4 Hz), 4.27 (2 H, q, J = 7.3 Hz), 3.91-3.98 (1 H, m), 3.34-3.51 (5 H, m), 3.09-3.21 (4 H, m), 2.75-2.89 (2 H, |

TABLE 2-continued

| | | | | | |
|---|---|---|---|---|---|
| 106 | Example 104 | Example 169 | 470.36 | [M + H]+ | m), 2.58-2.64 (2 H, m), 2.55 (1 H, dd, J = 12.3, 10.1 Hz), 2.44 (1 H, dd, J = 12.5, 3.7 Hz), 1.59 (3 H, t, J = 7.3 Hz)<br>8.84-8.87 (1 H, m), 8.61 (1 H, dd, J = 4.9, 1.6 Hz), 8.24 (1 H, d, J = 5.3 Hz), 7.99 (1 H, s), 7.89 (1 H, dt, J = 7.8, 1.9 Hz), 7.19-7.34 (3 H, m), 6.91-7.08 (2 H, m), 6.57 (1 H, d, J = 5.3 Hz), 4.27 (2 H, q, J = 7.3 Hz), 3.79-3.94 (2 H, m), 2.85-3.10 (4 H, m), 2.60 (2 H, m), 1.60 (3 H, t, J = 7.3 Hz), 1.27 (6 H, s) |
| 107 | Example 104 | Production Example 99 | 516.67 | [M + H]+ | 8.80-8.88 (1 H, m), 8.60 (1 H, dd, J = 5.0, 2.0 Hz), 8.23 (1 H, d, J = 5.2 Hz), 8.04 (1 H, s), 7.89 (1 H, dt, J = 7.7, 1.5 Hz), 7,24-7.42 (3 H, m), 7.00 (1 H, s), 6.66 (2 H, d, J = 8.8 Hz), 6.57 (1 H, d, J = 5.0 Hz), 4.70-4.85 (1 H, m), 4.37 (2 H, t, J = 5.3 Hz), 3.88-4.00 (2 H, m), 3.83 (2 H, t, J = 5.3 Hz), 3.39 (3 H, s), 3.25-3.37 (2 H, m), 2.53 (2 H, s), 1.52 (6 H, m). |
| 108 | Example 104 | Example 145 | 486.61 | [M + H]+ | 8.83 (1 H, s), 8.59 (1 H, dd, J = 4.8, 1.1 Hz), 8.21 (1 H, d, J = 5.2 Hz), 7.96 (1 H, s), 7.88 (1 H, dt, J = 7.4, 1.7 Hz), 7.21-7.44 (3 H, m), 7.00 (1 H, s), 6.66 (2 H, d, J = 9.3 Hz), 6.54 (1 H, d, J = 5.6 Hz), 4.70-4.85 (1 H, m), 4.26 (2 H, q, J = 7.4 Hz), 3.88-4.01 (2 H, m), 3.26-3.40 (2 H, m), 2.52 (2 H, s), 1.7-2.0 (1 H, br s), 1.58 (3 H, t, J = 7.4 Hz), 1.14 (6 H, s). |
| 109 | Example 104 | Example 168 | 486.53 | [M + H]+ | 8.84-8.88 (1 H, m), 8.58-8.65 (1 H, m), 8.23 (1 H, d, J = 4.9 Hz), 8.00 (1 H, s), 7.90 (1 H, dt, J = 7.8, 1.9 Hz), 7.28-7.35 (3 H, m), 6.87-6.98 (2 H, m), 6.57 (1 H, d, J = 5.3 Hz), 4.29 (2 H, q, J = 7.3 Hz), 3.95-4.07 (1 H, m), 3.54-3.84 (2 H, m), 3.43-3.54 (2 H, m), 3.42 (3 H, s), 2.54-2.96 (6 H, m), 1.60 (3 H, t, J = 7.4 Hz). |
| 110 | Example 104 | Example 137 | 543.49 | [M + H]+ | 8.87 (1 H, dd, J = 2.1, 0.8 Hz), 8.63 (1 H, dd, J = 4.9, 1.6 Hz), 8.24 (1 H, d, J = 4.9 Hz), 8.15 (1 H, s), 7.91 (1 H, dt, J = 8.1, 1.9 Hz), 7.29-7.38 (3 H, m), 7.08-7.15 (1 H, m), 6.81-6.89 (2 H, m), 6.53 (1 H, d, J = 4.9 Hz), 5.48-5.59 (1 H, m), 5.07-5.20 (4 H, m), 3.90-4.01 (1 H, m), 3.36-3.51 (5 H, m), 3.12-3.19 (4 H, m), 2.76-2.88 (2 H, m), 2.41-2.67 (4 H, m) |
| 111 | Example 104 | Production Example 97 | 559.44 | [M + H]+ | 8.82-8.87 (1 H, m), 8.59 (1 H, dd, J = 4.9, 1.6 Hz), 8.22 (1 H, d, J = 5.3 Hz), 8.02 (1 H, s), 7.88 (1 H, dt, J = 7.9, 2.0 Hz), 7.26-7.36 (4 H, m), 6.77-6.87 (2 H, m), 6.53 (1 H, d, J = 5.3 Hz), 4.15 (2 H, s), 3.88-4.00 (1 H, m), 3.28-3.57 (5 H, m), 3.06-3.22 (4 H, m), 2.74-2.88 (2 H, m), 2.39-2.68 (4 H, m), 1.27 (6 H, s) |
| 112 | | Example 159 | 469 | [M + H]+ | 8.80-8.85 (1 H, m), 8.60-8.62 (1 H, m), 8.23 (1 H, d, J = 4.9 Hz), 8.00 (1 H, s), 7.88-7.91 (1 H, m), 7.40 (2 H, d, J = 8.6 Hz), 7.30-7.38 (1 H, m), 7.06-7.11 (3 H, m), 6.57 (1 H, d, J = 5.1 Hz), 4.24-4.32 (2 H, m), 2.45-2.81 (12 H, m), 2.40 (3 H, s), 1.57-1.62 (3 H, m) |
| 113 | Example 112 | Production Example 102 | 440 | [M + H]+ | 8.84-8.85 (1 H, m), 8.60-8.62 (1 H, m), 8.24 (1 H, d, J = 5.1 Hz), 8.00 (1 H, s), 7.87-7.92 (1 H, m), 7.42 (2 H, d, J = 8.6 Hz), 7.30-7.34 (1 H, m), 7.10-7.17 (3 H, m), 6.57 (1 H, d, J = 5.1 Hz), 4.24-4.32 (2 H, m), 3.11-3.15 (2 H, m), 2.95 (1 H, m), 2.44 (3 H, s) 2.08-2.17 (2 H, m), 1.84-1.98 (3 H, m), 1.57-1.62 (3 H, m), 1.47-1.49 (1 H, m) |
| 114 | Example 112 | Production Example 71 | 440 | [M + H]+ | 8.85-8.86 (1 H, m), 8.61-8.63 (1 H, m), 8.23 (1 H, d, J = 5.1 Hz), 8.05 (1 H, s), 7.88-7.93 (1 H, m), 7.46-7.47 (1 H, m), 7.30-7.39 (2 H, m), 7.21 (1 H, t, J = 7.8 Hz), 7.10 (1 H, s), 6.88-6.91 (1 H, m), 6.54 (1 H, d, J = 5.1 Hz), 4.24-4.33 (2 H, m), 2.95-3.00 (2 H, m), 2.40-2.52 (1 H, m), 2.32 (3 H, s), 2.01-2.10 (2 H, m), 1.79-1.87 (4 H, m), 1.57-1.62 (3 H, m) |
| 115 | Example 112 | Example 171 | 426 | [M + H]+ | 8.85-8.86 (1 H, m), 8.60-8.62 (1 H, m), 8.23 (1 H, d, J = 5.1 Hz), 8.00 (1 H, s), 7.88-7.92 (1 H, m), 7.28-7.34 (3 H, m), 6.98-7.10 (1 H, m), 6.54 (1 H, d, J = 5.1 Hz), 4.24-4.32 (2 H, m), 2.87-2.92 (4 H, m), 2.56-2.58 (4 H, m), 2.38 (3 H, s), 1.50 (3 H, t, J = 7.3 Hz) |
| 116 | Example 112 | Production Example 90 | 469.47 | [M + H]+ | 8.84 (1 H, dd, J = 2.1, 0.8 Hz), 8.62 (1 H, dd, J = 4.9, 1.6 Hz), 8.29 (1 H, d, J = 5.3 Hz), 8.02 (1 H, s), 7.91 (1 H, dt, J = 7.9, 2.0 Hz), 7.50-7.56 (2 H, m), 7.31-7.37 (3 H, m), 7.23 (1 H, s), |

TABLE 2-continued

| | | | | | |
|---|---|---|---|---|---|
| | | | | | 6.64 (1 H, d, J = 5.3 Hz), 4.29 (2 H, q, J = 7.3 Hz), 3.44-3.83 (4 H, m), 2.36-2.71 (4 H, m), 2.33 (3 H, s), 1.61 (3 H, t, J = 7.4 Hz) |
| 117 | Example 112 | Production Example 95 | 495.27 | [M + H]+ | 8.84 (1 H, dd, J = 2.3, 1.0 Hz), 8.62 (1 H, dd, J = 4.6, 1.6 Hz), 8.29 (1 H, d, J = 5.3 Hz), 8.02 (1 H, s), 7.92 (1 H, dt, J = 8.1, 1.9 Hz), 7.49-7.56 (2 H, m), 7.28-7.38 (3 H, m), 7.23 (1 H, s), 6.63 (1 H, d, J = 5.3 Hz), 4.29 (2 H, q, J = 7.4 Hz), 2.93-3.57 (6 H, m), 2.30 (3 H, s), 1.66-2.04 (4 H, m), 1.61 (3 H, t, J = 7.4 Hz) |
| 118 | Example 112 | Production Example 95 | 549.57 | [M + H]+ | 8.83 (1 H, dd, J = 2.1, 0.8 Hz), 8.62 (1 H, dd, J = 4.9, 1.6 Hz), 8.28 (1 H, d, J = 5.3 Hz), 8.02 (1 H, s), 7.92 (1 H, dt, J = 7.9, 2.0 Hz), 7.52 (2 H, d, J = 8.6 Hz), 7.27-7.38 (3 H, m), 7.18 (1 H, s), 6.63 (1 H, d, J = 5.3 Hz), 4.30 (2 H, q, J = 7.3 Hz), 3.00-3.54 (6 H, m), 2.65-2.77 (1 H, m), 1.68-1.97 (6 H, m), 1.28-1.64 (9 H, m) |
| 119 | Example 112 | Production Example 90 | 497.44 | [M + H]+ | 8.82-8.85 (1 H, m), 8.62 (1 H, dd, J = 4.8, 1.5 Hz), 8.29 (1 H, d, J = 4.9 Hz), 8.02 (1 H, s), 7.87-7.95 (1 H, m), 7.54 (2 H, d, J = 8.6 Hz), 7.30-7.39 (3 H, m), 7.15 (1 H, s), 6.63 (1 H, d, J = 5.3 Hz), 4.30 (2 H, q, J = 7.4 Hz), 3.43-3.84 (4 H, m), 2.67-2.79 (1 H, m), 2.40-2.63 (4 H, m), 1.61 (3 H, t, J = 7.6 Hz), 1.06 (6 H, d, J = 6.6 Hz) |
| 120 | Example 112 | Production Example 90 | 537.33 | [M + H]+ | 8.84 (1 H, dd, J = 2.0, 1.6 Hz), 8.62 (1 H, dd, J = 4.9, 1.6 Hz), 8.29 (1 H, d, J = 5.3 Hz), 8.02 (1 H, s), 7.91 (1 H, dt, J = 7.9, 1.8 Hz), 7.53 (2 H, d, J = 8.6 Hz), 7.29-7.39 (3 H, m), 6.63 (1 H, d, J = 5.3 Hz), 4.29 (2 H, q, J = 7.3 Hz), 3.33-3.93 (4 H, m), 2.40-2.74 (4 H, m), 2.21-2.37 (1 H, m), 1.76-1.95 (4 H, m), 1.60 (3 H, t, J = 7.3 Hz), 1.03-1.39 (6 H, m) |
| 121 | Example 112 | Production Example 94 | 577.49 | [M + H]+ | 8.84 (1 H, dd, J = 2.1, 0.8 Hz), 8.63 (1 H, dd, J = 4.9, 1.6 Hz), 8.28 (1 H, d, J = 5.3 Hz), 7.89-7.95 (2 H, m), 7.50 (2 H, d, J = 7.8 Hz), 7.29-7.39 (5 H, m), 7.06-7.20 (3 H, m), 6.62 (1 H, d, J = 5.3 Hz), 5.38 (2 H, s), 3.34-3.90 (4 H, m), 2.67-2.80 (1 H, m), 2.40-2.64 (4 H, m), 1.06 (6 H, d, J = 6.3 Hz) |
| 122 | Example 112 | Production Example 91 | 497.30 | [M + H]+ | 8.82-8.85 (1 H, m), 8.63 (1 H, dd, J = 4.9, 1.6 Hz), 8.25 (1 H, d, J = 5.3 Hz), 8.10 (1 H, s), 7.91 (1 H, dt, J = 7.7, 2.1 Hz), 7.74-7.78 (1 H, m), 7.51-7.57 (1 H, m), 7.31-7.38 (1 H, m), 7.27 (1 H, d, J = 7.9 Hz), 7.16 (1 H, s), 7.00-7.06 (1 H, m), 6.59 (1 H, d, J = 5.3 Hz), 4.30 (2 H, q, J = 7.3 Hz), 3.39-3.91 (4 H, m), 2.36-2.82 (5 H, m), 1.61 (3 H, t, J = 7.3 Hz), 1.06 (6 H, d, J = 6.3 Hz) |
| 123 | Example 112 | Production Example 93 | 573.49 | [M + H]+ | 8.85 (1 H, dd, J = 2.1, 0.8 Hz), 8.63 (1 H, dd, J = 4.9, 1.6 Hz), 8.27 (1 H, d, J = 5.3 Hz), 7.92 (1 H, dt, J = 7.9, 2.0 Hz), 7.79 (1 H, s), 7.46-7.52 (2 H, m), 7.28-7.39 (5 H, m), 6.98-7.25 (4 H, m), 6.58 (1 H, d, J = 5.3 Hz), 4.45 (2 H, t, J = 7.4 Hz), 3.39-3.90 (4 H, m), 3.27 (2 H, t, J = 7.3 Hz), 2.39-2.79 (5 H, m), 1.06 (6 H, d, J = 6.6 Hz) |
| 124 | Example 112 | Production Example 92 | 561.27 | [M + H]+ | 8.82 (1 H, dd, J = 2.1, 0.8 Hz), 8.62 (1 H, dd, J = 4.8, 1.8 Hz), 8.32 (1 H, d, J = 5.3 Hz), 8.02 (1 H, s), 7.93 (1 H, dt, J = 7.9, 2.0 Hz), 7.62-7.71 (4 H, m), 7.30-7.40 (2 H, m), 6.70 (1 H, d, J = 5.3 Hz), 4.31 (2 H, q, J = 7.3 Hz), 2.60-2.92 (7 H, m), 2.11-2.23 (2 H, m), 1.40-1.65 (7 H, m), 1.01 (6 H, d, J = 6.6 Hz) |
| 125 | Example 112 | Example 171 | 468.40 | [M + H]+ | 8.83-8.88 (1 H, m), 8.61 (1 H, dd, J = 4.9, 1.6 Hz), 8.23 (1 H, d, J = 5.3 Hz), 8.00 (1 H, s), 7.90 (1 H, dt, J = 7.8, 1.9 Hz), 7.22-7.35 (3 H, m), 6.97-7.06 (2 H, m), 6.55 (1 H, d, J = 5.3 Hz), 4.60-4.73 (2 H, m), 4.28 (2 H, q, J = 7.3 Hz), 3.48-3.64 (1 H, m), 2.81-2.99 (4 H, m), 2.31-2.47 (4 H, m), 1.58 (3 H, t, J = 7.3 Hz). |
| 126 | Example 112 | Example 168 | 456.25 | [M + H]+ | 8.86 (1 H, dd, J = 2.1, 0.8 Hz), 8.62 (1 H, dd, J = 4.8, 1.8 Hz), 8.23 (1 H, d, J = 5.3 Hz), 8.00 (1 H, s), 7.89 (1 H, dt, J = 7.9, 2.0 Hz), 7.27-7.35 (2 H, m), 7.19-7.26 (1 H, m), 6.88-6.97 (2 H, m), 6.54 (1 H, d, J = 5.3 Hz), 4.28 (2 H, q, J = 7.5 Hz), 3.66 (2 H, s), 3.62 (2 H, t, J = 5.8 Hz), 3.40 (3 H, s), 2.84-2.92 (2 H, m), 2.73-2.82 (4 H, m), 1.57 (3 H, t, J = 7.3 Hz) |
| 127 | Example 112 | Production Example 101 | 413.38 | [M + H]+ | DMSO-d$_6$<br>13.45-13.62 (1 H, m), 9.14-9.20 (1 H, m), 8.69-8.73 (1 H, m), 8.50-8.65 (1 H, m), 8.28- |

TABLE 2-continued

| | | | | | |
|---|---|---|---|---|---|
| | | | | | 8.44 (2 H, m), 7.90-8.00 (1 H, m), 7.36-7.51 (1 H, m), 7.28 (2 H, d, J = 8.6 Hz), 6.74 (1 H, d, J = 4.9 Hz), 6.67 (2 H, d, J = 8.9 Hz), 2.98-3.05 (4 H, m), 2.42-2.48 (4 H, m), 2.22 (3 H, s) |
| 128 | Example 112 | Production Example 68 | 472.44 | [M + H]+ | DMSO-$d_6$ 9.31 (1 H, br s), 8.71 (1 H, s), 8.48-8.59 (1 H, m), 8.26-8.45 (2 H, m), 7.88-8.00 (1 H, m), 7.22-7.50 (2 H, m), 6.59-6.72 (1 H, m), 4.27-4.64 (5 H, m), 4.26 (2 H, q, J = 7.1 Hz), 3.40-3.61 (1 H, m), 2.69-2.83 (2 H, m), 1.69-2.02 (6 H, m), 1.40 (3 H, t, J = 7.1 Hz). |
| 129 | Example 112 | Example 168 | 412.38 | [M + H]+ | 8.82-8.89 (1 H, m), 8.61 (1 H, dd, J = 4.9, 1.6 Hz), 8.23 (1 H, d, J = 5.3 Hz), 7.99 (1 H, s), 7.89 (1 H, dt, J = 7.9, 2.0 Hz), 7.24-7.35 (3 H, m), 6.88-7.05 (2 H, m), 6.53 (1 H, d, J = 5.3 Hz), 4.28 (2 H, q, J = 7.3 Hz), 3.56 (2 H, s), 2.87 (2 H, t, J = 5.9 Hz), 2.70 (2 H, t, J = 5.9 Hz), 2.47 (3 H, s), 1.59 (3 H, t, J = 7.3 Hz). |
| 130 | Example 112 | Example 151 | 511.46 | [M + H]+ | 8.83-8.88 (1 H, m), 8.61 (1 H, dd, J = 4.9, 1.6 Hz), 8.21 (1 H, d, J = 4.9 Hz), 7.98 (1 H, s), 7.89 (1 H, dt, J = 7.9, 1.8 Hz), 7.27-7.41 (3 H, m), 7.08 (1 H, s), 6.82-6.89 (2 H, m), 6.52 (1 H, d, J = 5.3 Hz), 4.27 (2 H, q, J = 7.3 Hz), 4.00-4.11 (2 H, m), 3.34-3.48 (2 H, m), 3.12-3.22 (4 H, m), 2.69-2.79 (4 H, m), 2.41-2.57 (1 H, m), 1.77-1.88 (2 H, m), 1.54-1.69 (5 H, m) |
| 131 | Example 112 | Production Example 100 | 498.60 | [M + H]+ | 8.85-8.88 (1 H, m), 8.62 (1 H, dd, J = 4.9, 1.6 Hz), 8.26 (1 H, d, J = 5.3 Hz), 8.03 (1 H, s), 7.89 (1 H, dt, J = 7.7, 1.9 Hz), 7.27-7.34 (3 H, m), 7.07 (1 H, br s), 6.90 (1 H, d, J = 9.1 Hz), 6.59 (1 H, d, J = 4.9 Hz), 4.69-4.79 (4 H, m), 4.17 (2 H, s), 3.67-3.71 (1 H, m), 3.47 (2 H, s), 2.87 (2 H, t, J = 5.9 Hz), 2.59 (2 H, t, J = 5.9 Hz), 1.28 (6 H, s). |
| 132 | Example 112 | Production Example 82 | 526.54 | [M + H]+ | 8.84-8.88 (1 H, m), 8.60-8.67 (1 H, m), 8.23 (1 H, d, J = 5.3 Hz), 8.04 (1 H, s), 7.90 (1 H, dt, J = 7.9, 2.0 Hz), 7.30-7.51 (4 H, m), 7.07-7.25 (2H, m), 6.58 (1 H, d, J = 5.3 Hz), 4.63-4.73 (4 H, m), 4.18 (2 H, s), 3.44-3.57 (1 H, m), 2.79-2.95 (2 H, m), 2.43-2.54 (1 H, m), 1.75-1.99 (6H, m), 1.29 (6 H, s). |
| 133 | | Production Example 145 | 420 | [M + H]+ | 8.84-8.87 (2 H, m), 8.55-8.62 (2 H, m), 8.30 (1 H, d, J = 5.4 Hz), 8.02 (1 H, s), 7.84-7.93 (2 H, m), 7.61 (2 H, d, J = 8.1 Hz), 7.49 (2 H, d, J = 8.1 Hz), 7.31-7.38 (2 H, m), 7.21 (1 H, s), 6.64 (1 H, d, J = 5.4 Hz), 4.26-4.34 (2 H, m), 1.59-1.64 (3 H, m) |
| 134 | Example 133 | Production Example 145 | 420 | [M + H]+ | 8.86-8.87 (1 H, m), 8.60-8.64 (3 H, m), 8.31 (1 H, d, J = 5.4 Hz), 8.02 (1 H, s), 7.89-7.93 (1 H, m), 7.54-7.63 (4 H, m), 7.49-7.51 (2 H, m), 7.32-7.36 (1 H, m), 7.23 (1 H, s), 6.66 (1 H, d, J = 5.4 Hz), 4.26-4.34 (2 H, m), 1.59-1.64 (3 H, m) |
| 135 | | Production Example 58 | 228 | [M + 2H]2+ | 8.86-8.87 (1 H, m), 8.58-8.61 (1 H, m), 8.23 (1 H, d, J = 5.4 Hz), 8.07 (1 H, s), 7.88-7.92 (1 H, m), 7.28-7.39 (3 H, d, J = 8.9 Hz), 7.00 (1 H, s), 6.84 (2 H, d, J = 8.9 Hz), 6.57 (1 H, d, J = 5.1 Hz), 3.35 (8 H, s), 1.68 (9 H, s) |
| 136 | | Production Example 76 | 481.55 | [M + H]+ | 8.83-8.88 (1 H, m), 8.64 (1 H, dd, J = 4.8, 1.5 Hz), 8.26 (1 H, d, J = 5.3 Hz), 8.08 (1 H, s), 7.89 (1 H, dt, J = 8.0, 1.9 Hz), 7.28-7.37 (3 H, m), 6.79-6.93 (3 H, m), 6.53-6.58 (1 H, m), 4.81 (2 H, q, J = 8.2 Hz), 3.03-3.21 (8 H, m) |
| 137 | Example 136 | Production Example 77 | 455.48 | [M + H]+ | 8.84-8.90 (1 H, m), 8.63 (1 H, dd, J = 4.9, 1.6 Hz), 8.24 (1 H, d, J = 5.3 Hz), 8.16 (1 H, s), 7.92 (1 H, dt, J = 8.1, 1.9 Hz), 7.29-7.39 (3 H, m), 6.82-6.95 (3 H, m), 6.53 (1 H, d, J = 4.9 Hz), 5.49-5.61 (1 H, m), 5.08-5.20 (4 H, m), 3.08 (8 H, q, J = 6.0 Hz) |
| 138 | Example 136 | Production Example 86 | 517.26 | [M + H]+ | 8.84-8.89 (1 H, m), 8.62 (1 H, dd, J = 4.9, 1.6 Hz), 8.28 (1 H, d, J = 5.3 Hz), 7.89-7.97 (2 H, m), 7.46-7.51 (2 H, m), 7.33-7.45 (6 H, m), 7.28-7.32 (2 H, m), 7.10-7.20 (1 H, m), 6.63 (1 H, d, J = 5.3 Hz), 5.41 (2 H, s), 3.40-3.85 (4 H, m), 2.82-3.02 (4 H, m) |
| 139 | Example 136 | Production Example 75 | 507.43 | [M + H]+ | 8.86 (1 H, dd, J = 2.3, 0.7 Hz), 8.62 (1 H, dd, J = 4.6, 1.6 Hz), 8.21 (1 H, d, J = 5.3 Hz), 7.87-7.92 (2 H, m), 7.28-7.38 (5 H, m), 7.06-7.14 (2 H, m), 6.80-6.90 (3 H, m), 6.50 (1 H, d, J = 5.3 Hz), 5.36 (2 H, s), 3.02-3.12 (8 H, m) |

TABLE 2-continued

| | | | | | |
|---|---|---|---|---|---|
| 140 | Example 136 | Production Example 57 | 490.53 | [M + H]+ | 8.86-8.88 (1 H, m), 8.60-8.65 (2 H, m), 8.21-8.24 (1 H, m), 8.12-8.13 (1 H, m), 7.87-7.93 (1 H, m), 7.68-7.75 (1 H, m), 7.23-7.36 (5 H, m), 6.81-6.89 (3 H, m), 6.53-6.58 (1 H, m), 5.53 (2 H, s), 3.02-3.14 (8 H, m) |
| 141 | Example 136 | Production Example 80 | 490.59 | [M + H]+ | 8.85-8.87 (1 H, m), 8.61-8.68 (3 H, m), 8.22 (1 H, d, J = 5.3 Hz), 7.98 (1 H, s), 7.89 (1 H, dt, J = 7.9, 2.0 Hz), 7.67-7.73 (1 H, m), 7.29-7.39 (4 H, m), 6.82-6.93 (3 H, m), 6.51 (1 H, d, J = 5.3 Hz), 5.42 (2 H, s), 3.04-3.17 (8 H, m) |
| 142 | Example 136 | Production Example 78 | 503.55 | [M + H]+ | 8.87 (1 H, dd, J = 2.1, 0.8 Hz), 8.63 (1 H, dd, J = 4.9, 1.6 Hz), 8.20 (1 H, d, J = 5.3 Hz), 7.90 (1 H, dt, J = 7.9, 2.0 Hz), 7.78 (1 H, s), 7.28-7.37 (6 H, m), 7.16-7.22 (2 H, m), 6.82-6.94 (3 H, m), 6.47 (1 H, d, J = 5.3 Hz), 4.43 (2 H, t, J = 7.4 Hz), 3.27 (2 H, t, J = 7.4 Hz), 3.05-3.16 (8 H, m) |
| 143 | Example 136 | Production Example 55 | 453.52 | [M + H]+ | 8.84-8.87 (1 H, m), 8.61 (1 H, dd, J = 4.9, 1.6 Hz), 8.20 (1 H, d, J = 4.9 Hz), 7.98 (1 H, s), 7.89 (1 H, dt, J = 7.9, 2.0 Hz), 7.28-7.35 (3 H, m), 6.82 (1 H, s), 6.73 (2 H, d, J = 8.9 Hz), 6.50 (1 H, d, J = 4.9 Hz), 4.27 (2 H, q, J = 7.3 Hz), 3.60-3.68 (2 H, m), 3.36-3.44 (2 H, m), 2.84-2.91 (2 H, m), 1.77-1.92 (4 H, m), 1.58 (3 H, t, J = 7.3 Hz) |
| 144 | Example 136 | Production Example 56 | 454.53 | [M + H]+ | 8.84 (1 H, dd, J = 2.1, 0.8 Hz), 8.60 (1 H, dd, J = 4.8, 1.8 Hz), 8.22 (1 H, d, J = 2.9 Hz), 8.18 (1 H, d, J = 5.3 Hz), 7.99 (1 H, s), 7.88 (1 H, dt, J = 7.9, 2.0 Hz), 7.63 (1 H, dd, J = 9.1, 2.8 Hz), 7.28-7.34 (1 H, m), 6.76 (1 H, s), 6.52 (1 H, d, J = 5.1 Hz), 6.47 (1 H, d, J = 9.2 Hz), 4.27 (2 H, q, J = 7.4 Hz), 332 (2 H, dd, J = 11.7, 2.5 Hz), 3.62-3.69 (2 H, m), 2.99 (2 H, dd, J = 11.7, 2.1 Hz), 1.77-1.86 (4 H, m), 1.59 (3 H, t, J = 7.3 Hz) |
| 145 | Example 136 | Production Example 51 | 414.36 | [M + H]+ | 8.82-8.85 (1 H, m), 8.62 (1 H, dd, J = 4.6, 1.6 Hz), 8.22 (1 H, d, J = 5.1 Hz), 7.98 (1 H, s), 7.86-7.93 (1 H, m), 7.28-7.39 (3 H, m), 6.96 (1 H, s), 6.63-6.71 (2 H, m), 6.52-6.56 (1 H, m), 4.92-5.02 (1 H, m), 4.28 (2 H, q, J = 7.0 Hz), 3.76-3.98 (4 H, m), 1.59 (3 H, t, J = 7.3 Hz) |
| 146 | Example 136 | Production Example 50 | 468.48 | [M + H]+ | 8.83-8.85 (1 H, m), 8.62 (1 H, dd, J = 4.8, 1.8 Hz), 8.22 (1 H, d, J = 5.3 Hz), 7.98 (1 H, s), 7.90 (1 H, dt, J = 7.9, 2.0 Hz), 7.30-7.38 (3 H, m), 6.79-6.89 (3 H, m), 6.54 (1 H, d, J = 4.9 Hz), 4.39-4.51 (1H, m), 4.28 (2 H, q, J = 7.3 Hz), 3.62-3.69 (2 H, m), 2.10-2.18 (3 H, m), 1.82-1.93 (2 H, m), 1.56-1.74 (6 H, m) |
| 147 | Example 136 | Production Example 49 | 441.54 | [M + H]+ | 8.83-8.87 (1 H, m), 8.60 (1 H, dd, J = 4.8, 1.8 Hz), 8.21 (1 H, d, J = 5.3 Hz), 7.98 (1 H, s), 7.89 (1 H, dt, J = 7.9, 2.0 Hz), 7.28-7.45 (3 H, m), 6.79-7.03 (3 H, m), 6.51 (1 H, d, J = 4.9 Hz), 4.27 (2 H, q, J = 7.4 Hz), 3.50-3.62 (2 H, m), 2.61-2.94 (3 H, m), 1.87-1.98 (2 H, m), 1.59 (3 H, t, J = 7.4 Hz), 1.47-1.55 (2 H, m) |
| 148 | Example 136 | Production Example 73 | 445.49 | [M + H]+ | 8.66 (1 H, t, J = 1.5 Hz), 8.44 (1 H, d, J = 3.0 Hz), 8.26 (1 H, d, J = 5.3 Hz), 7.95 (1 H, s), 7.67 (1 H, ddd, J = 9.4, 2.8, 1.6 Hz), 7.28-7.35 (2 H, m), 6.99 (1 H, s), 6.81-6.88 (2 H, m), 6.57 (1 H, d, J = 4.9 Hz), 4.27 (2 H, q, J = 7.4 Hz), 3.03-3.13 (8 H, m), 1.59 (3 H, t, J = 7.4 Hz) |
| 149 | Example 136 | Production Example 129 | 463 | [M + H]+ | 8.84-8.85 (1 H, m), 8.63 (1 H, dd, J = 4.9, 1.6 Hz), 8.24 (1 H, d, J = 5.1 Hz), 8.04 (1 H, s), 7.86-7.90 (1 H, m), 7.29-7.35 (3 H, m), 6.84-6.88 (3 H, m), 6.54 (1 H, d, J = 5.1 Hz), 5.99-6.43 (1 H, m), 4.50-4.61 (2 H, m), 3.04-3.11 (8 H, m) |
| 150 | Example 136 | Production Example 130 | 464 | [M + H]+ | 8.82-8.83 (1 H, m), 8.63 (1 H, dd, J = 5.1, 1.6 Hz), 8.22-8.24 (2 H, m), 8.04 (1 H, s), 7.85-7.89 (1 H, m), 7.63-7.67 (1 H, m), 7.29-7.33 (1 H, m), 6.77 (1 H, s), 6.54-6.59 (2 H, m), 5.99-6.43 (1 H, m), 4.50-4.62 (2 H, m), 3.44-3.48 (4 H, m), 3.00-3.03 (4 H, m) |
| 151 | Example 136 | Production Example 121 | 427 | [M + H]+ | 8.55-8.86 (1 H, m), 8.61-8.62 (1 H, m), 8.21 (1 H, d, J = 5.1 Hz), 7.98 (1 H, s), 7.87-7.91 (1 H, m), 7.35 (2 H, d, J = 8.6 Hz), 7.30-7.31 (1 H, m), 6.93 (1 H, s), 6.86 (2 H, d, J = 8.9 Hz), 6.51 (1 H, d, J = 5.4 Hz), 4.23-4.31 (2 H, m), 3.05-3.12 (8 H, m), 1.58-1.63 (3 H, m) |
| 152 | Example 136 | Production Example 123 | 445 | [M + H]+ | 8.82-8.83 (1 H, m), 8.61 (1 H, dd, J = 4.9, 1.6 Hz), 8.24 (1 H, d, J = 4.9 Hz), 8.01 (1 H, s), 7.88-7.92 (1 H, m), 7.47-7.53 (1 H, m), 7.31-7.35 (1 H, m), 7.01-7.05 (1 H, m), 6.96 (1 H, s), |

TABLE 2-continued

| | | | | | |
|---|---|---|---|---|---|
| | | | | | 6.83-6.90 (1 H, m), 6.57 (1 H, d, J = 5.1 Hz), 4.25-4.33 (2 H, m), 3.01-3.08 (8 H, m), 1.57-1.63 (3 H, m) |
| 153 | Example 136 | Production Example 132 | 463 | [M + H]+ | 8.80-8.81 (1 H, m), 8.60-8.63 (1 H, m), 8.25 (1 H, d, J = 5.4 Hz), 8.02 (1 H, s), 7.89-7.93 (1 H, m), 7.32-7.37 (1 H, m), 7.08-7.16 (2 H, m), 6.98 (1 H, s), 6.61 (1 H, d, J = 5.1 Hz), 4.25-4.36 (2 H, m), 3.08-3.13 (4 H, m), 2.97-3.01 (4 H, m), 1.58-1.64 (3 H, m) |
| 154 | Example 136 | Production Example 141 | 441 | [M + H]+ | 8.84-8.85 (1 H, m), 8.60-8.62 (1 H, m), 8.22 (1 H, d, J = 5.4 Hz), 8.01 (1 H, s), 7.88-7.92 (1 H, m), 7.29-7.36 (3 H, m), 6.82 (1 H, d, J = 8.4 Hz), 6.88 (1 H, s), 6.52 (1 H, d, J = 4.9 Hz), 4.24-4.32 (2 H, m), 3.01-3.04 (4 H, m), 2.83-2.87 (4 H, m), 2.29 (3 H, s), 1.57-1.63 (3 H, m) |
| 155 | Example 136 | Production Example 133 | 428 | [M + H]+ | 8.83-8.84 (1 H, m), 8.60-8.61 (1 H, m), 8.26 (1 H, d, J = 2.7 Hz), 8.20 (1 H, d, J = 5.1 Hz), 7.98 (1 H, s), 7.85-7.90 (1 H, m), 7.71-7.74 (1 H, m), 7.28-7.33 (1 H, m), 6.87 (1 H, s), 6.55-6.60 (2 H, m), 4.27 (2 H, q, J = 7.3 Hz), 3.65-3.69 (4 H, m), 3.17-3.21 (4 H, m), 1.57-1.62 (3 H, m) |
| 156 | Example 136 | Production Example 62 | 514.49 | [M + H]+ | 8.84-8.87 (1 H, m), 8.63 (1 H, dd, J = 4.9, 1.6 Hz), 8.23 (1 H, d, J = 5.3 Hz), 7.99 (1 H, s), 7.89 (1 H, dt, J = 7.9, 2.0 Hz), 7.49-7.68 (4 H, m), 7.29-7.37 (3 H, m), 6.82-6.91 (3 H, m), 6.52 (1 H, d, J = 5.3 Hz), 5.42 (2 H, s), 3.01-3.12 (8 H, m) |
| 157 | Example 136 | Production Example 64 | 514.57 | [M + H]+ | 8.82-8.88 (1 H, m), 8.61 (1 H, dd, J = 4.9, 1.6 Hz), 8.23 (1 H, d, J = 4.9 Hz), 8.14 (1 H, s), 7.88 (1 H, dt, J = 7.9, 1.8 Hz), 7.73 (1 H, d, J = 7.6 Hz), 7.57-7.66 (1 H, m), 7.47 (2 H, dd, J = 6.9, 5.3 Hz), 7.27-7.36 (3 H, m), 6.81-6.95 (3 H, m), 6.54 (1 H, d, J = 5.3 Hz), 5.61 (2 H, s), 2.99-3.14 (8 H, m) |
| 158 | Example 136 | Production Example 142 | 427 | [M + H]+ | 8.85-8.86 (1 H, m), 8.60-8.63 (1 H, m), 8.23 (1 H, d, J = 5.4 Hz), 8.03 (1 H, s), 7.88-7.92 (1 H, m), 7.27-7.35 (3 H, m), 7.16-7.20 (1H, m), 7.01-7.03 (1H, m), 6.54-6.63 (2H, m), 4.24-4.31 (2H, m), 3.14-3.18 (4H, m), 3.01-3.06 (4H, m), 1.57-1.62 (3H, m) |
| 159 | Example 136 | Production Example 143 | 455 | [M + H]+ | 8.84-8.85 (1 H, m), 8.60-8.62 (1 H, m), 8.24 (1 H, d, J = 5.1 Hz), 8.00 (1 H, s), 7.87-7.92 (1 H, m), 7.40 (2 H, d, J = 8.4 Hz), 7.30-7.35 (1 H, m), 7.11 (2 H, d, J = 8.6 Hz), 6.98 (1 H, s), 6.56 (1 H, d, J = 4.9 Hz), 4.24-4.32 (2 H, m), 2.93-2.97 (4 H, m), 2.75-2.81 (2 H, m), 2.54-2.61 (6 H, m), 1.57-1.63 (3 H, m) |
| 160 | Example 136 | Production Example 136 | 441 | [M + H]+ | 8.84-8.86 (1 H, m), 8.60-8.62 (1 H, m), 8.21 (1 H, d, J = 5.1 Hz), 7.98 (1 H, s), 7.87-7.91 (1 H, m), 7.28-7.36 (3 H, m), 7.01 (1 H, s), 6.86-6.89 (2 H, m), 6.51 (1 H, d, J = 5.4 Hz), 4.23-4.31 (2 H, m), 3.44-3.50 (1 H, m), 3.31-3.38 (1 H, m), 2.98-3.06 (1 H, m), 2.69-2.79 (1 H, m), 2.50-2.57 (1 H, m), 1.67-1.97 (3 H, m), 1.56-1.62 (3 H, m), 1.48 (2 H, s), 1.21-1.31 (1 H, m) |
| 161 | Example 136 | Production Example 137 | 441 | [M + H]+ | 8.84-8.85 (1 H, m), 8.60-8.63 (1 H, m), 8.21 (1 H, d, J = 5.1 Hz), 7.99 (1 H, s), 7.87-7.91 (1 H, m), 7.29-7.37 (3 H, m), 6.85-6.91 (3 H, m), 6.51 (1 H, d, J = 4.9 Hz), 4.24-4.32 (2 H, m), 3.47-3.51 (1 H, m), 3.31-3.39 (1 H, m), 2.97-3.06 (1 H, m), 2.69-2.79 (1 H, m), 2.50-2.57 (1 H, m), 1.68-1.97 (3 H, m), 1.60 (3 H, t, J = 7.3 Hz), 1.40-1.51 (2 H, m), 1.15-1.30 (1 H, m) |
| 162 | Example 136 | Production Example 147 | 426 | [M + H]+ | 8.77-8.88 (1 H, m), 8.54 (1 H, dd, J = 4.6, 1.6 Hz), 8.17 (1 H, d, J = 4.9 Hz), 7.93 (1 H, s), 7.80-7.85 (1 H, m), 7.34 (2 H, d, J = 8.4 Hz), 7.23-7.27 (1 H, m), 7.05 (2 H, d, J = 8.6 Hz), 6.97 (1 H, s), 6.49 (1 H, d, J = 5.4 Hz), 4.21 (2 H, q, J = 7.3 Hz), 3.14-3.18 (2 H, m), 2.66-2.74 (2 H, m), 2.49-2.56 (1 H, m), 1.58-1.81 (4 H, m), 1.53 (3 H, t, J = 7.3 Hz) |
| 163 | Example 136 | Production Example 128 | 452 | [M + H]+ | 8.84-8.85 (1 H, m), 8.60-8.62 (1 H, m), 8.23 (1 H, d, J = 5.1 Hz), 8.00 (1 H, s), 7.88-7.91 (1 H, m), 7.37-7.42 (2 H, m), 7.30-7.35 (1 H, m), 7.06-7.18 (3 H, m), 6.55 (1 H, m), 4.24-4.32 (2 H, m), 3.61-3.63 (2 H, m), 2.90-2.96 (1 H, m), 2.29-2.34 (1 H, m), 1.72-1.86 (5 H, m), 1.52-1.62 (6 H, m) |
| 164 | Example 136 | Production Example 120 | 460 | [M + H]+ | 8.83-8.84 (1 H, m), 8.60-8.62 (1 H, m), 8.23 (1 H, d, J = 5.1 Hz), 7.98 (1 H, s), 7.87-7.92 (1 H, m), 7.37 (2 H, d, J = 8.9 Hz), 7.29-7.34 (1 H, |

TABLE 2-continued

| | | | | | |
|---|---|---|---|---|---|
| | | | | | m), 6.87-6.94 (3 H, m), 6.55 (1 H, d, J = 5.1 Hz), 4.87-4.88 (0.5 H, m), 4.69-4.70 (0.5 H, m), 4.20-4.35 (3 H, m), 3.31-3.41 (1 H, m), 3.12-3.19 (1 H, m), 2.64-2.91 (2 H, m), 1.90-1.97 (2 H, m), 1.57-1.62 (3 H, m) |
| 165 | Example 136 | Production Example 122 | 442 | [M + H]+ | 8.85 (1 H, dd, J = 2.2, 0.8 Hz), 8.63 (1 H, dd, J = 5.1, 1.6 Hz), 8.25 (1 H, d, J = 5.4 Hz), 8.04 (1 H, s), 7.89-7.93 (1 H, m), 7.31-7.36 (2 H, m), 7.14-7.20 (1 H, m), 7.02-7.07 (2 H, m), 6.55-6.60 (2 H, m), 4.34-4.42 (1 H, m), 4.28 (2 H, q, J = 7.3 Hz), 3.11-3.20 (2 H, m), 2.70-2.79 (2 H, m), 1.99-2.09 (2 H, m), 1.68-1.76 (3 H, m), 1.61 (3 H, t, J = 7.3 Hz) |
| 166 | Example 136 | Production Example 131 | 445 | [M + H]+ | 8.86-8.87 (1 H, m), 8.54-8.56 (1 H, m), 8.21 (1 H, d, J = 2.7 Hz), 8.02 (1 H, d, J = 2.7 Hz), 7.85-7.89 (1 H, m), 7.20-7.25 (1 H, m), 7.08-7.12 (2 H, m), 6.69-6.76 (3 H, m), 4.26-4.34 (2 H, m), 3.02-3.08 (8 H, m), 1.57-1.63 (3 H, m) |
| 167 | Example 136 | Production Example 134 | 492 | [M + H]+ | 8.85-8.86 (1 H, m), 8.60-8.62 (1 H, m), 8.26 (1 H, d, J = 5.4 Hz), 8.01 (1 H, s), 7.88-7.92 (1 H, m), 7.75 (1 H, s), 7.66 (1 H, s), 7.48 (2 H, d, J = 8.4 Hz), 7.37 (2 H, d, J = 8.6 Hz), 7.29-7.34 (1 H, m), 7.04 (1 H, s), 6.58 (1 H, d, J = 5.1 Hz), 4.25-4.33 (3 H, m), 3.30-3.61 (2 H, m), 2.81-2.89 (2 H, m), 2.33-2.37 (2 H, m), 1.99-2.05 (2 H, m), 1.58-1.64 (3 H, m) |
| 168 | Example 136 | Production Example 125 | 398 | [M + H]+ | 8.85-8.86 (1 H, m), 8.60 (1 H, dd, J = 5.1, 1.6 Hz), 8.23 (1 H, d, J = 5.1 Hz), 8.00 (1 H, s), 7.88-7.92 (1 H, m), 7.24-7.34 (3 H, m), 7.04 (1 H, s), 6.91 (1 H, d, J = 8.9 Hz), 6.55 (1 H, d, J = 4.9 Hz), 4.24-4.32 (2 H, m), 4.00 (2 H, s), 3.13-3.18 (2 H, m), 2.76-2.80 (2 H, m), 1.60 (3 H, t, J = 7.3 Hz) |
| 169 | Example 136 | Production Example 126 | 398 | [M + H]+ | 8.72-8.73 (1 H, m), 8.45 (1 H, dd, J = 5.1, 1.6 Hz), 8.26-8.28 (2 H, m), 7.99-8.04 (1 H, m), 7.35-7.41 (1 H, m), 7.13-7.16 (2 H, m), 6.83-6.86 (1 H, m), 6.78 (1 H, d, J = 5.4 Hz), 4.30 (2 H, q, J = 7.3 Hz), 3.82 (2 H, s), 3.06-3.11 (2 H, m), 2.75-2.79 (2 H, m), 1.53-1.59 (3 H, m) |
| 170 | Example 136 | Production Example 124 | 398 | [M + H]+ | 8.87-8.88 (1 H, m), 8.60-8.62 (1 H, m), 8.22 (1 H, d, J = 5.1 Hz), 7.98 (1 H, s), 7.87-7.91 (1 H, m), 7.28-7.33 (1 H, m), 6.82-6.87 (2 H, m), 6.76 (1 H, d, J = 1.9 Hz), 6.59-6.62 (1 H, m), 6.52 (1 H, d, J = 5.1 Hz), 4.23-4.31 (2 H, m), 3.26-3.30 (2 H, m), 2.68-2.73 (2 H, m), 1.90-1.96 (2 H, m), 1.56-1.62 (3 H, m) |
| 171 | Example 136 | Production Example 127 | 412 | [M + H]+ | 8.86-8.87 (1 H, m), 8.60-8.62 (1 H, m), 8.23-8.27 (1 H, m), 7.99 (1 H, d, J = 4.9 Hz), 7.88-7.93 (1 H, m), 7.28-7.33 (3 H, m), 7.00-7.05 (2 H, m), 6.56-6.61 (1 H, m), 4.28 (2 H, q, J = 7.3 Hz), 3.13-3.23 (4 H, m), 2.88-2.92 (4 H, m), 1.60 (3 H, t, J = 7.3 Hz) |
| 172 | | Production Example 105 | 456.40 | [M + H]+ | CD$_3$OD 8.71-8.76 (1 H, m), 8.43-8.50 (1 H, m), 8.27-8.32 (2 H, m), 8.00-8.05 (1 H, m), 7.14-7.46 (3 H, m), 6.76-6.89 (2 H, m), 4.31 (2 H, q, J = 7.5 Hz), 4.09 (2 H, s), 3.56 (2 H, s), 3.22-3.37 (2 H, m), 2.87-2.99 (2 H, m), 1.56 (3 H, t, J = 7.3 Hz). |
| 173 | Example 172 | Production Example 106 | 485.48 | [M + H]+ | CD$_3$OD 8.69-8.71 (1 H, m), 8.48 (1 H, dd, J = 5.1, 1.5 Hz), 8.28 (1 H, s), 8.23 (1 H, d, J = 5.3 Hz), 7.98-8.05 (1 H, m), 7.36-7.45 (1 H, m), 7.24 (2 H, d, J = 8.9 Hz), 6.72-6.81 (3 H, m), 4.31 (2 H, q, J = 7.3 Hz), 3.12-3.19 (4 H, m), 3.05 (2 H, s), 2.68-2.77 (4 H, m), 1.56 (3 H, t, J = 7.3 Hz). |
| 174 | | Production Example 149 | 485 | [M + H]+ | 8.85-8.86 (1 H, m), 8.60-8.62 (1 H, m), 8.23 (1 H, d, J = 5.4 Hz), 7.97 (1 H, s), 7.86-7.91 (1 H, m), 7.37 (2 H, d, J = 8.9 Hz), 7.28-7.33 (1 H, m), 6.89 (1 H, s), 6.84-6.87 (2 H, d, J = 8.6 Hz), 6.56 (1 H, d, J = 5.1 Hz), 4.21-4.32 (4 H, m), 3.82-3.86 (1 H, m), 3.61-3.64 (1 H, m), 3.42-3.46 (2 H, m), 3.11-3.15 (4 H, m), 1.57-1.62 (3 H, m) |
| 175 | Example 174 | Production Example 148 | 456 | [M + H]+ | 8.85-8.87 (1 H, m), 8.58-8.62 (1 H, m), 8.26 (1 d, J = 5.1 Hz), 7.98-7.99 (1 H, s), 7.91-7.92 (1 H, m), 7.29-7.37 (3 H, m), 6.99-7.07 (2 H, m), 6.60 (1 H, d, J = 5.1 Hz), 4.73 (1 H, s), 4.39 (1 H, s), 4.24-4.32 (4 H, m), 3.85-3.90 (1 H, m), 3.69-3.72 (1 H, m), 3.46-3.51 (1 H, m), 2.85-2.87 (2 H, m), 1.58-1.63 (3 H, m) |

TABLE 2-continued

| | | | | | |
|---|---|---|---|---|---|
| 176 | | Production Example 59 | 455.49 | [M + H]+ | 8.85 (1 H, dd, J = 2.3, 1.0 Hz), 8.61 (1 H, dd, J = 4.9, 1.6 Hz), 8.21 (1 H, d, J = 4.9 Hz), 7.98 (1 H, s), 7.89 (1 H, dt, J = 8.1, 1.9 Hz), 7.28-7.39 (3 H, m), 7.02 (1 H, s), 6.85-6.94 (2 H, m), 6.51 (1 H, d, J = 5.3 Hz), 4.27 (2 H, q, J = 7.4 Hz), 3.16 (4 H, t, J = 5.6 Hz), 1.54-1.79 (7 H, m), 1.18 (3 H, s) |
| 177 | Example 176 | Production Example 61 | 469.53 | [M + H]+ | 8.84-8.87 (1 H, m), 8.61 (1 H, dd, J = 4.6, 1.6 Hz), 8.21 (1 H, d, J = 5.3 Hz), 7.98 (1 H, s), 7.89 (1 H, dt, J = 7.9, 2.0 Hz), 7.28-7.37 (3 H, m), 6.86-6.96 (3 H, m), 6.51 (1 H, d, J = 5.3 Hz), 4.27 (2 H, q, J = 7.4 Hz), 3.22-3.31 (2 H, m), 3.03-3.14 (2 H, m), 1.67-1.80 (2 H, m), 1.42-1.63 (7 H, m), 0.93 (3 H, t, J = 7.4 Hz) |
| 178 | Example 176 | Production Example 63 | 483.59 | [M + H]+ | |
| 179 | | Production Example 107 | 442.47 | [M + H]+ | 8.84-8.89 (1 H, m), 8.58 (1 H, dd, J = 4.9, 1.6 Hz), 8.25 (1 H, d, J = 4.9 Hz), 7.98 (1 H, s), 7.87 (1 H, dt, J = 7.9, 2.0 Hz), 6.94-7.26 (5 H, m), 6.58 (1 H, d, J = 5.3 Hz), 4.28 (2 H, q, J = 7.4 Hz), 3.73 (2 H, t, J = 5.1 Hz), 3.59 (2 H, s), 2.76-2.90 (4 H, m), 2.72 (2 H, t, J = 5.3 Hz), 1.59 (3 H, t, J = 7.4 Hz) |
| 180 | | Production Example 146 | 508 | [M + H]+ | 8.84-8.85 (1 H, m), 8.59-8.62 (1 H, m), 8.27 (1 H, d, J = 5.1 Hz), 8.17 (1 H, s), 8.00 (1 H, s), 7.89-7.92 (1 H, m), 7.56-7.59 (2 H, m), 7.45-7.48 (2 H, m), 7.27-7.35 (2 H, m), 6.62 (1 H, d, J = 5.1 Hz), 4.25-4.33 (2 H, m), 3.54-3.58 (4 H, m), 2.53-2.58 (4 H, m), 2.36 (3 H, s), 1.58-1.63 (3 H, m) |

When the following synthesis literature was described in the text and table, the compounds were synthesized according to the description of the documents.

[Synthesis literature 1]: Huang et. al., WO 2011025927,
[Synthesis literature 2]: Fernandez et. al., WO 2013112323,
[Synthesis literature 3]: Muehlhausen et. al., J. Labelled Compd. Rad., 52(1), 13-22; 2009,
[Synthesis literature 4]: Wishart et. al., US 20110152243,
[Synthesis literature 5]: Xu et. al., WO 2015006754,
[Synthesis literature 6]: Venkateshappa et. al., WO 2015025197,
[Synthesis literature 7]: Chen et. al., WO 2014048165,
[Synthesis literature 8]: Dobler et. al., WO 2007038459,
[Synthesis literature 9]: Capraro et. al., WO 2005054238,
[Synthesis literature 10]: Banik et. al., J. Am. Chem. Soc., 138(15), 5000-5003; 2016,
[Synthesis literature 11]: Cecere et. al., WO 2016030310,
[Synthesis literature 12]: Harrison et. al., WO 2015092431,
[Synthesis literature 13]: Skerlj et. al., WO 2016073895,
[Synthesis literature 14]: Mou et. al., Bioorg. Med. Chem. Lett., 25(15), 3057-3061; 2015,
[Synthesis literature 15]: Bolin et. al., WO 2010017040,
[Synthesis literature 16]: Foitzik et. al., WO 2014026242,
[Synthesis literature 17]: Hansen et. al., WO 2013170115,
[Synthesis literature 18]: Gao et. al., WO 2008144483,
[Synthesis literature 19]: Villa et. al., Eur. J. Med. Chem., 36(6), 495-506; 2001,
[Synthesis literature 20]: Tang et. al., Tetrahedron, 69(5), 1427-1433; 2013,
[Synthesis literature 21]: Wang et. al., J. Med. Chem., 59(8), 3964-3979; 2016,
[Synthesis literature 22]: Phillips et. al., Eur. J. Med. Chem., 106, 120-131; 2015,
[Synthesis literature 23]: Urbanek et. al., Bioorg. Med. Chem. Lett., 23(2), 543-547; 2013,
[Synthesis literature 24]: Heo et. al., WO 2016006974,
[Synthesis literature 25]: Crawford et. al., WO 2013067260,
[Synthesis literature 26]: Devlin et. al., WO 2014027199,
[Synthesis literature 27]: Chaff et. al., WO 2009079597,
[Synthesis literature 28]: Player et. al., WO 2007033232,
[Synthesis literature 29]: Kanojia et. al., Bioorg. Med. Chem. Lett., 10(24), 2819-2823; 2000,
[Synthesis literature 30]: Chong et. al., WO 9921845,
[Synthesis literature 31]: Kamenecka et. al., J. Med. Chem., 53(1), 419-431; 2010,
[Synthesis literature 32]: Xie et. al., Org. Lett., 16(6), 1768-1771; 2014,
[Synthesis literature 33]: McCall et. al., J. Med. Chem., 29(1), 133-137; 1986,
[Synthesis literature 34]: Kley et. al., WO 2004026829,
[Synthesis literature 35]: Davenport et. al., WO 2009121812,
[Synthesis literature 36]: Breslin et. al., WO 2010071885,
[Synthesis literature 37]: Du et. al., WO 2016049211,
[Synthesis literature 38]: Kemp et. al., WO 2010034982,
[Synthesis literature 39]: Brain et. al., WO 2007140222,
[Synthesis literature 40]: Lo-Alfredsson et. al., WO 2010132015,
[Synthesis literature 41]: Jia et. al., WO 2015084998,
[Synthesis literature 42]: Campbell et. al., WO 2013043232,
[Synthesis literature 43]: Mollard et. al., WO 2014151871,
[Synthesis literature 44]: Hopkins et. al., WO 2015089337,
[Synthesis literature 45]: Peters et. al., WO 2010063784,
[Synthesis literature 46]: Thomson et. al., WO 2003123145,
[Synthesis literature 47]: Wan et. al., WO 2013170774,
[Synthesis literature 48]: Xi et. al., WO 2013138210,
[Synthesis literature 49]: Hikita et. al., JP 2007070323,
[Synthesis literature 50]: Chen et. al., WO 2012129344.

Test Example 1

BMP Signal Inhibitory Effect

A BMP signal inhibitory activity of a compound of the present invention was evaluated according to the following method.

MDA-231-D-BREFluc/Rluc cells prepared according to the method described in Y. Katsuno et al., Oncogene, 27, 6322 (2008) were incubated at 37° C. for 2 hours together with test compounds, and BMP-6 (commercially available from R&D System, 507-BM-020) was then added thereto, and the mixture was additionally incubated at 37° C. for 30 minutes. A Lysis Buffer and Acceptor mix of AlphaScreen SureFire SMAD1 (p-Ser463/465) assay kit (commercially available from Perkin Elmer, TGRSM1S10K) were sequentially added thereto, the mixture was incubated at room temperature for 2 hours, and AlphaScreen Protein A kit (commercially available from Perkin Elmer, 6760617) was then added thereto, and standard AlphaScreen settings of Alpha Technology—compatible plate reader (commercially available from Perkin Elmer, EnSpire) was used for measurement. An inhibitory effect was determined using test compounds with respective concentrations, and a concentration ($IC_{50}$) indicating 50% of the maximal inhibitory concentration was calculated.

The results are shown in the following table.

TABLE 3

| Example | $IC_{50}$ (nM) |
|---|---|
| 1 | 6.9 |
| 2 | 40.7 |
| 3 | 26.7 |
| 4 | 16.3 |
| 5 | 16.9 |
| 6 | 29.2 |
| 7 | 144.5 |
| 8 | 6.8 |
| 9 | 23.5 |
| 10 | 5.8 |
| 11 | 29.4 |
| 12 | 6.6 |
| 13 | 26.8 |
| 14 | 36.4 |
| 15 | 30.1 |
| 16 | 12.8 |
| 17 | 22.6 |
| 18 | 30.8 |
| 19 | 23.3 |
| 20 | 11.8 |
| 21 | 39.0 |
| 22 | 19.0 |
| 23 | 33.8 |
| 24 | 5.3 |
| 25 | 48.5 |
| 26 | 18.5 |
| 27 | 58.5 |
| 28 | 24.6 |
| 29 | 29.4 |
| 30 | 32.9 |
| 31 | 19.7 |
| 32 | 21.3 |
| 33 | 7.8 |
| 34 | 17.3 |
| 35 | 22.5 |
| 36 | 15.9 |
| 37 | 31.3 |
| 38 | 16.4 |
| 39 | 11.2 |
| 40 | 5.0 |
| 41 | 11.9 |
| 42 | 36.9 |
| 43 | 5.2 |
| 44 | 14.5 |
| 45 | 12.1 |
| 46 | 18.8 |
| 47 | 10.2 |
| 48 | 21.2 |
| 49 | 28.1 |
| 50 | 6.3 |
| 51 | 18.3 |
| 52 | 13.3 |
| 53 | 22.0 |
| 54 | 8.2 |
| 55 | 21.6 |

TABLE 3-continued

| Example | $IC_{50}$ (nM) |
|---|---|
| 56 | 17.6 |
| 57 | 13.0 |
| 58 | 4.4 |
| 59 | 25.2 |
| 60 | 6.4 |
| 61 | 7.0 |
| 62 | 10.0 |
| 63 | 3.9 |
| 64 | 4.0 |
| 65 | 3.3 |
| 66 | 6.4 |
| 67 | 5.3 |
| 68 | 6.8 |
| 69 | 13.0 |
| 70 | 33.6 |
| 71 | 22.8 |
| 72 | 13.4 |
| 73 | 7.2 |
| 74 | 39.0 |
| 75 | 14.8 |
| 76 | 46.1 |
| 77 | 51.3 |
| 78 | 12.7 |
| 79 | 35.7 |
| 80 | 26.7 |
| 81 | 21.0 |
| 82 | 18.4 |
| 83 | 14.3 |
| 84 | 19.3 |
| 85 | 7.3 |
| 86 | 12.9 |
| 87 | 29.7 |
| 88 | 5.5 |
| 89 | 5.7 |
| 90 | 21.6 |
| 91 | 21.3 |
| 92 | 11.9 |
| 93 | 3.8 |
| 94 | 24.3 |
| 95 | 14.8 |
| 96 | 20.9 |
| 97 | 15.2 |
| 98 | 23.4 |
| 99 | 20.0 |
| 100 | 18.6 |
| 101 | 70.8 |
| 102 | 50.4 |
| 103 | 10.4 |
| 104 | 16.4 |
| 105 | 33.7 |
| 106 | 3.5 |
| 107 | 24.4 |
| 108 | 13.3 |
| 109 | 5.7 |
| 110 | 32.8 |
| 111 | 27.3 |
| 112 | 11.7 |
| 113 | 8.0 |
| 114 | 0.9 |
| 115 | 1.1 |
| 116 | 15.1 |
| 117 | 12.0 |
| 118 | 8.6 |
| 119 | 5.0 |
| 120 | 6.1 |
| 121 | 19.6 |
| 122 | 23.6 |
| 123 | 12.6 |
| 124 | 16.0 |
| 125 | 10.0 |
| 126 | 4.0 |
| 127 | 22.4 |
| 128 | 32.0 |
| 129 | 1.8 |
| 130 | 12.4 |
| 131 | 16.7 |
| 132 | 24.9 |
| 133 | 18.7 |

TABLE 3-continued

| Example | IC$_{50}$ (nM) |
|---------|----------------|
| 134 | 21.8 |
| 135 | 11.7 |
| 136 | 13.3 |
| 137 | 35.6 |
| 138 | 22.4 |
| 139 | 16.2 |
| 140 | 31.9 |
| 141 | 55.2 |
| 142 | 7.3 |
| 143 | 9.2 |
| 144 | 16.7 |
| 145 | 16.4 |
| 146 | 13.5 |
| 147 | 14.1 |
| 148 | 14.8 |
| 149 | 9.1 |
| 150 | 18.8 |
| 151 | 3.6 |
| 152 | 7.2 |
| 153 | 6.5 |
| 154 | 7.0 |
| 155 | 8.5 |
| 156 | 24.3 |
| 157 | 19.7 |
| 158 | 18.5 |
| 159 | 15.2 |
| 160 | 15.8 |
| 161 | 12.6 |
| 162 | 4.5 |
| 163 | 4.9 |
| 164 | 11.4 |
| 165 | 22.6 |
| 166 | 40.0 |
| 167 | 12.4 |
| 168 | 1.5 |
| 169 | 1.6 |
| 170 | 22.7 |
| 171 | 1.3 |
| 172 | 38.3 |
| 173 | 47.6 |
| 174 | 37.0 |
| 175 | 10.8 |
| 176 | 7.3 |
| 177 | 8.5 |
| 178 | 14.8 |
| 179 | 5.7 |
| 180 | 9.1 |

Test Example 2

ALK Enzyme Inhibitory Effect

Evaluation of an inhibitory effect of a compound of the present invention with respect to ALK2 (R206H), ALK2, ALK3, and ALK6 was requested to Reaction Biology Corporation (One Great Valley Parkway, Suite 2, Malvern, Pa. 19355, USA.). Evaluation conditions were described in the following web pages. http://www.reactionbiology.corrilwebapps/site/Kinase_Assay_Protocol.aspx http://www.reactionbiology.corrilwebapps/site/KinaseDetail.aspx?page=Kinases&id=1

Test Example 2-1

An overview of evaluation of an inhibitory effect of a compound of the present invention with respect to ALK2 (R206H) is as follows.

In a buffer solution (20 mM HEPES, pH 7.5, 10 mM MgCl$_2$, 2 mM MnCl$_2$, 1 mM EGTA, 0.02% Brij 35, 0.02 mg/mL BSA, 0.1 mM Na$_3$VO$_4$, 2 mM DTT, 1% DMSO), human ALK2 (http://www.expasy.org/uniprot/Q04771) in which Arg$^{206}$ was mutated with His, and a substrate (20 µM casein) were incubated at room temperature for 20 minutes together with a test compound, 33P-ATP (specific radioactivity: 10 Ci/L) was then added thereto so that the final ATP concentration was 10 µM, and the mixture was additionally incubated at room temperature for 2 hours. The reaction mixture was filtered using a P81 ion exchange filter, and a kinase activity was determined by measuring a radioactivity bound to the filter. An inhibitory effect was determined using test compounds with respective concentrations, and a concentration (IC$_{50}$) indicating 50% of the maximum inhibitory concentration was calculated.

ALK2 (R206H) inhibitory effects of representative compounds are shown as IC$_{50}$ values in the following table.

TABLE 4

| Example | IC$_{50}$ (nM) |
|---------|----------------|
| 3 | 13.5 |
| 8 | 18.7 |
| 15 | 29.1 |
| 16 | 5.5 |
| 17 | 13.9 |
| 22 | 25.6 |
| 23 | 42.2 |
| 27 | 15.1 |
| 31 | 13.2 |
| 32 | 6.1 |
| 33 | 5.7 |
| 36 | 28.3 |
| 37 | 7.5 |
| 38 | 13.5 |
| 39 | 37.6 |
| 43 | 24.9 |
| 44 | 13.6 |
| 45 | 14.7 |
| 46 | 21.0 |
| 47 | 11.6 |
| 49 | 26.0 |
| 51 | 8.0 |
| 54 | 11.5 |
| 55 | 23.8 |
| 64 | 12.6 |
| 65 | 6.7 |
| 67 | 31.1 |
| 71 | 17.0 |
| 73 | 31.2 |
| 76 | 1.3 |
| 77 | 7.5 |
| 78 | 18.5 |
| 81 | 33.8 |
| 82 | 9.2 |
| 84 | 38.3 |
| 87 | 43.6 |
| 89 | 10.7 |
| 93 | 7.1 |
| 94 | 46.9 |
| 96 | 28.2 |
| 97 | 14.3 |
| 98 | 46.1 |
| 99 | 48.2 |
| 101 | 31.8 |
| 102 | 14.5 |
| 104 | 11.0 |
| 105 | 9.9 |
| 110 | 45.0 |
| 111 | 30.2 |
| 113 | 16.3 |
| 117 | 6.3 |
| 129 | 2.7 |
| 130 | 17.7 |
| 131 | 26.0 |
| 137 | 17.1 |
| 140 | 49.2 |
| 142 | 18.7 |
| 145 | 26.9 |
| 147 | 17.3 |
| 148 | 17.0 |

TABLE 4-continued

| Example | IC$_{50}$ (nM) |
|---|---|
| 149 | 5.6 |
| 151 | 9.4 |
| 154 | 22.3 |
| 155 | 16.0 |
| 156 | 5.4 |
| 157 | 5.6 |
| 163 | 31.0 |
| 166 | 82.4 |
| 167 | 34.6 |
| 168 | 10.9 |
| 169 | 9.4 |
| 171 | 11.0 |
| 172 | 16.3 |
| 173 | 27.2 |
| 176 | 26.4 |
| 177 | 3.0 |

Test Example 2-2

An overview of evaluation of an inhibitory effect of a compound of the present invention with respect to ALK2 is as follows.

In a buffer solution (20 mM HEPES, pH 7.5, 10 mM MgCl$_2$, 2 mM MnCl$_2$, 1 mM EGTA, 0.02% Brij 35, 0.02 mg/mL BSA, 0.1 mM Na$_3$VO$_4$, 2 mM DTT, 1% DMSO), human ALK2 (http://www.expasy.org/uniprot/Q04771) and a substrate (20 μM casein) were incubated at room temperature for 20 minutes together with test compound, 33P-ATP (specific radioactivity: 10 Ci/L) was then added thereto so that the final ATP concentration was 10 μM, and the mixture was additionally incubated at room temperature for 2 hours. The reaction mixture was filtered using a P81 ion exchange filter, and a kinase activity was determined by measuring a radioactivity bound to the filter. An inhibitory effect was determined using test compounds with respective concentrations, and a concentration (IC$_{50}$) indicating 50% of the maximum inhibitory concentration was calculated.

ALK2 inhibitory effects of representative compounds are shown as IC$_{50}$ values in the following table.

TABLE 5

| Example | IC$_{50}$ (nM) |
|---|---|
| 3 | 24.2 |
| 15 | 45.0 |
| 16 | 6.6 |
| 17 | 54.0 |
| 19 | 25.0 |
| 27 | 17.7 |
| 33 | 6.1 |
| 37 | 10.4 |
| 38 | 26.4 |
| 41 | 68.0 |
| 46 | 25.5 |
| 49 | 67.0 |
| 71 | 40.0 |
| 75 | 28.0 |
| 101 | 18.0 |
| 104 | 13.2 |
| 117 | 7.9 |
| 124 | 61.5 |
| 126 | 15.0 |
| 129 | 33.0 |
| 135 | 54.0 |
| 137 | 46.2 |
| 142 | 87.2 |
| 143 | 27.0 |
| 144 | 56.0 |
| 148 | 51.0 |

TABLE 5-continued

| Example | IC$_{50}$ (nM) |
|---|---|
| 149 | 62.5 |
| 150 | 25.0 |
| 151 | 34.0 |
| 152 | 15.0 |
| 155 | 57.0 |
| 156 | 6.1 |
| 162 | 25.0 |
| 163 | 38.0 |
| 165 | 57.0 |
| 167 | 36.1 |
| 168 | 43.0 |
| 169 | 18.0 |
| 171 | 17.0 |
| 175 | 46.8 |
| 176 | 66.0 |
| 177 | 3.5 |
| 179 | 31.0 |

Test Example 2-3

An overview of evaluation of an inhibitory effect of a compound of the present invention with respect to ALK3 is as follows.

In a buffer solution (20 mM HEPES, pH 7.5, 10 mM MgCl$_2$, 2 mM MnCl$_2$, 1 mM EGTA, 0.02% Brij 35, 0.02 mg/mL BSA, 0.1 mM Na$_3$VO$_4$, 2 mM DTT, 1% DMSO), human ALK3 (http://www.expasy.org/uniprot/P36894) and a substrate (20 μM casein) were incubated at room temperature for 20 minutes together with a test compound, 33P-ATP (specific radioactivity: 10 Ci/L) was then added thereto so that the final ATP concentration was 10 and the mixture was additionally incubated at room temperature for 2 hours. The reaction mixture was filtered using a P81 ion exchange filter, and a kinase activity was determined by measuring a radioactivity bound to the filter. An inhibition rate when the concentration of the test compound was 300 nM or 370 nM was determined.

ALK3 inhibitory effects of representative compounds are shown as an inhibition rate at 300 nM in the following table.

TABLE 6

| Example | Inhibition rate at 300 nM (%) |
|---|---|
| 3 | 52.0 |
| 15 | 51.4 |
| 17 | 50.4 |
| 19 | 59.3 |
| 23 | 52.0 |
| 29 | 66.1 |
| 38 | 53.3 |
| 49 | 52.2 |
| 71 | 48.0 |
| 75 | 67.5 |
| 101 | 48.8* |
| 104 | 65.8 |
| 126 | 59.0 |
| 127 | 55.2* |
| 129 | 55.7 |
| 135 | 60.0 |
| 137 | 47.9 |
| 139 | 54.3 |
| 142 | 62.7 |
| 143 | 57.0 |
| 144 | 46.0 |
| 149 | 63.5 |
| 150 | 53.0 |
| 151 | 56.1* |

TABLE 6-continued

| Example | Inhibition rate at 300 nM (%) |
|---|---|
| 152 | 53.0 |
| 155 | 48.8* |
| 162 | 49.5 |
| 163 | 47.6 |
| 167 | 67.5 |
| 168 | 67.3 |
| 169 | 66.6 |
| 171 | 67.1 |
| 175 | 74.6 |
| 176 | 62.4 |
| 179 | 62.4 |

*inhibition rate at 370 nM

Test Example 2-4

An overview of evaluation of an inhibitory effect of a compound of the present invention with respect to ALK6 is as follows.

In a buffer solution (20 mM HEPES, pH 7.5, 10 mM MgCl$_2$, 2 mM MnCl$_2$, 1 mM EGTA, 0.02% Brij 35, 0.02 mg/mL BSA, 0.1 mM Na$_3$VO$_4$, 2 mM DTT, 1% DMSO), human ALK6 (http://www.expasy.org/uniprot/O00238) and a substrate (20 µM casein) were incubated at room temperature for 20 minutes together with a test compound, 33P-ATP (specific radioactivity: 10 Ci/L) was then added thereto so that the final ATP concentration was 10 and the mixture was additionally incubated at room temperature for 2 hours. The reaction mixture was filtered using a P81 ion exchange filter, and a kinase activity was determined by measuring a radioactivity bound to the filter. An inhibition rate when the concentration of the test compound was 300 nM or 370 nM was determined.

ALK6 inhibitory effects of representative compounds are shown as an inhibition rate at 300 nM in the following table.

TABLE 7

| Example | Inhibition rate at 300 nM (%) |
|---|---|
| 3 | 79.6 |
| 15 | 90.2 |
| 17 | 88.0 |
| 19 | 88.4 |
| 25 | 47.7* |
| 29 | 91.3 |
| 38 | 88.9 |
| 41 | 78.0 |
| 49 | 91.6 |
| 71 | 76.0 |
| 75 | 92.9 |
| 101 | 70.4* |
| 104 | 93.5 |
| 124 | 87.0 |
| 126 | 85.0 |
| 127 | 82.8* |
| 129 | 92.2 |
| 135 | 77.0 |
| 137 | 85.3 |
| 138 | 83.8 |
| 139 | 90.6 |
| 142 | 92.6 |
| 143 | 91.0 |
| 144 | 86.0 |
| 148 | 79.4 |
| 149 | 86.5 |
| 150 | 82.0 |
| 151 | 93.0* |
| 152 | 82.0 |
| 155 | 86.5* |
| 162 | 94.2 |
| 163 | 96.2 |
| 167 | 92.2 |
| 168 | 93.9 |
| 169 | 96.5 |
| 171 | 98.3 |
| 175 | 93.6 |
| 176 | 88.5 |
| 179 | 94.3 |

*inhibition rate at 370 nM

The invention claimed is:

1. A compound of Formula (I) or a pharmacologically acceptable salt or an ester thereof,

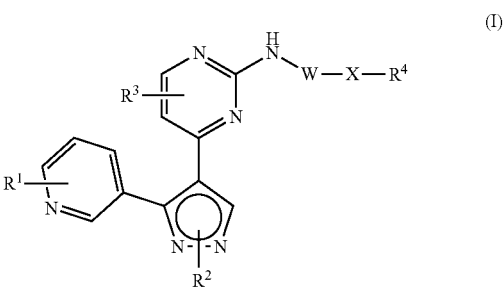

wherein,
R$^1$ represents a group selected from H and a "substituent group A",
R$^2$ represents a group selected from
  H;
  a lower alkyl group;
  a lower alkyl group substituted with 1 to 3 substituents selected from a "substituent group B" or an oxo group; and
  the "substituent group B,"
R$^3$ represents
  H,
  a halogen atom, or
  a lower alkyl group,
W represents a group selected from
  a phenylene group;
  a phenylene group substituted with 1 to 3 substituents selected from the "substituent group A";
  a bivalent group in which a phenylene group and a heterocyclyl group are condensed;
  a bivalent group in which a phenylene group and a heterocyclyl group are condensed and substituted with 1 to 3 substituents selected from the "substituent group A",
  a bivalent pyridyl group;
  a bivalent group in which a pyridyl group and a heterocyclyl group are condensed; and
  a bivalent pyrazolyl group;
X represents a group selected from
  a single bond;
  a group selected from a "substituent group C" including the sequences in reverse order;
  a lower alkylene group; and a lower alkylene group substituted with groups selected from the "substituent group C" including the sequences in reverse order;

$R^4$ represents a group selected from:
  H;
  a lower alkyl group;
  a lower alkyl group substituted with 1 to 3 substituents selected from the "substituent group B", an oxo group and a lower alkyl group;
  a $C_{3-6}$ cycloalkyl group;
  a —C(O)$R^5$ group;
  a heteroaryl group;
  a heteroaryl group substituted with 1 to 3 substituents selected from a "substituent group E";
  a heterocyclyl group; and
  a heterocyclyl group substituted with 1 to 3 substituents selected from a "substituent group D,"

$R^5$ represents
  an OH group,
  a lower alkyl group, or
  a lower alkoxy group, $R^6$ represents
  H or
  a lower alkyl group;

$R^7$ represents
  H or
  a lower alkyl group; or $R^6$ and $R^7$, together, form
  a lower alkylene group or
  a lower alkylene group in which one carbon atom is replaced with an —O— group, an —$NR^8$— group, or an —S(O)$_p$— group (p represents 0, 1 or 2);

$R^8$ represents
  H or
  a lower alkyl group;

the "substituent group A" represents
  a lower alkyl group,
  a lower alkoxy group,
  a cyano group,
  a nitro group,
  an —N($R^6$)$R^7$ group or
  a halogen atom, the "substituent group B" represents
  an OH group;
  an —N($R^6$)$R^7$ group;
  an —N($R^6$)COR$^5$ group;
  a halogen atom,
  a —C(O)$R^5$ group;
  a —C(O)N($R^6$)$R^7$ group;
  a $C_{3-6}$ cycloalkyl group;
  a halo-lower alkyl group;
  a heterocyclyl group;
  a heterocyclyl group substituted with 1 to 3 substituents selected from the "substituent group A";
  an aryl group;
  an aryl group substituted with 1 to 3 substituents selected from the "substituent group A";
  a pyridyl group;
  a pyridyl group substituted with 1 to 3 substituents selected from the "substituent group A";
  a lower alkoxy group;
  a halo-lower alkoxy group; or
  a $C_{3-6}$ cycloalkyl lower alkoxy group, the "substituent group C" represents
  an —O— group,
  a —C(O)— group,
  a —C(O)O— group,
  a —C(O)NR$^8$— group,
  an —NR$^8$— group,
  an —S— group,
  an —S(O)— group,
  an —S(O)$_2$— group,
  an —S(O)$_2$NR$^8$— group or
  an —NR$^8$S(O)$_2$— group;

the "substituent group D" represents
  a lower alkyl group;
  a lower alkyl group substituted with 1 to 3 substituents selected from the "substituent group B" and an oxo group;
  an oxo group;
  a cyano group;
  a halogen atom;
  an —N($R^6$)$R^7$ group;
  an —N($R^6$)COR$^5$ group;
  a —CO-lower alkylene-OH group;
  a —C(O)$R^5$ group;
  a —C(O)N($R^6$)$R^7$ group;
  a heterocyclyl group;
  a heterocyclyl group substituted with 1 to 3 substituents selected from the "substituent group A";
  a $C_{3-6}$ cycloalkyl group;
  an aryl group;
  a lower alkyl group substituted with 1 to 3 substituents selected from the "substituent group B," an oxo group and a COOH group, or
  an aryl group substituted with 1 to 3 substituents selected from the "substituent group A," and the "substituent group E" represents
  an OH group;
  a halogen atom;
  a lower alkyl group;
  a halo-lower alkyl group;
  a lower alkyl group substituted with 1 to 3 substituents selected from the "substituent group B" and an oxo group;
  a heterocyclyl group; or
  a heterocyclyl group substituted with 1 to 3 substituents selected from the "substituent group D".

2. The compound or a pharmacologically acceptable salt or an ester thereof according to claim 1, wherein $R^1$ is H or a halogen atom.

3. The compound or a pharmacologically acceptable salt or an ester thereof according to claim 1,
wherein
  $R^2$ is a group selected from
    a lower alkyl group;
    a lower alkyl group substituted with 1 to 3 substituents selected from the "substituent group B" and an oxo group; and
    the "substituent group B".

4. The compound or a pharmacologically acceptable salt or an ester thereof according to claim 1,
wherein
  $R^2$ is a group selected from
    a lower alkyl group;
    a lower alkyl group substituted with 1 to 3 substituents selected from the "substituent group B" and an oxo group;
    a $C_{3-6}$ cycloalkyl group; and
    a heterocyclyl group.

5. The compound or a pharmacologically acceptable salt or an ester thereof according to claim 1, wherein $R^3$ represents H or a halogen atom.

6. The compound or a pharmacologically acceptable salt or an ester thereof according to claim 1,
wherein
W represents a group selected from
a phenylene group;
a phenylene group substituted with 1 to 3 substituents selected from the "substituent group A";
a bivalent group in which a phenylene group and a heterocyclyl group are condensed;
a bivalent pyridyl group; and
a bivalent pyrazolyl groups.

7. The compound or a pharmacologically acceptable salt or an ester thereof according to claim 1,
wherein
W represents a group selected from
a phenylene group,
a bivalent group in which a phenylene group and a heterocyclyl group are condensed;
a bivalent pyridyl group; and
a bivalent pyrazolyl group.

8. The compound or a pharmacologically acceptable salt or an ester thereof according to claim 1,
wherein
X represents a group selected from
a single bond; and
—O— group, a —C(O)— group, a —C(O)NR$^8$— group, an —NR$^8$C(O)— group, an —S(O)$_2$— group, an —S(O)$_2$NR$^8$— group, or an —NR$^8$S(O)$_2$— group including the sequences in reverse order;
a lower alkylene group; and
a lower alkylene group substituted with an —O— group, a —C(O)— group, a —C(O)NR$^8$— group, an —NR$^8$C(O)— group, an —S(O)$_2$— group, an —S(O)$_2$NR$^8$— group, or an —NR$^8$S(O)$_2$— group including the sequences in reverse order.

9. The compound or a pharmacologically acceptable salt or an ester thereof according to claim 1,
wherein
X represents a group selected from
a single bond; and
an —O— group, a —C(O)— group, a —C(O)NR$^8$— group, an —S(O)$_2$— group, or an —S(O)$_2$NR$^8$— group including the sequences in reverse order;
a lower alkylene group; and
a lower alkylene group substituted with an —O— group or a —C(O)— group including the sequences in reverse order.

10. The compound or a pharmacologically acceptable salt or an ester thereof according to claim 1,
wherein
R$^4$ represents a group selected from
H;
a lower alkyl group;
a lower alkyl group substituted with 1 to 3 substituents selected from the "substituent group B," an oxo group and a lower alkyl group;
a C$_{3-6}$ cycloalkyl group;
a —C(O)R$^5$ group;
a heteroaryl group;
a heteroaryl group substituted with 1 to 3 substituents selected from the "substituent group E";
a heterocyclyl group; and
a heterocyclyl group substituted with 1 to 3 substituents selected from the "substituent group D".

11. The compound or a pharmacologically acceptable salt or an ester thereof according to claim 1,
wherein
R$^4$ represents a group selected from
H;
a lower alkyl group;
a lower alkyl group substituted with 1 to 3 substituents selected from the "substituent group B," an oxo group and a lower alkyl group;
a C$_{3-6}$ cycloalkyl group;
a heteroaryl group;
a heteroaryl group substituted with 1 to 3 substituents selected from the "substituent group E";
a heterocyclyl group; and
a heterocyclyl group substituted with 1 to 3 substituents selected from the "substituent group D".

12. The compound or a pharmacologically acceptable salt or an ester thereof according to claim 1,
wherein
a "heterocyclyl" group in the "heterocyclyl" group and the "heterocyclyl" group substituted with 1 to 3 substituents selected from the "substituent group D" in R$^4$ is a group selected from the followings:

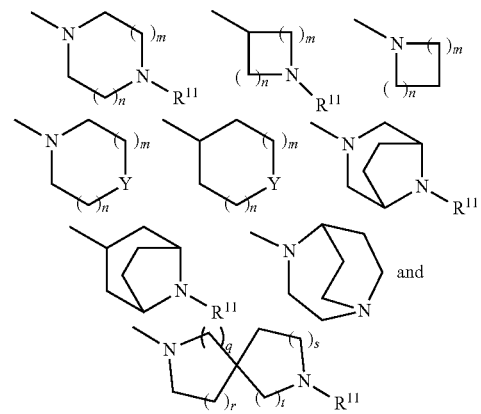

wherein, R$^{11}$ represents H or a "substituent group D,"
Y represents an —O— group, or —S(O)$_p$— group,
m and n may be the same as or different from each other; 1 or 2,
p is 0, 1 or 2, and
q, r, s and t may be the same as or different from each other; 0, 1 or 2; provided that q and t are not both 0.

13. The compound or a pharmacologically acceptable salt or an ester thereof according to claim 1,
wherein
R$^5$ is an OH group or a lower alkyl group.

14. The compound or a pharmacologically acceptable salt or an ester thereof according to claim 1,
wherein
R$^6$ and R$^7$, together, form a lower alkylene group.

15. The compound or a pharmacologically acceptable salt or an ester thereof according to claim 1,
wherein
the "substituent group A" is a lower alkyl group, a cyano group or a halogen atom.

16. The compound or a pharmacologically acceptable salt or an ester thereof according to claim 1,
wherein
the "substituent group B" is
an OH group,
an —N(R$^6$)R$^7$ group,
a halogen atom, a C<sub>3-6</sub> cycloalkyl group,
a heterocyclyl group,
an aryl group,
an aryl group substituted with 1 to 3 substituents selected from the "substituent group A,"
a pyridyl group,
a lower alkoxy group,
a halo-lower alkoxy group,
a —C(O)N($R^5$)$R^7$ group, or
a $C_{3-6}$ cycloalkyl lower alkoxy group.

17. The compound or a pharmacologically acceptable salt or an ester thereof according to claim 1,
wherein
the "substituent group B" is
an OH group,
an —N($R^6$)$R^7$ group,
a halogen atom,
a $C_{3-6}$ cycloalkyl group,
a heterocyclyl group,
an aryl group,
an aryl group substituted with 1 to 3 substituents selected from the "substituent group A,"
a lower alkoxy group,
a halo-lower alkoxy group, or
a $C_{3-6}$ cycloalkyl lower alkoxy group.

18. The compound or a pharmacologically acceptable salt or an ester thereof according to claim 1,
wherein
the "substituent group C" is
an —O— group,
a —C(O)— group,
a —C(O)$NR^8$— group,
an —S(O)$_2$— group, or
an —S(O)$_2NR^8$— group.

19. The compound or a pharmacologically acceptable salt or an ester thereof according to claim 1,
wherein
the "substituent group C" is
an —O— group,
a —C(O)— group,
a —C(O)$NR^8$— group, or
an —S(O)$_2NR^8$— group.

20. The compound or a pharmacologically acceptable salt or an ester thereof according to claim 1,
wherein
the "substituent group D" is
a lower alkyl group;
a lower alkyl group substituted with 1 to 3 substituents selected from the "substituent group B" and an oxo group;
an oxo group;
a cyano group;
a halogen atom;
an —N($R^6$)$R^7$ group;
an —N($R^6$)$COR^5$ group;
a —CO-lower alkylene-OH group;
a —C(O)$R^5$ group;
a —C(O)N($R^6$)$R^7$ group;
a heterocyclyl group;
a heterocyclyl group substituted with 1 to 3 substituents selected from the "substituent group A";
a $C_{3-6}$ cycloalkyl group; or
an aryl group.

21. The compound or a pharmacologically acceptable salt or an ester thereof according to claim 1,
wherein
the "substituent group D" is
a lower alkyl group;
a lower alkyl group substituted with 1 to 3 substituents selected from the "substituent group B" and an oxo group;
a halogen atom;
an oxo group;
a cyano group;
an —N($R^6$)$R^7$ group;
a —CO-lower alkylene-OH group;
a —C(O)$R^5$ group;
a heterocyclyl group;
a $C_{3-6}$ cycloalkyl group; or
an aryl group.

22. The compound or a pharmacologically acceptable salt or an ester thereof according to claim 1,
wherein
the "substituent group E" is
a lower alkyl group;
a halo-lower alkyl group;
a lower alkyl group substituted with 1 to 3 substituents selected from the "substituent group B" and an oxo group;
a heterocyclyl group; or
a heterocyclyl group substituted with 1 to 3 substituents selected from the "substituent group D".

23. The compound or a pharmacologically acceptable salt or an ester thereof according to claim 1,
wherein
the "substituent group E" is
a lower alkyl group;
a halo-lower alkyl group; or
a heterocyclyl group.

24. The compound or a pharmacologically acceptable salt or an ester thereof according to claim 1,
wherein
the group of —W—X—$R^4$, together, forms the followings:

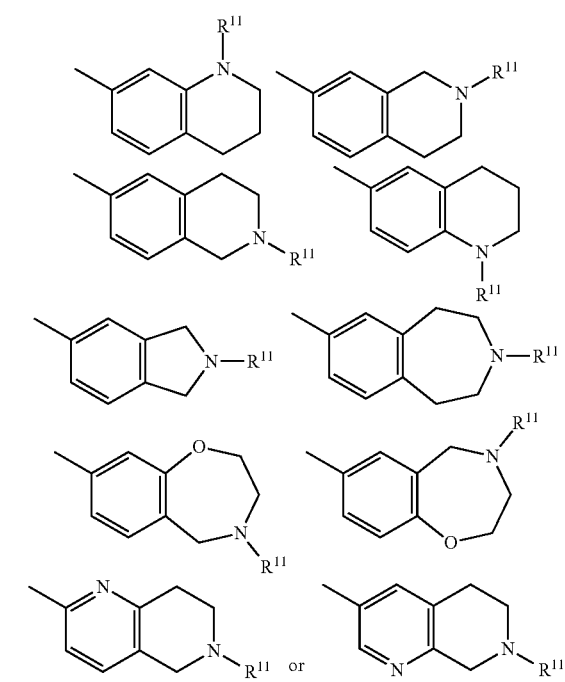

wherein, $R^{11}$ is H or a "substituent group D".

25. The compound or a pharmacologically acceptable salt or an ester thereof according to claim 1, wherein
the compound is any of the following compounds:
(4-(tert-butyl)piperazin-1-yl) (4-((4-(1-ethyl-3-(pyridin-3-yl)-1H-pyrazol-4-yl)pyrimidin-2-yl)amino)phenyl)methanone;
(4-((4-(1-ethyl-3-(pyridin-3-yl)-1H-pyrazol-4-yl)pyrimidin-2-yl)amino)phenyl) (4-(4-fluorophenyl)piperazine-1-yl)methanone;
2-methyl-N-(4-(1-(oxetan-3-yl)-3-(pyridin-3-yl)-1H-pyrazol-4-yl)pyrimidin-2-yl)-1,2,3,4-tetrahydroisoquinolin-6-amine;
2-methyl-N-(4-(3-(pyridin-3-yl)-1-((tetrahydrofuran-3-yl)methyl)-1H-pyrazol-4-yl)pyrimidin-2-yl)-1,2,3,4-tetrahydroisoquinolin-6-amine;
N-(4-(1-(2-methoxyethyl)piperidin-4-yl)phenyl)-4-(1-(oxetan-3-yl)-3-(pyridin-3-yl)-1H-pyrazol-4-yl)pyrimidin-2-amine;
4-(1-ethyl-3-(pyridin-3-yl)-1H-pyrazol-4-yl)-N-(4-(4-(oxetan-3-yl)piperazin-1-yl)phenyl)pyrimidin-2-amine;
4-(1-ethyl-3-(pyridin-3-yl)-1H-pyrazol-4-yl)-N-(4-(4-isopropylpiperazin-1-yl)phenyl)pyrimidin-2-amine;
4-(1-ethyl-3-(pyridin-3-yl)-1H-pyrazol-4-yl)-N-(4-(4-(2-methoxyethyl)piperazin-1-yl)phenyl)pyrimidin-2-amine;
N-(4-(1-ethyl-1H-pyrazol-4-yl)phenyl)-4-(1-ethyl-3-(pyridin-3-yl)-1H-pyrazol-4-yl)pyrimidin-2-amine;
2-(4-(4-((4-(1-ethyl-3-(pyridin-3-yl)-1H-pyrazol-4-yl)pyrimidin-2-yl)amino)phenyl)piperazin-1-yl)-1-(piperidin-1-yl)ethan-1-one;
N-(4-(4-cyclopropylpiperazin-1-yl)phenyl)-4-(1-ethyl-3-(pyridin-3-yl)-1H-pyrazol-4-yl)pyrimidin-2-amine;
N-(4-(4-(cyclopropylmethyl)piperazin-1-yl)phenyl)-4-(1-ethyl-3-(pyridin-3-yl)-1H-pyrazol-4-yl(pyrimidin-2-amine;
N-(4-(4-(cyclopropylmethyl)piperazin-1-yl)phenyl)-4-(1-(2-methoxyethyl)-3-(pyridin-3-yl)-1H-pyrazol-4-yl)pyrimidin-2-amine;
4-(1-(2-methoxyethyl)-3-(pyridin-3-yl)-1H-pyrazol-4-yl)-N-(4-(4-(2-methoxyethyl)piperazin-1-yl)phenyl)pyrimidin-2-amine;
N-(4-(1H-1,2,4-triazol-1-yl)phenyl)-4-(1-ethyl-3-(pyridin-3-yl)-1H-pyrazol-4-yl)pyrimidin-2-amine;
4-(1-ethyl-3-(pyridin-3-yl)-1H-pyrazol-4-yl)-N-(4-(2-(4-(2-methoxyethyl)piperazin-1-yl)ethyl)phenyl)pyrimidin-2-amine;
N-(4-(1H-imidazol-1-yl)phenyl)-4-(1-ethyl-3-(pyridin-3-yl)-1H-pyrazol-4-yl)pyrimidin-2-amine;
4-(1-ethyl-3-(pyridin-3-yl)-1H-pyrazol-4-yl)-N-(3-fluoro-4-(1-methylpiperidin-4-yl)phenyl)pyrimidin-2-amine;
4-(1-ethyl-3-(pyridin-3-yl)-1H-pyrazol-4-yl)-N-(4-(4-methylpiperazin-1-yl)phenyl)pyrimidin-2-amine;
4-(1-ethyl-3-(pyridin-3-yl)-1H-pyrazol-4-yl)-N-(3-methoxy-4-(4-methylpiperazin-1-yl)phenyl)pyrimidin-2-amine;
4-(1-ethyl-3-(pyridin-3-yl)-1H-pyrazol-4-yl)-N-(4-(piperidin-1-yl)phenyl)pyrimidin-2-amine;
4-(1-ethyl-3-(pyridin-3-yl)-1H-pyrazol-4-yl)-N-(4-(1-(2-methoxyethyl)pyrrolidin-3-yl)phenyl)pyrimidin-2-amine;
N-(4-(4-(2-(2,2-difluoroethoxy)ethyl)piperazin-1-yl)phenyl)-4-(1-ethyl-3-(pyridin-3-yl)-1H-pyrazol-4-yl)pyrimidin-2-amine;
1-(4-(4-((4-(1-ethyl-3-(pyridin-3-yl)-1H-pyrazol-4-yl)pyrimidin-2-yl)amino)-1H-pyrazol-1-yl)piperidin-1-yl)-2-methylpropan-2-ol;
4-(1-ethyl-3-(pyridin-3-yl)-1H-pyrazol-4-yl)-N-(1-(1-(2-methoxyethyl)piperidin-4-yl)-1H-pyrazol-4-yl)pyrimidin-2-amine oxalate;
4-(1-ethyl-3-(pyridin-3-yl)-1H-pyrazol-4-yl)-N-(4-(1-(2-methoxyethyl)piperidin-4-yl)phenyl)pyrimidin-2-amine;
N-(4-(1-(2-methoxyethyl)-3-(pyridin-3-yl)-1H-pyrazol-4-yl)pyrimidin-2-yl)-2-methylisoindolin-5-amine;
N-(4-(1-ethyl-3-(pyridin-3-yl)-1H-pyrazol-4-yl)pyrimidin-2-yl)-2-(2-methoxyethyl)isoindolin-5-amine;
N-(4-(1-(2-methoxyethyl)-3-(pyridin-3-yl)-1H-pyrazol-4-yl)pyrimidin-2-yl)-2-methyl-1,2,3,4-tetrahydroisoquinolin-6-amine;
2-methyl-1-(4-(2-((2-methyl-1,2,3,4-tetrahydroisoquinolin-6-yl)amino)pyrimidin-4-yl)-3-(pyridin-3-yl)-1H-pyrazol-1-yl)propan-2-ol;
3-cyclopropyl-N-(4-(1-ethyl-3-(pyridin-3-yl)-1H-pyrazol-4-yl)pyrimidin-2-yl)-2,3,4,5-tetrahydro-1H-benzo[d]azepin-7-amine;
N-(4-(1-ethyl-3-(pyridin-3-yl)-1H-pyrazol-4-yl)pyrimidin-2-yl)-4-methyl-2,3,4,5-tetrahydrobenzo[f] [1,4] oxazepin-8-amine;
N-(4-(4-(dimethylamino)-4-methylpiperidin-1-yl)phenyl)-4-(1-ethyl-3-(pyridin-3-yl)-1H-pyrazol-4-yl)pyrimidin-2-amine;
4-(1-(2-methoxyethyl)-3-(pyridin-3-yl)-1H-pyrazol-4-yl)-N-(4-(piperazin-1-yl)phenyl)pyrimidin-2-amine;
N-(4-(4-(2-methoxyethyl)piperazin-1-yl)phenyl)-4-(3-(pyridin-3-yl)-1-(tetrahydrofuran-3-yl)-1H-pyrazol-4-yl)pyrimidin-2-amine;
N-(4-(4-(2-methoxyethyl)piperazin-1-yl)phenyl)-4-(1-((3-methyloxetan-3-yl)methyl)-3-(pyridin-3-yl))-1H-pyrazol-4-yl)pyrimidin-2-amine;
4-(1-ethyl-3-(pyridin-3-yl)-1H-pyrazol-4-yl)-N-(4-(4-((1-methylpyrrolidin-2-yl)methyl)piperazin-1-yl)phenyl)pyrimidin-2-amine;
1-(4-(2-((4-(4-(2-methoxyethyl)piperazin-1-yl)phenyl)amino)pyrimidin-4-yl)-3-(pyridin-3-yl)-1H-pyrazol-1-yl)-2-methylpropan-2-ol;
2-((4-(2-((4-(4-(2-methoxyethyl)piperazin-1-yl)phenyl)amino)pyrimidin-4-yl)-3-(pyridin-3-yl)-1H-pyrazol-1-yl)methyl)benzonitrile;
4-(1-ethyl-3-(pyridin-3-yl)-1H-pyrazol-4-yl)-N-(4-(8-(2-methoxyethyl)-8-azabicyclo[3.2.1] octan-3-yl)phenyl)pyrimidin-2-amine;
N-(4-(1-ethyl-3-(pyridin-3-yl)-1H-pyrazol-4-yl)pyrimidin-2-yl)-2-((tetrahydrofuran-2-yl)methyl)-1,2,3,4-tetrahydroisoquinoline-7-amine;
N-(4-(1-ethyl-3-(pyridin-3-yl)-1H-pyrazol-4-yl)pyrimidin-2-yl)-2-((tetrahydrofuran-2-yl)methyl)-1,2,3,4-tetrahydroisoquinolin-6-amine;
N-(4-(1-ethyl-3-(pyridin-3-yl)-1H-pyrazol-4-yl)pyrimidin-2-yl)-3-(2-methoxyethyl)-2,3,4,5-tetrahydro-1H-benzo[d]azepin-7-amine;
N-(4-(4-((4,4-dimethyloxetan-2-yl)methyl)piperazin-1-yl)phenyl)-4-(1-ethyl-3-(pyridin-3-yl)-1H-pyrazol-4-yl)pyrimidin-2-amine;
4-(1-ethyl-3-(pyridin-3-yl)-1H-pyrazol-4-yl)-N-(4-(4-((tetrahydrofuran-3-yl)methyl)piperazin-1-yl)phenyl)pyrimidin-2-amine;
4-(1-(oxetan-3-yl)-3-(pyridin-3-yl)-1H-pyrazol-4-yl)-N-(4-(4-(oxetan-3-yl)piperazin-1-yl)phenyl)pyrimidin-2-amine;
N-(4-(4-(2-methoxyethyl)piperazin-1-yl)phenyl)-4-(1-(oxetan-3-ylmethyl)-3-(pyridin-3-yl)-1H-pyrazol-4-yl)pyrimidin-2-amine;
1-(4-(4-((4-(1-ethyl-3-(pyridin-3-yl)-1H-pyrazol-4-yl)pyrimidin-2-yl)amino)phenyl)piperazin-1-yl)-2-methylpropan-2-ol;
1-(4-(4-((4-(1-ethyl-3-(pyridin-3-yl)-1H-pyrazol-4-yl)pyrimidin-2-yl)amino)phenyl)piperazin-1-yl)-3-methoxypropan-2-ol;

1-(7-((4-(1-ethyl-3-(pyridin-3-yl)-1H-pyrazol-4-yl)pyrimidin-2-yl)amino)-3,4-dihydroisoquinoline-2(1H)-yl)-2-methylpropan-2-ol;
1-(6-((4-(1-ethyl-3-(pyridin-3-yl)-1H-pyrazol-4-yl)pyrimidin-2-yl)amino)-3,4-dihydroisoquinolin-2(1H)-yl)-3-methoxypropan-2-ol;
4-(1-ethyl-3-(pyridin-3-yl)-1H-pyrazol-4-yl)-N-(4-(1-methylpiperidin-3-yl)phenyl)pyrimidin-2-amine;
4-(1-ethyl-3-(pyridin-3-yl)-1H-pyrazol-4-yl)-N-(3-(1-methylpiperidin-4-yl)phenyl)pyrimidin-2-amine;
N-(4-(1-ethyl-3-(pyridin-3-yl)-1H-pyrazol-4-yl)pyrimidin-2-yl)-3-methyl-2,3,4,5-tetrahydro-1H-benzo[d]azepin-7-amine;
(4-((4-(1-ethyl-3-(pyridin-3-yl)-1H-pyrazol-4-yl)pyrimidin-2-yl)amino)phenyl) (8-methyl-3,8-diazabicyclo[3.2.1]octan-3-yl)methanone;
(8-cyclopentyl-3,8-diazabicyclo[3.2.1]octan-3-yl) (4-((4-(1-ethyl-3-(pyridin-3-yl)-1H-pyrazol-4-yl)pyrimidin-2-yl)amino)phenyl)methanone;
(4-((4-(1-ethyl-3-(pyridin-3-yl)-1H-pyrazol-4-yl)pyrimidin-2-yl)amino)phenyl) (4-isopropylpiperazin-1-yl)methanone;
(4-cyclohexylpiperazin-1-yl) (4-((4-(1-ethyl-3-(pyridin-3-yl)-1H-pyrazol-4-yl)pyrimidin-2-yl)amino)phenyl)methanone;
N-(4-(1-ethyl-3-(pyridin-3-yl)-1H-pyrazol-4-yl)pyrimidin-2-yl)-3-(oxetan-3-yl)-2,3,4,5-tetrahydro-1H-benzo[d]azepin-7-amine;
N-(4-(1-ethyl-3-(pyridin-3-yl)-1H-pyrazol-4-yl)pyrimidin-2-yl)-2-(2-methoxyethyl)-1,2,3,4-tetrahydroisoquinolin-6-amine;
N-(4-(1-ethyl-3-(pyridin-3-yl)-1H-pyrazol-4-yl)pyrimidin-2-yl)-2-methyl-1,2,3,4-tetrahydroisoquinolin-6-amine;
4-(1-ethyl-3-(pyridin-3-yl)-1H-pyrazol-4-yl)-N-(4-(4-(tetrahydro-2H-pyran-4-yl)piperazin-1-yl)phenyl)pyrimidin-2-amine;
2-methyl-1-(4-(2-((2-(oxetan-3-yl)-1,2,3,4-tetrahydroisoquinolin-6-yl)amino)pyrimidin-4-yl)-3-(pyridin-3-yl)-1H-pyrazol-1-yl)propan-2-ol;
4-(1,1-dimethylethyl)-3-(pyridin-3-yl)-1H-pyrazol-4-yl)-N-(4-(piperazin-1-yl)phenyl)pyrimidin-2-amine;
4-(1-(oxetan-3-yl)-3-(pyridin-3-yl)-1H-pyrazol-4-yl)-N-(4-(piperazin-1-yl)phenyl)pyrimidin-2-amine;
4-(1-phenethyl-3-(pyridin-3-yl)-1H-pyrazol-4-yl)-N-(4-(piperazin-1-yl)phenyl)pyrimidin-2-amine;
N-(4-(3,8-diazabicyclo[3.2.1]octan-3-yl)phenyl)-4-(1-ethyl-3-(pyridin-3-yl)-1H-pyrazol-4-yl)pyrimidin-2-amine;
N-(4-(azetidin-3-yloxy)phenyl)-4-(1-ethyl-3-(pyridin-3-yl)-1H-pyrazol-4-yl)pyrimidin-2-amine;
N-(4-(4-aminopiperidin-1-yl)phenyl)-4-(1-ethyl-3-(pyridin-3-yl)-1H-pyrazol-4-yl)pyrimidin-2-amine;
4-(1-ethyl-3-(5-fluoropyridin-3-yl)-1H-pyrazol-4-yl)-N-(4-(piperazin-1-yl)phenyl)pyrimidin-2-amine;
4-(1-(2,2-difluoroethyl)-3-(pyridin-3-yl)-1H-pyrazol-4-yl)-N-(4-(piperazin-1-yl)phenyl)pyrimidine-2-amine;
4-(1-ethyl-3-(pyridin-3-yl)-1H-pyrazol-4-yl)-N-(4-(piperazin-1-yl)phenyl)pyrimidin-2-amine;
4-(1-ethyl-3-(pyridin-3-yl)-1H-pyrazol-4-yl)-N-(3-fluoro-4-(piperazin-1-yl)phenyl)pyrimidin-2-amine;
N-(3,5-difluoro-4-(piperazin-1-yl)phenyl)-4-(1-ethyl-3-(pyridin-3-yl)-1H-pyrazol-4-yl)pyrimidin-2-amine;
4-(1-ethyl-3-(pyridin-3-yl)-1H-pyrazol-4-yl)-N-(3-methyl-4-(piperazin-1-yl)phenyl)pyrimidin-2-amine;
4-(1-ethyl-3-(pyridin-3-yl)-1H-pyrazol-4-yl)-N-(6-(piperazin-1-yl)pyridin-3-yl)pyrimidin-2-amine;
3-((4-(2-((4-(piperazin-1-yl)phenyl)amino)pyrimidin-4-yl)-3-(pyridin-3-yl)-1H-pyrazol-1-yl)methyl)benzonitrile;
2-((4-(2-((4-(piperazin-1-yl)phenyl)amino)pyrimidin-4-yl)-3-(pyridin-3-yl)-1H-pyrazol-1-yl)methyl)benzonitrile;
4-(1-ethyl-3-(pyridin-3-yl)-1H-pyrazol-4-yl)-N-(4-(piperidin-4-yl)phenyl)pyrimidin-2-amine;
N-(4-(8-azabicyclo[3.2.1]octan-3-yl)phenyl)-4-(1-ethyl-3-(pyridin-3-yl)-1H-pyrazol-4-yl)pyrimidin-2-amine;
4-(1-ethyl-3-(pyridin-3-yl)-1H-pyrazol-4-yl)-N-(4-(1-(piperidin-4-yl)-1H-pyrazol-4-yl)phenyl)pyrimidin-2-amine;
N-(4-(1-ethyl-3-(pyridin-3-yl)-1H-pyrazol-4-yl)pyrimidin-2-yl)-1,2,3,4-tetrahydroisoquinolin-6-amine;
N-(4-(1-ethyl-3-(pyridin-3-yl)-1H-pyrazol-4-yl)pyrimidin-2-yl)-1,2,3,4-tetrahydroisoquinolin-7-amine;
N-(4-(1-ethyl-3-(pyridin-3-yl)-1H-pyrazol-4-yl)pyrimidin-2-yl)-2,3,4,5-tetrahydro-1H-benzo[d]azepin-7-amine;
2-(6-((4-(1-ethyl-3-(pyridin-3-yl)-1H-pyrazol-4-yl)pyrimidin-2-yl)amino)-3,4-dihydroisoquinolin-2(1H)-yl)acetic acid;
2-(4-(4-((4-(1-ethyl-3-(pyridin-3-yl)-1H-pyrazol-4-yl)pyrimidin-2-yl)amino)phenyl)piperazin-1-yl)acetic acid;
N-(4-(4-amino-4-methylpiperidin-1-yl)phenyl)-4-(1-ethyl-3-(pyridin-3-yl)-1H-pyrazol-4-yl)pyrimidin-2-amine;
N-(4-(4-amino-4-ethylpiperidin-1-yl)phenyl)-4-(1-ethyl-3-(pyridin-3-yl)-1H-pyrazol-4-yl)pyrimidin-2-amine;
2-(7-((4-(1-ethyl-3-(pyridin-3-yl)-1H-pyrazol-4-yl)pyrimidin-2-yl)amino)-3,4-dihydroisoquinolin-2(1H)-yl)ethan-1-ol; and
4-(1-ethyl-3-(pyridin-3-yl)-1H-pyrazol-4-yl)-N-(4-(3-(4-methylpiperazin-1-yl)-1H-1,2,4-triazol-1-yl)phenyl)pyrimidin-2-amine.

26. The compound or a pharmacologically acceptable salt or an ester thereof according to claim 1,
wherein
the compound is any of the following compounds:
4-(1-ethyl-3-(pyridin-3-yl)-1H-pyrazol-4-yl)-N-(4-(4-(oxetan-3-yl)piperazin-1-yl)phenyl)pyrimidin-2-amine;
4-(1-ethyl-3-(pyridin-3-yl)-1H-pyrazol-4-yl)-N-(4-(4-(2-methoxyethyl)piperazin-1-yl)phenyl)pyrimidin-2-amine;
N-(4-(1-ethyl-1H-pyrazol-4-yl)phenyl)-4-(1-ethyl-3-(pyridin-3-yl)-1H-pyrazol-4-yl)pyrimidin-2-amine;
N-(4-(4-(cyclopropylmethyl)piperazin-1-yl)phenyl)-4-(1-ethyl-3-(pyridin-3-yl)-1H-pyrazol-4-yl)pyrimidin-2-amine;
N-(4-(1H-1,2,4-triazol-1-yl)phenyl)-4-(1-ethyl-3-(pyridin-3-yl)-1H-pyrazol-4-yl)pyrimidin-2-amine;
4-(1-ethyl-3-(pyridin-3-yl)-1H-pyrazol-4-yl)-N-(4-(4-methylpiperazin-1-yl)phenyl)pyrimidin-2-amine;
1-(4-(4-((4-(1-ethyl-3-(pyridin-3-yl)-1H-pyrazol-4-yl)pyrimidin-2-yl)amino)-1H-pyrazol-1-yl)piperidin-1-yl)-2-methylpropan-2-ol;
N-(4-(1-(2-methoxyethyl)-3-(pyridin-3-yl)-1H-pyrazol-4-yl)pyrimidin-2-yl)-2-methyl-1,2,3,4-tetrahydroisoquinolin-6-amine;
2-methyl-1-(4-(2-((2-methyl-1,2,3,4-tetrahydroisoquinolin-6-yl)amino)pyrimidin-4-yl)-3-(pyridin-3-yl)-1H-pyrazol-1-yl)propan-2-ol;
N-(4-(1-ethyl-3-(pyridin-3-yl)-1H-pyrazol-4-yl)pyrimidin-2-yl)-2-((tetrahydrofuran-2-yl)methyl)-1,2,3,4-tetrahydroisoquinolin-6-amine;
N-(4-(1-ethyl-3-(pyridin-3-yl)-1H-pyrazol-4-yl)pyrimidin-2-yl)-3-(2-methoxyethyl)-2,3,4,5-tetrahydro-1H-benzo[d]azepin-7-amine;
4-(1-(oxetan-3-yl)-3-(pyridin-3-yl)-1H-pyrazol-4-yl)-N-(4-(4-(oxetan-3-yl)piperazin-1-yl)phenyl)pyrimidin-2-amine;
N-(4-(1-ethyl-3-(pyridin-3-yl)-1H-pyrazol-4-yl)pyrimidin-2-yl)-2-methyl-1,2,3,4-tetrahydroisoquinolin-6-amine;
4-(1-(2,2-difluoroethyl)-3-(pyridin-3-yl)-1H-pyrazol-4-yl)-N-(4-(piperazin-1-yl)phenyl)pyrimidin-2-amine;

4-(1-ethyl-3-(pyridin-3-yl)-1H-pyrazol-4-yl)-N-(4-(piperazin-1-yl)phenyl)pyrimidin-2-amine;
4-(1-ethyl-3-(pyridin-3-yl)-1H-pyrazol-4-yl)-N-(6-(piperazin-1-yl)pyridin-3-yl)pyrimidin-2-amine;
N-(4-(1-ethyl-3-(pyridin-3-yl)-1H-pyrazol-4-yl)pyrimidin-2-yl)-1,2,3,4-tetrahydroisoquinolin-6-amine;
N-(4-(1-ethyl-3-(pyridin-3-yl)-1H-pyrazol-4-yl)pyrimidin-2-yl)-1,2,3,4-tetrahydroisoquinolin-7-amine;
N-(4-(1-ethyl-3-(pyridin-3-yl)-1H-pyrazol-4-yl)pyrimidin-2-yl)-2,3,4,5-tetrahydro-1H-benzo[d]azepin-7-amine; and
N-(4-(4-amino-4-ethylpiperidin-1-yl)phenyl)-4-(1-ethyl-3-(pyridin-3-yl)-1H-pyrazol-4-yl)pyrimidin-2-amine.

* * * * *